(12) United States Patent
Baier et al.

(10) Patent No.: US 11,707,615 B2
(45) Date of Patent: Jul. 25, 2023

(54) MEDICAL PUMP

(71) Applicant: DEKA Products Limited Partnership, Manchester, NH (US)

(72) Inventors: Michael J. Baier, Dunbarton, NH (US); David Blumberg, Jr., Deerfield, NH (US); Hugh J. Boddington, Concord, NH (US); Thomas A. Friedrich, Loudon, NH (US); Paul G. Girouard, Allenstown, NH (US); Larry B. Gray, Merrimack, NH (US); David C. Nivens, Hollis, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 482 days.

(21) Appl. No.: 16/542,789

(22) Filed: Aug. 16, 2019

(65) Prior Publication Data
US 2020/0054823 A1 Feb. 20, 2020

Related U.S. Application Data

(60) Provisional application No. 62/765,100, filed on Aug. 16, 2018.

(51) Int. Cl.
*A61M 39/28* (2006.01)
*A61M 5/142* (2006.01)
*A61M 5/145* (2006.01)

(52) U.S. Cl.
CPC ...... *A61M 39/285* (2013.01); *A61M 5/14228* (2013.01); *A61M 39/287* (2013.01); *A61M 2005/14533* (2013.01)

(58) Field of Classification Search
CPC .. A61M 39/28; A61M 39/284; A61M 39/285; A61M 39/286; A61M 39/287
See application file for complete search history.

(56) References Cited

U.S. PATENT DOCUMENTS

| 788,603 | A | * | 5/1905 | Rowell | A61M 39/284 |
| | | | | | 251/9 |
| 2,546,852 | A | | 3/1951 | Ruckle | |

(Continued)

FOREIGN PATENT DOCUMENTS

| AU | 736366 B2 | 7/2001 |
| CN | 1938061 A | 3/2007 |

(Continued)

OTHER PUBLICATIONS

AAMI and FDA, Infusing Patients Safely: Priority Issues from the AAMI/FDA Infusion Device Summit, Symposium, Oct. 5-6, 2010, pp. 1-48, AAMI, Arlington, VA, USA.

(Continued)

*Primary Examiner* — William R Carpenter
(74) *Attorney, Agent, or Firm* — Ira Stickler

(57) ABSTRACT

A pump for treating a patient is disclosed that includes a spring-biased plunger biased toward actuation against a tube; a cam shaft configured to actuate the spring-based plunger; a lever actuatable between a closed position and an open position; a shaft coupled to the lever, the shaft having a central axis centrally along the length of the shaft, the shaft coupled to the lever to rotate around the central axis in accordance with actuation of the lever; and a lift cam pivotally coupled to the shaft, wherein the lift cam pivots around a lift cam axis, the lift cam axis of the lift cam is parallel to the central axis of the shaft, and the lift cam engages with the spring-based plunger to lift the spring-biased plunger off of the cam shaft as the shaft rotates in accordance with actuating the lever to the open position.

3 Claims, 145 Drawing Sheets

(56) References Cited

U.S. PATENT DOCUMENTS

| | | | |
|---|---|---|---|
| 2,570,560 A | 10/1951 | Katcher | |
| 2,877,714 A | 3/1959 | Sorg et al. | |
| 3,128,716 A | 4/1964 | Stallman et al. | |
| 3,173,372 A | 3/1965 | Baldwin | |
| 3,384,336 A | 5/1968 | Pulman | |
| 3,644,068 A | 2/1972 | Lepak | |
| 3,658,445 A | 4/1972 | Pulman et al. | |
| 3,981,633 A | 9/1976 | Wall | |
| 4,236,880 A | 12/1980 | Archibald | |
| 4,273,121 A | 6/1981 | Jassawalla | |
| 4,277,226 A | 7/1981 | Archibald | |
| 4,278,085 A | 7/1981 | Shim | |
| 4,303,376 A | 12/1981 | Siekmann | |
| 4,312,493 A | 1/1982 | Stauffer | |
| D263,997 S | 4/1982 | Preussner | |
| 4,373,525 A | 2/1983 | Kobayashi | |
| 4,392,849 A | 7/1983 | Petre et al. | |
| 4,561,830 A | 12/1985 | Bradley | |
| 4,648,812 A | 3/1987 | Kobayashi et al. | |
| D289,395 S | 4/1987 | Bowers | |
| 4,705,464 A | 11/1987 | Arimond | |
| 4,725,205 A | 2/1988 | Cannon et al. | |
| 4,728,265 A | 3/1988 | Cannon | |
| D309,662 S | 7/1990 | Gorton | |
| 4,952,124 A | 8/1990 | Ogami | |
| 5,039,279 A | 8/1991 | Natwick et al. | |
| 5,055,001 A | 10/1991 | Natwick et al. | |
| 5,055,013 A | 10/1991 | Faeser | |
| 5,078,362 A | 1/1992 | Lawless et al. | |
| 5,087,245 A | 2/1992 | Doan | |
| 5,103,211 A | 4/1992 | Daoud et al. | |
| 5,116,203 A | 5/1992 | Natwick et al. | |
| 5,131,816 A | 7/1992 | Brown et al. | |
| 5,158,437 A | 10/1992 | Natwick et al. | |
| 5,180,287 A | 1/1993 | Natwick et al. | |
| 5,213,573 A | 5/1993 | Sorich et al. | |
| 5,219,279 A | 6/1993 | Natwick et al. | |
| RE34,413 E | 10/1993 | McCullough | |
| 5,256,157 A | 10/1993 | Samiotes et al. | |
| 5,322,422 A | 6/1994 | Natwick et al. | |
| D348,730 S | 7/1994 | Walker et al. | |
| 5,357,827 A | 10/1994 | Natwick et al. | |
| 5,364,371 A | 11/1994 | Kamen | |
| D353,667 S | 12/1994 | Tsubota et al. | |
| 5,395,321 A | 3/1995 | Kawahara et al. | |
| 5,413,252 A | 5/1995 | Magnus et al. | |
| 5,478,211 A | 12/1995 | Dominiak et al. | |
| 5,482,446 A | 1/1996 | Williamson et al. | |
| 5,505,709 A | 4/1996 | Funderburk et al. | |
| 5,577,891 A | 11/1996 | Loughnane et al. | |
| 5,609,576 A | 3/1997 | Voss et al. | |
| 5,637,095 A | 6/1997 | Nason et al. | |
| 5,681,285 A | 10/1997 | Ford et al. | |
| 5,695,473 A | 12/1997 | Olsen | |
| D390,654 S | 2/1998 | Alsberg et al. | |
| 5,720,923 A | 2/1998 | Haff et al. | |
| D393,072 S | 3/1998 | Rogler | |
| 5,755,563 A | 5/1998 | Clegg et al. | |
| 5,781,442 A | 7/1998 | Engleson et al. | |
| 5,781,881 A | 7/1998 | Stegmann | |
| 5,791,881 A | 8/1998 | Moubayed et al. | |
| 5,800,387 A | 9/1998 | Duffy et al. | |
| 5,836,910 A | 11/1998 | Duffy et al. | |
| 5,842,841 A | 12/1998 | Danby et al. | |
| 5,868,712 A | 2/1999 | Briggs et al. | |
| 5,938,413 A | 8/1999 | Makino et al. | |
| 5,954,697 A | 9/1999 | Srisathapat et al. | |
| D425,017 S | 5/2000 | Leung | |
| 6,064,797 A | 5/2000 | Crittendon et al. | |
| 6,106,249 A | 8/2000 | Barak | |
| 6,117,115 A * | 9/2000 | Hill | A61M 5/16813 604/250 |
| 6,158,965 A | 12/2000 | Butterfield et al. | |
| 6,193,480 B1 | 2/2001 | Butterfield | |
| D440,575 S | 4/2001 | Wang et al. | |
| 6,228,047 B1 | 5/2001 | Dadson | |
| 6,234,773 B1 | 5/2001 | Hill et al. | |
| 6,241,704 B1 | 6/2001 | Peterson et al. | |
| 6,253,968 B1 | 7/2001 | Van Dijk et al. | |
| 6,261,262 B1 | 7/2001 | Briggs et al. | |
| 6,267,559 B1 | 7/2001 | Mossman et al. | |
| 6,305,908 B1 | 10/2001 | Hermann et al. | |
| 6,328,712 B1 | 12/2001 | Cartledge | |
| 6,346,886 B1 | 2/2002 | De La Huerga | |
| 6,347,553 B1 | 2/2002 | Morris et al. | |
| 6,348,777 B1 | 2/2002 | Brown et al. | |
| 6,358,225 B1 | 3/2002 | Butterfield | |
| 6,362,591 B1 | 3/2002 | Moberg | |
| 6,362,887 B1 | 3/2002 | Meisberger | |
| 6,394,771 B2 | 5/2002 | Butterfield | |
| 6,408,330 B1 | 6/2002 | DeLaHuerga | |
| 6,416,291 B1 | 7/2002 | Butterfield et al. | |
| 6,422,057 B1 | 7/2002 | Anderson | |
| 6,475,180 B2 | 11/2002 | Peterson et al. | |
| 6,503,221 B1 | 1/2003 | Briggs et al. | |
| 6,519,569 B1 | 2/2003 | White et al. | |
| D475,134 S | 5/2003 | Randolph | |
| 6,561,262 B1 | 5/2003 | Osakabe et al. | |
| 6,616,633 B1 | 9/2003 | Butterfield et al. | |
| 6,629,955 B2 | 10/2003 | Morris et al. | |
| 6,635,033 B1 | 10/2003 | Hill et al. | |
| 6,690,338 B1 | 2/2004 | Maguire, Jr. | |
| D491,523 S | 6/2004 | Chi et al. | |
| 6,776,152 B2 | 8/2004 | Gray et al. | |
| 6,790,198 B1 | 9/2004 | White et al. | |
| D499,740 S | 12/2004 | Ombao et al. | |
| 6,869,425 B2 | 3/2005 | Briggs et al. | |
| 6,916,159 B2 | 7/2005 | Rush et al. | |
| D512,151 S | 11/2005 | Ward et al. | |
| 6,997,905 B2 | 2/2006 | Gillespie, Jr. et al. | |
| 7,104,763 B2 | 9/2006 | Bouton et al. | |
| 7,206,715 B2 | 4/2007 | Vanderveen et al. | |
| 7,217,108 B2 | 5/2007 | Herwig et al. | |
| 7,258,534 B2 | 8/2007 | Fathallah et al. | |
| D551,243 S | 9/2007 | Young | |
| 7,267,661 B2 | 9/2007 | Susi | |
| D557,272 S | 12/2007 | Glaser et al. | |
| D559,262 S | 1/2008 | Young | |
| D568,814 S | 5/2008 | Hung | |
| 7,520,859 B2 | 4/2009 | Nunome | |
| 7,553,291 B2 | 6/2009 | Duffy et al. | |
| 7,553,295 B2 | 6/2009 | Susi | |
| 7,556,616 B2 | 7/2009 | Fathallah et al. | |
| 7,561,986 B2 | 7/2009 | Vanderveen et al. | |
| 7,565,301 B2 | 7/2009 | Moubayed et al. | |
| D599,373 S | 9/2009 | Kobayashi et al. | |
| D604,740 S | 11/2009 | Matheny et al. | |
| 7,611,498 B2 | 11/2009 | Hasler | |
| 7,611,503 B2 | 11/2009 | Spohn et al. | |
| 7,621,893 B2 | 11/2009 | Moberg et al. | |
| 7,632,249 B2 | 12/2009 | Momeni et al. | |
| 7,651,489 B2 | 1/2010 | Estes et al. | |
| 7,654,976 B2 | 2/2010 | Peterson et al. | |
| 7,668,731 B2 | 2/2010 | Martucci et al. | |
| 7,678,071 B2 | 3/2010 | Lebel et al. | |
| 7,699,806 B2 | 4/2010 | Ware et al. | |
| 7,713,241 B2 | 5/2010 | Cartledge et al. | |
| 7,727,222 B2 | 6/2010 | Da Silva et al. | |
| 7,736,354 B2 | 6/2010 | Gelfand et al. | |
| 7,743,975 B2 | 6/2010 | Miller | |
| 7,762,989 B2 | 7/2010 | Simpson | |
| D622,730 S | 8/2010 | Krum et al. | |
| D625,322 S | 10/2010 | Guntaur et al. | |
| D625,323 S | 10/2010 | Matsushima et al. | |
| 7,819,843 B2 | 10/2010 | Mann et al. | |
| 7,873,489 B2 | 1/2011 | Dolgos et al. | |
| 7,890,881 B2 | 2/2011 | Skidgel | |
| 7,893,876 B2 | 2/2011 | Brown et al. | |
| 7,895,053 B2 | 2/2011 | Holland et al. | |
| D633,517 S | 3/2011 | Weir et al. | |
| 7,896,572 B2 | 3/2011 | Fathallah et al. | |
| 7,896,842 B2 | 3/2011 | Palmroos et al. | |
| 7,904,822 B2 | 3/2011 | Monteleone et al. | |
| 7,911,353 B2 | 3/2011 | Bedingfield | |

(56) References Cited

U.S. PATENT DOCUMENTS

| | | |
|---|---|---|
| 7,933,780 B2 | 4/2011 | De La Huerga |
| 7,934,912 B2 | 5/2011 | Voltenburg, Jr. et al. |
| 7,938,796 B2 | 5/2011 | Moubayed et al. |
| 7,941,534 B2 | 5/2011 | de la Huerga |
| 7,945,452 B2 | 5/2011 | Fathallah et al. |
| D640,376 S | 6/2011 | Amano et al. |
| D640,377 S | 6/2011 | Amano et al. |
| 7,955,060 B2 | 6/2011 | Gottschalk |
| 7,976,508 B2 | 7/2011 | Hoag |
| 7,981,082 B2 | 7/2011 | Wang et al. |
| 8,025,634 B1 | 9/2011 | Moubayed et al. |
| 8,029,253 B2 | 10/2011 | Rotem et al. |
| 8,032,226 B2 | 10/2011 | Miller et al. |
| 8,062,008 B2 | 11/2011 | Voltenburg, Jr. et al. |
| 8,062,257 B2 | 11/2011 | Moberg et al. |
| D649,973 S | 12/2011 | Matas |
| 8,075,514 B2 | 12/2011 | Butterfield et al. |
| 8,082,112 B2 | 12/2011 | Butterfield et al. |
| 8,083,503 B2 | 12/2011 | Voltenburg, Jr. et al. |
| D652,050 S | 1/2012 | Chaudhri |
| 8,105,269 B2 | 1/2012 | Zhou |
| 8,105,282 B2 | 1/2012 | Susi et al. |
| 8,109,898 B2 | 2/2012 | Wolff |
| 8,118,778 B2 | 2/2012 | Haylor et al. |
| D655,301 S | 3/2012 | Ray et al. |
| 8,133,197 B2 | 3/2012 | Blomquist et al. |
| 8,134,459 B2 | 3/2012 | Smith et al. |
| 8,142,400 B2 | 3/2012 | Rotem et al. |
| 8,149,131 B2 | 4/2012 | Blomquist |
| 8,150,493 B2 | 4/2012 | Susi |
| D660,313 S | 5/2012 | Williams et al. |
| 8,177,739 B2 | 5/2012 | Cartledge et al. |
| 8,182,461 B2 | 5/2012 | Pope et al. |
| 8,185,322 B2 | 5/2012 | Schroeder et al. |
| D662,051 S | 6/2012 | Saunders et al. |
| 8,192,394 B2 | 6/2012 | Estes et al. |
| 8,197,235 B2 | 6/2012 | Davis |
| 8,211,061 B2 | 7/2012 | Sen |
| 8,231,578 B2 | 7/2012 | Fathallah et al. |
| D664,988 S | 8/2012 | Gleasman et al. |
| D665,401 S | 8/2012 | Rai et al. |
| D666,208 S | 8/2012 | Spears et al. |
| 8,235,938 B2 | 8/2012 | Eggers et al. |
| 8,250,483 B2 | 8/2012 | Blomquist |
| 8,257,066 B2 | 9/2012 | Kasai et al. |
| D668,262 S | 10/2012 | Gleasman et al. |
| D669,096 S | 10/2012 | Katsura |
| D669,165 S | 10/2012 | Estes et al. |
| D671,550 S | 11/2012 | Chen et al. |
| D671,551 S | 11/2012 | Deng et al. |
| 8,308,457 B2 | 11/2012 | Rotem et al. |
| 8,313,308 B2 | 11/2012 | Lawless et al. |
| D673,168 S | 12/2012 | Frijlink et al. |
| 8,337,168 B2 | 12/2012 | Rotem et al. |
| D675,224 S | 1/2013 | Lee et al. |
| 8,359,338 B2 | 1/2013 | Butterfield et al. |
| D675,727 S | 2/2013 | Collins et al. |
| 8,371,832 B2 | 2/2013 | Rotem et al. |
| D678,320 S | 3/2013 | Kanalakis, Jr. et al. |
| 8,414,523 B2 | 4/2013 | Blomquist et al. |
| 8,435,206 B2 | 5/2013 | Evans et al. |
| D685,817 S | 7/2013 | Kunieda et al. |
| D689,195 S | 9/2013 | Nelsen |
| D690,729 S | 10/2013 | Abratowski et al. |
| D691,259 S | 10/2013 | Estes et al. |
| D692,378 S | 10/2013 | Esses |
| D696,684 S | 12/2013 | Yuk et al. |
| D696,686 S | 12/2013 | Yuk et al. |
| D698,362 S | 1/2014 | Ramesh et al. |
| D701,232 S | 3/2014 | Na et al. |
| D704,213 S | 5/2014 | Agnew |
| D705,244 S | 5/2014 | Arnold et al. |
| D705,248 S | 5/2014 | McCormack et al. |
| D708,626 S | 7/2014 | Klein et al. |
| D708,627 S | 7/2014 | Klein et al. |
| D709,085 S | 7/2014 | Wen |
| D712,920 S | 9/2014 | Sloo et al. |
| D715,320 S | 10/2014 | McCormack et al. |
| D716,332 S | 10/2014 | Chotin et al. |
| D717,814 S | 11/2014 | Zuckerberg et al. |
| D718,776 S | 12/2014 | Hobbs et al. |
| D718,777 S | 12/2014 | Hobbs et al. |
| D718,778 S | 12/2014 | Hobbs et al. |
| D719,963 S | 12/2014 | Hobbs et al. |
| D719,964 S | 12/2014 | Hobbs et al. |
| D721,719 S | 1/2015 | Lee |
| D722,612 S | 2/2015 | Lee et al. |
| D722,614 S | 2/2015 | Williams et al. |
| D723,052 S | 2/2015 | Lai et al. |
| D725,670 S | 3/2015 | Zhang et al. |
| D728,779 S | 5/2015 | Sabin et al. |
| D731,509 S | 6/2015 | Sueishi et al. |
| D732,062 S | 6/2015 | Kwon |
| D732,063 S | 6/2015 | Kwon |
| D732,567 S | 6/2015 | Moon et al. |
| D733,740 S | 7/2015 | Lee et al. |
| D733,741 S | 7/2015 | Lee et al. |
| D735,319 S | 7/2015 | Sabin et al. |
| D735,746 S | 8/2015 | Zuckerberg et al. |
| D736,370 S | 8/2015 | Sabin et al. |
| D740,848 S | 10/2015 | Bolts et al. |
| D741,358 S | 10/2015 | Seo et al. |
| 9,151,646 B2 | 10/2015 | Kamen et al. |
| D745,661 S | 12/2015 | Collins et al. |
| D749,206 S | 2/2016 | Johnson et al. |
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| D756,386 S | 5/2016 | Kendler et al. |
| D758,399 S | 6/2016 | Kendler et al. |
| D760,288 S | 6/2016 | Kendler et al. |
| D760,289 S | 6/2016 | Kendler et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| 9,408,966 B2 | 8/2016 | Kamen |
| D767,756 S | 9/2016 | Sabin |
| 9,435,455 B2 | 9/2016 | Peret et al. |
| D768,716 S | 10/2016 | Kendler et al. |
| 9,465,919 B2 | 10/2016 | Kamen et al. |
| 9,488,200 B2 | 11/2016 | Kamen et al. |
| D774,645 S | 12/2016 | Gill et al. |
| 9,518,958 B2 | 12/2016 | Wilt et al. |
| 9,636,455 B2 | 5/2017 | Kamen et al. |
| D789,516 S | 6/2017 | Gill et al. |
| 9,675,756 B2 | 6/2017 | Kamen et al. |
| 9,677,555 B2 | 6/2017 | Kamen et al. |
| 9,687,417 B2 | 6/2017 | Demers et al. |
| D792,963 S | 7/2017 | Gill |
| D795,424 S | 8/2017 | Sloss |
| D795,805 S | 8/2017 | Gray et al. |
| 9,719,964 B2 | 8/2017 | Blumberg |
| 9,724,465 B2 | 8/2017 | Peret et al. |
| 9,724,466 B2 | 8/2017 | Peret et al. |
| 9,724,467 B2 | 8/2017 | Peret et al. |
| 9,730,731 B2 | 8/2017 | Langenfeld et al. |
| 9,744,300 B2 | 8/2017 | Kamen et al. |
| 9,746,093 B2 | 8/2017 | Peret et al. |
| 9,746,094 B2 | 8/2017 | Peret et al. |
| 9,759,343 B2 | 9/2017 | Peret et al. |
| 9,759,369 B2 | 9/2017 | Gray et al. |
| 9,772,044 B2 | 9/2017 | Peret et al. |
| D799,025 S | 10/2017 | Johnson et al. |
| D801,519 S | 10/2017 | Sabin et al. |
| 9,789,247 B2 | 10/2017 | Kamen et al. |
| D802,118 S | 11/2017 | Peret et al. |
| D803,386 S | 11/2017 | Sabin et al. |
| D803,387 S | 11/2017 | Bodwell et al. |
| D804,017 S | 11/2017 | Sabin |
| 9,808,572 B2 | 11/2017 | Kamen et al. |

(56) References Cited

U.S. PATENT DOCUMENTS

| | | |
|---|---|---|
| D805,183 S | 12/2017 | Sabin et al. |
| 9,856,990 B2 | 1/2018 | Peret et al. |
| D813,376 S | 3/2018 | Peret et al. |
| D814,021 S | 3/2018 | Sabin |
| D815,730 S | 4/2018 | Collins et al. |
| D816,685 S | 5/2018 | Kendler et al. |
| D816,829 S | 5/2018 | Peret et al. |
| D817,479 S | 5/2018 | Sabin et al. |
| D817,480 S | 5/2018 | Sabin et al. |
| 9,968,730 B2 | 5/2018 | Blumberg, Jr. et al. |
| 9,976,665 B2 | 5/2018 | Peret et al. |
| 10,044,791 B2 | 8/2018 | Kamen et al. |
| 10,082,241 B2 | 9/2018 | Janway et al. |
| 10,088,346 B2 | 10/2018 | Kane et al. |
| 10,108,785 B2 | 10/2018 | Kamen et al. |
| 10,113,660 B2 | 10/2018 | Peret et al. |
| 10,126,267 B2 | 11/2018 | Blumberg, Jr. |
| 10,183,114 B2 | 1/2019 | Lee |
| 10,185,812 B2 | 1/2019 | Kamen et al. |
| 10,202,970 B2 | 2/2019 | Kamen et al. |
| 10,202,971 B2 | 2/2019 | Kamen et al. |
| 10,220,135 B2 | 3/2019 | Kamen et al. |
| 10,228,683 B2 | 3/2019 | Peret et al. |
| 10,242,159 B2 | 3/2019 | Kamen et al. |
| 10,245,374 B2 | 4/2019 | Kamen et al. |
| 10,265,463 B2 | 4/2019 | Biasi et al. |
| 10,288,057 B2 | 5/2019 | Kamen et al. |
| 10,314,955 B2 * | 6/2019 | Friedman ............ C12N 5/0653 |
| 10,316,834 B2 | 6/2019 | Kamen et al. |
| D854,145 S | 7/2019 | Collins |
| 10,380,321 B2 | 8/2019 | Kamen et al. |
| 10,391,241 B2 | 8/2019 | Desch et al. |
| D860,437 S | 9/2019 | Collins |
| 10,426,517 B2 | 10/2019 | Langenfeld et al. |
| 10,436,342 B2 | 10/2019 | Peret et al. |
| 10,453,157 B2 | 10/2019 | Kamen et al. |
| 10,468,132 B2 | 11/2019 | Kamen et al. |
| 10,471,402 B2 | 11/2019 | Demers et al. |
| 10,478,261 B2 | 11/2019 | Demers et al. |
| 10,488,848 B2 | 11/2019 | Peret et al. |
| 10,561,787 B2 | 2/2020 | Kamen et al. |
| 10,563,681 B2 | 2/2020 | Kamen et al. |
| 10,571,070 B2 | 2/2020 | Gray et al. |
| 10,655,779 B2 | 5/2020 | Janway et al. |
| 10,670,182 B2 | 6/2020 | Janway et al. |
| 10,718,445 B2 | 7/2020 | Yoo |
| 10,722,645 B2 | 7/2020 | Kamen et al. |
| 10,739,759 B2 | 8/2020 | Peret et al. |
| 10,753,353 B2 | 8/2020 | Kamen et al. |
| 10,761,061 B2 | 9/2020 | Wilt et al. |
| 10,839,953 B2 | 11/2020 | Kamen et al. |
| 10,844,970 B2 | 11/2020 | Peret et al. |
| D905,848 S | 12/2020 | Sloss et al. |
| 10,857,293 B2 | 12/2020 | Kamen et al. |
| 10,872,685 B2 | 12/2020 | Blumberg, Jr. et al. |
| 10,876,868 B2 | 12/2020 | Kane et al. |
| 10,894,638 B2 | 1/2021 | Peret et al. |
| 10,911,515 B2 | 2/2021 | Biasi et al. |
| 2001/0044602 A1 | 11/2001 | Angersbach et al. |
| 2002/0165503 A1 | 11/2002 | Morris et al. |
| 2003/0106553 A1 | 6/2003 | Vanderveen |
| 2003/0190246 A1 | 10/2003 | Corwin et al. |
| 2003/0217962 A1 | 11/2003 | Childers et al. |
| 2004/0158193 A1 | 8/2004 | Bui et al. |
| 2005/0029277 A1 | 2/2005 | Tachibana |
| 2005/0050301 A1 | 3/2005 | Whittle et al. |
| 2005/0267827 A1 | 12/2005 | Grant, Jr. et al. |
| 2006/0005081 A1 | 1/2006 | Seth et al. |
| 2006/0140798 A1 | 6/2006 | Kutsuzawa |
| 2006/0253163 A1 | 11/2006 | Stubbs et al. |
| 2006/0258985 A1 | 11/2006 | Russell |
| 2007/0109325 A1 | 5/2007 | Eveleigh |
| 2007/0116585 A1 | 5/2007 | Scalzi |
| 2007/0215155 A1 | 9/2007 | Marx et al. |
| 2008/0038128 A1 | 2/2008 | Haar |
| 2009/0040875 A1 | 2/2009 | Buzescu et al. |
| 2009/0088687 A1 | 4/2009 | Yardimci et al. |
| 2009/0107902 A1 | 4/2009 | Childers et al. |
| 2009/0112155 A1 | 4/2009 | Zhao et al. |
| 2009/0138005 A1 | 5/2009 | Prakash et al. |
| 2009/0144620 A1 | 6/2009 | Bauchot et al. |
| 2009/0153058 A1 | 6/2009 | Feng et al. |
| 2009/0153463 A1 | 6/2009 | Arrizza et al. |
| 2009/0203329 A1 | 8/2009 | White et al. |
| 2009/0270810 A1 | 10/2009 | DeBelser et al. |
| 2009/0276167 A1 | 11/2009 | Glaser et al. |
| 2009/0286692 A1 | 11/2009 | Wainwright et al. |
| 2010/0036322 A1 | 2/2010 | Rotem |
| 2010/0040481 A1 * | 2/2010 | Wolff ............... A61M 5/16831 417/53 |
| 2010/0114027 A1 | 5/2010 | Jacobson et al. |
| 2010/0153872 A1 | 6/2010 | Ahn et al. |
| 2010/0169389 A1 | 7/2010 | Weber et al. |
| 2010/0169783 A1 | 7/2010 | Weber et al. |
| 2010/0228222 A1 | 9/2010 | Williams et al. |
| 2011/0004186 A1 | 1/2011 | Butterfield |
| 2011/0085778 A1 | 4/2011 | Iwase et al. |
| 2011/0161806 A1 | 6/2011 | Stern et al. |
| 2011/0172594 A1 | 7/2011 | Yodfat et al. |
| 2011/0190694 A1 | 8/2011 | Lanier, Jr. et al. |
| 2011/0231204 A1 | 9/2011 | De La Huerga |
| 2011/0241878 A1 | 10/2011 | Hoag |
| 2011/0264033 A1 | 10/2011 | Jensen et al. |
| 2011/0271221 A1 | 11/2011 | Lategan |
| 2011/0282416 A1 | 11/2011 | Hamann et al. |
| 2011/0301472 A1 | 12/2011 | Grober et al. |
| 2011/0313789 A1 | 12/2011 | Kamen et al. |
| 2011/0318198 A1 | 12/2011 | Johnson et al. |
| 2011/0318208 A1 | 12/2011 | Goldor et al. |
| 2011/0320049 A1 | 12/2011 | Chossat et al. |
| 2012/0004624 A1 | 1/2012 | Brown et al. |
| 2012/0016295 A1 | 1/2012 | Tsoukalis |
| 2012/0029941 A1 | 2/2012 | Malave et al. |
| 2012/0035581 A1 | 2/2012 | Travis |
| 2012/0053533 A1 | 3/2012 | Butterfield et al. |
| 2012/0066609 A1 | 3/2012 | Howard et al. |
| 2012/0078222 A1 | 3/2012 | Smith et al. |
| 2012/0079416 A1 | 3/2012 | Fagans |
| 2012/0083760 A1 | 4/2012 | Ledford et al. |
| 2012/0124174 A1 | 5/2012 | Nudelman et al. |
| 2012/0130308 A1 | 5/2012 | Silkaitis et al. |
| 2012/0157920 A1 | 6/2012 | Flachbart et al. |
| 2012/0172802 A1 | 7/2012 | Blomquist |
| 2012/0176394 A1 | 7/2012 | Vik et al. |
| 2012/0177507 A1 | 7/2012 | Bennett et al. |
| 2012/0179130 A1 | 7/2012 | Barnes et al. |
| 2012/0185267 A1 | 7/2012 | Kamen |
| 2012/0209197 A1 | 8/2012 | Lanigan et al. |
| 2012/0241525 A1 | 9/2012 | Borges et al. |
| 2012/0254044 A1 | 10/2012 | Flanagan et al. |
| 2012/0266964 A1 | 10/2012 | West et al. |
| 2012/0283638 A1 | 11/2012 | Susi |
| 2012/0283691 A1 | 11/2012 | Barnes et al. |
| 2012/0310205 A1 | 12/2012 | Lee et al. |
| 2012/0323212 A1 | 12/2012 | Murphy et al. |
| 2013/0012880 A1 | 1/2013 | Blomquist |
| 2013/0023848 A1 | 1/2013 | Nelson et al. |
| 2013/0045115 A1 | 2/2013 | Flachbart et al. |
| 2013/0053820 A1 | 2/2013 | Estes et al. |
| 2013/0091191 A1 | 4/2013 | Levin et al. |
| 2013/0104120 A1 | 4/2013 | Arrizza et al. |
| 2013/0127870 A1 | 5/2013 | Baudel et al. |
| 2013/0133036 A1 | 5/2013 | Wang et al. |
| 2013/0138074 A1 | 5/2013 | Travis et al. |
| 2013/0141329 A1 | 6/2013 | Halbert et al. |
| 2013/0177455 A1 | 7/2013 | Kamen |
| 2013/0182381 A1 | 7/2013 | Gray |
| 2013/0184676 A1 | 7/2013 | Kamen et al. |
| 2013/0188040 A1 | 7/2013 | Kamen et al. |
| 2013/0191513 A1 | 7/2013 | Kamen |
| 2013/0197693 A1 | 8/2013 | Kamen |
| 2013/0204188 A1 | 8/2013 | Kamen |
| 2013/0272773 A1 | 10/2013 | Kamen |
| 2013/0281965 A1 | 10/2013 | Kamen |

(56) References Cited

U.S. PATENT DOCUMENTS

| | | |
|---|---|---|
| 2013/0297330 A1 | 11/2013 | Kamen |
| 2013/0310990 A1 | 11/2013 | Peret et al. |
| 2013/0317753 A1 | 11/2013 | Kamen |
| 2013/0317837 A1 | 11/2013 | Ballantyne |
| 2013/0318429 A1 | 11/2013 | Dantas et al. |
| 2013/0325154 A1 | 12/2013 | Oh et al. |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0207057 A1 | 7/2014 | Zhu |
| 2014/0227021 A1 | 8/2014 | Kamen |
| 2014/0237419 A1 | 8/2014 | Ryu |
| 2014/0243745 A1 | 8/2014 | Ueda et al. |
| 2014/0318639 A1 | 10/2014 | Peret |
| 2014/0343492 A1 | 11/2014 | Kamen |
| 2014/0359443 A1 | 12/2014 | Hwang |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0018766 A1 | 1/2015 | Nakanishi et al. |
| 2015/0023808 A1 | 1/2015 | Zhu |
| 2015/0033823 A1 | 2/2015 | Blumberg, Jr. |
| 2015/0089364 A1 | 3/2015 | Meller et al. |
| 2015/0151057 A1 | 6/2015 | Nakanishi |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0314083 A1 | 11/2015 | Blumberg, Jr. et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo |
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0262977 A1 | 9/2016 | Demers et al. |
| 2016/0319850 A1 | 11/2016 | Kamen et al. |
| 2016/0339229 A1 | 11/2016 | Hung et al. |
| 2016/0346056 A1 | 12/2016 | Demers et al. |
| 2016/0362234 A1 | 12/2016 | Peret et al. |
| 2017/0011202 A1 | 1/2017 | Kamen et al. |
| 2017/0045478 A1 | 2/2017 | Wilt et al. |
| 2017/0216516 A1 | 8/2017 | Dale et al. |
| 2017/0224909 A1 | 8/2017 | Kamen et al. |
| 2017/0259230 A1 | 9/2017 | Demers et al. |
| 2017/0266378 A1 | 9/2017 | Kamen et al. |
| 2017/0268497 A1 | 9/2017 | Kamen et al. |
| 2017/0284968 A1 | 10/2017 | Blumberg, Jr. |
| 2017/0296745 A1 | 10/2017 | Kamen et al. |
| 2017/0303969 A1 | 10/2017 | Langenfeld et al. |
| 2017/0321841 A1 | 11/2017 | Gray et al. |
| 2017/0333623 A1 | 11/2017 | Kamen et al. |
| 2017/0335988 A1 | 11/2017 | Peret et al. |
| 2018/0038501 A1 | 2/2018 | Peret et al. |
| 2018/0066648 A1 | 3/2018 | Kamen et al. |
| 2018/0080605 A1 | 3/2018 | Janway et al. |
| 2018/0106246 A1 | 4/2018 | Kamen et al. |
| 2018/0128259 A1 | 5/2018 | Kamen et al. |
| 2018/0224012 A1 | 8/2018 | Peret et al. |
| 2018/0228964 A1 | 8/2018 | Blumberg, Jr. et al. |
| 2018/0252359 A1 | 9/2018 | Janway et al. |
| 2018/0278676 A1 | 9/2018 | Kamen et al. |
| 2019/0009018 A1 | 1/2019 | Kamen et al. |
| 2019/0033104 A1 | 1/2019 | Kane et al. |
| 2019/0041362 A1 | 2/2019 | Blumberg, Jr. |
| 2019/0049029 A1 | 2/2019 | Peret et al. |
| 2019/0134298 A1 | 5/2019 | Kamen et al. |
| 2019/0139640 A1 | 5/2019 | Kamen et al. |
| 2019/0154026 A1 | 5/2019 | Kamen et al. |
| 2019/0170134 A1 | 6/2019 | Kamen et al. |
| 2019/0175821 A1 | 6/2019 | Kamen et al. |
| 2019/0179289 A1 | 6/2019 | Peret et al. |
| 2019/0189272 A1 | 6/2019 | Kamen et al. |
| 2019/0219047 A1 | 7/2019 | Kamen et al. |
| 2019/0249657 A1 | 8/2019 | Kamen et al. |
| 2019/0298913 A1 | 10/2019 | Biasi et al. |
| 2019/0316948 A1 | 10/2019 | Karol et al. |
| 2019/0328964 A1 | 10/2019 | Desch et al. |
| 2019/0341146 A1 | 11/2019 | Kamen et al. |
| 2019/0365421 A1 | 12/2019 | Langenfeld et al. |
| 2020/0025305 A1 | 1/2020 | Peret et al. |
| 2020/0051190 A1 | 2/2020 | Kamen et al. |
| 2020/0054823 A1 | 2/2020 | Baier et al. |
| 2020/0066388 A1 | 2/2020 | Kamen et al. |
| 2020/0070113 A1 | 3/2020 | Demers et al. |
| 2020/0078127 A1 | 3/2020 | Demers et al. |
| 2020/0171241 A1 | 6/2020 | Kamen et al. |
| 2020/0173469 A1 | 6/2020 | Kamen et al. |
| 2020/0182400 A1 | 6/2020 | Gray et al. |
| 2020/0278078 A1 | 9/2020 | Janway et al. |
| 2020/0347949 A1 | 11/2020 | Yoo |
| 2020/0371497 A1 | 11/2020 | Peret et al. |
| 2020/0386220 A1 | 12/2020 | Kamen et al. |
| 2020/0393414 A1 | 12/2020 | Wilt et al. |
| 2021/0023296 A1 | 1/2021 | Langenfeld et al. |

FOREIGN PATENT DOCUMENTS

| | | |
|---|---|---|
| EP | 69350 A1 | 1/1983 |
| EP | 477551 A1 | 4/1992 |
| EP | 681847 A2 | 11/1995 |
| EP | 960627 A2 | 12/1999 |
| EP | 1640028 A2 | 3/2006 |
| EP | 1722310 A1 | 11/2006 |
| EP | 2319551 A2 | 5/2011 |
| EP | 2700424 A1 | 2/2014 |
| EP | 2700424 B1 | 1/2018 |
| FR | 2273264 A1 | 12/1975 |
| GB | 2020735 | 11/1979 |
| GB | 2020735 A | 11/1979 |
| JP | S58163843 A | 9/1983 |
| JP | 07171213 A | 7/1995 |
| JP | 10503688 A | 3/1996 |
| JP | 8191890 | 7/1996 |
| JP | 08509898 A | 10/1996 |
| JP | 11500338 A | 3/1997 |
| JP | 2000504964 A | 2/1998 |
| JP | 11148462 A | 6/1999 |
| JP | 200349779 A | 12/2000 |
| JP | 2004523305 | 8/2004 |
| JP | 2006514856 A | 5/2006 |
| JP | 2007516798 T | 6/2007 |
| JP | 3957322 B9 | 8/2007 |
| JP | 2007528236 A | 10/2007 |
| JP | 2007530860 A | 11/2007 |
| JP | 2009521998 A | 6/2009 |
| JP | 2011245354 A | 12/2011 |
| WO | WO9304285 A1 | 3/1993 |
| WO | WO9310835 A1 | 6/1993 |
| WO | WO9524229 A2 | 9/1995 |
| WO | WO9603168 A1 | 2/1996 |
| WO | WO9734084 A1 | 9/1997 |
| WO | WO9737703 A1 | 10/1997 |
| WO | WO9814234 A1 | 4/1998 |
| WO | WO02068018 A2 | 9/2002 |
| WO | WO2002068018 A2 | 9/2002 |
| WO | WO02100262 A1 | 12/2002 |
| WO | WO03094091 A1 | 11/2003 |
| WO | WO2004012043 A2 | 2/2004 |
| WO | WO2004029853 A2 | 4/2004 |
| WO | WO2004035116 A1 | 4/2004 |
| WO | WO2004094919 A1 | 11/2004 |

(56) References Cited

FOREIGN PATENT DOCUMENTS

| | | |
|---|---|---|
| WO | WO2005065750 A1 | 7/2005 |
| WO | WO2005089263 A2 | 9/2005 |
| WO | WO2005094919 A1 | 10/2005 |
| WO | WO2006008465 A1 | 1/2006 |
| WO | WO2006086723 A2 | 8/2006 |
| WO | WO2008022880 A1 | 2/2008 |
| WO | WO2009055639 A2 | 4/2009 |
| WO | WO2009055639 A3 | 7/2009 |
| WO | WO2009055639 A4 | 11/2009 |
| WO | WO2010129720 A2 | 11/2010 |
| WO | WO2011021098 A1 | 2/2011 |
| WO | WO2011066556 A1 | 6/2011 |
| WO | WO2011080193 A1 | 7/2011 |
| WO | WO2011091998 A1 | 8/2011 |
| WO | WO2011119810 A1 | 9/2011 |
| WO | WO2013095459 A9 | 6/2013 |
| WO | WO2013096713 A2 | 6/2013 |
| WO | WO2013096718 A2 | 6/2013 |
| WO | WO2013096722 A2 | 6/2013 |
| WO | WO2013096909 A2 | 6/2013 |
| WO | WO2013176770 A2 | 11/2013 |
| WO | WO2013177357 A1 | 11/2013 |
| WO | WO2014100557 A2 | 6/2014 |
| WO | WO2014100571 A2 | 6/2014 |
| WO | WO2014100658 A1 | 6/2014 |
| WO | WO2014100687 A2 | 6/2014 |
| WO | WO2014100736 A2 | 6/2014 |
| WO | WO2014100744 A2 | 6/2014 |
| WO | WO2014144557 A2 | 9/2014 |
| WO | WO2015017275 A1 | 2/2015 |
| WO | WO2017137421 A1 | 8/2017 |
| WO | WO2019142125 A1 | 7/2019 |

OTHER PUBLICATIONS

Alaris Medical Systems, Signature Edition GOLD: Infusion Pump Models 7130/7131 and 7230/7231, directions for use, 132 pgs., ALARIS Medical Systems, Inc. (Publication date unknown but assumed to be prior to the filing date.).
B. Braun, B. Braun Space Infusion Systems: Automated Infusion Systems, brochure, 24 pgs., B. Braun Melsungen AG (Publication date unknown but assumed to be prior to the filing date.).
B. Braun, B. Braun SpaceStation MRI: Automated Infusion Systems, B. Braun Melsungen AG; (available not before Feb. 2008); No. 6064504; 2 pgs.
B. Braun, Infusomat Space and Accessories, Date of last revision: Nov. 2010, 68 pgs., B. Braun Meslungen AG; www.bbraun.com.
B. Braun, Outlook 200 with DoseScan, Operator's Manual, 2003, 73 pgs., B. Braun Medical Inc.
B. Braun, Outlook ES Safety Infusion System, © 2008, 16 pgs., Bethlehem, PA, United States, B. Braun Medical Inc.
B. Braun, SpaceControl for Automated Glucose Control, instructions for use, Date of last revision: Dec. 2010, 44 pgs., B. Braun Melsungen AG.
B. Braun, Technical Data, 5 pgs., B. Braun Melsungen AG; (Publication date unknown but assumed to be prior to the filing date.).
B. Braun, Vista basic Infusion Pump: Quick Reference, manual, 950853—Rev Jun. 2002, 2 pgs., B. Braun Medical Inc.
B. Braun, Vista Basic: Software IFVB, instructions for use, 2002, 3 pgs., B. Bran Medical Inc.
Baxter, Flo-Gard 6201: Volumetric Infusion Pump, Service Manual, 1992/1995, 202 pgs., Baxter Healthcare Corporation, United States.
Butterfield, Alaris SE Pump, Monitoring and Detection of IV Line Occlusions, 2010, 4 pgs., CareFusion Corporation.
Carayon et al., Observing Nurse Interaction with Infusion Pump Technologies, Advances in Patient Safety, pp. 349-364, vol. 2: Observing Medication Administration; Study 2001-2004.
Cardinal Health, Alaris DS Docking Station, Technical Service Manual, 2002-2007, pp. 1-31, Issue 2, Cardinal Health, Inc.
Cardinal Health, Alaris GP Volumetric Pump, Technical Service Manual, 2006-2008, pp. 1-84, Issue 3, Cardinal Health, Inc.
Cardinal Health, Alaris GW Volumetric Pump, Technical Service Manual, 2003-2006, pp. 1-77, Issue 4, Cardinal Health, Inc.
Cardinal Health, IVAC Variable Pressure Volumetric Pump: Models 571 & 572, Technical Service Manual.
Service Manual, 1994-2008, pp. 1-104, Issue 2, Cardinal Health, Inc.
Cardinal Health, IVAC Volumetric Pump: Models 597 & 598, Technical Service Manual, 1998-2006, pp. 1-76, Issue 3, Cardinal Health, Inc.
Care Everywhere, Gateway User Manual: V1.0.13 W/CQI 1.6: For use with the Sigma Spectrum Pump: Care Everywhere Document No. CE-100-003-IFU, manual, 1-55, CareEverywhere LLC, 9 Tech Circle, Natick, MA, USA. © 2010.
Carefusion, Alaris SE Pump: Models 7100/7130 and 7200/7230, User Manual, Apr. 2011, 134 pgs., CareFusion Corporation.
Carefusion, Directions for Use: Alaris System (with Alaris PC unit, Model 8015), directions for use, Dec. 2011, 360 pgs., CareFusion Corporation.
Carefusion, Infusion Products, brochure, 2011, 16 pgs., CareFusion Corporation.
Carefusion, MedSystem III Infusion Pump Model 2865: With Advanced Dose Rate Calculation and Drug List Editor, User Manual, Nov. 2012, 102 pgs., CareFusion Corporation.
ECRI Institute, Evaluation: Large-Volume Infusion Pumps, Health Devices, Dec. 2009, pp. 402-410, Dec. 2009 issue, ECRI Institute, www.ecri.org.
ECRI Institute, Healthcare Product Comparison System: Infusion Pumps, General Purpose, 2007, pp. 1-54, ECRI Institute.
ECRI, Product Comparison: Infusion Pumps, General-Purpose, Aug. 2005, pp. 1-47, ECRI.
FDA, Medical Devices: SEDASYS Computer-Assisted Personalized Sedation System—P080009, Recently-Approved Devices, May 24, 2013, 2 pgs., U.S. Food and Drug Administration.
First Examination Report from The Intellectual Property Office of New Zealand for Application 626630, dated Apr. 1, 2015, 2 pgs.
First Examination Report from The Intellectual Property Office of New Zealand for Application 702122, dated Nov. 3, 2015, 5 pgs.
Fresenius Deutchsland, Technisches Handbuch: Volumed micro-VP5000, 101 pgs., Fresenius Deutschland; (Publication date unknown but assumed to be prior to the filing date.).
Fresenius Kabi, Applix Smart—Enteral Feeding Pump: Instructions for Use, manual, Feb. 2011, 40 pgs., Fresenius Kabi AG.
Fresenius Kabi, Applix Smart: Technical Guide, service manual, 50 pgs., Fresenius Kabi; (Publication date unknown but assumed to be prior to the filing date.).
Fresenius Kabi, Volumat Agilia, customer presentation, 29 pgs., Fresenius Kabi; (Publication date unknown but assumed to be prior to the filing date.).
Fresenius Kabi, Volumat MC Agilia: Advanced Volumetric Infusion Pump, Medical Devices, specifications, 2 pgs., Fresenius Kabi; (Publication date unknown but assumed to be prior to the filing date.).
Fresenius Medical Care, multiFiltrate Service Manual, service manual, 150 pgs., Fresenius Medical Care multiFiltrate; (Publication date unknown but assumed to be prior to the filing date.).
Fresenius Transfusions GMBH, Fresenius HemoCare: Technical Manual for com.tec, service manual, 342 pgs., Fresenius Transfusions GmbH; (Publication date unknown but assumed to be prior to the filing date.).
Fresenius USA, Inc., Fresenius 2008H Hemodialysis System, Troubleshooting Guide, 1998-1999, 90 pgs., Fresenius USA, Inc.
Fresenius Vial S.A., Optima PT-VS-ST: Technical Manual, service manual, 2007, 106 pgs., Fresenius Vial S.A.
Gieras, Innovative Infusion Pump Technologies, Jun. 15, 2010, pp. 1-53, IEEE.
Goldman et al., Advancing the Adoption of Medical Device "Plug-and-Play" Interoperability to Improve Patient Safety and Healthcare Efficiency, a white paper from the MD PnP Program, 2006-2009 (rev Sep. 2009), pp. 1-3, MD PnP Program.
Hawk, III, The Role of Color Coding in Medication Error Reduction, Action of the AMA House of Delegates 2004 Annual Meeting: Report of the Council on Scientific Affairs, CSA Report 5-A-04, pp. 1-8.

(56) References Cited

OTHER PUBLICATIONS

Hoenich et al., Research & Technology: The Current Status and Future Directions of Hemodialysis Machine Technology, Hemodialysis Horizons, pp. 38-44, AAMI.org; (Publication date unknown but assumed to be prior to the filing date.).
Hofmann, Modeling Medical Devices for Plug-and-Play Interoperability, Master of Engineering thesis, Massachusetts Institute of Technology, Jun. 2007, pp. 1-187, Robert Matthew Hofmann, MMVII.
Infusion Nurses Society, Infusion Nursing: Standards of Practice, Journal of Infusion Nursing, 2011, 115 pgs., vol. 34, No. 1S, Jan./Feb. 2011 issue, Infusion Nurses Society.
Infusion Nurses Society, Policies and Procedures for Infusion Nursing, 2011, pts. 1-162, 4th edition, Infusion Nurses Society.
International Search Report & Written Opinion dated Oct. 1, 2013, received in International patent application No. PCT/US2012/071490, 20 pgs.
International Search Report & Written Opinion dated Dec. 4, 2013, received in International patent application No. PCT/US2013/032445, 20 pgs.
International Search Report & Written Opinion dated Nov. 7, 2013, received in International patent application No. PCT/US2013/042350, 18 pgs.
International Preliminary Report on Patentability dated Jul. 3, 2014, received in International patent application No. PCT /US2012/071490, 14 pgs.
International Preliminary Report on Patentability dated Dec. 4, 2014, received in International patent application No. PCT/US2013/032445, 12 pgs.
International Preliminary Report on Patentability dated Dec. 4, 2014, received in International patent application No. PCT/US2013/042350, 13 pgs.
Invitation to Pay Additional Fees and, Where Applicable, Protest Fees, dated May 28, 2013, received in International patent application PCT /US2012/071490, 8 pgs.
Invitation to Pay Additional Fees and, Where Applicable, Protest Fee dated Sep. 9, 2013, received in International patent application No. PCT/US2013/032445, 10 pgs.
Invitation to Pay Additional Fees and, Where Applicable, Protest Fee dated Sep. 26, 2013, received in International patent application No. PCT/US2013/042350, 7 pgs.
Israelski, The Symbiq (Next-Generation) IV Infusion Pump: A Feature-Filled "Intelligent" Pump Developed with and for the End-User, May 2007, 4 pgs., Hospira, Inc.
Jetley et al., Safety Requirements based Analysis of Infusion Pump Software, 4 pgs., US Food and Drug Administration; (Publication date unknown but assumed to be prior to the filing date.).
King et al., Prototyping Closed Loop Physiologic Control with the Medical Device Coordination Framework, 200X, 11 pgs., MD PnP www.mdpnp.org; (Publication date unknown but assumed to be prior to the filing date.).
MHRA, Volumetric Pump—Fresenius Vial MVP MS, evaluation, Feb. 2004, pp. 1-16, MHRA.
National Patient Safety Agency, Design for Patient Safety: A Guide to the Design of Electronic Infusion Devices, booklet, 2010, pp. 1-96, Edition 1, National Patient Safety Agency, London, USA.
Nemeth et al., Making Information Technology a Team Player in Safety: The Case of Infusion Devices, Advances in Patient Safety: Interface Design for Infusion Devices, pp. 319-330, vol. 1; (Publication date unknown but assumed to be prior to the filing date.).
Notice for Reason for Rejection, dated Nov. 17, 2015, received in Japanese patent application No. 2015-514014 with English Translation, 9 pgs.
Notice for Reason for Rejection, dated Oct. 6, 2015, received in Japanese patent application No. 2014-548986 with English Translation,10 pgs.
Pfiedler Enterprises, A Comprehensive Surgical Checklist: Using Technology to Help Optimize Preparedness, Patient Safety and Performance (A Continuing Education Self-Study Activity), 2011, pp. 1-20, Pfiedler Enterprises.

Prusch et al., IV Interoperability: Smart Pump and BCMA Integration, Oct. 5, 2010, Lancaster General Health; 13 pgs.
Rafferty, Proposal for Wireless Transmission of Non-invasive Respiratory Data to the Servo Module of an Opioid Infusion-Pump for Real-Time Patient Safety Feedback Control, 1pg., Yale School of Medecine; (Publication date unknown but assumed to be prior to the filing date.).
Search Report and Written Opinion from The Intellectual Property Office of Singapore for Application 11201403511Y, dated Nov. 28, 2014, 20 pgs.
Sigma, Service Manual Sigma International Model Spectrum Infusion Pump, Service Manual, Aug. 2009, 58 pgs., SIGMA International, Inc., Medina, New York, United States.
Technical Data: Infusomat Space, Perfusor Space, 7 pgs.; (Publication date unknown but assumed to be prior to the filing date.).
Vanderveen, Technology Focus: Using Data to Improve Smart Intravenous Infusion Pumps, Human Factors Horizons, 2010, pp. 57-63, Human Factors Horizons.
Written Opinion from The Intellectual Property Office of Singapore for Application 11201403511Y, dated Jun. 19, 2015, 11 pgs.
Invitation to Pay Additional Fees and, Where Applicable, Protest Fee dated Jan. 25, 2016, received in International patent application No. PCT/US2015/049952, 7 pgs.
International Search Report and Written Opinion Apr. 7, 2016, received in International patent application No. PCT/US2015/049952, 18 pgs.
Extended European Search Report & Written Opinion dated Jul. 18, 2016, received in European patent application No. 16166215.0, 9 pgs.
First Examination Report from IP Australia for Australian Application 2012358221, dated Sep. 28, 2016, 3 pgs.
Notice of Acceptance from IP Australia for Australian Application 2012358221, dated Dec. 13, 2016, 3 pgs.
First Rule 71(3) Communication from the European Patent Office for EPO Application No. 12 826 641.8-116, dated Jun. 23, 2015, 8 pgs.
Second Rule 71(3) Communication from the European Patent Office for EPO Application No. 12 826 641.8-116, dated Jan. 28, 2016, 8 pgs.
Decision to Grant from the European Patent Office for EPO Application No. 12 826 641.8-116, dated Jul. 21, 2016, 3 pgs.
Second Examination Report from The Intellectual Property Office of New Zealand for Application 626630, dated Dec. 23, 2015, 2 pgs.
Notice of Acceptance and Extract from The Intellectual Property Office of New Zealand for Application 626630, dated May 30, 2016, 4 pgs.
Notice of Intention to Refuse Patent Application and Examination Report from The Intellectual Property Office of Singapore for Application 11201403511Y, dated May 4, 2016, 12 pgs.
First Examination Report from the IP Australia of the Australian Government for Australian Patent Application No. 2013266864, dated Oct. 31, 2016, 3 pgs.
First Office Action dated Aug. 30, 2016, received in Republic of China Patent Application No. 201380039475.5, 10 pgs.
Notification of Paying the Restoration Fee for Unity of Invention dated May 20, 2016, received in Republic of China Patent Application No. 201380039475.5, 1 pgs.
Report of substantive examination from Superintendent of Industry and Commerce of Colombia for Patent Application 14.283.126, dated Jun. 24, 2016, 6 pgs.
Article 94(3) Communication from the European Patent Office for EPO Application No. 13 728 549.0-1662, dated Mar. 4, 2016, 3 pgs.
Notice for Reason for Rejection, dated Nov. 17, 2015, received in Japanese patent application No. 2015-514014, 4 pgs.
Decision to Grant, dated Jun. 7, 2016, received in Japanese patent application No. 2015-514014, 3 pg.
Further Examination Report (Second) from The Intellectual Property Office of New Zealand for Application 702122, dated Nov. 9, 2016, 2 pgs.
First Examination Report from The Intellectual Property Office of New Zealand for Application 714766, dated Jun. 8, 2016, 2 pgs.

(56) References Cited

OTHER PUBLICATIONS

Further (Second) Examination Report from The Intellectual Property Office of New Zealand for Application 714766, dated Aug. 26, 2016, 2 pgs.
Further (Third) Examination Report from The Intellectual Property Office of New Zealand for Application 714766, dated Dec. 23, 2015, 2 pgs.
Notice of Acceptance and Extract from The Intellectual Property Office of New Zealand for Application 714766, dated Nov. 16, 2016, 4 pgs.
First Examination report from the New Zealand Intellectual Property Office for New Zealand IP No. 720136, dated Jun. 8, 2016, 2 pgs.
First Examination report from the New Zealand Intellectual Property Office for New Zealand IP No. 724959, dated Oct. 31, 2016, 3 pgs.
First Examination Report from The Intellectual Property Office of New Zealand for Application 720767, dated Sep. 5, 2016, 4 pgs.
Notice of Acceptance from The Intellectual Property Office of New Zealand for Application 720767, dated Dec. 14, 2016, 1 pg.
Decision to Grant, dated Jul. 26, 2016, received in Japanese patent application No. 2014-548986, 3 pg.
Notice of Eligibility for Grant and Examination Review Report from The Intellectual Property Office of Singapore for Application 11201403511Y, dated Jan. 31, 2017, 7 pgs.
Notice of Acceptance from the IP Australia of the Australian Government for Australian Patent Application No. 2013266864, dated Mar. 24, 2017, 3 pgs.
International Preliminary Report on Patentability and Written Opinion Mar. 21, 2017, received in International patent application No. PCT/US2015/049952, 11 pgs.
Further Examination report from the New Zealand Intellectual Property Office for New Zealand IP No. 720136, dated Dec. 22, 2016, 2 pgs.
Report of substantive examination from Superintendent of Industry and Commerce of Colombia for Patent Application 14.283.126, dated Jan. 17, 2017, 6 pgs.
Further Examination report from the New Zealand Intellectual Property Office for New Zealand IP No. 724959, dated Apr. 26, 2017, 2 pgs.
Second Office Action dated May 15, 2017, received in Republic of China Patent Application No. 201380039475.5, 10 pgs.
Rule 161 Communication from the European Patent Office for Patent Application 15771376.9, dated May 8, 2017, 2 pgs.
Notice for Reason for Rejection, dated Jun. 6, 2017, received in Japanese patent application National Publication No. 2016-132343, 2 pgs.
First Examination Report from The Intellectual Property Office of New Zealand for Application 735908, dated Oct. 26, 2017, 3 pgs.
Notice for Reason for Rejection, dated Aug. 29, 2017, received in Japanese patent application National Publication No. 2016-161815, 5 pgs.
European Examination Report (Article 94(3) EPC Communication) dated Dec. 14, 2017, received in European patent application No. 16 166 215.0-1664, 3 pgs.
Communication of the Substantive Examination Result dated Nov. 23, 2017, from the Mexican Institute of Industrial Property for application MX/a/2014/014321,5 pgs.
First Examination Report from IP Australia for Australian Application 2018200015, dated Jan. 16, 2018, 2 pgs.
Written Opinion dated Feb. 14, 2020, received in International patent application No. PCT/US2019/046838, 12 pgs.
U.S. Appl. No. 61/578,649, filed Dec. 21, 2011.
PCT/US12/71490, filed Dec. 21, 2012, WO2013096909A1.
U.S. Appl. No. 13/725,790, filed Dec. 21, 2012, US20130177455A1.
U.S. Appl. No. 13/840,339, filed Mar. 15, 2013, US20130336814A1.
PCT/US13/32445, filed Mar. 15, 2013, WO2013176770A1.
U.S. Appl. No. 62/052,008, filed Sep. 18, 2014.
U.S. Appl. No. 14/853,300, filed Sep. 14, 2015, US20160158437A1.
PCT/US15/49952, filed Sep. 14, 2015, WO/2016/044146A1.
U.S. Appl. No. 14/873,515, filed Oct. 2, 2015, US20160097382A1.
U.S. Appl. No. 15/584,376, filed May 2, 2017, US20170266378A1.
U.S. Appl. No. 15/616,325, filed Jun. 7, 2017, US20170268497A1.
U.S. Appl. No. 15/808,099, filed Nov. 9, 2017, US20180066648A1.
U.S. Appl. No. 15/841,961, filed Dec. 14, 2017, US20180106246A1.
U.S. Appl. No. 15/866,581, filed Jan. 10, 2018, US20180128259A1.
U.S. Appl. No. 29/651,489, filed Aug. 16, 2018.
U.S. Appl. No. 62/765,100, filed Aug. 16, 2018.
U.S. Appl. No. 16/259,257, filed Jan. 28, 2019, US20190154026A1.
U.S. Appl. No. 16/271,046, filed Feb. 8, 2019, US20190170134A1.
U.S. Appl. No. 16/359,134, filed Mar. 20, 2019, US20190219047A1.
U.S. Appl. No. 16/377,453, filed Apr. 8, 2019, US20190298913A1.
U.S. Appl. No. 16/389,042, filed Apr. 19, 2019, US20190249657A1.
PCT/US19/46838, filed Aug. 16, 2019, WO20200371216A1.
U.S. Appl. No. 17/000,538, filed Aug. 24, 2020, US20200386220A1.
U.S. Appl. No. 17/111,998, filed Dec. 4, 2020.
First Office Action English Translation dated Aug. 30, 2016, received in Republic of China Patent Application No. 201380039475.5, 10 pgs.
U.S. Appl. No. 17/332,153, filed May 27, 2021.

\* cited by examiner

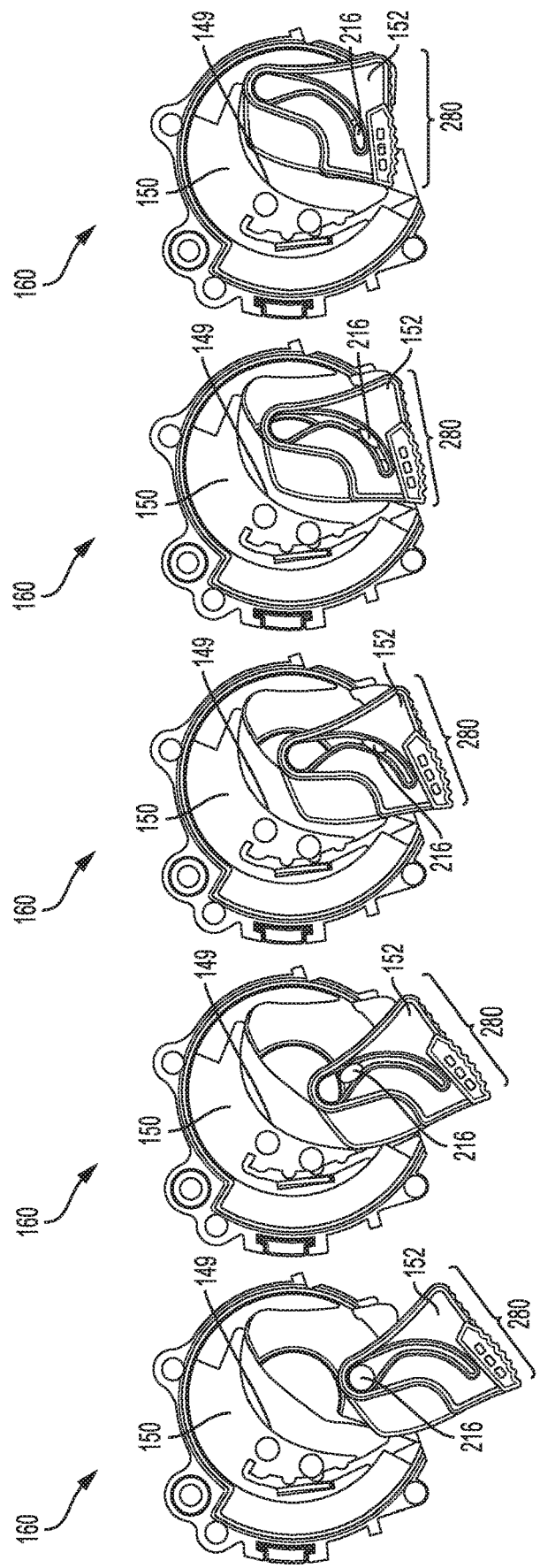

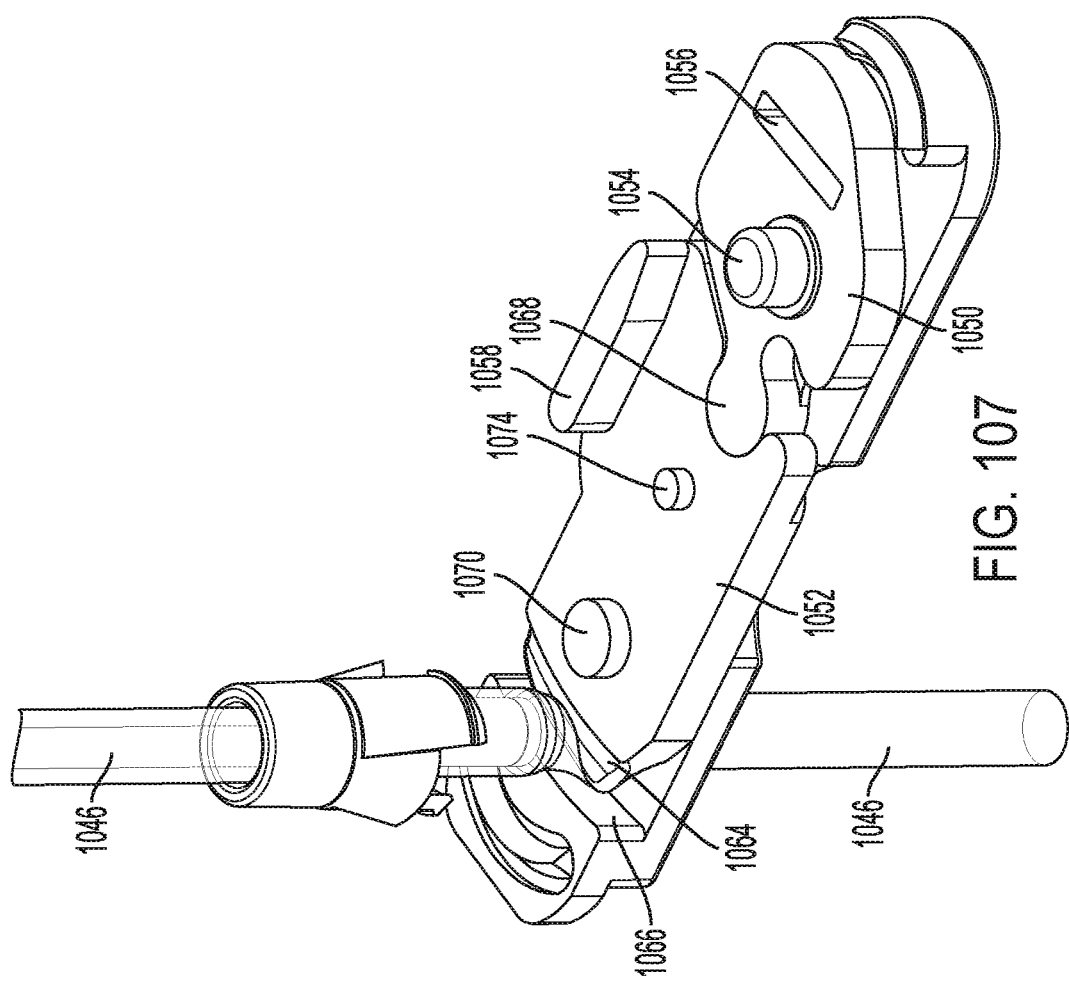

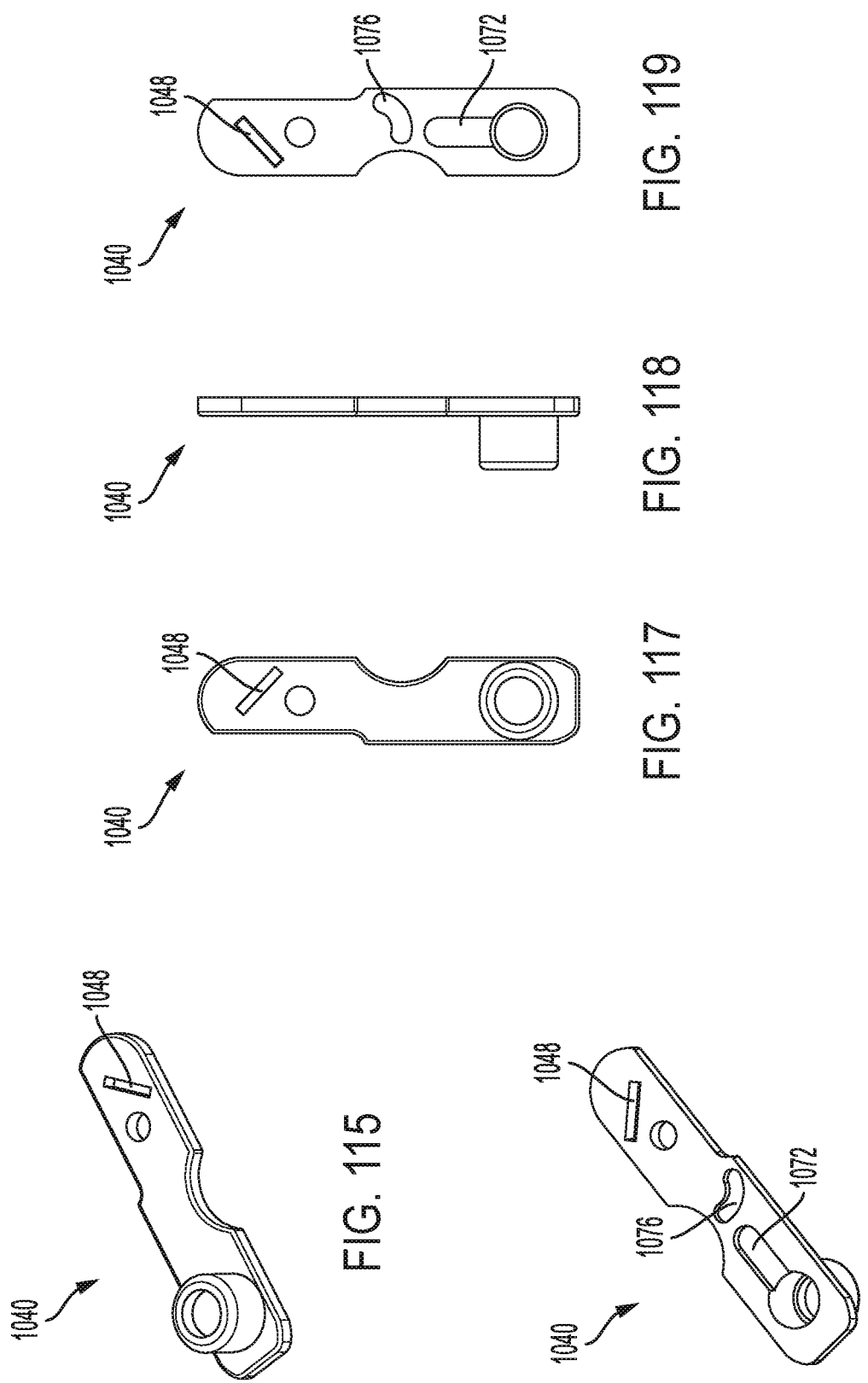

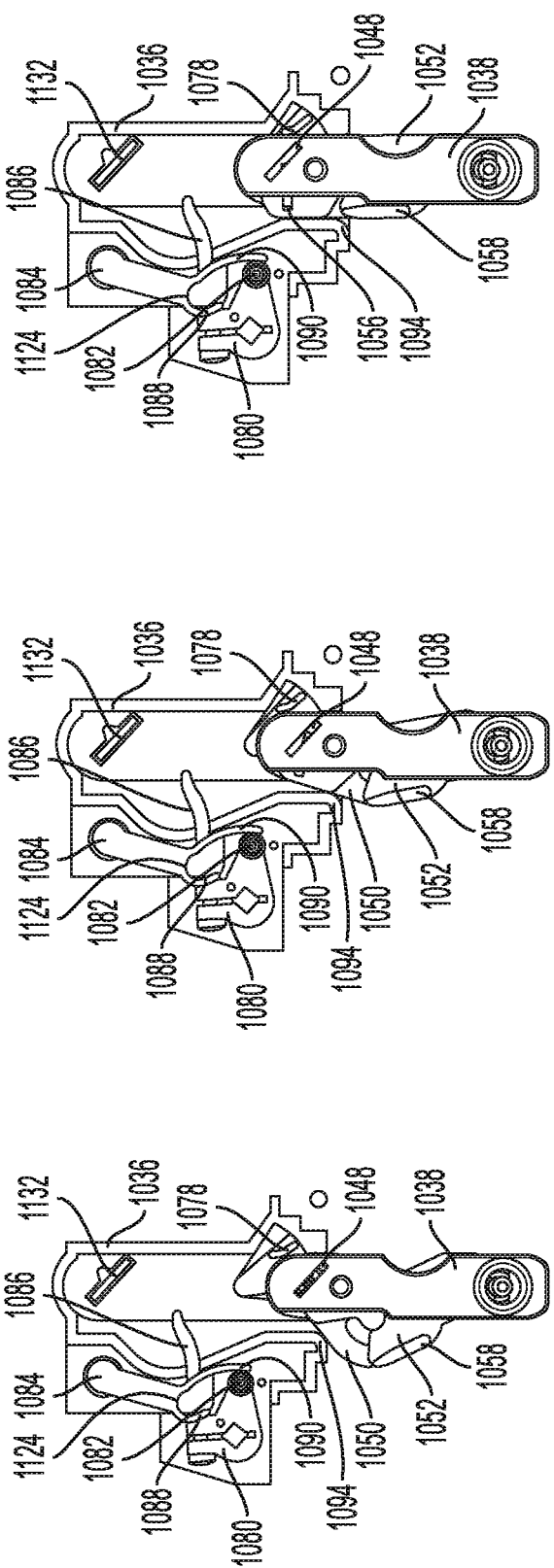
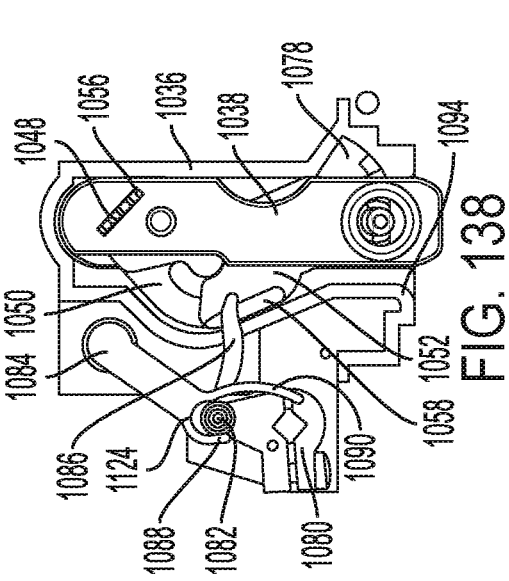
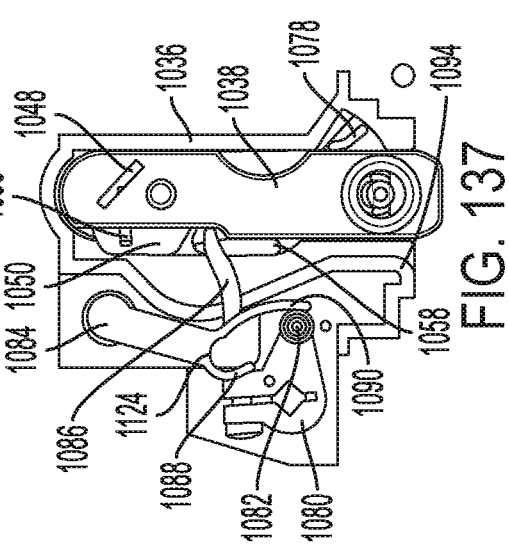

MEDICAL PUMP

CROSS REFERENCE TO RELATED APPLICATIONS

The present application is a Non-Provisional Application which claims the benefit of U.S. Provisional Patent Application Ser. No. 62/765,100, filed Aug. 16, 2018 and entitled Medical Pump, which is hereby incorporated herein by reference in its entirety.

BACKGROUND

Relevant Field

The present disclosure relates to medical pumps. More particularly, the present disclosure relates to medical pump, such as a peristaltic pump, for infusing fluid into a patient.

Description of Related Art

Peristaltic pumps are used in a variety of applications including medical applications. In medical applications, peristaltic pumps are used to infuse a patient with a fluid and typically have the benefit of isolating the medical fluid being infused into a patient in while maintaining sterility. Some peristaltic pumps work by compressing or squeezing a length of flexible tubing thereby preventing the fluid being infused from coming into contact with the pump or internal pump mechanism. A mechanical mechanism of the peristaltic pump pinches a portion of the tubing to push fluid trapped in the tubing in the direction of the patient. There are rotary peristaltic pumps and finger peristaltic pumps.

Rotary peristaltic pumps typically move liquids through flexible tubing placed in an arc-shaped raceway. Rotary peristaltic pumps are generally made of two to four rollers placed on a roller carrier driven rotationally by a motor. A typical rotary peristaltic pump has a rotor assembly with pinch rollers that apply pressure to the flexible tubing at spaced locations to provide a squeezing action on the tubing against a counter surface. The occlusion of the tubing creates increased pressure ahead of the squeezed area and reduced pressure behind that area, thereby forcing a liquid through the tubing as the rotor assembly moves the pinch rollers along the tubing. In order to operate, there must always be an occlusion zone; in other words, at least one of the rollers is always pressing on the tube.

Finger peristaltic pumps are made of a series of fingers moving in cyclical fashion to flatten a flexible tube against a counter surface. The fingers move essentially vertically to form a zone of occlusion that moves fluid from upstream to downstream. The most commonly used finger pumps are linear, meaning that the counter surface is flat and the fingers are parallel. In this case, the fingers are controlled by a series of cams arranged one behind another, each cam cooperating with a finger. These cams may be placed in a helically offset manner on a shared shaft driven rotationally by a motor. There are also rotary-finger peristaltic pumps, which attempt to combine the advantages of roller pumps with those of finger pumps. In this type of pump, the counter surface is not flat, but arc-shaped, and the fingers are arranged radially inside the counter surface. In this case, a shared cam with multiple knobs placed in the center of the arc is used to activate the fingers.

SUMMARY

In accordance with an embodiment of the present disclosure, pump for treating a patient includes a spring-biased plunger, a cam shaft, a lever, a shaft, and a lift cam. The spring-biased plunger is biased toward actuation against a tube. The cam shaft actuates the spring-based plunger. The lever is actuatable between a closed position and an open position. The shaft is coupled to the lever and has a central axis centrally along the length of the shaft. The shaft is coupled to the lever to rotate around the central axis in accordance with actuation of the lever. The lift cam is pivotally coupled to the shaft. The lift cam pivots around a lift cam axis. The lift cam axis of the lift cam is parallel to the central axis of the shaft. The lift cam engages with the spring-based plunger to lift the spring-biased plunger off of the cam shaft as the shaft rotates in accordance with actuating the lever to the open position.

The pump may include a torsion spring to bias the lift cam to rotate toward the spring-biased plunger, a first bevel gear coupled to the lever that rotates as the lever is actuated, a second bevel gear disposed on the shaft to rotate therewith. The first bevel gear can engage with the second bevel gear. The lift cam may include an arcuate outer surface configured to engage with the spring-based plunger. The pump may include a spring to bias the shaft to rotate along the central axis of the shaft where the central axis of the shaft is offset from the lift cam axis. The pump may include shaft spring coupled to the shaft. The shaft spring can actuate the lever to an open position or a closed position. The shaft spring can actuate the lever in an over-center action. The lift cam can actuate an end effector away from a tube when the lift cam lifts the spring-biased plunger off the cam shaft and the lift cam can actuate an end effector toward the shaft when the lift cam lifts the spring-biased plunger off the cam shaft.

In another embodiment of the present disclosure, a pump for treating a patient includes a door, a door catch, a latching sled, and a hook cam. The door has an door-open position and a door-closed position. The door catch catches the door when the door is in the door-closed position. The latching sled latches the door catch and unlatches the door catch. The latch sled includes a cam follower and the hook cam engages with the cam follower, The hook cam includes a hook to actuate the latching sled to unlatch the door catch.

The latching sled may include a sled base to actuate toward and away from the shaft and a claw coupled to the sled base. The sled base may be coupled to the cam follower. The claw may be pivotably coupled to the sled base, e.g., at an axis of the cam follower. A sled spring may be coupled the claw to bias the claw. The sled spring can bias the claw toward the shaft and/or the sled spring biases the claw away the shaft. The pump may include a block configured to allow the sled base to slide back and forth within a channel of the block. The sled spring may be coupled to the block. The claw may be pivotably coupled to the sled base adjacent to the cam follower of the latching sled and/or the claw can be pivotably coupled to each side of the cam follower of the latching sled. The pump may include a pin where: the claw is pivotably coupled to the pin on each side of the cam follower of the latching sled, the cam follower rotates around the pin, the pin defines a pin axis, the hook cam rotates around a cam axis, and the pin axis is parallel to the cam axis.

The pump may include a shaft disposed along the cam axis such that the hook cam rotates with the shaft. The pump may include a block wherein the sled base slides within the block, an anchor coupled to the block; and a spring coupled to a claw and the anchor. The anchor may be a pin.

The pump may include a shaft having the hook cam disposed thereon and a lever coupled to a shaft. The hook cam can engage with the cam follower when the lever is in a closed position. When the lever is actuated to the open position, the hook cam may rotate such that the hook of the hook cam latches onto the cam follower of the latching sled and pulls the latching sled toward the shaft. The hook cam may define a retraction space configured to receive the latching sled when the latching sled is fully actuated toward the hook cam. The door catch may be actuatable between a catching position and a locking position.

The pump may include a spring coupled to a door catch where the spring pushes the door catch such that the door catch is bi-stable in the catching position or the locking position. The spring may bias the door catch to a closer one of the catching position or the locking position when the door catch is therebetween. The stability may be caused by an over center action of the spring.

The door catch may include a door-catch hold. The latching sled may include a claw pivotably coupled to the latching sled. The hook cam may be actuated to hook onto the latching sled and retract the latching sled toward the hook cam. The claw of the latching sled may grasp onto the door-catch hold and actuate the door catch from the locking position to the catching position. The hook cam may be actuated to hook onto the latching sled and retract the latching sled toward the hook cam. The block may actuate an end of the claw away from the sled base where the end of the claw is opposite to the pivotable coupling.

The door catch may include a channel, a pin catch, a door catch, and a door-catch anchor. The channel pivots the door catch. The pin catch catches the pin. The door catch hold engagements with a claw of the latching sled. The door-catch anchor may couple to a door-catch spring to make the door catch bi-stable.

In some embodiments of the present disclosure, a pump for treating a patient includes a carriage housing, a carriage, and a pivot. The carriage is disposed within the carriage housing and receives a slide camp. The carriage is pivotable within the housing and the housing includes a tube retainer to retain a tube when the carriage is pivoted within the carriage housing. The pivot pivots the carriage around an axis and may be a gear connector.

The pump may include a pawl pivotably coupled to the carriage housing to engage with a slot of the carriage to stop rotation of the carriage in a first pivot direction. A pawl spring may be coupled to the carriage housing and the pawl to bias the pawl against the carriage. The pump may include a lifter pin configured to actuate in response to closing a door on the pump and a lift coupled to the pawl and configured to receive the lifter pin. The lifter may pin include a lifter spring to lift the lift when a predetermined amount of force is applied to the lifter pin from the door being closed.

The pump may include a pawl pivotably coupled to the carriage housing and to engage with a slot of the carriage to stop rotation of the carriage in a first pivot direction, a lever, and a shaft. The lever is actuatable from an open position to a closed position. The shaft may be coupled to the lever and to the carriage. When the pawl is engaged with the slot of the carriage, the lever may be prevented from going from the open position to the closed position when the carriage cannot rotate in the first pivot direction.

The pump may include a coupling on the shaft to allow the lever to actuate a predetermined amount from the open position to the closed position when the pawl is engaged with the slot of the carriage. The carriage may further include a cover configured to cover an opening of the carriage housing when the carriage is rotationally positioned in a fluid flow position.

In another embodiment of the present disclosure, an apparatus includes a carriage housing and a pivot. The carriage housing includes a carriage rotatable within the carriage housing and one or more tube retainers offset from an axis of rotation of the carriage. The at least one tube retainer receives and retains a fluid tube in a substantially stationary position while the carriage rotates within the carriage housing. The pivot mechanism may be coupled to the carriage and connects to a rotating device to rotate the carriage about the axis in response to rotation of the rotating device. The carriage housing may receive a tube clamp for rotation inside the carriage housing by the carriage such that, when the fluid tube is retained by the at least one tube retainer and the carriage rotates about the axis, the tube clamp constricts or opens the tube depending on the direction of rotation of the carriage. The one or more tube retainers may include respective tube retainers aligned through at least a portion of a top and a bottom of the carriage housing at respective vertically aligned locations. The apparatus may include a light emitting device and an optical sensor.

The carriage housing may include a window to receive light from the light emitting device pass at least a portion of the received light through the carriage housing to the sensor when the tube clamp is received into the carriage housing. The portion of the received light may include a pattern defined by one or more holes in the tube clamp.

In other embodiment of the present disclosure, a pump for treating a patient includes a lever, a shaft, and a shaft spring. The lever may be actuatable between a closed position and an open position. The shaft may be coupled to the lever and may have a central axis centrally along the length of the shaft. The shaft may be coupled to the lever to rotate around the central axis in accordance with actuation of the lever. The shaft spring may be coupled to the shaft to actuate the lever to an open position or a closed position in an over-center action. A first bevel gear may be coupled to the lever and rotates as the lever is actuated. A second bevel gear may disposed on the shaft to rotate therewith where the first bevel gear engages with the second bevel gear.

In other embodiment of the present disclosure, an apparatus includes a substantially flat body portion and a head portion. The substantially flat body portion is for insertion into a housing and has an arcuate slot within the body. The arcuate slot has a receiving portion at one end of the body and an occluding portion, narrower than the receiving portion, at another end of the body portion. The head portion transverse to the substantially flat body portion and configured to increase an amount of force applied to the body portion during insertion into the housing. The arcuate slot is positioned such that when a stationary fluid tube is received into the receiving portion, and the body is rotated in a first direction about an axis transverse to the body, the tube traverses into the occluding portion.

In another embodiment of the present disclosure, a slide clamp includes a body where the body defines an arcuate slot configured to receive a pinchable tube. The arcuate slot includes a flowing portion and an occluding portion. The slide clamp may be rotated within a carriage. The slide clamp may include a stabilizer coupled to the body. The slide clamp may include a thumb rest coupled to the body. The thumb rest may include an extension, and the extension can includes a plurality of slide-clamp identification holes.

In another embodiment of the present disclosure, a carriage assembly includes a carriage housing and a carriage. The carriage can have an opening and the carriage may disposed within the carriage housing and configured to rotate along a rotational axis. The carriage may receive a slide clamp disclosed herein. The carriage housing may include a window to determine an identification in accordance with a plurality of slide-clamp identification holes of the slide clamp. The carriage assembly may be disposed within a peristaltic pump. Rotation of the carriage from a first rotational position to a second rotational position may position a tube within the arcuate slot from the occluding portion to the flowing portion. When the carriage is in the second position, a cover of the carriage may cover the opening of the carriage housing. The carriage may include a slide-clamp retainer configured to retain the slide clamp within the carriage. The slide-clamp retainer may include a spring body and a retainer hook.

In another embodiment of the present disclosure, a modular pump system includes a central unit and a medical-device assembly. The central unit includes a first central-unit connector, a central-unit switchable power circuit, and a first signal generating circuit. The first central-unit connector has a power pin and a communication pin. The central-unit switchable power circuit is coupled to the power pin of the first central-unit connector. The switchable power circuit may switch between a power-on mode where power is thereby applied to the power pin of the first central-unit connector and a power-off mode where power is thereby not applied to the power pin of the first central-unit connector. The first signal generating circuit may generate a first signal on the communication pin of the first central-unit connector.

The medical-device assembly includes a first medical-device connector, a module-detect controller, and a power receiver circuit. The first medical-device connector may have a power pin and a communication pin. The first medical-device connector may be used for connecting to the first central-unit connector thereby connecting the power pin of the first central-unit connector to the power pin of the first medical-device connector and connecting the communication pin of the first central-unit connector to the communication pin of the first medical-device connector. The module-detect controller may passively indicate a request to receive power through the power pin of the first medical-device connector. The power receiver circuit may be coupled to the module-detect controller to provide power to the module-detect controller. The power receiver circuit may be coupled to the power pin of the first medical-device connector and the communication pin of the first medical-device connector. The power receiver circuit can power the module-detect circuit from the signal on the communication pin when the switchable power circuit is in the power-off mode and from the power pin when the switchable power circuit is in power-on mode using the power applied to the power pin of the first medical-device connector received through the power pin of the first central-unit connector.

The module-detect controller may alter an impedance coupled to the communication pin to thereby passively indicate the request to receive the power, alter a resistance coupled to the communication pin to thereby passively indicate the request to receive the power, and/or activate a resistor coupled to the communication pin to thereby passively indicate the request to receive the power.

The module-detect controller may allow a current to flow through the resistor to a ground to thereby add a resistance to the communication pin to thereby passively indicate the request to receive the power. The module-detect controller may be coupled to the resistor via an open-drain driver pin and the open-drain driver pin may activate the resistor by entering into a low-impedance mode. The low-impedance mode may be is implemented by a transistor in an active mode.

The first central unit may switch to the power-on mode when the module-detect controller of the medical-device assembly passively requests power to thereby supply power to the module detect controller from the power pin of the first central-unit connector to the power pin of the first medical-device connector.

The medical-device assembly may include a second medical-device connector having a power pin and a communication pin. The medical-device assembly may further include a second signal generating circuit configured to generate a second signal on the communication pin of the second medical-device connector. The second signal generating circuit may generates the second signal after the central-unit switchable power circuit switches to the power-on mode. The second signal generating circuit may generate the second signal after the module-detect controller passively indicates the request to receive the power. /the medical-device assembly may include a detection circuit to detect a passive request to communicate power from the power pin of the first medical-device connector to the power pin of the second medical-device connector. The medical-device assembly may include a crossbar switch connecting the power pin of the first medical-device connector to the power pin of the second medical-device connector. The crossbar switch may be closed when the detection circuit detects the passive request to communicate power to the power pin of the second medical-device connector.

In yet another embodiment of the present disclosure, a central unit includes a left central-unit connector, a left switchable power circuit, a right central-unit connector, a right switchable power circuit, one or more signal generating circuits, a left load-detect circuit, and a right load-detect circuit. The left central-unit connector has a left power pin and a left communication pin. The left switchable power circuit is coupled to the power pin of the first central-unit connector. The left switchable power circuit switches between a power-on mode where power is thereby applied to the left power pin of the left central-unit connector and a power-off mode where power is thereby not applied to the left power pin of the left central-unit connector. The right central-unit connector has a right power pin and a right communication pin. The right switchable power circuit is coupled to the power pin of the right central-unit connector. The right switchable power circuit switches between a power-on mode where power is thereby applied to the right power pin of the right central-unit connector and a power-off mode where power is thereby not applied to the right power pin of the right central-unit connector. The one or more signal generating circuits may generate a signal on the left communication pin of the left central-unit connector and/or the right communication pin of the right central-unit connector. The left load-detect circuit may detect a passive indication of request for power of a left connected medical-device assembly. The left switchable power circuit may switch to a power-on mode when the left load-detect circuit detects the passive indication of request for power of the left connected medical-device assembly. The right load-detect circuit may detect a passive indication of request for power of a right connected medical-device assembly. The right switchable power circuit may switch to a power-on mode when the right load-detect circuit detects the passive indication of request for power of the right connected medical-device assembly.

The left load-detect circuit may detects a change in impedance of the left communication pin of the left central-unit connector to determine that the passive indication of the request for power of a right connected medical-device assembly has been received. The left load-detect circuit may detect an increased impedance of the left communication pin of the left central-unit connector to determine that the passive indication of the request for power of a right connected medical-device assembly has been received. The left load-detect circuit may detect an increase in resistance of the left communication pin of the left central-unit connector to determine that the passive indication of the request for power of a right connected medical-device assembly has been received.

In another embodiment of the present disclosure, a medical-device assembly comprises: a left medical-device connector having a left power pin and a left communication pin; a right medical-device connector having a right power pin and a right communication pin; a module-detect controller configured to passively indicate a request to receive power through the left power pin of the left medical-device connector or to passively indicate a request to receive power through the right power pin of the right medical-device connector; and a power receiver circuit coupled to the module-detect controller to provide power to the module-detect controller, wherein the power receiver circuit is coupled to the power pin of the left medical-device connector and the left communication pin of the left medical-device connector, wherein the power receiver circuit powers the module-detect circuit from a received signal from one of the left communication pin of the left medical-device connector or the right communication pin of the right medical-device connector; a left signal generating circuit configured to generate a left signal on the left communication pin of the left medical-device connector when active; a right signal generating circuit configured to generate a right signal on the right communication pin of the right medical-device connector when active; and a crossbar switch connecting the left power pin of the left medical-device connector to the right power pin of the right medical-device connector.

The power receiver circuit may power the module-detect controller only when the received signal is received via only one of the left communication pin or the right communication pin. The module-detect controller may passively indicate a request to receive power through the left communication pin when the received signal is received from the left communication pin. The module-detect controller is configured to non-simultaneously: passively indicate a request through the left communication pin to receive power from the left power pin when the received signal is received from the left communication pin or passively indicate a request through the right communication pin to receive power from the right power pin when the received signal is received from the right communication pin. The module-detect controller may passively indicate a request through the left communication pin to receive power from the left power pin when the received signal is received from the left communication pin and passively indicate a request through the right communication pin to receive power from the right power pin when the received signal is received from the right communication pin. The module-detect controller may provide only one request to receive power where the one request to receive power being one of the request to receive power through the left power pin or the request to receive power through the right power pin. The left signal generating circuit may be coupled to the module-detect controller and the left signal generating circuit is operatively coupled to the module-detect controller.

The module-detect controller may instruct the left signal generating circuit to generate the left signal on the left communication pin when the received signal is received via the right communication pin of the right medical-device connector. The module-detect controller may be configured to instruct the right signal generating circuit to generate the right signal on the right communication pin when the received signal is received via the left communication pin of the left medical-device connector. The module-detect controller may be configured to generate only one of the right signal and the left signal by instructing only one of the right signal generating circuit and the left signal generating circuit. The right signal generating circuit and the left signal generating circuit may be integrated together with the module-detect controller on a semiconductor device.

The module-detect controller may be configured to passively indicate a request to receive power through the left power pin of the left medical-device connector by adding a first resistance to the left communications pin of the left medical-device connector. The module-detect controller may be configured to activate a first resistor coupled to the left communication pin to thereby passively indicate the request to receive the power through the left power pin. The module-detect controller may be configured to allow a current to flow through the first resistor to a ground to thereby add the resistance to the left communication pin to thereby passively indicate the request to receive the power through the left power pin. The module-detect controller may be coupled to the first resistor via a left open-drain driver pin when the left open-drain driver pin activates the resistor by entering into a low-impedance mode. The module-detect controller may be configured to passively indicate a request to receive power through the right power pin of the right medical-device connector by adding a second resistance to the right communications pin of the right medical-device connector. The module-detect controller may be configured to activate a second resistor coupled to the right communication pin to thereby passively indicate the request to receive the power through the right power pin. The module-detect controller may be configured to allow a current to flow through the second resistor to a ground to thereby add the second resistance to the right communication pin to thereby passively indicate the request to receive the power through the right power pin. The module-detect controller may be coupled to the second resistor via a right open-drain driver pin, wherein the right open-drain driver pin activates the second resistor by entering into an another low-impedance mode.

In another embodiment of the present disclosure, a circuit comprises: a bus interface configured to interface with a bus; a bus transceiver configured to receive a bus-received signal and output a bus-transmit signal; a transceiver circuit in operative communication with the bus interface and the bus transceiver, the transceiver circuit having an RF switch and signal-sense circuit, the RF switch having an ON-mode and an OFF-mode, the RF switch configured to receive a common carrier signal from the bus interface and couple the common carrier signal to a ground when in the ON-mode, wherein the RF switch is operatively coupled to the bus-transmit signal of the bus transceiver to switch between the ON-mode and the OFF-mode is accordance with the bus-transmit signal, the signal-sense circuit configured to generate the bus-receive signal in accordance with the common carrier signal.

The common carrier signal may be a spread spectrum signal. The signal-sense circuit may be a logarithmic power detector configured to detect the common carrier signal. The signal-sense circuit may include a comparator configured to compare output from the logarithmic power detector to generate the bus-receive signal, a splitter coupled to the bus interface, and/or a comparator configured to receive an output from the logarithmic power detector for comparison with a reference voltage to thereby generate the bus-receive signal. The RF switch may be a loading FET and/or a pin-diode.

In another embodiment of the present disclosure, a modular pump system, comprises: a central unit comprising: a first bus interface configured to interface with a bus; a common-carrier signal generator configured to generate a common carrier signal on the bus; a first bus transceiver configured to receive a first bus-received signal and output a first bus-transmit signal; a first transceiver circuit in operative communication with the first bus interface and the first bus transceiver, the first transceiver circuit having a first RF switch and a first signal-sense circuit, the first RF switch having an ON-mode and an OFF-mode, the first RF switch configured to receive the common carrier signal from the first bus interface and couple the common carrier signal to a ground when in the ON-mode, wherein the first RF switch is operatively coupled to the first bus-transmit signal of the first bus transceiver to switch between the ON-mode and the OFF-mode is accordance with the bus-transmit signal, the first signal-sense circuit configured to generate the bus-receive signal in accordance with the common carrier signal; a medical-device assembly comprising: a second bus interface configured to interface with the bus to receive the common carrier signal; a second bus transceiver configured to receive a bus-received signal and output a bus-transmit signal; a second transceiver circuit in operative communication with the second bus interface and the second bus transceiver, the second transceiver circuit having a second RF switch and a second signal-sense circuit, the second RF switch having an ON-mode and an OFF-mode, the second RF switch configured to receive the common carrier signal from the second bus interface and couple the common carrier signal to a ground when in the ON-mode, wherein the second RF switch is operatively coupled to the second bus-transmit signal of the second bus transceiver to switch between the ON-mode and the OFF-mode is accordance with the bus-transmit signal, the second signal-sense circuit configured to generate the bus-receive signal in accordance with the common carrier signal.

In another embodiment of the present disclosure, a modular pump system comprises: a central unit comprising: a first bus interface configured to interface with a bus; a common-carrier signal generator configured to generate a common carrier signal on the bus; a first bus transceiver configured to receive a first bus-received signal and output a first bus-transmit signal; a first transceiver circuit in operative communication with the first bus interface and the first bus transceiver, the first transceiver circuit having a first signal-sense circuit, wherein the first transceiver circuit is operatively coupled to the first bus-transmit signal of the first bus transceiver to switch to switch the common-carrier signal on or off in accordance with the bus-transmit signal, the first signal-sense circuit configured to generate the bus-receive signal in accordance with the common carrier signal; a medical-device assembly comprising: a second bus interface configured to interface with the bus to receive the common carrier signal; a second bus transceiver configured to receive a bus-received signal and output a bus-transmit signal; a second transceiver circuit in operative communication with the second bus interface and the second bus transceiver, the second transceiver circuit having a second RF switch and a second signal-sense circuit, the second RF switch having an ON-mode and an OFF-mode, the second RF switch configured to receive the common carrier signal from the second bus interface and couple the common carrier signal to a ground when in the ON-mode, wherein the second RF switch is operatively coupled to the second bus-transmit signal of the second bus transceiver to switch between the ON-mode and the OFF-mode is accordance with the bus-transmit signal, the second signal-sense circuit configured to generate the bus-receive signal in accordance with the common carrier signal.

In another embodiment of the present disclosure, a modular pump system comprises: a plurality of medical device assemblies configured to physically couple together, wherein one of the plurality of medical device assemblies comprises: a first transceiver coil coupled to a first end; a second transceiver coil coupled to a second end; a transmission line coupled to the first transceiver coil and the second transceiver coil, the transmission line configured to provide electromagnetic communications between the first transceiver coil and the second transceiver coil; and a resonator magnetically coupled to one of the first transceiver coil and the second transceiver coil. The resonator may be a split-ring resonator. The transmission line may be an embedded strip line. The first transceiver coil, the second transceiver coil, the transmission line, and the resonator may be embedded within a Printed Circuit Board with a ground plane.

In another embodiment of the present disclosure, a modular pump system comprises: a first medical device assembly comprises: a first transceiver coil coupled to a first end; a second transceiver coil coupled to a second end; a first transmission line coupled to the first transceiver coil and the second transceiver coil, the transmission line configured to provide electromagnetic communications between the first transceiver coil and the second transceiver coil; and a first resonator magnetically coupled to one of the first transceiver coil and the second transceiver coil; and a second medical device assembly comprises: a third transceiver coil coupled to a first end; a fourth transceiver coil coupled to a second end;a second transmission line coupled to the third transceiver coil and the fourth transceiver coil, the second transmission line configured to provide electromagnetic communications between the third transceiver coil and the fourth transceiver coil; and a second resonator magnetically coupled to one of the third transceiver coil and the fourth transceiver coil. The first and second medical device assemblies are configured to couple together in spaced relation where the first transceiver coil of the first medical device assembly is adjacent to the third transceiver coil of the second medical device assembly. The first transceiver coil may be about 4 millimeters from the third transceiver coil. Each of the first, second, third, and fourth transceiver coils may include a surrounding magnetic shield.

In another embodiment of the present disclosure, a pump includes a lever, a shaft, a pin, an interlock arm, and a gripper finger. The lever is actuatable between a closed position and an open position. The shaft has a central axis centrally along a length of the shaft and is coupled to the lever to actuate in response to actuation of the lever. The pin is disposed a predetermined distance from the central axis of the shaft and actuates on a path at least partially around the central axis of the shaft in accordance with a rotation of the shaft. The interlock arm is pivotally coupled to the pump and has a catch formed by a first finger, a second finger, and a catch well. The first finger and the second finger are coupled to the catch well. The gripper finger disposed on the interlock arm and forms an end effector configured to actuate a slide clamp.

The interlock arm can receive the pin to thereby pivot around the pivot to actuate the gripper finger toward or away from a carriage. The gripper finger may be disposed on the first finger of the interlock arm. The first finger and the second finger may guide the pin to the catch well. The gripper finger may grip onto a flange of a slide-clamp assembly. A door-securing arm may be operatively coupled to the shaft to pull a door against the pump. A tube shutter may be used to open when a slide-clamp assembly is inserted into a carriage of the pump.

In another embodiment of the present disclosure, a pump for treating a patient includes a lever, a first linkage, a second linkage, a spring, a track, a shaft, and first and second bevel gears. The lever is actuatable between a closed position and an open position. The first linkage is coupled to the lever. The second linkage is coupled to the first bevel gear. The spring is coupled to the first linkage and the second linkage. The track is configured to guide the first linkage and the second linkage. The shaft has a central axis centrally along a length of the shaft. The second bevel gear is coupled to the first bevel gear and the shaft, and the second bevel gear configured to rotate the shaft. The spring may be a torsion spring with a first end coupled to the first linkage and a second end coupled to the second linkage. The first linkage may include guides to guide the first linkage along the track. The second linkage may include guides to guide the second linkage along the track.

In another embodiment of the present disclosure, a slide-clamp assembly includes a top housing, a bottom housing, a backstop, a tube coupling, and first and second links. The top housing has a first end and a second end. The bottom housing has a first end and a second end. The backstop is positioned between the top housing and the bottom housing. The backstop is disposed at or near the first end of the top housing and the first end of the bottom housing. The tube coupling is coupled to the first end of the top housing and configured to pass a tube through the first end of the top housing and the first end of the bottom housing. The tube coupling is further configured to pass the tube adjacent to the backstop. The first link is disposed within a track. The second link is coupled to the second end of one of the top housing and a second end of the bottom housing. The first link and the second link may be coupled to each other. The track may be defined by the top housing and the bottom housing. The first link may pivot within the track. The first link may include a plunger on an end adjacent to the backstop to occlude fluid flow through the tube when actuated toward the backstop. The first link may include a flange configured to couple to an end effector. The second link may include a shutter aperture. The top housing or the bottom housing may include a housing aperture configured to align with the shutter aperture of the second link when the first link and the second link are positioned in a non-occluding position. The top housing or the bottom housing may include an identification aperture configured to align with the shutter aperture of the second link when the first link and the second link are positioned in a non-occluding position. The second link may include a notch configured to at least partially align with a housing aperture of at least one of the top housing and the bottom housing when the second link is in an occluding position. A shutter aperture of the second link may at least partially align with the housing aperture when the second link is in the occluding position. The second link may include an identification aperture. The first link and the second link may be configured for being positionally bi-stable. The top housing and the bottom housing may form a finger groove configured for user actuation of the first link.

In another embodiment of the present disclosure, a slide-clamp assembly includes a housing a slide clamp, and a tube coupling. The housing may have a top side and a bottom side, The slide clamp has an arcuate slot pivotally disposed between the top side and the bottom side of the housing where one end of the arcuate slot is non-occluding. The tube coupling is positioned to pass a tube through the arcuate slot. The slide-clamp assembly may be configured such that a rotational angle of the slide-clamp relative to the housing via a pivot corresponds to an occlusion or a non-occlusion of fluid flowing through the tube. The slide-clamp may include a notch. The notch may be configured to cooperate with an end effector of a gripper finger. The slide clamp may include an exposed portion that extends away from the housing. The exposed portion defines an identification aperture.

The housing may define an indentation configured for user actuation of the slide-clamp along the pivot. The top side and bottom side may at least partially surround the slide clamp. The housing may be adjacent to only one side of the slide clamp. An identification aperture may be disposed on the slide clamp.

In another embodiment of the present disclosure, a slide-clamp assembly includes a backstop and a plunger. The backstop is dispose a tube adjacent thereto. The plunger actuates the tube against the backstop by linearly actuating the plunger toward the backstop and at least partially rotating the plunger along an axis. The plunger may be coupled to a guide configured to actuate toward and away from the backstop along a track, wherein the guide is pivotably coupled to the track.

In another embodiment of the present disclosure, a slide-clamp assembly includes a housing and a linkage. The housing has an housing aperture. The linkage is rotatably coupled to the housing and has a first position and a second position. The linkage may include an opening configure to align with the housing aperture to indicate the linkage is in the first position. The linkage may include a second opening configured to align with the housing aperature to indicate the linkage is in the second position. The opening may be an identification aperature. The second opening may be a position aperature configured to indicate the linkage is in the second position.

The carriage may include an image sensor having an image sensor opening configured to alight with the housing aperature when the slide-clamp assembly is fully inserted into the carriage. The image sensor may be configured to detect a misalignment of the housing aperature with the image sensor opening. The image sensor may detect the misalign when a number sensed from one of the opening and the second opening does not correspond to a valid value of a set of valid values. A processor configured to interface with the image sensor.

BRIEF DESCRIPTION OF THE DRAWINGS

These and other aspects will become more apparent from the following detailed description of the various embodiments of the present disclosure with reference to the drawings wherein:

FIGS. 49-53 show a sequence of event to illustrate the slide clamp of FIGS. 43-48 being inserted in the carriage assembly of the peristaltic pump of FIG. 1 in accordance with an embodiment of the present disclosure;

FIGS. 107-109 show several viewsf of the slide-clamp assembly of FIGS. 102-105 with the top housing removed in accordance with an embodiment of the present disclosure;

FIGS. 115-119 show several views of the top housing of the slide-clamp assembly of FIGS. 102-105 in accordance with an embodiment of the present disclosure;

FIGS. 134-138 show the slide-clamp assembly of FIGS. 102-105 being inserted into a carriage, in accordance with an embodiment of the present disclosure;

DETAILED DESCRIPTION

Figure 1:
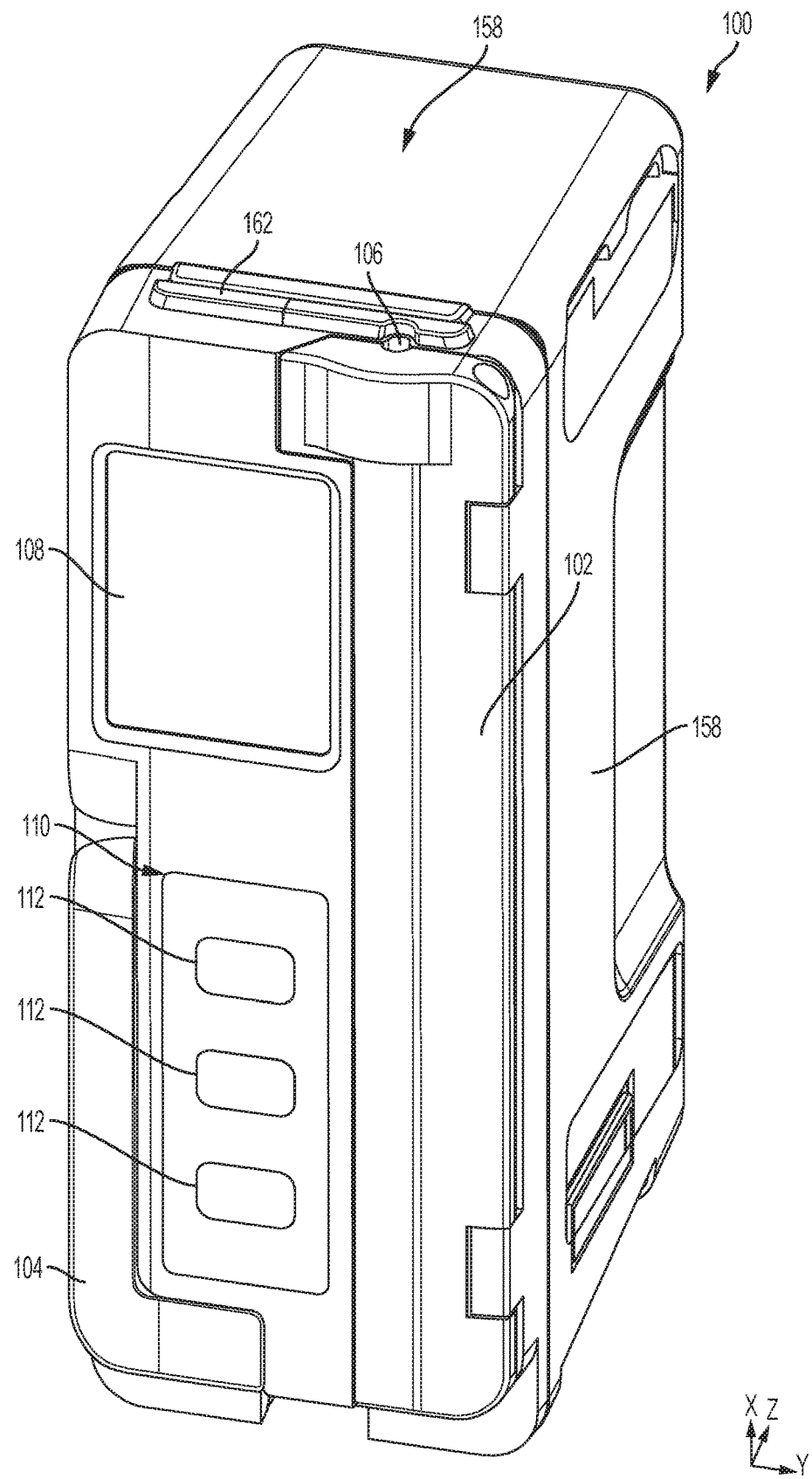
FIG. 1 shows the front of a peristaltic pump in accordance with an embodiment of the present disclosure.

FIG. 1 shows the front of a pump 100. The pump 100 may be a standalone device that couples to an IV pole (not shown) directly, e.g., by using a clamp (not shown). Additionally or alternatively, the pump 100 may be modular such that one or more pumps 100 can be coupled together with a central unit and/or with other medical devices. Although a peristaltic pump 100 is described throughout this specification, additional embodiments may include syringe pumps or other pump types where applicable or where it would be apparent to one of ordinary skill in the relevant art.

The pump 100 includes a pump housing 158 and a door 102 coupled to the pump housing 158. The door 102 is pivotably coupled to the pump 100 such that an infusion set having a slide clamp 152 (see FIGS. 39-44) and a tube 216 (See FIGS. 4-5) may be loaded and secured within the pump 100 by the door 102 (described in more detail below). A hole 106 is shown so that the door 102 may be shut without pinching the tube 216. Kinks or pinches within the tube 216 may occlude fluid flow within the tube 216.

The pump 100 includes a button panel 110 with buttons 112 for user input and a screen 108. The screen 108 provides visual information, such as menus and status information, that can be used by a caregiver to program and interact with the control software of the pump 100 using the buttons 112. In some embodiments, the screen 108 may be a touch screen configured to receive user input via user touch. The pump 100 also includes a lever 104 that can be used to open the door 102 and lock the door 102 as described in more detail below.

The pump 100 also includes a light bar 162. The light bar 162 may illuminate based upon the status of the pump 100. For example, the light bar 162 may blink green when the pump 100 is infusing fluid into a patient and blink red when the pump 100 is not operating or is experiencing an error condition or fault. The light bar 162 may blink yellow when an occlusion is detected and intervention is needed to clear the occlusion, etc.

Figure 2:
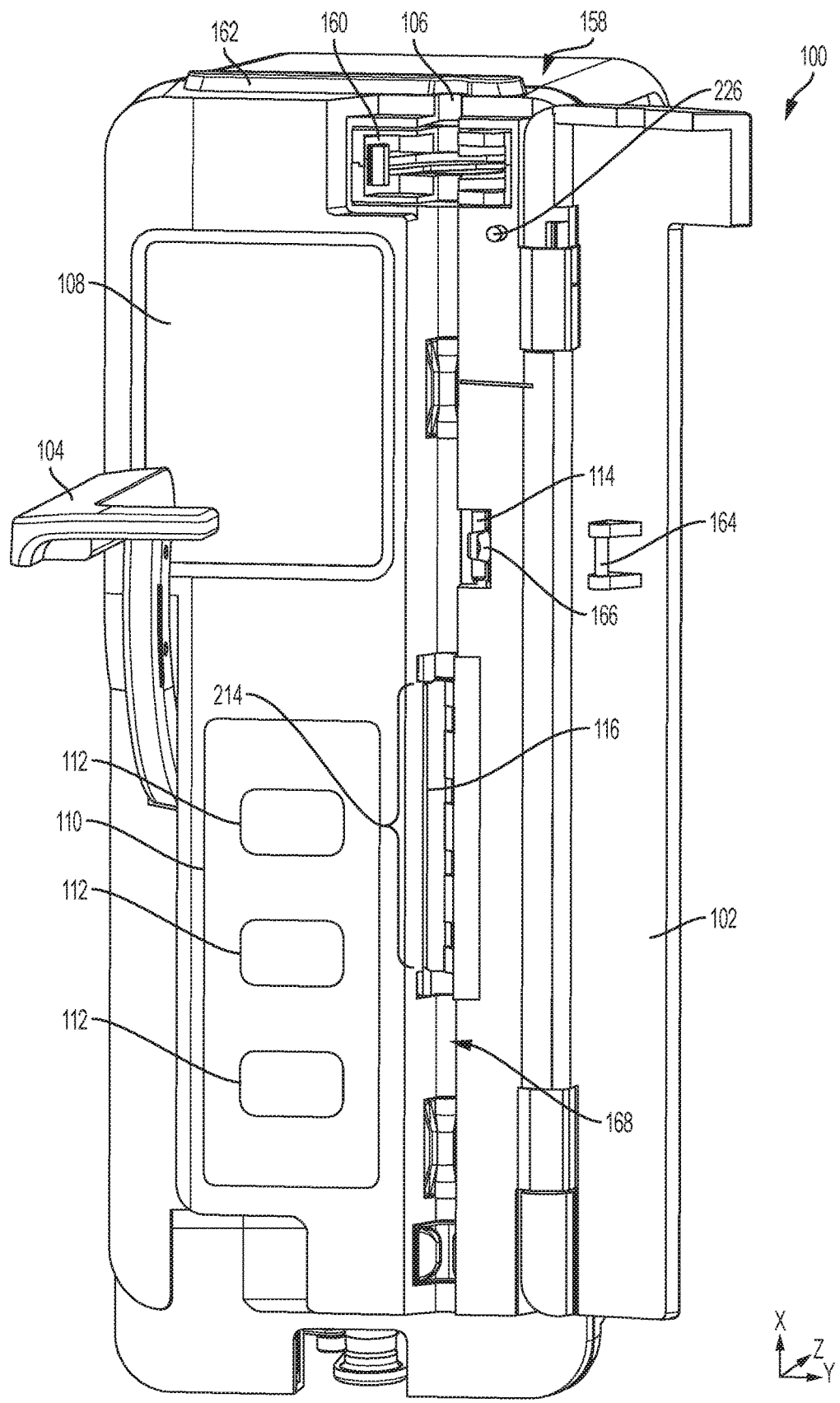
FIG. 2 shows the peristaltic pump of FIG. 1 with the door open and the lever in the open position in accordance with an embodiment of the present disclosure.

FIG. 2 shows the peristaltic pump 100 of FIG. 1 with the door 102 open and the lever 104 in the open position. When the lever 104 is shut and the door 102 is properly closed, a door catch 114 secures the door 102 shut by holding on to a hold 164. The hold 164 may be a pin that interfaces with a pin catch 166. When the lever 104 is actuated to the open position as shown in FIG. 2, the door catch 114 releases the hold 164. The door 102 may be spring biased such that the door 102 swings open when the door catch 114 releases the hold 164.

Actuation of the lever 104 into the open position also retracts the spring-biased plunger 116. Actuation of the spring-biased plunger 116 allows a tube 216 to be loaded into a raceway 168. Having the spring-biased plunger 116 actuated into the raceway 168 would make insertion of a tube 216 into the raceway 168 more difficult or impossible because it would block the raceway 168.

Figure 3:
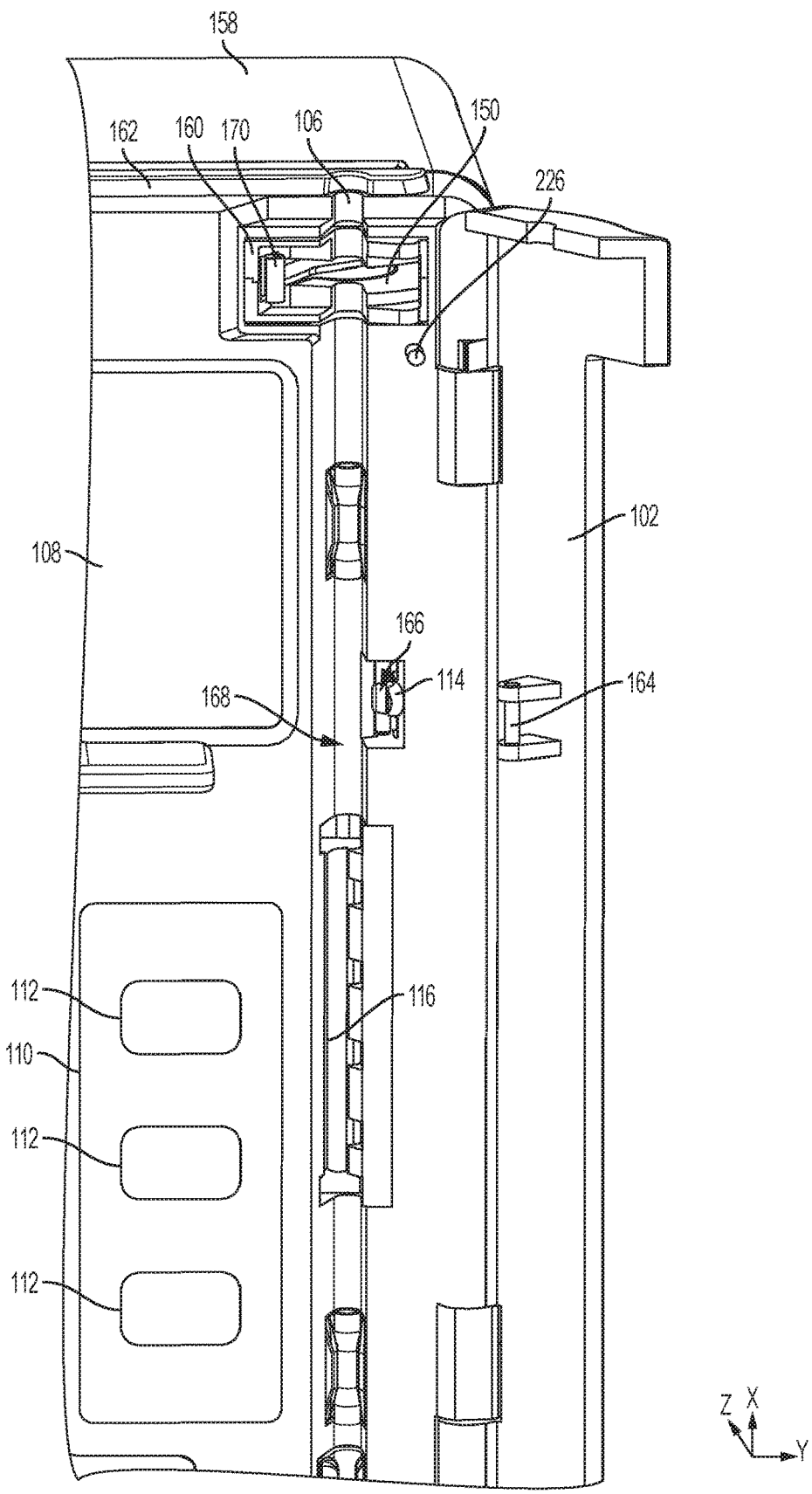
FIG. 3 shows a close up view of the opened door of the peristaltic pump of FIG. 1 in accordance with an embodiment of the present disclosure.
Figure 4:
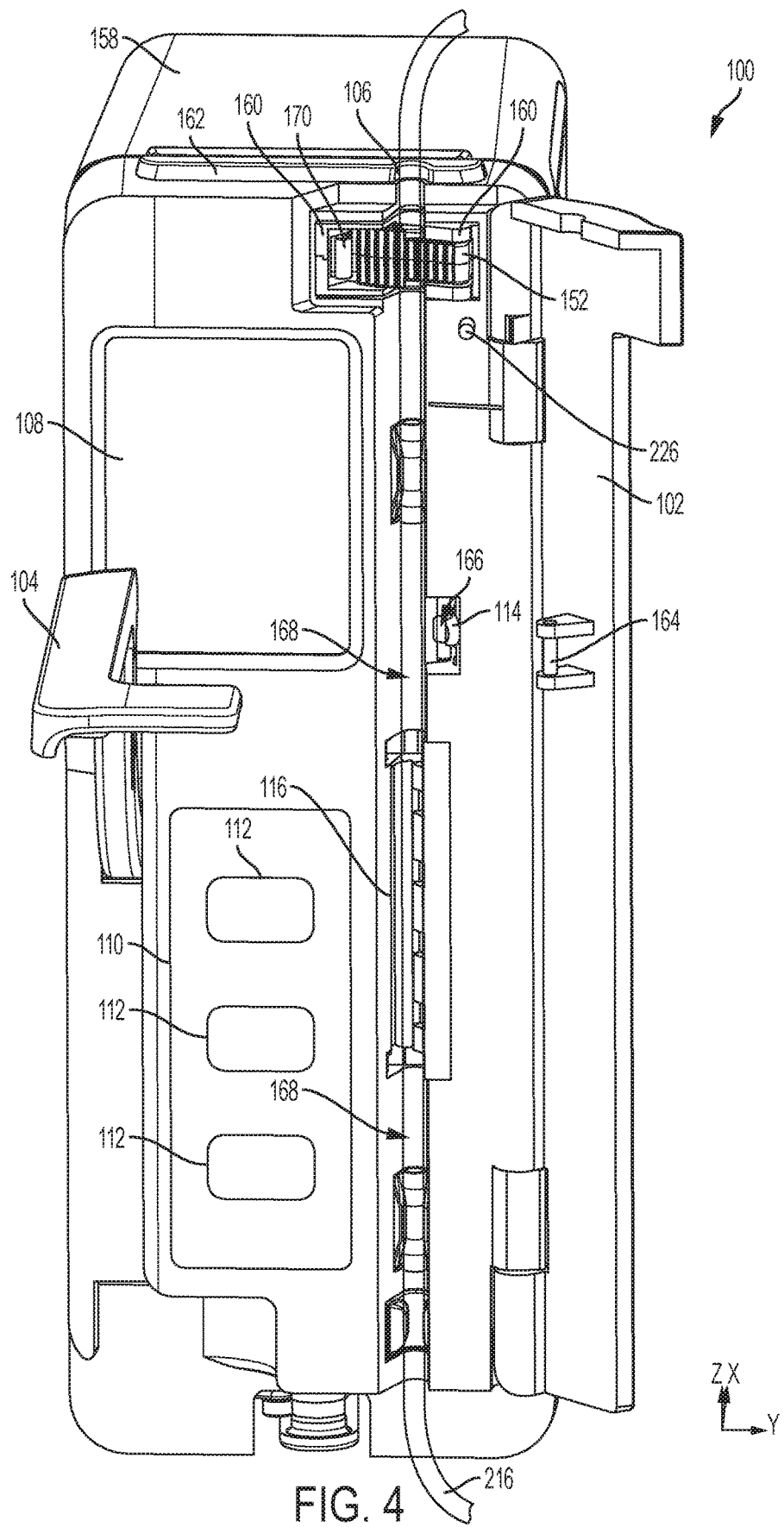
FIG. 4 shows the peristaltic pump of FIG. 1 with the door open and a slide clamp loaded into the carriage of the peristaltic pump in accordance with an embodiment of the present disclosure.
Figure 5:
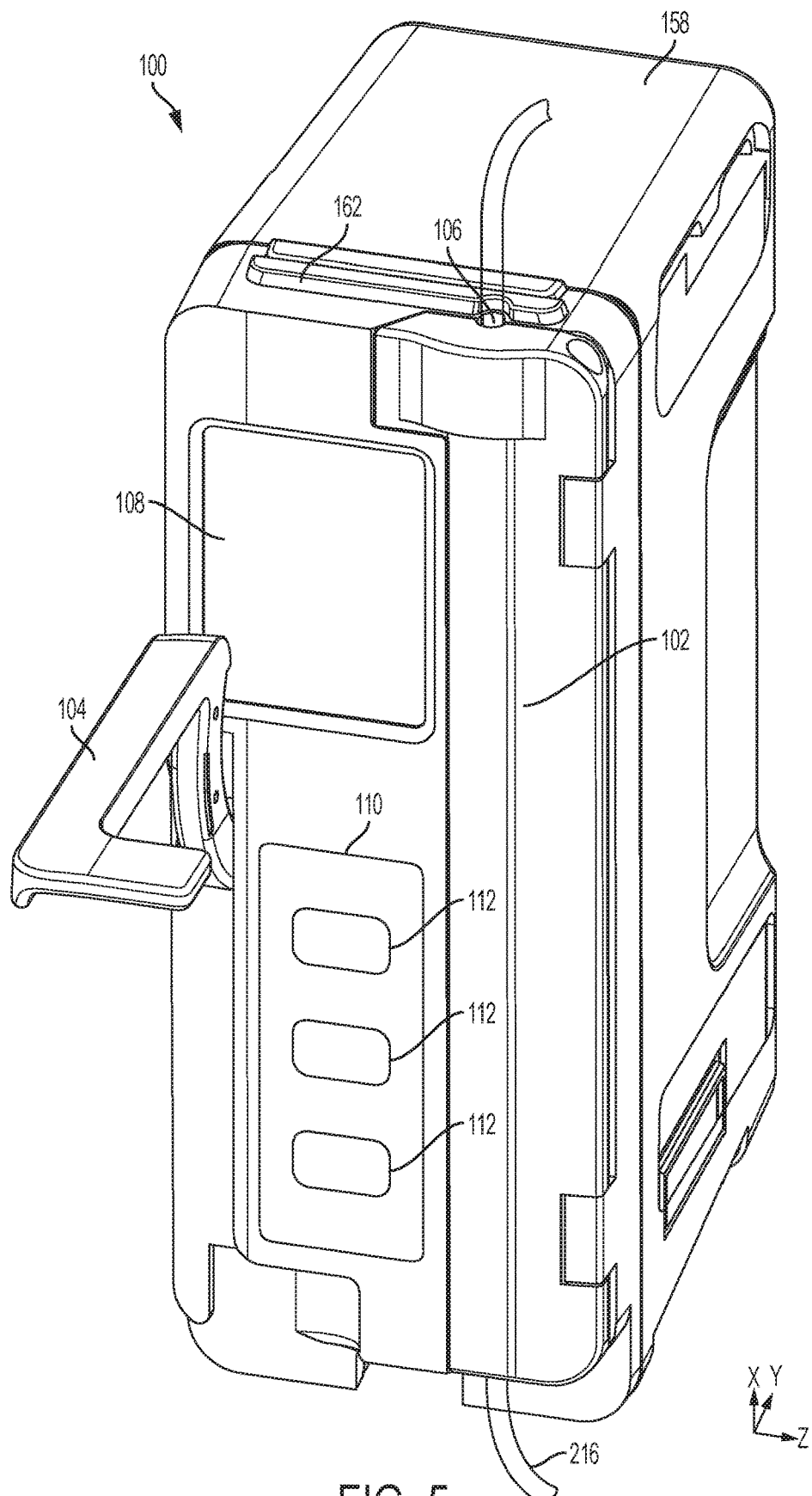
FIG. 5 shows the peristatic pump of FIG. 1 after the slide clamp has been loaded into the carriage and the door has been shut, but prior to closing the lever, in accordance with an embodiment of the present disclosure.

FIG. 3 shows a close up view of the door 102 of the peristaltic pump 100 (see FIG. 1) in the open position. The carriage assembly 160 is also easily seen in FIG. 3. A slide clamp 152 (see FIGS. 39-44) may be inserted into the carriage assembly 160 so that a carriage 150 retains the slide clamp 152. A slide-clamp retainer 170 can retain the slide clamp 152 in the carriage 150. FIG. 4 shows the slide clamp 152 loaded into the carriage 150 of the peristaltic pump 100. Thereafter, the door 102 may be shut with the slide clamp 152 inserted therein as shown in FIG. 5. Because the lever 104 is still in the open position, the door 102 may be reopened because the door catch 114 has not locked the door 102. When the lever 104 is actuated down into the closed position, then the door 102 will be locked by the door catch 114.

Figure 6:
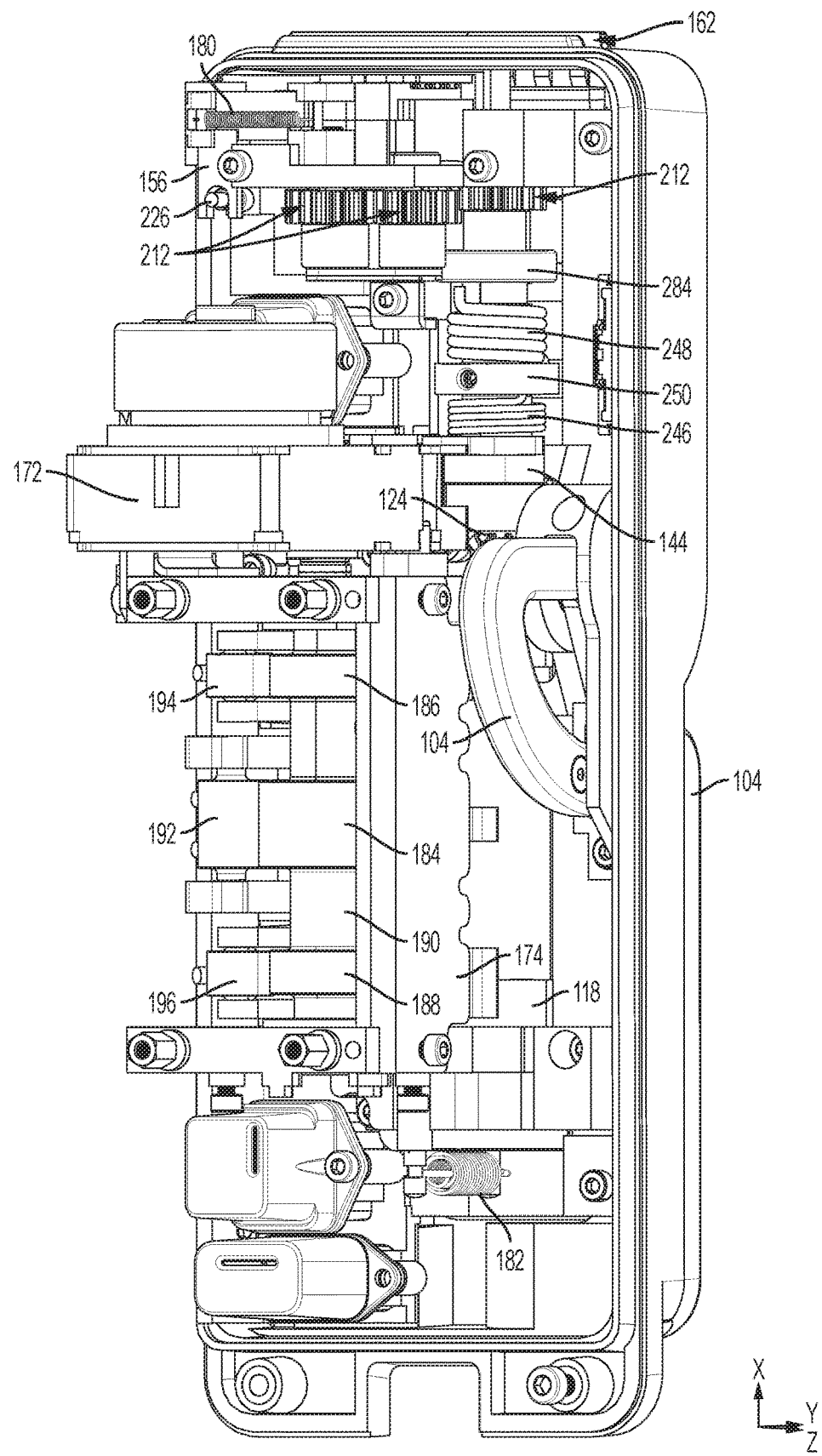
FIG. 6 shows the back of the pump of FIG. 1 with the back housing, cabling and electronic circuit boards, removed in accordance with an embodiment of the present disclosure.
Figure 7:
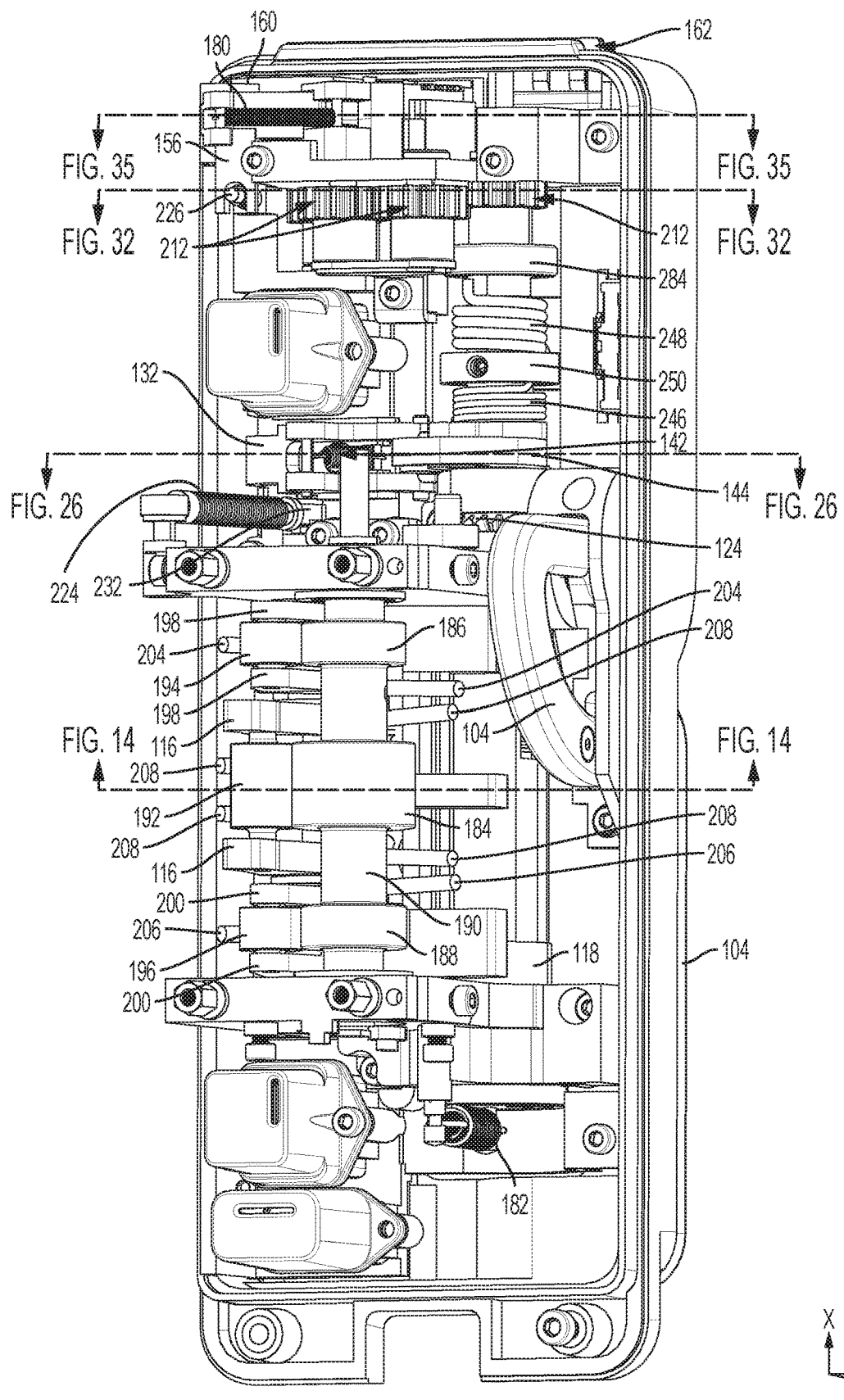
FIG. 7 shows the pump as shown in FIG. 6, but with the motor removed in accordance with an embodiment of the present disclosure.

FIG. 6 shows the back of the pump 100 of FIG. 1 with the back housing, cabling and electronic circuit boards, removed. However, in FIG. 6, a motor 172 and a brace 174 are visible. FIG. 7 shows the pump 100 as shown in FIG. 6, but with the motor 172 and the brace 174 removed for additional clarity.

In FIG. 7, a cam shaft 190 is shown with a plunger cam 184, an inlet-valve cam 186, and an outlet-valve cam 188 disposed on the cam shaft 190. A plunger-cam follower 192 pivots along a pivot shaft 202 (see FIG. 14) as the plunger-cam follower 192 follows the plunger cam 184. The inlet valve 198 pivots along the pivot shaft 202 (see FIG. 14) as the inlet-valve cam follower 194 follows the inlet-valve cam follower 194. And, the outlet valve 200 pivot along the pivot shaft 202 (see FIG. 14) as the outlet-valve cam follower 196 follows the outlet-valve cam 188.

Figure 8:
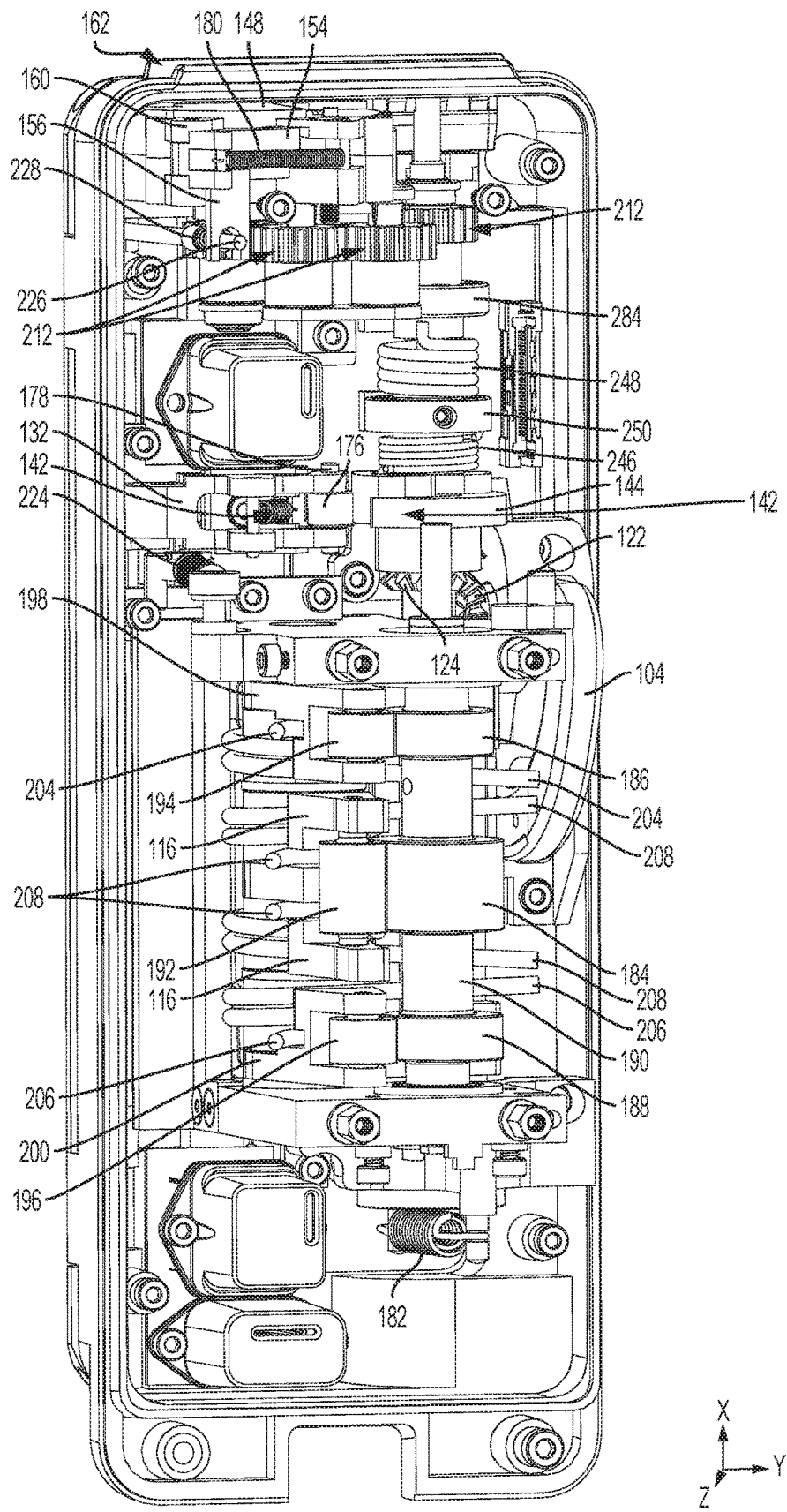
FIG. 8 shows the pump as shown in FIG. 7 but at another angle in accordance with an embodiment of the present disclosure.
Figure 9:
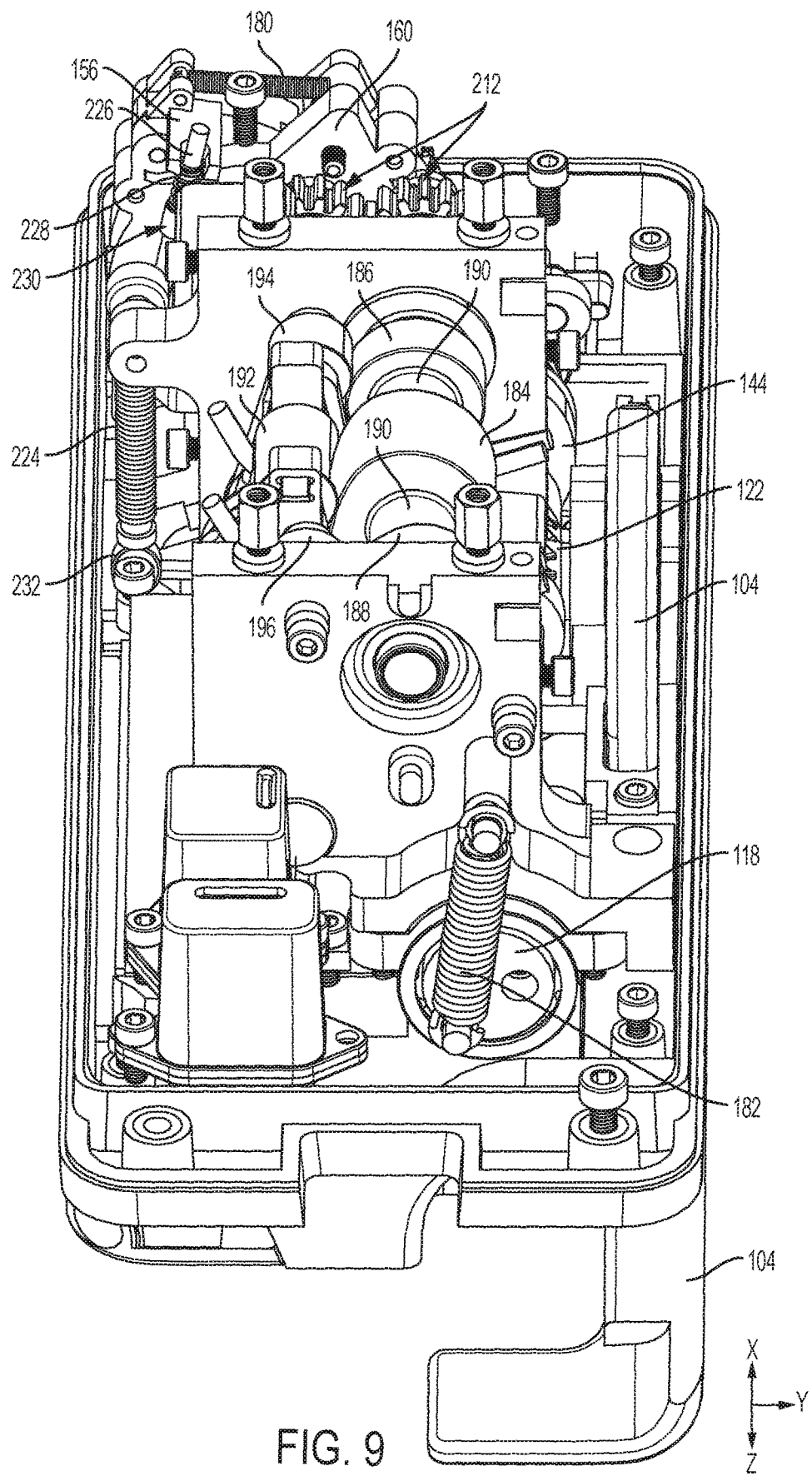
FIG. 9 shows the pump as shown in FIG. 7, but at a bottom-up angle from the back of the pump, in accordance with an embodiment of the present disclosure.

An inlet-valve torsion spring 204 biases the inlet-valve cam follower 194 against the inlet-valve cam 186 and toward the tube 216. An outlet-valve torsion spring 206 biases the outlet-valve cam follower 196 against the outlet-valve cam 188. Also, a pair of plunger torsion springs 208 biases the plunger-cam follower 192 against the plunger cam 184 and therefore also biases the spring-biased plunger 116 toward the tube 216. FIG. 8 shows the pump 100 as shown in FIG. 7 but at another angle, and FIG. 9 shows the pump 100 as shown in FIG. 7, but at a bottom-up angle from the back of the pump 100.

Actuation of the lever 104 actuates the main shaft 118. A shaft spring 182 is shown that pulls the main shaft 118 into one of two positions making the lever 104 actuate toward one of the open or closed position depending upon the angle of the main shaft 118. That is, the shaft spring 182 makes the lever 104 operate with an over-center action with regard to the force the shaft spring 182 exerts on the main shaft 118. The force from the shaft spring 182 exerts on the main shaft 118 is also exerted on the lever 104 because of the mechanical coupling between the main shaft 118 and the lever 104. This over-center action biases the main shaft 118 such that the lever 104 is biased toward either the closed position or the open position, depending upon if the lever 104 is between an intermediate position and the closed position or is between the intermediate position and the open position.

Figure 10:
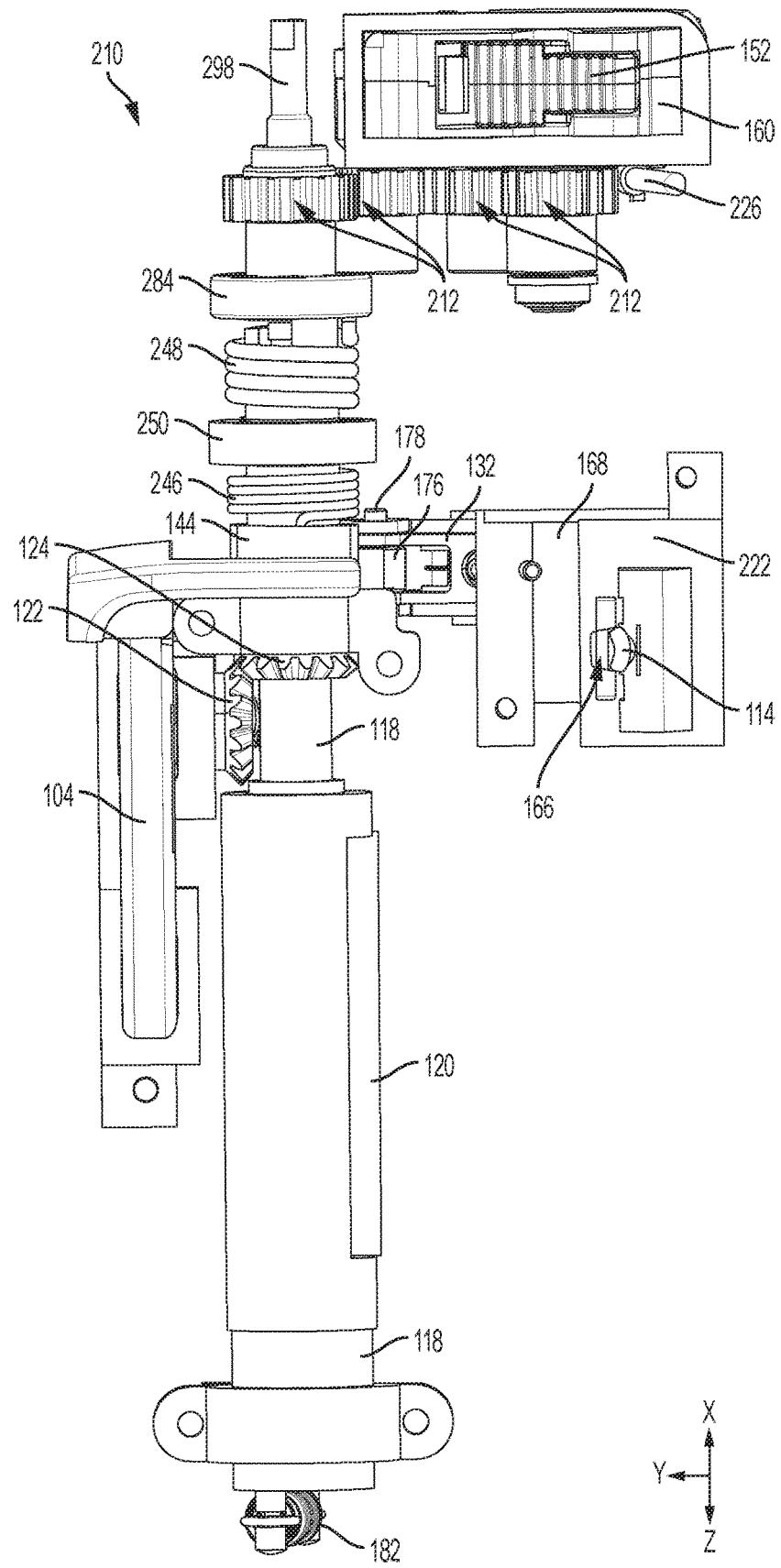
FIG. 10 shows a front view of a mechanical assembly including the shaft coupled to the lever of the pump of FIG. 1 with the lever in the open position in accordance with an embodiment of the present disclosure.
Figure 11:
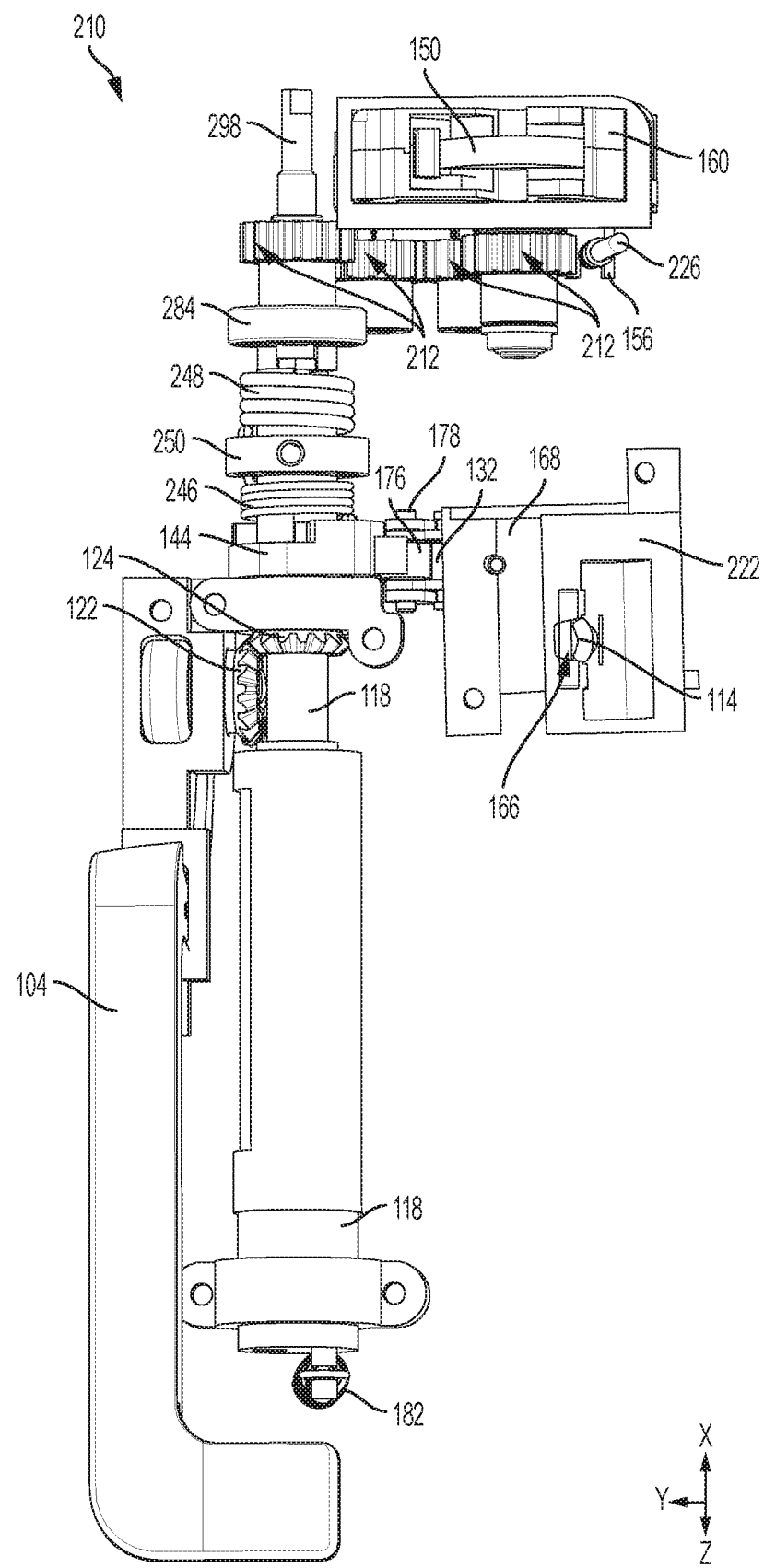
FIG. 11 shows the mechanical assembly of FIG. 10 with the lever in the closed position in accordance with an embodiment of the present disclosure.
Figure 12:
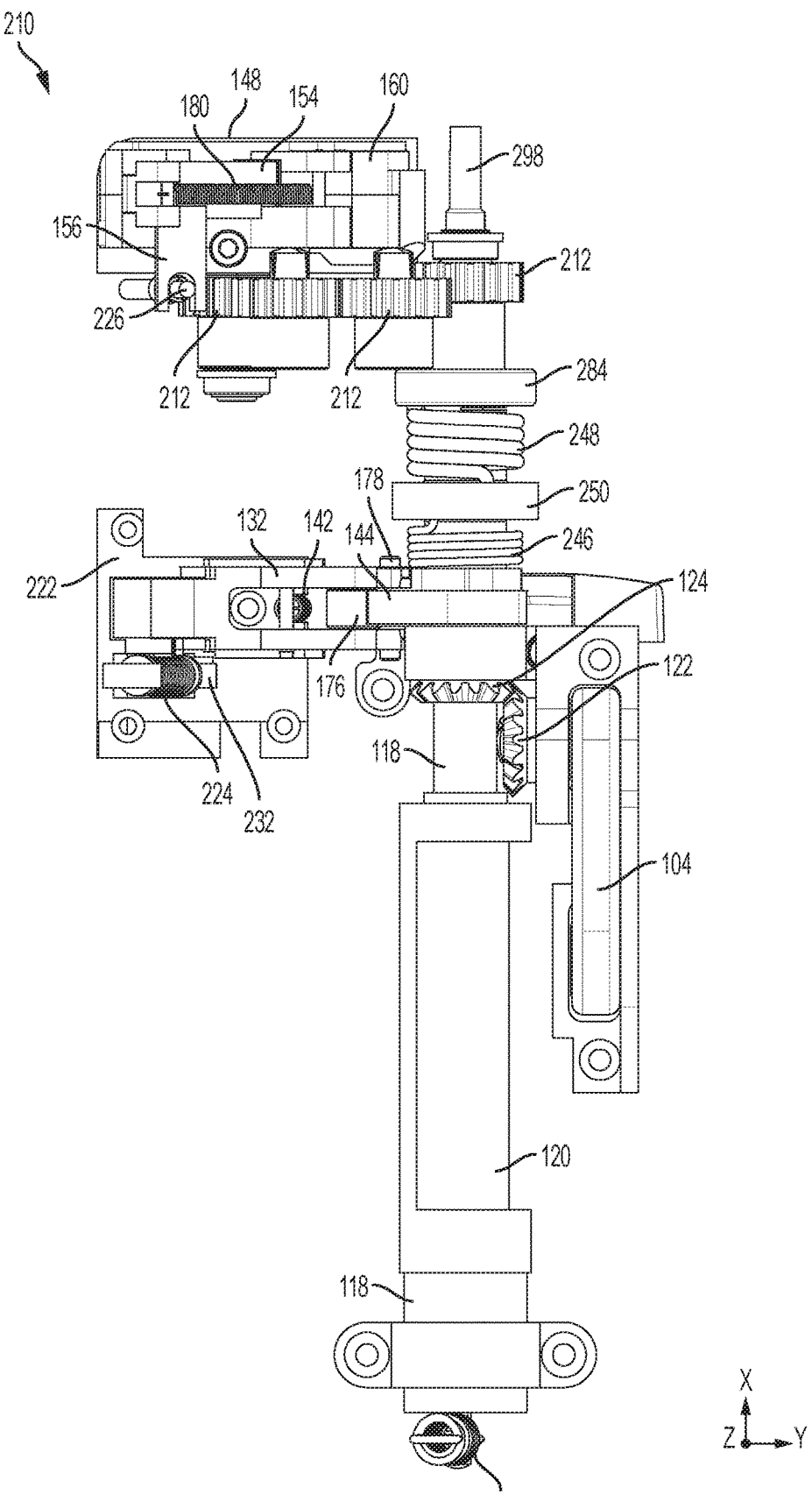
FIG. 12 shows the back view of the mechanical assembly of FIG. 10 with the lever in the open position in accordance with an embodiment of the present disclosure.
Figure 13:
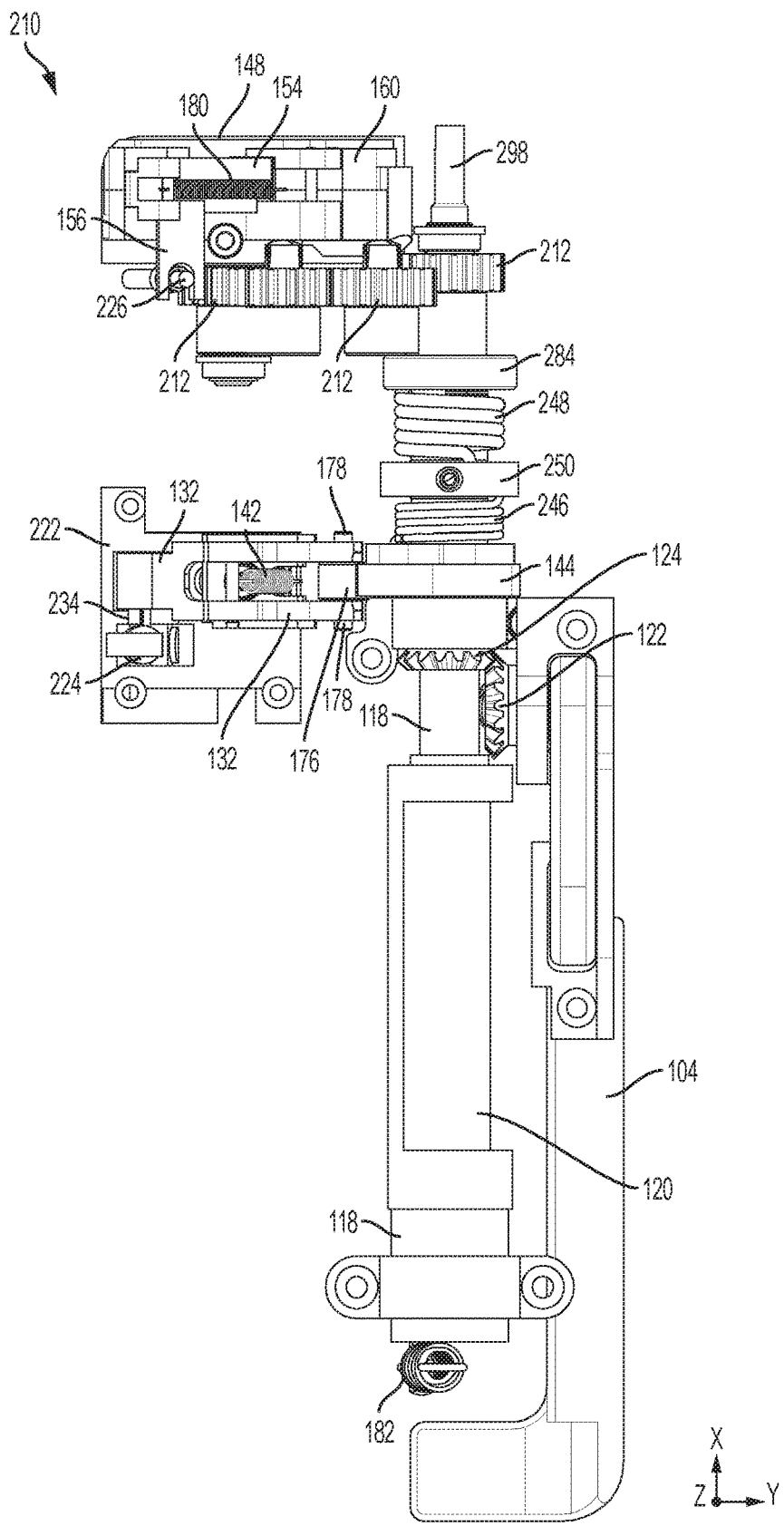
FIG. 13 shows the back view of the mechanical assembly of FIG. 10 with the lever in the closed position in accordance with an embodiment of the present disclosure.

Referring to FIGS. 10-13, FIG. 10 shows a front view of a mechanical assembly 210 including the main shaft 118 coupled to the lever 104 with the lever 104 in the open position, and FIG. 11 shows the mechanical assembly 210 of FIG. 10 with the lever 104 in the closed position. FIG. 12 shows the back view of the mechanical assembly 210 of FIG. 10 with the lever 104 in the open position and FIG. 13 shows the back view of the mechanical assembly 210 of FIG. 10 with the lever 104 in the closed position. The mechanical assembly 210 may be found within the pump 100 of FIG. 1.

The lever 104 is coupled to the first bevel gear 122 and rotates with movement of the lever 104. That is, the lever 104 is coupled to the first bevel gear 122 to actuate the first bevel gear 122. The first bevel gear 122 is coupled to the second bevel gear 124, and the second bevel gear 124 is coupled to the main shaft 118. In combination, actuation of the lever 104 causes the main shaft 118 to rotate around its central axis.

Generally, an upper shaft 298 rotates with the main shaft 118. However, the upper shaft 298 is not directly coupled to main shaft 118 and may, in certain circumstances, rotate separately from the main shaft 118. A more detailed description of the circumstances in which the upper shaft 298 rotates apart from the main shaft 118 is described below with reference to FIGS. 31-32.

Rotation of the main shaft 118 causes a lift cam 120 to rotate. The rotation of the lift cam 120 can actuate the spring-biased plunger 116, the inlet valve 198, and the outlet valve 200 away from a tube 216 and out of the raceway 168. That is, the spring-biased plunger 116, the inlet valve 198, and the outlet valve 200 are retracted away from the tube 216 and into the end-effector port 214 (See FIGS. 2-4). Additional details of the lift cam 120 are described below.

Referring again to FIGS. 10-13, when the lever 104 is in the open position, as shown in FIGS. 10 and 12, the latching sled 132 is configured so that the door catch 114 will allow the door 102 (see FIG. 1) to open and shut freely without locking the door 102. However, the door catch 114 is biased toward holding the door 102 or releasing the door 102. When the lever 104 is in the closed position (see FIGS. 11 and 13), the latching sled 132 allows the door 102 (see FIG. 1) to shut by allowing the door catch 114 to receive the hold 164 (see FIG. 4). However, when the lever 104 is in the closed position and the door 102 is shut, the latching sled 132 will lock the door 102 by preventing the door catch 114 from releasing the hold 164 (see FIG. 4) after it is locked by the latching sled 132. Details of the latching sled 132 are described below.

Also shown in FIGS. 10-13, the carriage assembly 160 can been seen. A carriage housing 148 receives a slide clamp 152 within the carriage 150 for rotation therein. Gears 212 rotate the carriage 150 as the lever 104 is actuated such that the slide clamp 152 can be inserted into the carriage 150 when the lever 104 is in the open position as shown in FIG. 10. After insertion of the slide clamp 152, actuation of the lever 104 to the closed position (shown in FIGS. 11 and 13) rotates the carriage 150 and rotates the slide clamp 152 to unkink the tube 216 so that fluid may flow through the tube 216. Details of the carriage assembly 160 are described below.

Figure 14:
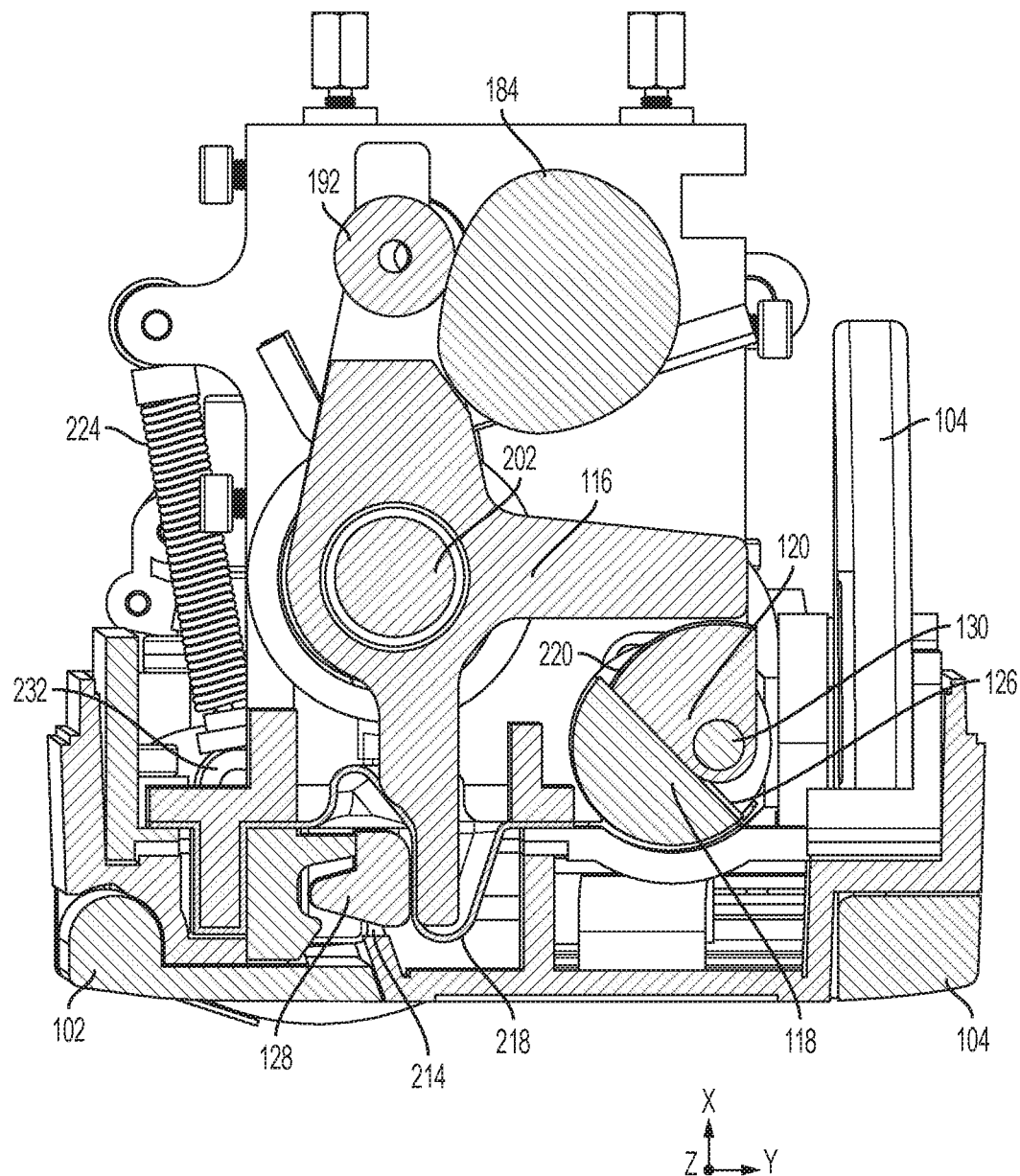
FIG. 14 is a cross-sectional view of the peristaltic pump of FIG. 1 showing the lift cam when the lever is in the closed position in accordance with an embodiment of the present disclosure.
Figure 15:
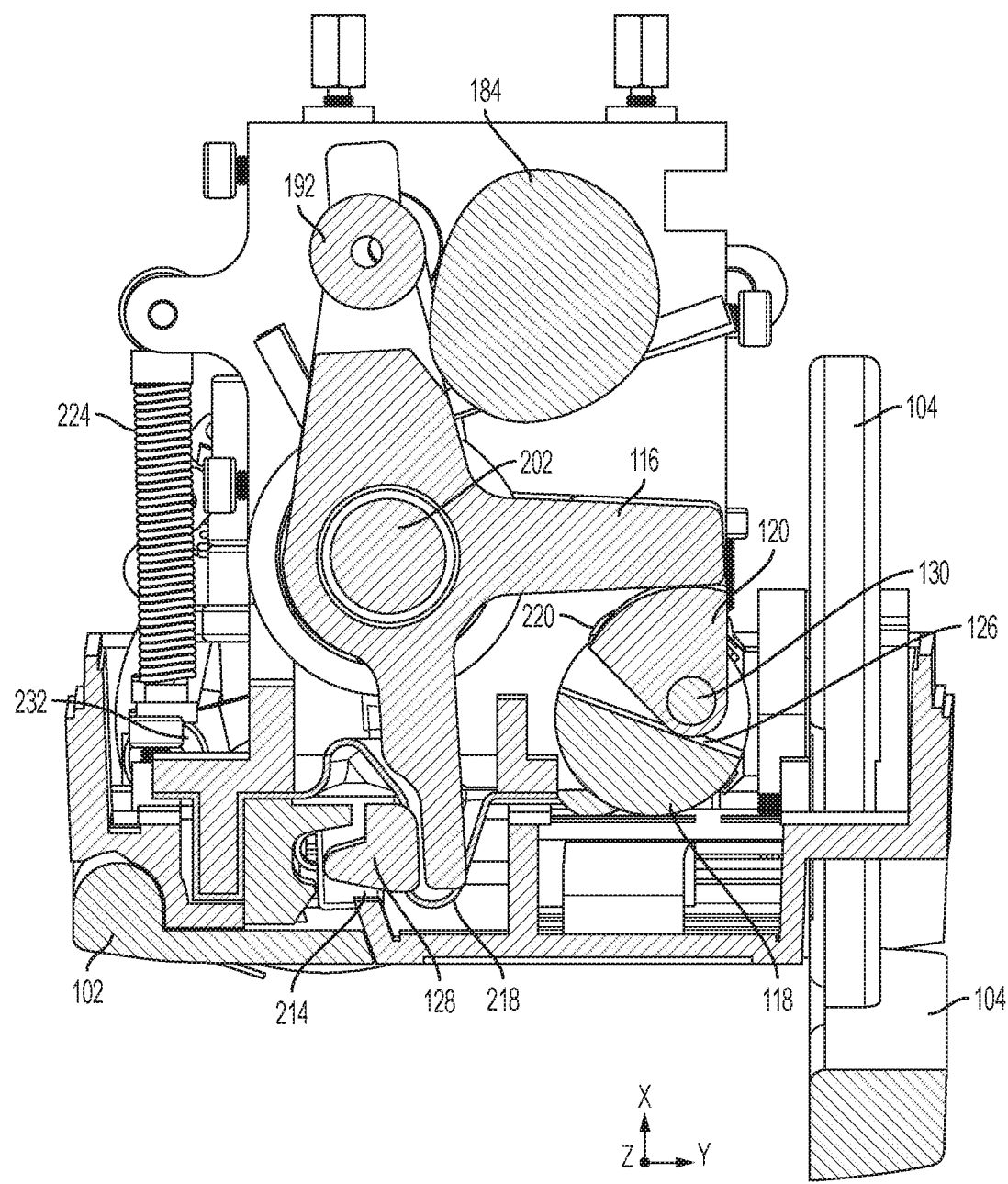
FIG. 15 is a cross-sectional view of the peristaltic pump of FIG. 1 showing the lift cam when the lever is in between the closed position and the open position in accordance with an embodiment of the present disclosure.
Figure 16:
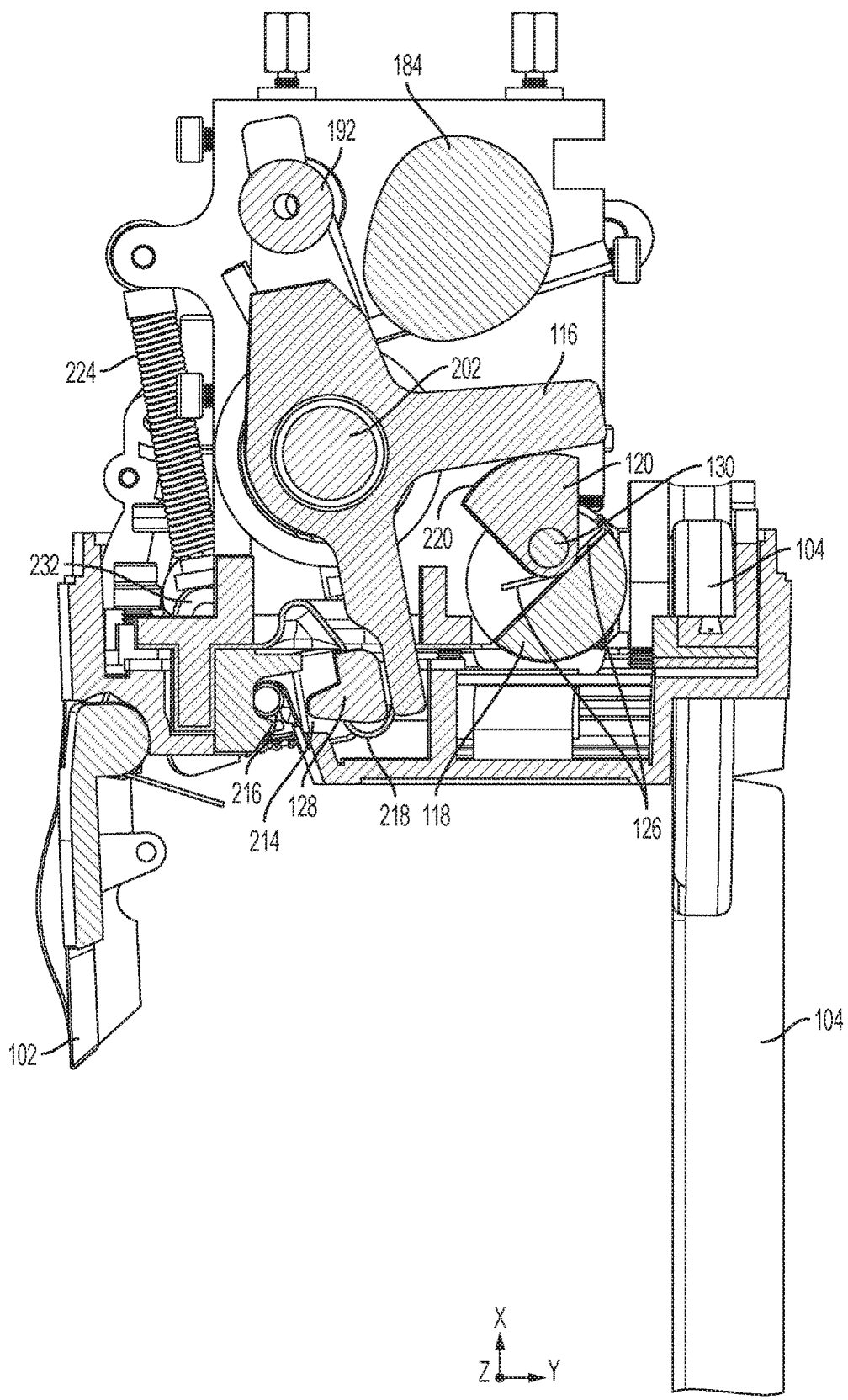
FIG. 16 is a cross-sectional view of the peristaltic pump of FIG. 1 showing the lift cam when the lever is in the open position in accordance with an embodiment of the present disclosure.

Please refer now to FIGS. 14-16 for reference with the following description of the operation of the lift cam 120. FIGS. 14-16 all show cross-sectional views along the same plane. FIG. 14 is a cross-sectional view of the peristaltic pump 100 showing the lift cam 120 when the lever 104 is in the closed position. FIG. 15 is a cross-sectional view of the peristaltic pump 100 showing the lift cam 120 when the lever 104 is in between the closed position and the open position; And FIG. 16 is a cross-sectional view of the peristaltic pump 100 showing the lift cam 120 when the lever 104 is in the open position.

As shown in FIG. 14, the lift cam 120 is disposed on the main shaft 118 for rotation along a lift-cam pin 130. The axis of the lift-cam pin 130 is offset from a central axis of the main shaft 118. The lift cam 120 is biased by a cam-lifter torsion spring 126 in a counter-clockwise direction as shown in FIG. 14, however, one of ordinary skill in the art would know how to configure the pump 100 for clockwise bias.

In FIG. 14, the lift cam 120 is not engaged with the spring-biased plunger 116 and the position of the spring-biased plunger 116 is based upon the rotational position of the plunger cam 184 and/or the fill volume of a tube 216. The spring-biased plunger 116 includes an end effector 128 that engages with the tube 216 disposed in the raceway 168.

The end effector 128 of the spring-biased plunger 116 is shown in FIG. 14 as being in an extended position and thereby protrudes out of the end-effector port 214 (thus engaging with the tube 216). A seal 218 prevents fluid ingress or egress through the end-effector port 214 even though the end effector 128 is secured to the spring-biased plunger 116.

As is easily seen in FIG. 15, as the lever 104 is actuated toward the open position, the main shaft 118 rotates and the lift cam 120 engages with the spring-biased plunger 116. Because an outer surface 220 of the lift cam 120 frictionally engages the spring-biased plunger 116, the lift cam 120 rotates as the lever 104 is actuated into the open position as shown in FIG. 15.

FIG. 16 shows the lever 104 in the fully open position in which the lift cam 120 has fully lifted the spring-biased plunger 116 such that the end effector 128 is fully retracted within the end-effector port 214. The tube 216 is visibly present in FIG. 16 because of the retraction of the spring-biased plunger 116. Also, note that the plunger-cam follower 192 has been actuated away from the plunger cam 184 such that it no longer touches the plunger cam 184. The lift cam 120 actuates the inlet valve 198 and the outlet valve 200 in a similar manner That is, the lift cam 120 also engages with the inlet valve 198 and the outlet valve 200, which are also spring biased.

Figure 17:
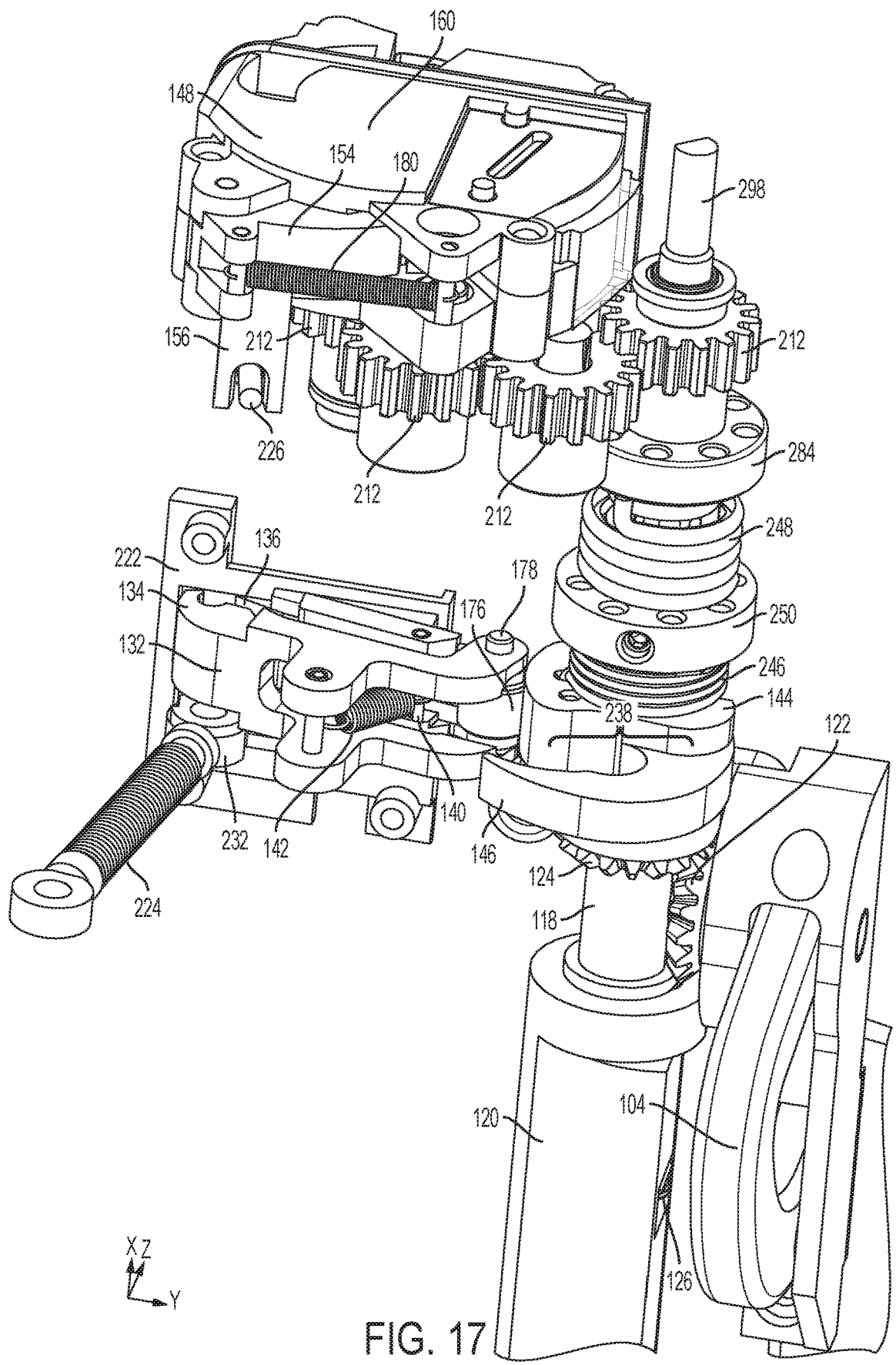
FIG. 17 shows a close-up view of the latching sled of the mechanical assembly of the peristaltic pump of FIG. 1 when the lever is in the closed position in accordance with an embodiment of the present disclosure.
Figure 18:
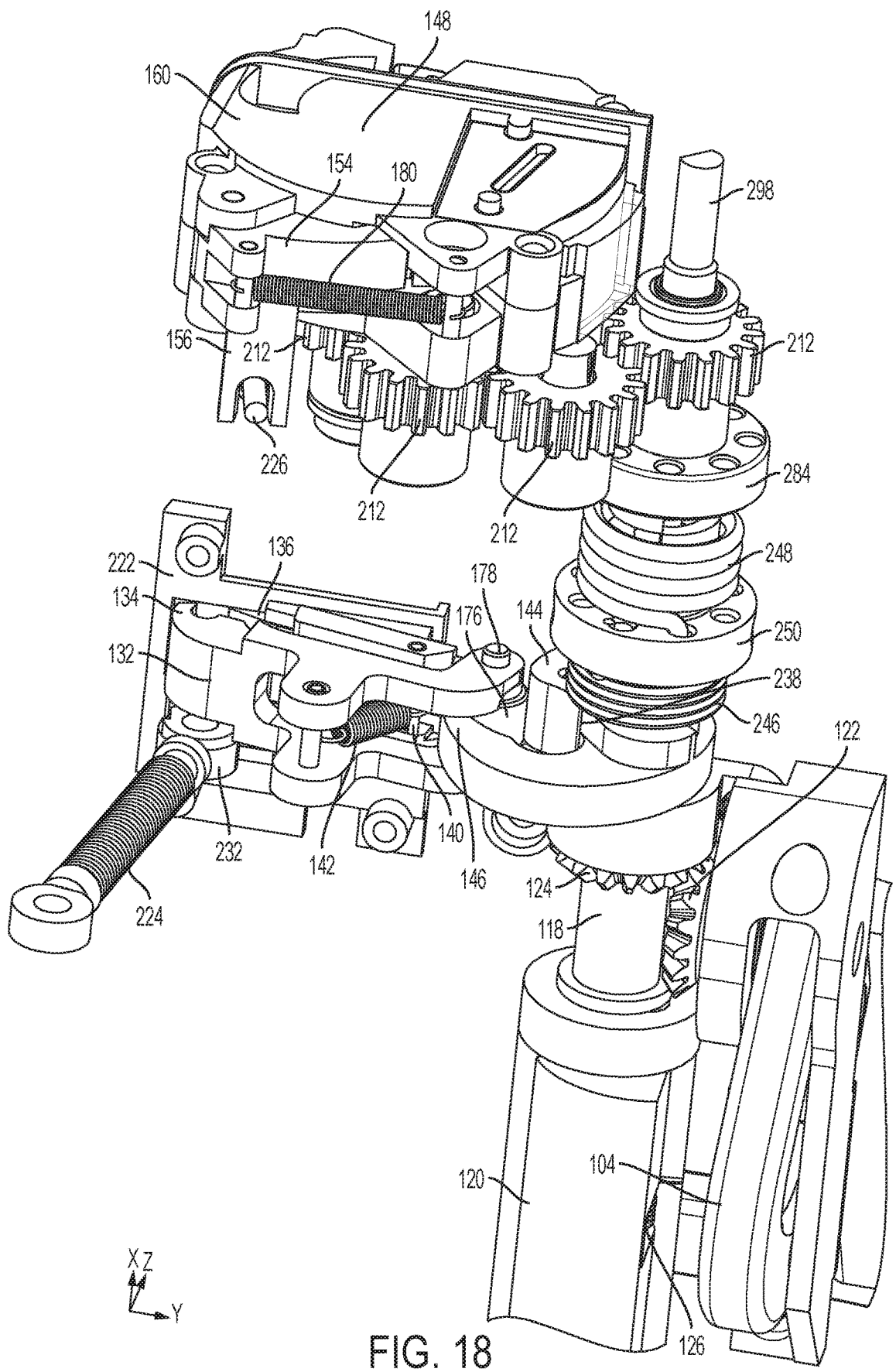
FIG. 18 shows a close-up view of the latching sled of the mechanical assembly of the peristaltic pump of FIG. 1 when the lever is between the closed position and the open position in accordance with an embodiment of the present disclosure.
Figure 19:
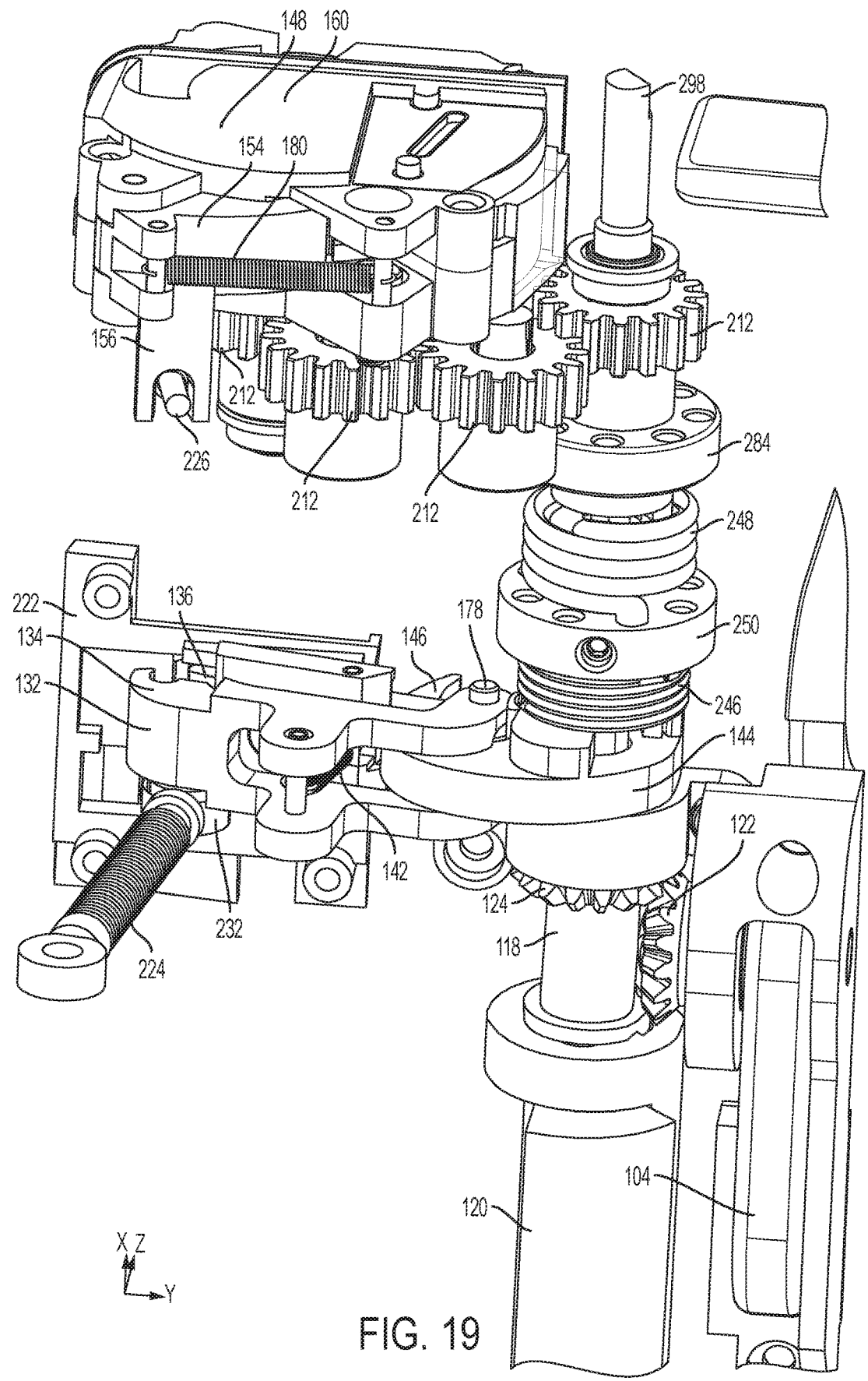
FIG. 19 shows a close-up view of the latching sled of the mechanical assembly of the peristaltic pump of FIG. 1 when the lever is in the open position in accordance with an embodiment of the present disclosure.

Referring to FIGS. 17-19, FIG. 17 shows a close-up view of the latching sled 132 of the mechanical assembly 210 of the peristaltic pump 100 of FIG. 1 when the lever 104 is in the closed position. FIG. 18 shows a close-up view of the latching sled 132 when the lever 104 is between the closed position and the open position; And FIG. 19 shows a close-up view of the latching sled 132 when the lever 104 is in the open position.

FIG. 17 shows the lever 104 in the closed position and hence the latching sled 132 is in the extended position. When the latching sled 132 is in the extended position, the claw 134 is actuated away from the main shaft 118 because of the abutment of the sled cam follower 176 with the hook cam 144. That is, the hook cam 144 engages with the sled cam follower 176 such that the hook cam 144 extends the sled cam follower 176 maximally away from the main shaft 118. Therefore, FIG. 17 shows the condition where the hook cam 144 has actuated the latching sled 132 to its fully extended position.

When the latching sled 132 is in the extended position, the door 102 and the door catch 114 may initially be unlocked, but as soon as the door catch 114 is actuated to the closed position (e.g., when the door 102 is shut), a door-catch hold 234 of the door catch 114 is locked between the claw 134 and the sled base 136. That is, once the door catch 114 has rotated into the locked position, the latching sled 132 prevents it from being opened because the latching sled 132 is in the extended (or locking) position.

FIG. 18 shows the lever 104 in a partially actuated position where the hook 146 of the hook cam 144 hooks onto the sled cam follower 176. The hook cam 144 includes a retraction space 238 so that the sled cam follower 176 can be pulled toward the main shaft 118. FIG. 19 shows the lever 104 in the fully open position such that the hook 146 of the hook cam 144 has fully retracted the latching sled 132. As the claw 134 was pushed toward the hook cam 144, the claw 134 pulled the door catch 114 into the open (or unlatched position), which in turn, opened the door 102.

Figure 25:
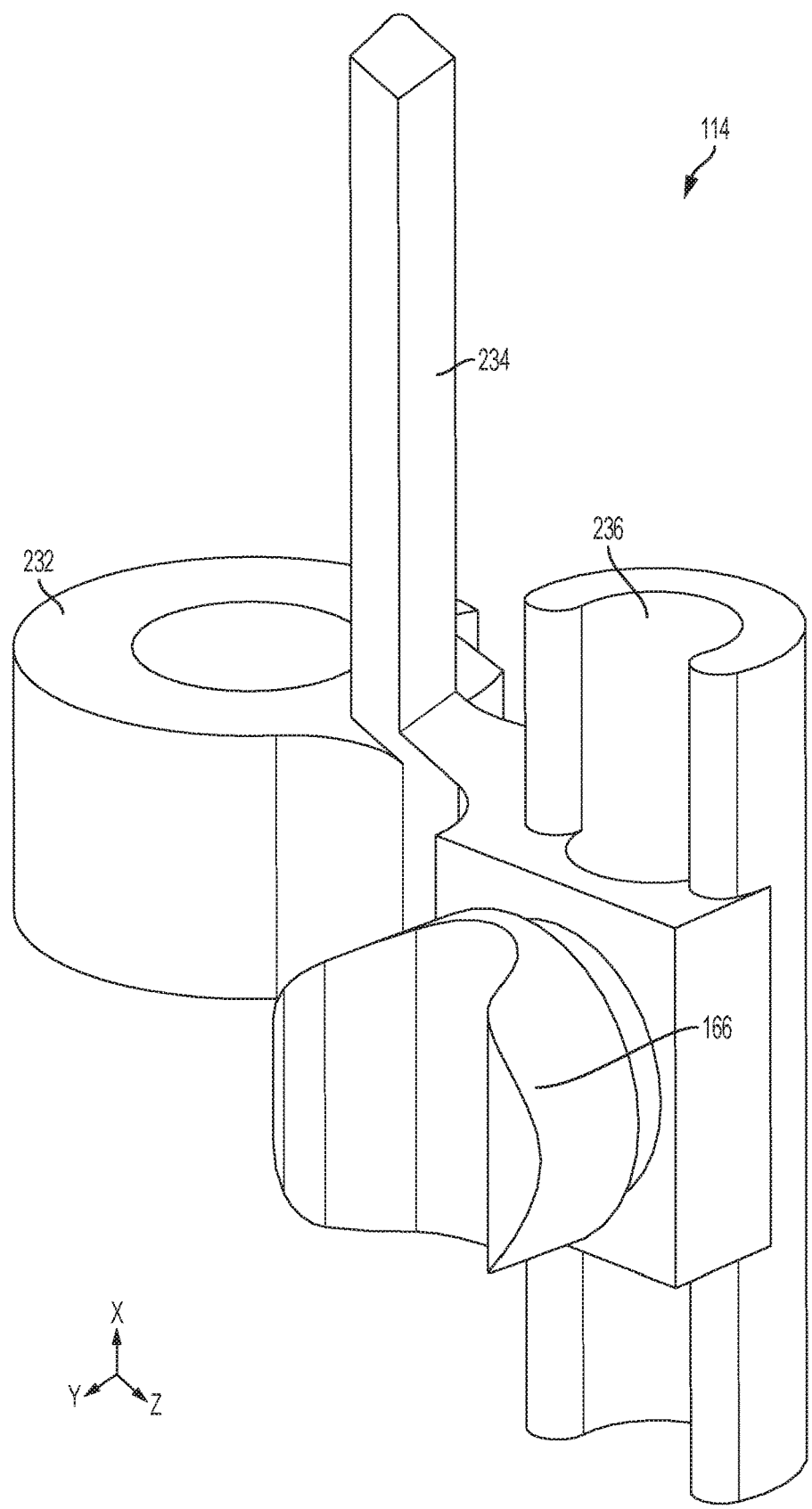
FIG. 25 shows the door catch for the peristaltic pump of FIG. 1 in accordance with an embodiment of the present disclosure.

Referring to FIGS. 2, 19 and 25, when the lever 104 was actuated from the closed position to the open position, the claw 134 pulled on the door-catch hold 234 such that the door catch 114 was rotated along its channel 236 which rotated the pin catch 166 to a position where it no longer locks the hold 164 of the door 102. Because the door 102 may be spring-biased open, the door 102 may swing open when the door catch 114 no longer locks onto the hold 164 of the door 102.

Referring again to FIG. 19, the latching sled 132 is coupled to a door-catch spring 224 that is coupled to the door-catch anchor 232. The door-catch spring 224 pushes against the door-catch anchor 232 which makes the door catch 114 actuate with an "over center" action. The over center action of the door-catch spring 224 makes the door catch 114 bi-stable in the locked position or in the open position. As shown in FIG. 19, when the claw 134 is in a retracted position, the door catch 114 is free to actuate freely between the open position and the locked (or closed) position because the claw 134 has been actuated free from the door-catch hold 234 (see FIG. 25)

Figure 20:
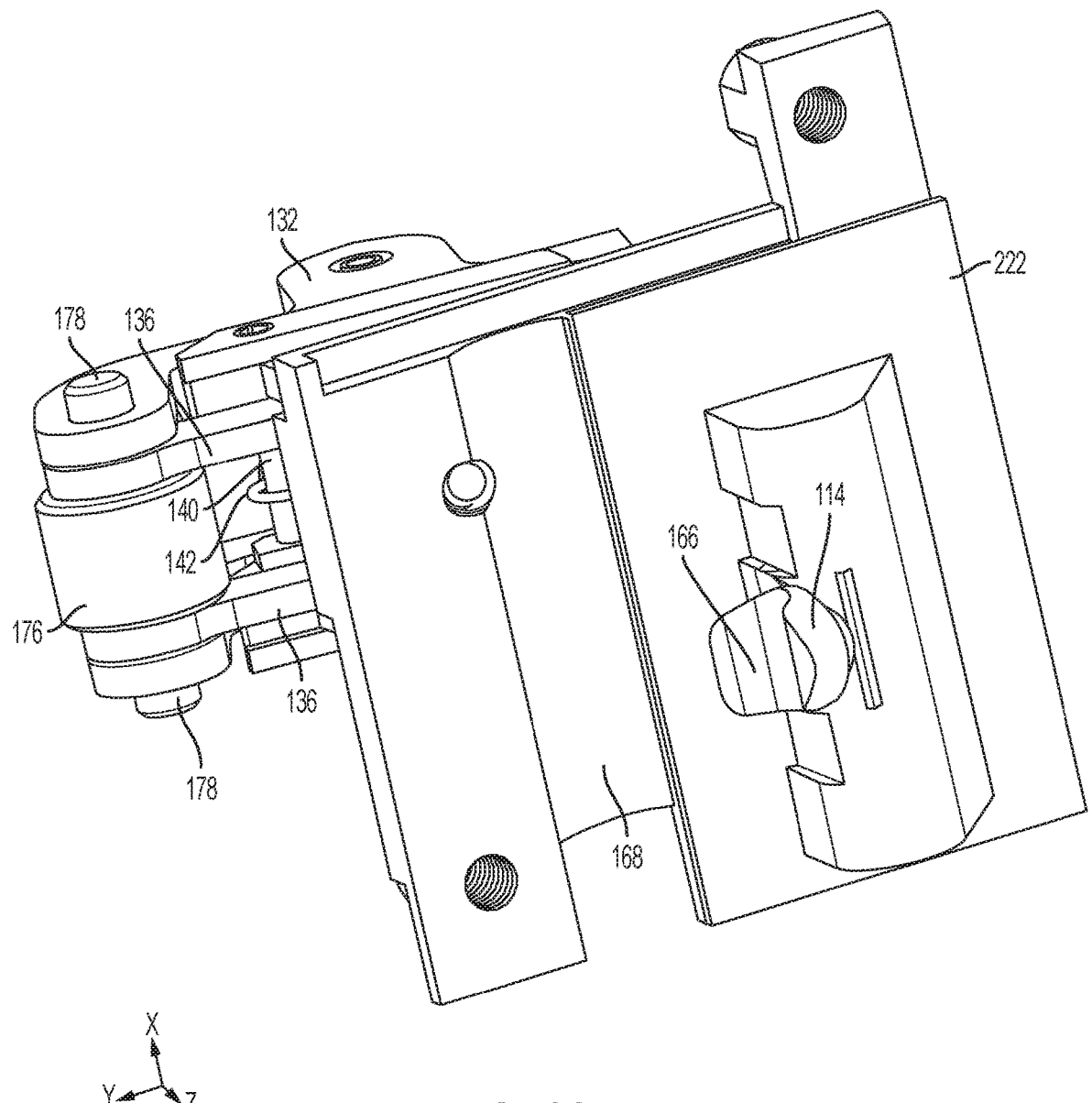
FIG. 20 shows the door catch and latching sled of the peristaltic pump of FIG. 1 from the front side of the pump in accordance with an embodiment of the present disclosure.
Figure 21:
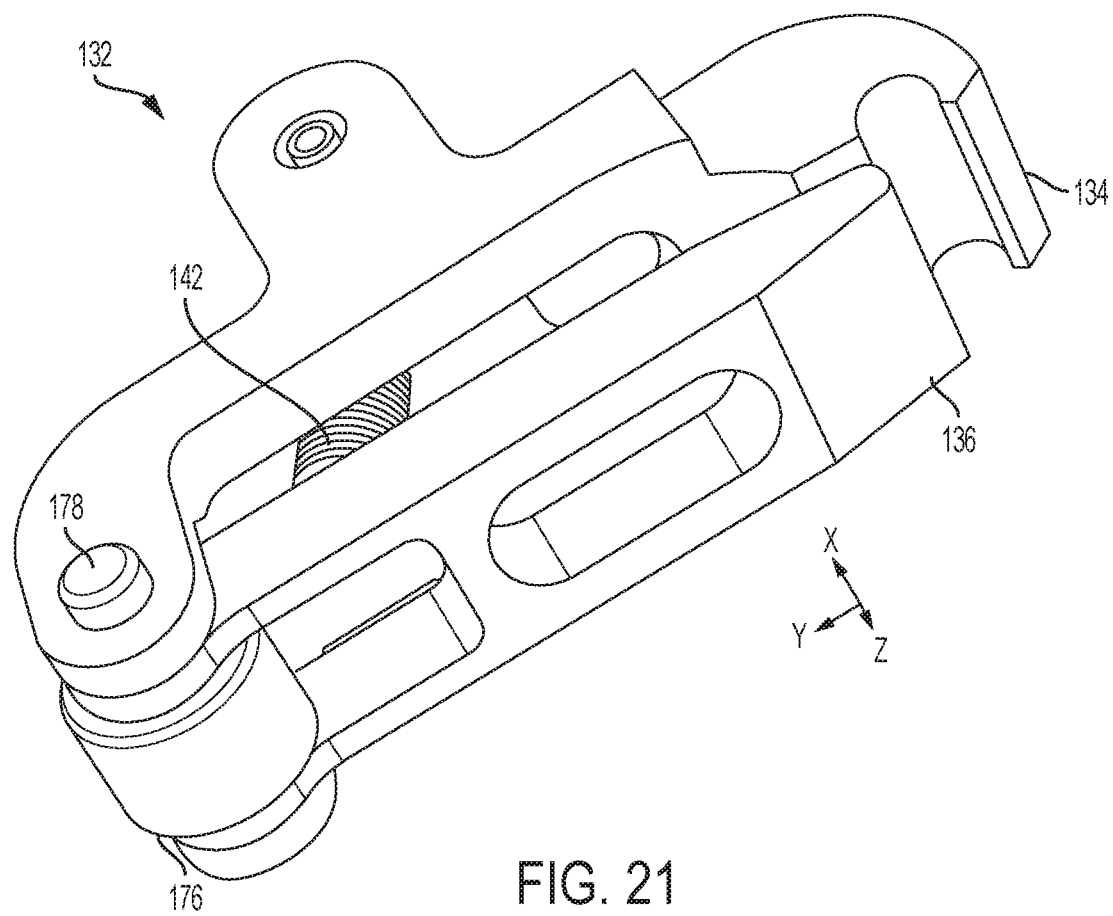
FIG. 21 shows the latching sled of the peristaltic pump in accordance with an embodiment of the present disclosure.

FIG. 20 shows the door catch 114 and latching sled 132 of the peristaltic pump 100 of FIG. 1 from the front side of the pump 100. A door-catch interface 222 separates the outside, in which the pin catch 166 protrudes outside the door-catch interface 222, from the internal parts of the door catch 114 in which the latching sled 132 operates on. FIG. 21 shows the latching sled 132 including a sled base 136 and a claw 134 pivotally coupled to the sled base 136 about an axis of the sled cam follower 176. The sled cam follower 176 is secured to both the sled base 136 and the claw 134 via a sled pin 178. A sled spring 142 is coupled to the claw 134. The sled base 136 slides back and forth in a block 138 of the door-catch interface 222 as shown in FIG. 22.

Figure 22:
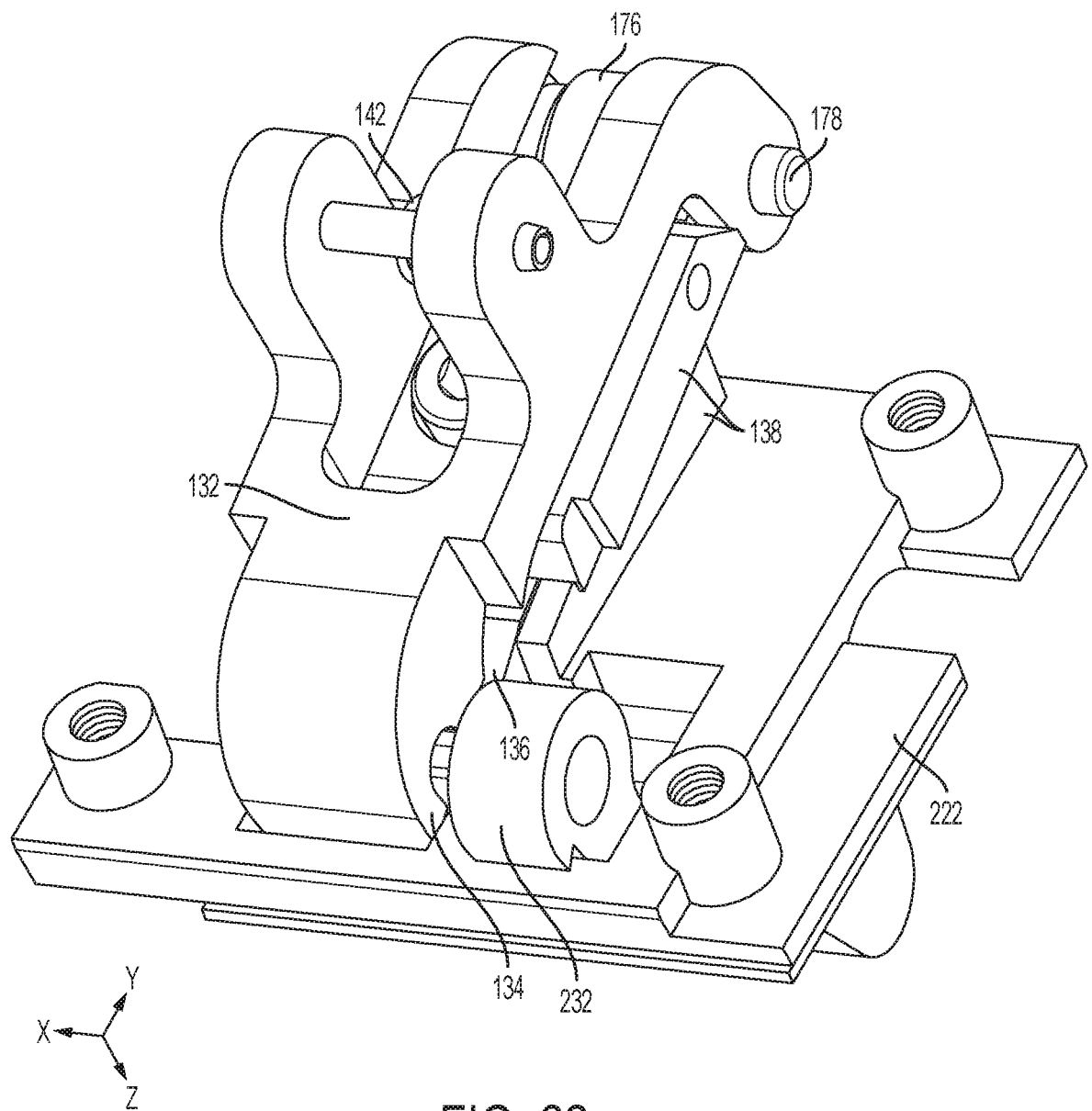
FIG. 22 shows the door catch and latching sled of the peristaltic pump of FIG. 1 from the back side of the pump, the claw of the latching sled is in a locking position in accordance with an embodiment of the present disclosure.

FIG. 22 shows the door catch 114 and latching sled 132 of the peristaltic pump 100 of FIG. 1 from the back side of the pump 100. The claw 134 of the latching sled 132 is in a locking position. The sled spring 142 is coupled to the claw 134 and to an anchor pin 140 of the block 138. The sled spring 142 biases the claw 134 toward the sled base 136 and biases the latching sled 132 toward the door-catch hold 234. However, the position of the sled base 136 within the block 138 is controlled by the hook cam 144 (See FIG. 19).

Figure 23:
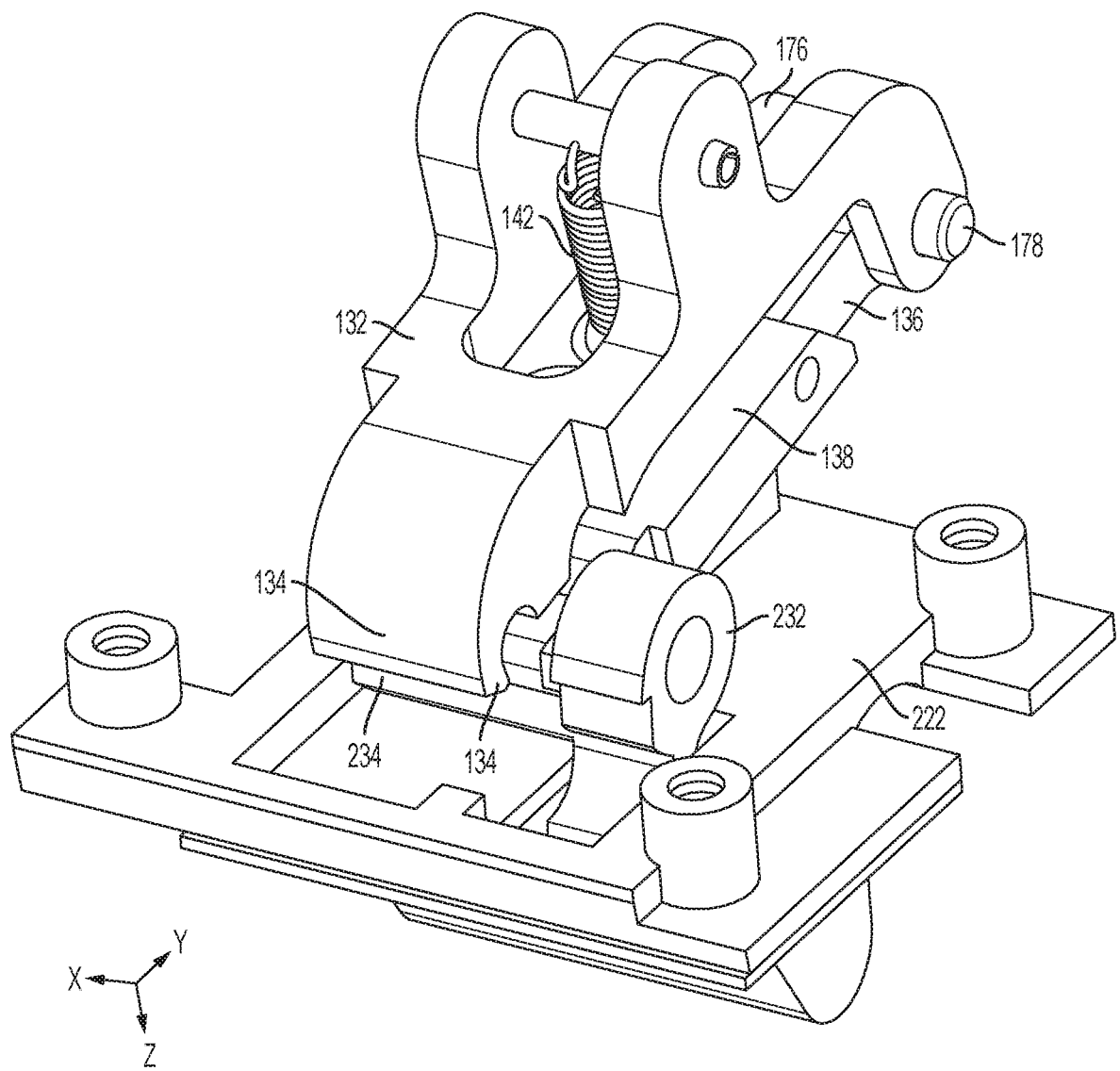
FIG. 23 shows the door catch and latching sled of the peristaltic pump of FIG. 1 from the back side of the pump, the claw of the latching sled is in a retracted position in accordance with an embodiment of the present disclosure.

FIG. 23 shows the door catch 114 and latching sled 132 where the claw 134 of the latching sled 132 is in a retracted position. As is easily seen in FIG. 23, the door-catch hold 234 has been pulled back by the claw 134. In this position, wherein the latching sled 132 has been pulled back because the lever 104 has been actuated to the open position, the door-catch hold 234 is free to actuated between the two positions shown in FIGS. 22 and 23 because the claw 134 has been lifted up away from the door-catch hold 234. The force of the door-catch spring 224 on the door-catch anchor 232 pushes the door-catch hold 234 into one of the positions of FIGS. 22 and 23.

Figure 24:
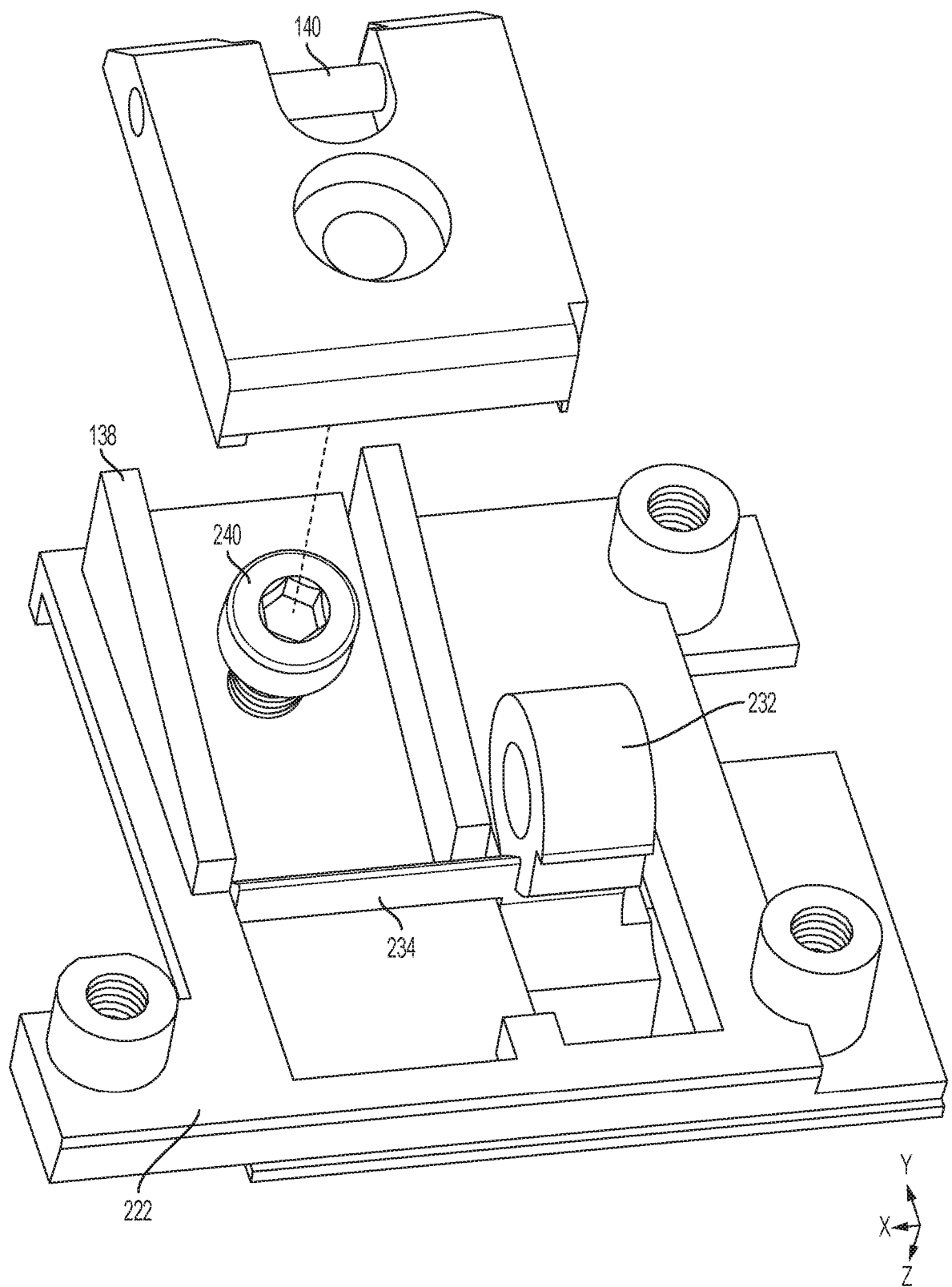
FIG. 24 shows the door catch and a portion of the block that seats the latching sled for the peristaltic pump of FIG. 1 in accordance with an embodiment of the present disclosure.

FIG. 24 shows the door catch 114 and a portion of the block 138 that seats the latching sled 132 for the peristaltic pump 100 of FIG. 1. Also show in exploded view is the anchor pin 140 on the top portion of the block 138 that is secured to the bottom portion of the block 138 by a screw 240. Easily seen in FIG. 24, the door-catch hold 234 is actuatable between the two position. FIG. 25 shows the door catch 114, which is rotatable along a pivot defined by the channel 236. The channel 236 may receive any device that makes the door catch 114 pivotable, such as a pin, flange, or protrusion on the door-catch interface 222.

Figure 26:
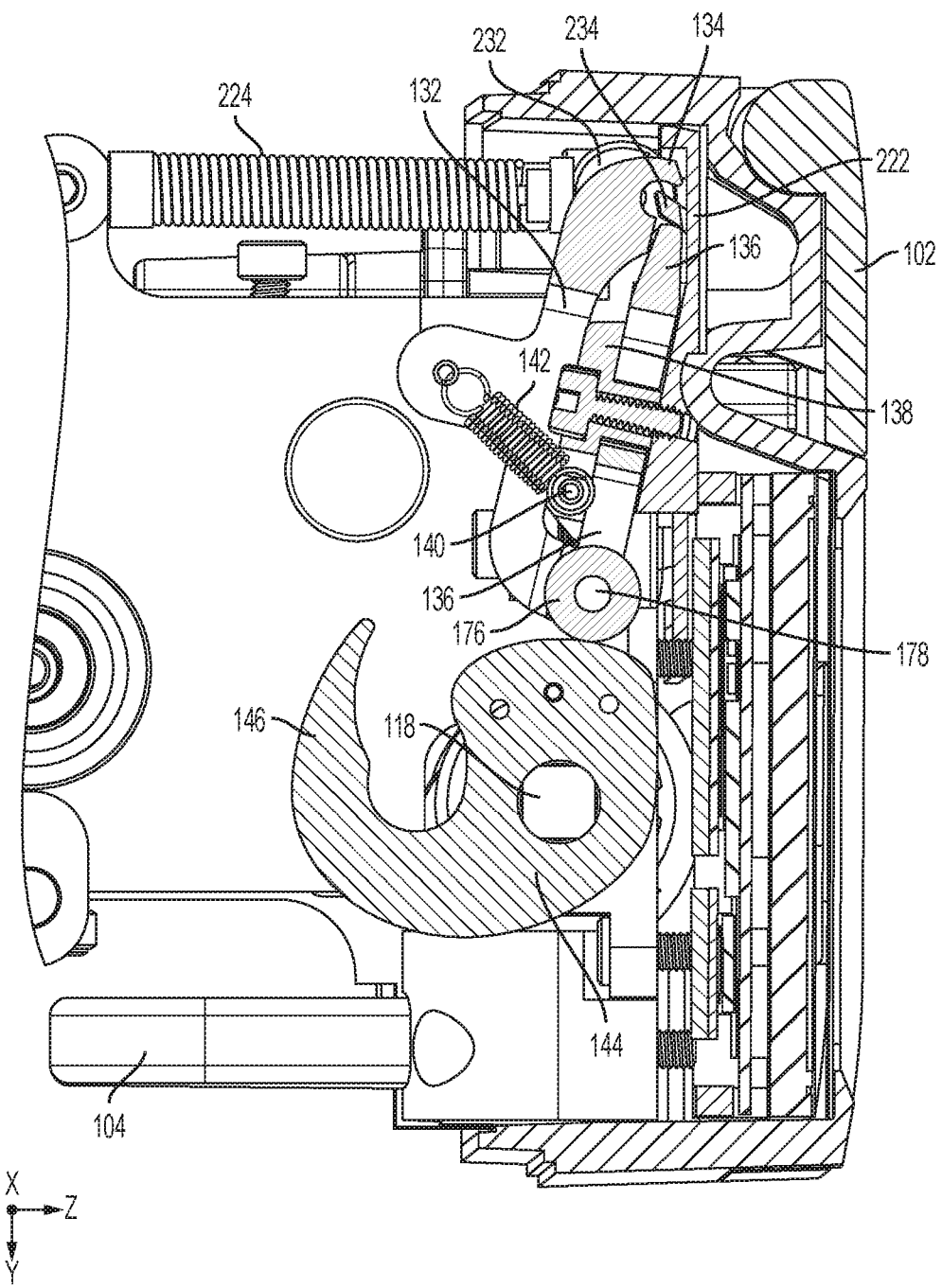
FIG. 26 shows a cross-sectional view of the peristaltic pump of FIG. 1 with a hook cam in a non-hooking position in accordance with an embodiment of the present disclosure.
Figure 27:
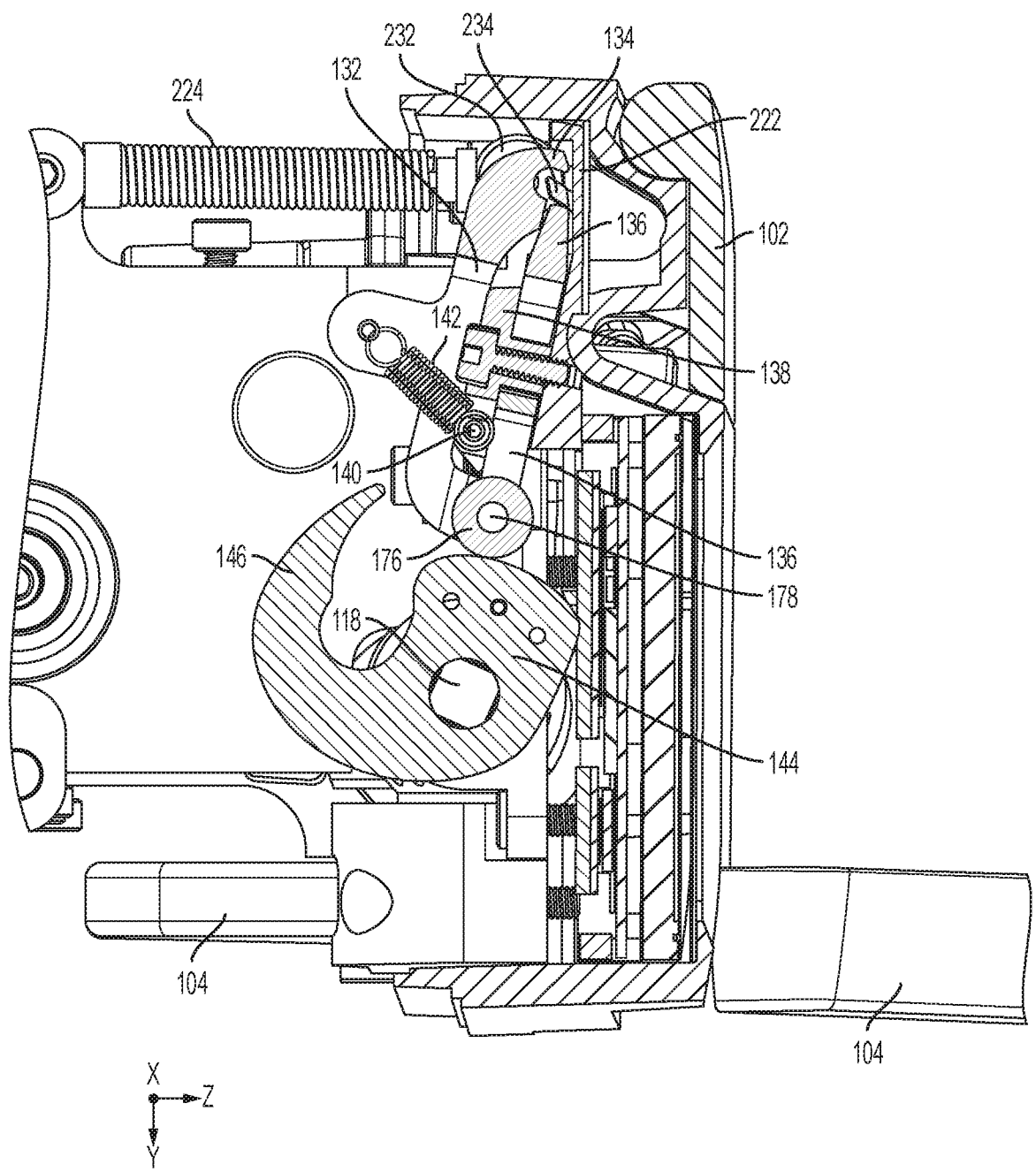
FIG. 27 shows the cross-sectional view of FIG. 26, but with the hook cam partially actuated toward the cam follower of the latching sled in accordance with an embodiment of the present disclosure.
Figure 28:
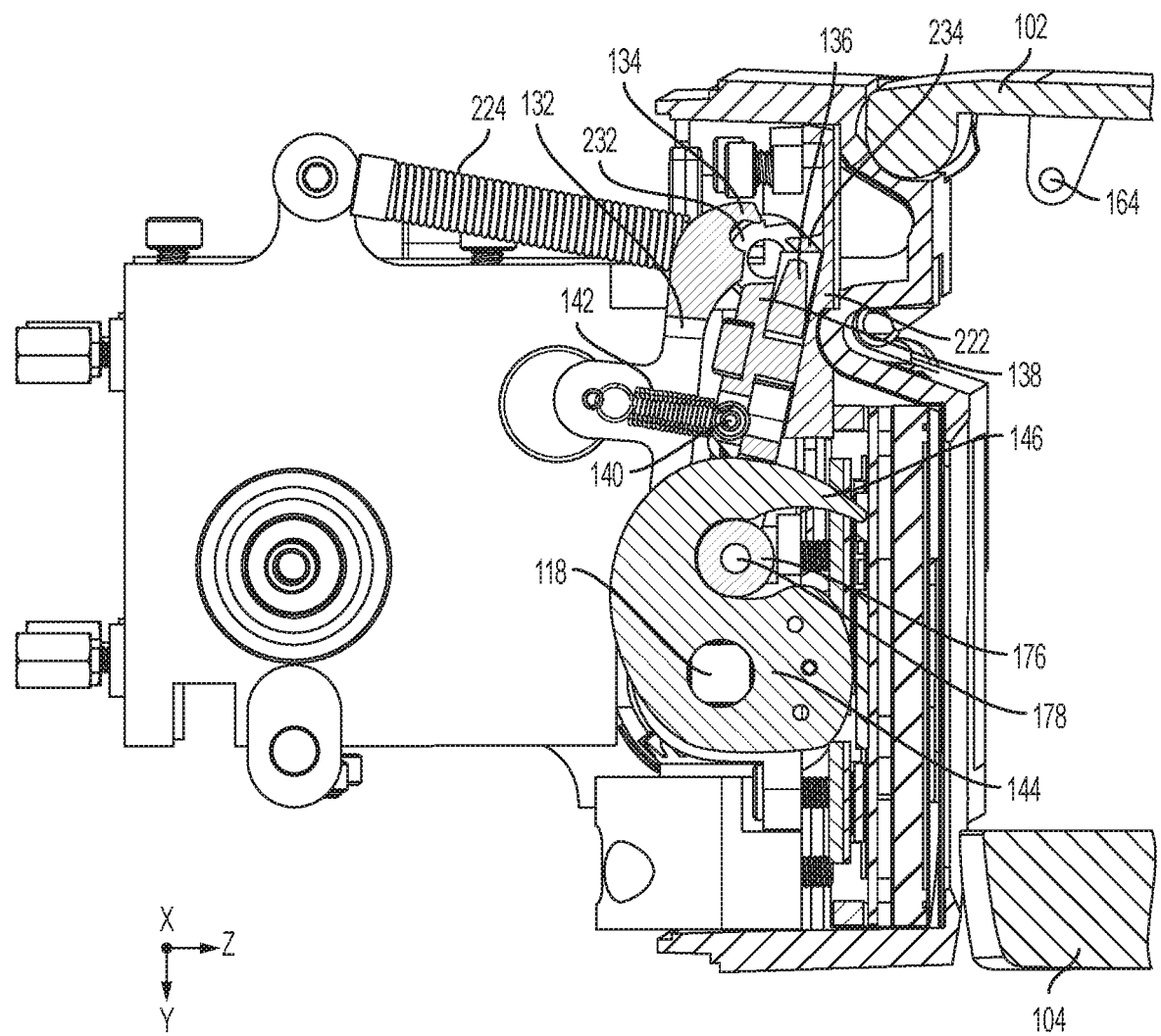
FIG. 28 shows the cross-sectional view of FIG. 26, but with the hook cam fully actuated such that the hook has coupled to the cam follower of the latching sled and has fully retracted the latching sled in accordance with an embodiment of the present disclosure.

Refer now to FIGS. 26-28: FIG. 26 shows a cross-sectional view of the peristaltic pump 100 of FIG. 1 with a hook cam 144 in a non-hooking position; FIG. 27 shows the cross-sectional view of FIG. 26, but with the hook cam 144 partially actuated toward the cam follower of the latching sled 132; And FIG. 28 shows the cross-sectional view of FIG. 26, but with the hook cam 144 fully actuated such that the hook 146 has coupled to the cam follower of the latching sled 132 and has fully retracted the latching sled 132.

Figure 29:
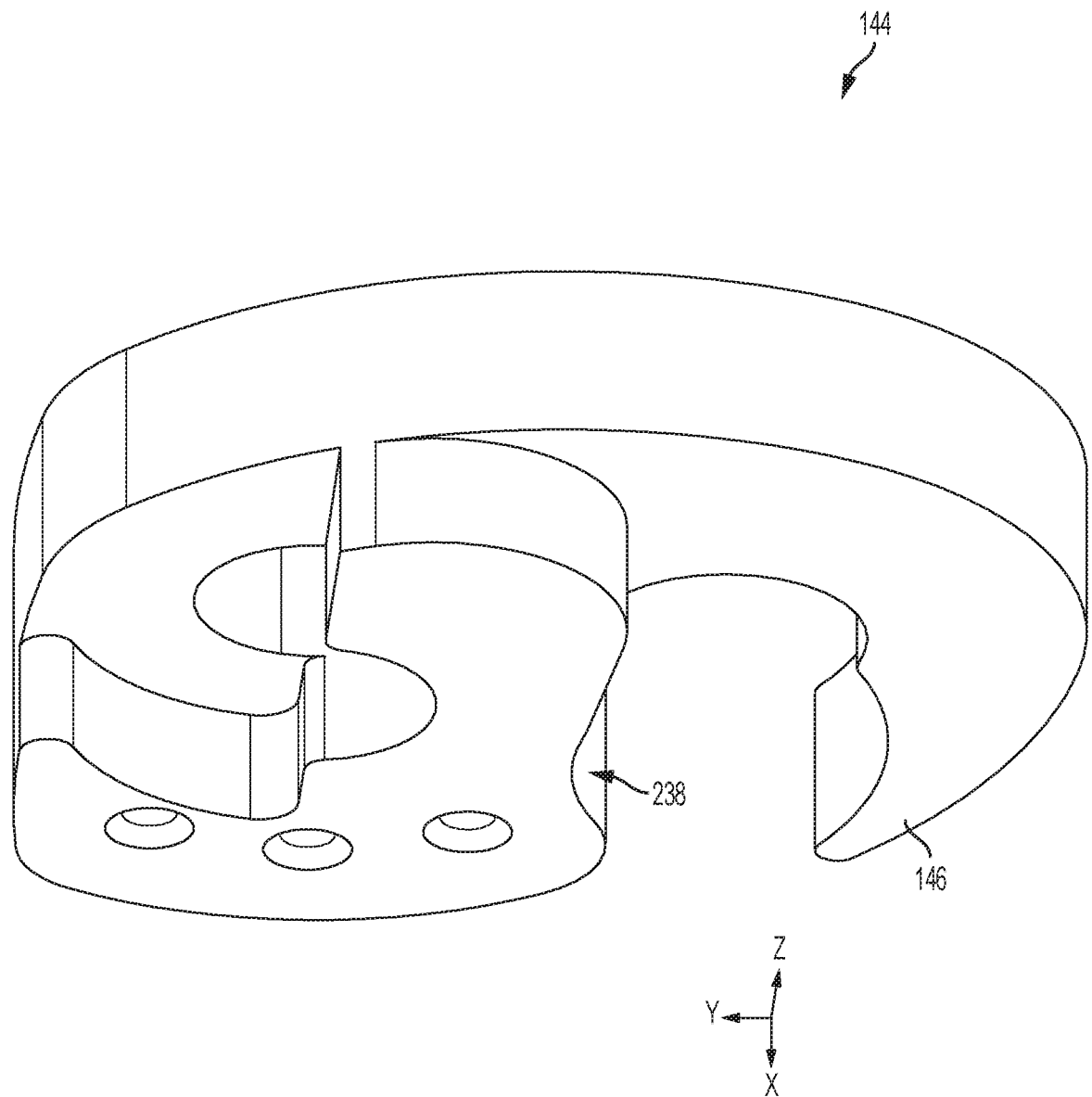
FIG. 29 shows the hook cam of the peristaltic pump of FIG. 1 in accordance with an embodiment of the present disclosure.

As can be seen through the sequence of FIGS. 26, 27, and 28, the hook 146 of the hook cam 144 grabs onto the sled cam follower 176 and retracts the latching sled 132. As the claw 134 is pulled back, the door-catch hold 234 is retraced within it. The door catch 114 is then in the unlocked state as shown in FIG. 28. When the door 102 is fully opened as shown in FIG. 28, the door-catch hold 234 is able to freely actuate between the open and closed position. The door-catch spring 224 pushes against the door-catch anchor 232 such that the door catch 114 is bi-stable between the positions shown in FIGS. 26 and 28. Also, it is easily viewable in FIG. 28 that the block 138 lifts up the claw 134 as it is retracted by the hook cam 144 despite the sled spring 142. That is, the surface of the block 138 provides a cam action against the claw 134 to lift up the claw 134 when the latching sled 132 is retracted by the hook cam 144. The sled spring 142 biases the claw 134 toward the sled base 136. FIG. 29 shows the hook cam 144 with a close up to illustrate the retraction space 238 which allows a portion of the claw 134 to retract more closely to the main shaft 118.

Figure 30:
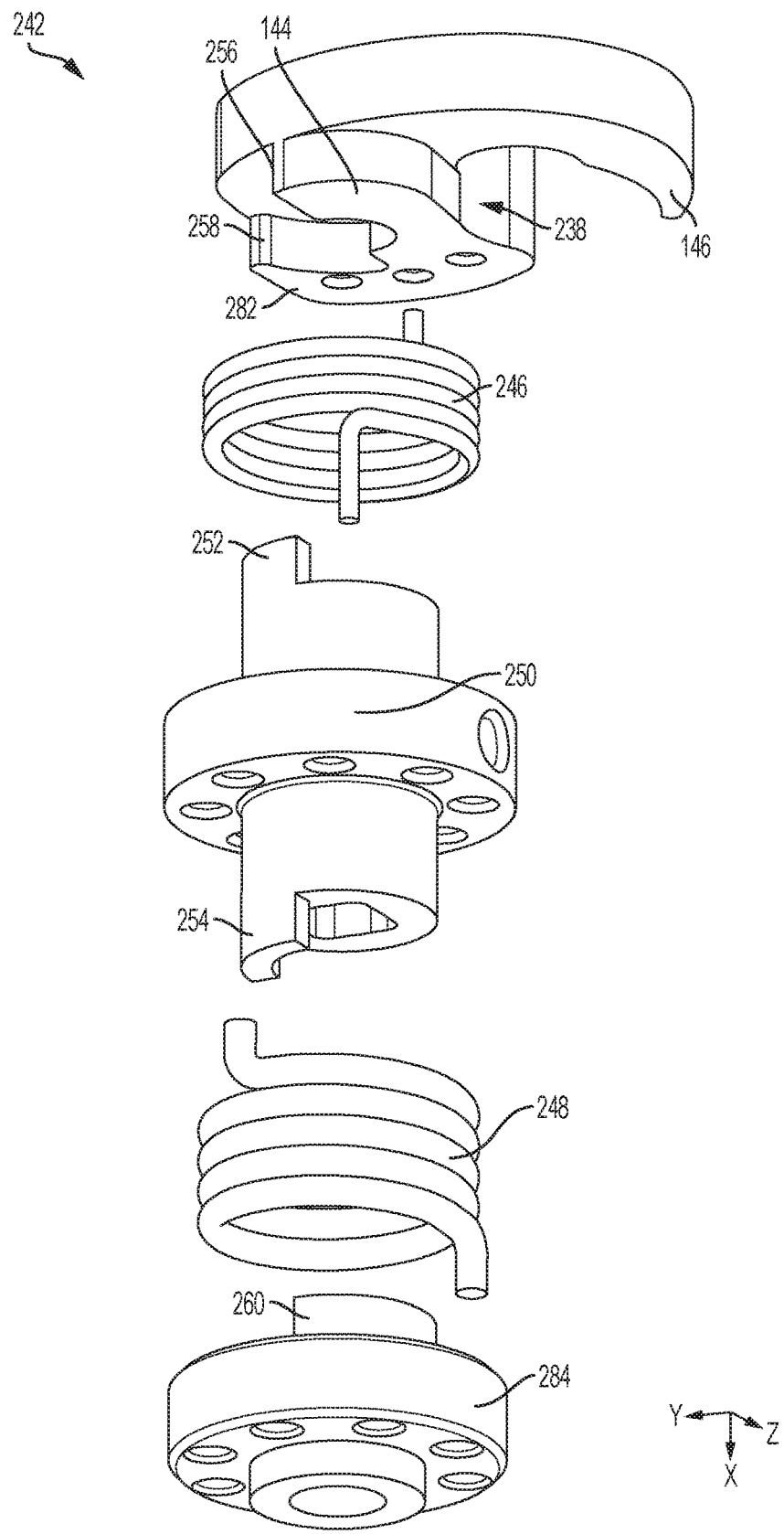
FIG. 30 shows an exploded view of a coupling for coupling together the main shaft to the upper shaft of the peristaltic pump of FIG. 1 in accordance with an embodiment of the present disclosure.
Figure 31:
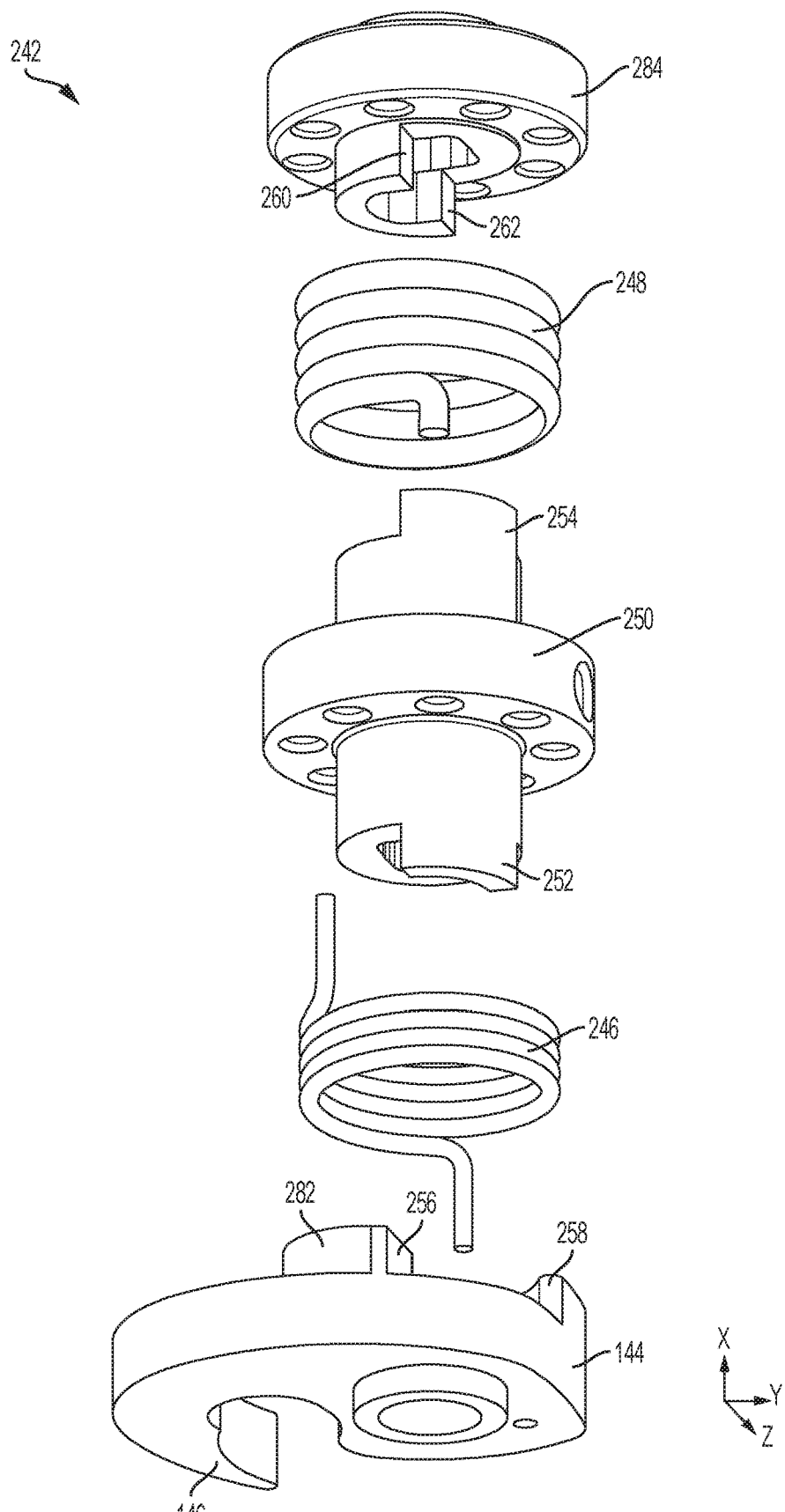
FIG. 31 shows an exploded view of the coupling of FIG. 30 but from another viewing angle in accordance with an embodiment of the present disclosure.

FIG. 30 shows an exploded view of a coupling 242 for coupling together the main shaft 118 to the upper shaft 298 of the peristaltic pump 100 of FIG. 1, and FIG. 31 shows an exploded view of the coupling 242 of FIG. 30 but from another viewing angle.

Referring to both FIGS. 30 and 31, the coupling 242 includes a middle connector 250, a first connector 282, and a second connector 284. The embodiment shown herein shows the hook cam 144 and the first connector 282 integrated together. The middle connector 250 is rigidly coupled to the main shaft 118. The hook cam 144 rotates around the main shaft 118 (see FIG. 19). The second connector 284 is rigidly coupled to the upper shaft 298 (see FIG. 19).

The middle connector 250 includes a first flange 252 that can interface with one of a first stop 256 of the first connector 282 or a second stop 258 of the first connector 282. The middle connector 250 also includes a second flange 254 that can interface with a third stop 260 or a fourth stop 262 of the second connector 284. The first flange 252 engages with the first stop 256 of the first connector 282 such that when the lever 104 is actuated from the closed position to the open position, the rotation of the main shaft 118 rotates the middle connector 250 (via direct coupling) to press the first flange 252 against the first stop 256 to thereby actuate the hook cam 144 to retract the latching sled 132. Likewise, the second flange 254 engages with the third stop 260 such that when the lever 104 is actuated from the closed position to the open position, the rotation of the main shaft 118 rotates the middle connector 250 (via direct coupling) to press the second flange 254 against the third stop 260 to rotate the second connector 284 with the main shaft 118; because the upper shaft 298 is directly coupled to second connector 284, the interface of the second flange 254 with the third stop 260 causes the main shaft 118 and the upper shaft 298 to rotate with each other when the lever 104 is actuated from the closed position to the open position.

A first shaft spring 246 torsionally biases the middle connector 250 relative to the first connector 282, and the second shaft spring 248 torsionally biases the middle connector 250 relative to the second connector 284. The coupling 242 allows the main shaft 118 to continue to rotate a predetermined amount when the gears 212 are locked and thereby causing the upper shaft 298 to remain stationary. Although described in greater detail below, a pawl 154 of the carriage assembly 160 (see FIG. 33) can prevent the carriage 150 from rotating and can prevent the gears 212 (see FIGS. 32-33) from also rotating. Because the gears 212 are rigidly coupled to the upper shaft 298, when the gears 212 are prevented from rotating, the upper shaft 298 is also prevented from rotating.

That is, a user trying to actuate the lever 104 to the closed position while the door 102 is open will be prevented from closing the lever 104 to keep it closed because once a user lets go of the lever 104, the lever 104 will quickly spring back to the open position. Rather than rigidly stopping any actuation of the lever 104 as the user attempts to actuate the lever 104 to the closed position while the door 102 is open, the coupling 242 provides a spring resistance until the lever 104 is in the fully closed position. The main shaft 118 is not shown in FIGS. 30-31, however as previously mentioned, the main shaft 118 is rotationally disconnected from the upper shaft 298 thereby allowing them to rotate independently. When the door 102 is open, the coupling 242 allows a predetermined amount of actuation of the lever 104 toward the closed position until the lever 104 is fully closed, or in other embodiments, the coupling 242 prevents any additional actuation. When the door 102 is closed, the upper portion of the main shaft 118 is not locked and the lever 104 can be freely actuated to the closed position.

When the door 102 is open and the user tries to actuate the lever 104 from the open position to the closed position, the main shaft 118 continues to rotate. Because the main shaft 118 is coupled to the middle connector 250, the middle connector 250 will rotate with actuation of the lever 104; however, the second connector 284 will not rotate because the gears 212 are locked by virtue of the door 102 being open which thereby locks the upper shaft 298 and the first connector 282 will also not rotate because the hook cam 144 cannot overcome the bias of the door-catch spring 224 that holds the latching sled 132 in the retracted position. Referring to FIGS. 30-31, in this situation, the middle connector 250 will rotate because it is connected to the main shaft 118 and the first connector 282 and the second connector 284 will remain stationary as the user attempts to close the lever 104 with the door 102 open. The hook cam 144 does not rotate in this situation because it is rigidly connected to the first connector 282. The first flange 252 will leave the first stop 256 thereby charging the first shaft spring 246 and the second flange 254 will leave the third stop 260 thereby charging the second shaft spring 248. If the user lets go of the lever 104, it will quickly open because of the charging of the first shaft spring 246 and the second shaft spring 248. Alternatively, if the user, while holding the lever 104 in the fully closed position against the biasing of the first shaft spring 246 and the second shaft spring 248, attempts to close the door 102, the lifter pin 226 will actuate causing the lifter spring 228 to press against the lift 156. However, because the pawl 154 (see FIG. 33) is locked under force (via the first shaft spring 246 and the second shaft spring 248), the lifter spring 228 cannot overcome the force needed to lift the lift 156 and release the carriage 150 (described in more detail below). Nonetheless, the latching sled 132 may overcome the spring 224 (through assistance of the door 102 causing actuation of the door catch 114) thereby allowing the hook cam 144 to rotate such that the first stop 256 again engages the first flange 252; however, as soon as the user lets go of the lever 104, the lever 104 will quickly open causing the hook cam 144 to quickly retract the latching sled 132 again because of charge of the second shaft spring 248.

Figure 32:
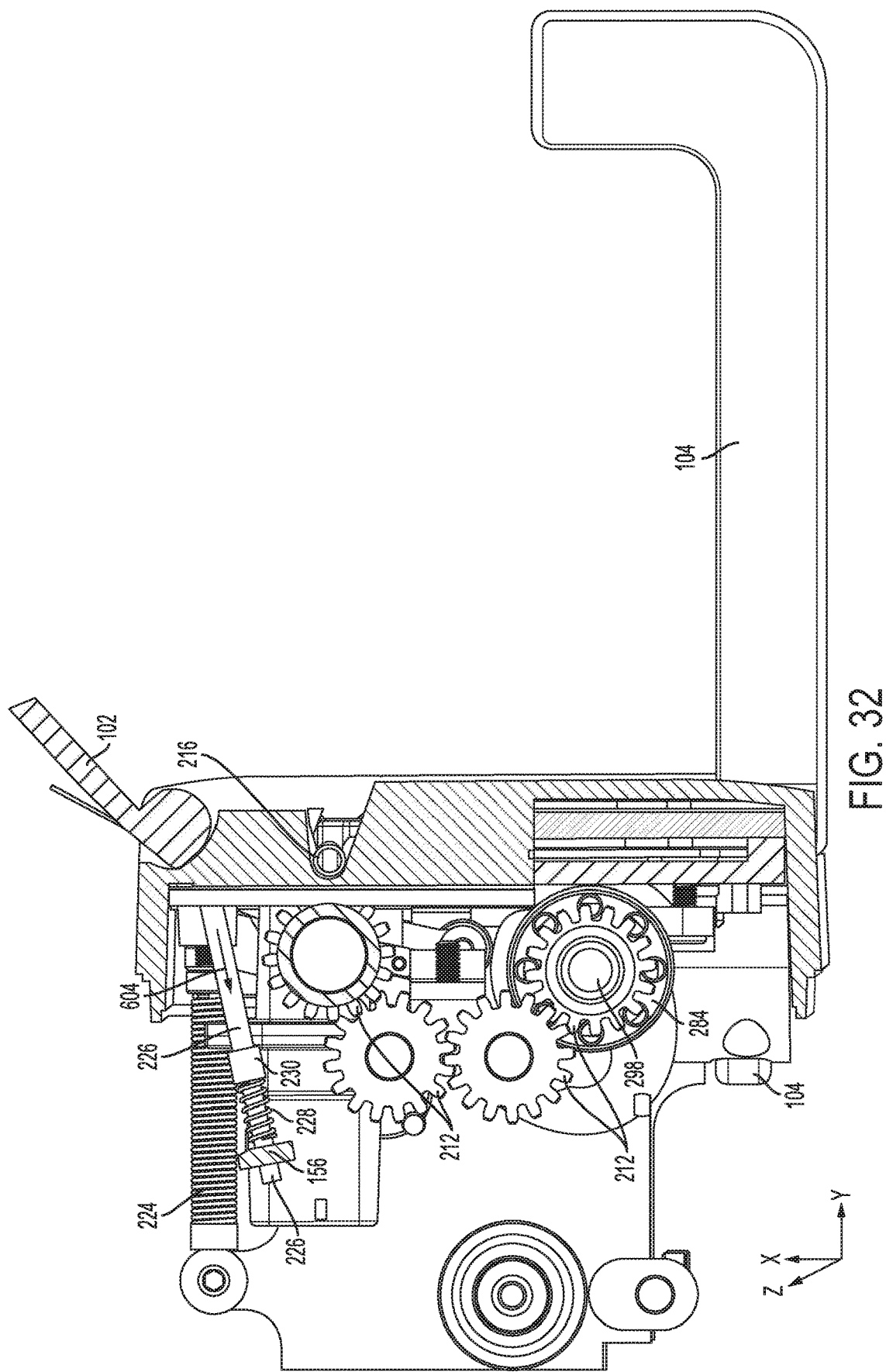
FIG. 32 shows a cross-sectional view of the peristaltic pump of FIG. 1 to illustrate the gears to actuate a carriage by actuation of the main shaft with the door open and the lifter pin actuated toward the open door in accordance with an embodiment of the present disclosure.
Figure 33:
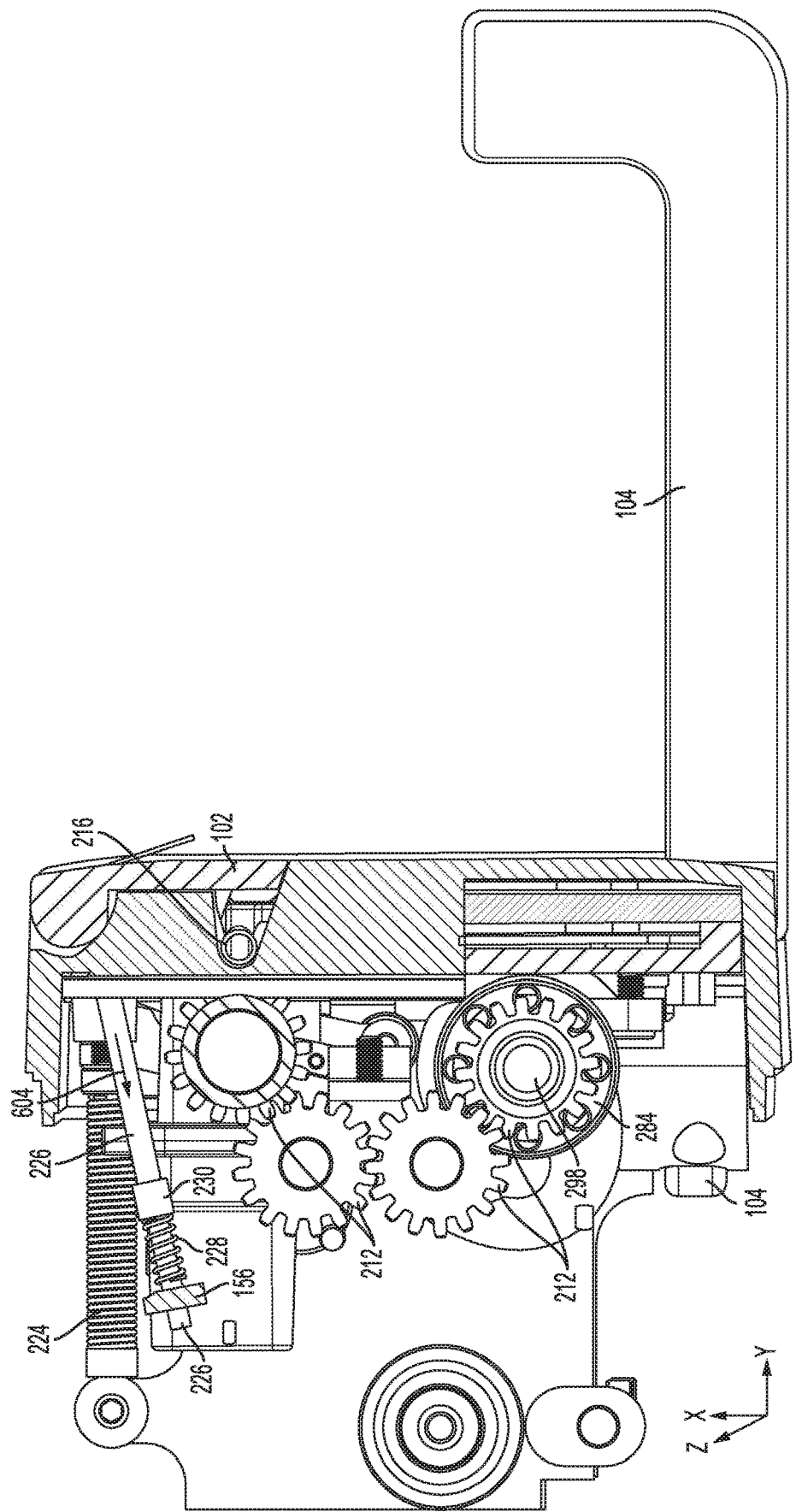
FIG. 33 shows the same cross-sectional view as in FIG. 32 but with the door closed which thereby actuates the lifter pin away from the door to compress the spring which actuates the lift in accordance with an embodiment of the present disclosure.
Figure 34:
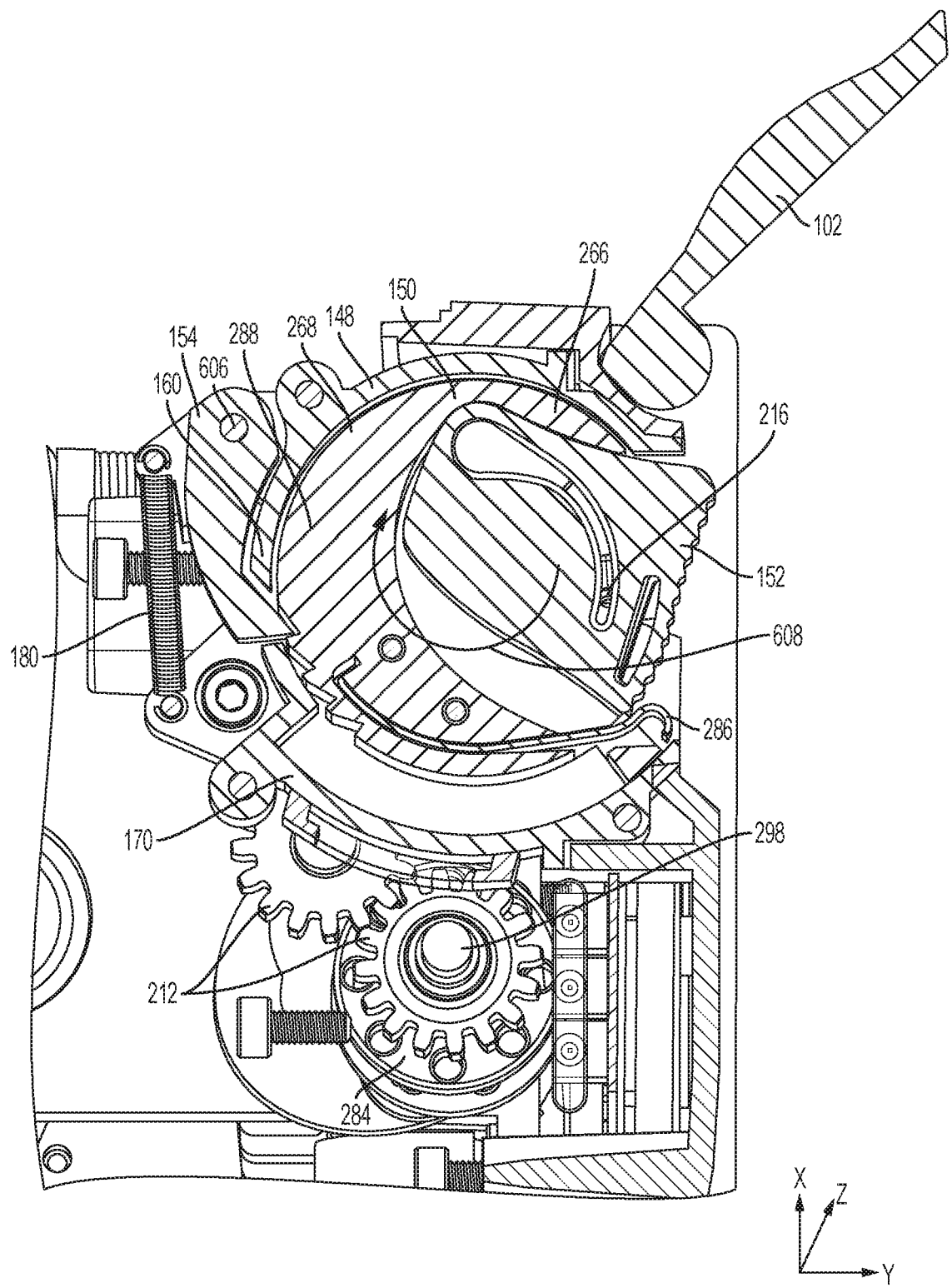
FIG. 34 shows a cross-sectional view of the peristaltic pump of FIG. 1 to show a cross-sectional view of the carriage assembly with the door open and the lever open in accordance with an embodiment of the present disclosure.
Figure 35:
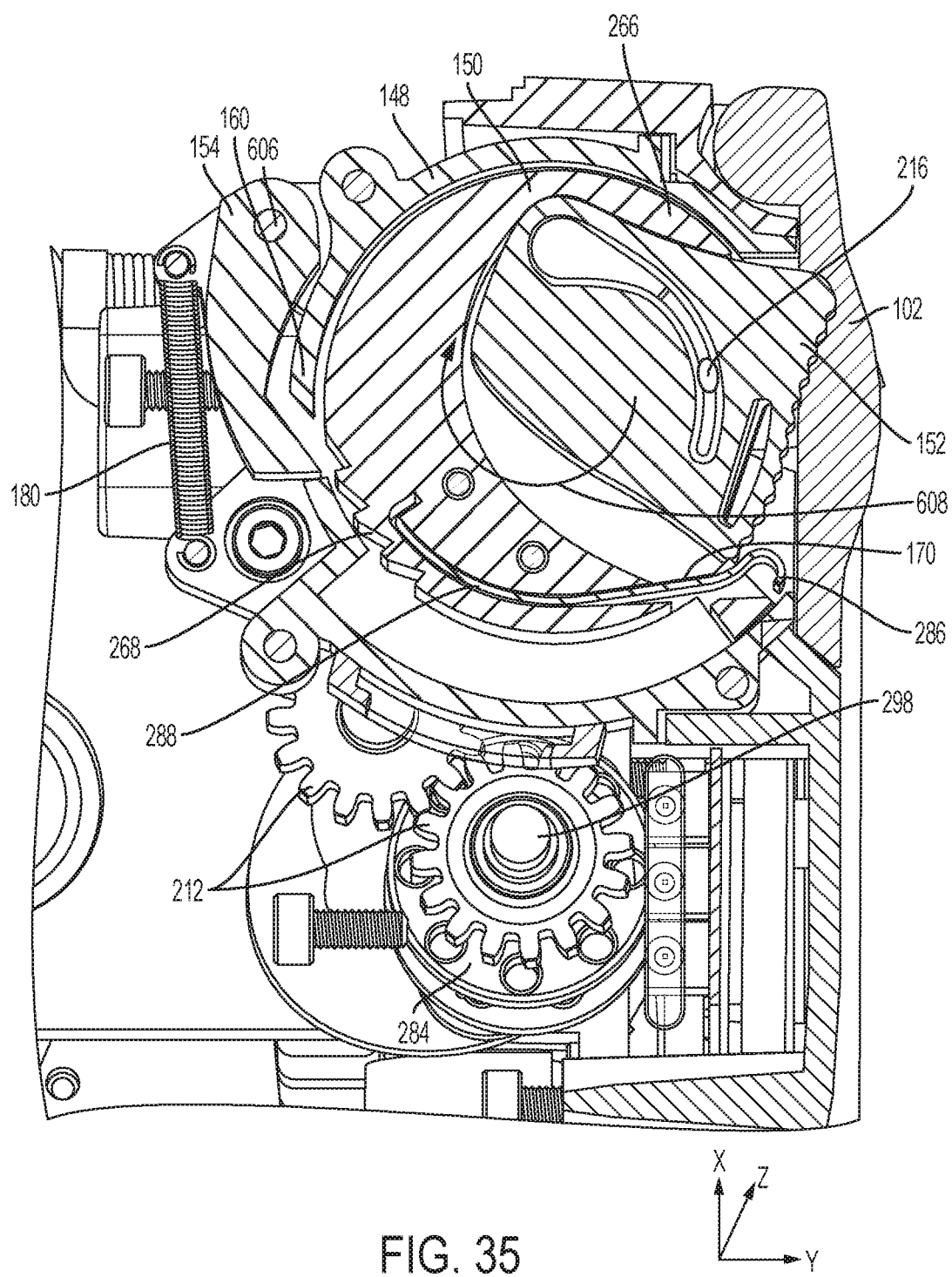
FIG. 35 shows the same cross-sectional view as in FIG. 34 but the door is closed which actuates the pawl in accordance with an embodiment of the present disclosure.

FIG. 32 shows a cross-sectional view of the peristaltic pump 100 of FIG. 1. The gears 212 can actuate the carriage 150 by actuation of the main shaft 118. That is, the gears 212 couple the main shaft 118 to the carriage 150 (see FIGS. 34-36) so that the carriage 150 (see FIGS. 34-36) can rotate. Rotation of the carriage 150 causes the tube 216 to either be in an occluding position or a non-occluding position within the slide clamp 152. FIGS. 32, 34, 35 correspond to the carriage 150 being in a position that positions the tube 216 to be occluded within the slide clamp 152, while FIG. 36 corresponds to the carriage 150 being in a position that positions the tube 216 to be non-occluded within the slide clamp 152. FIG. 33 shows the lifter pin 226 in the position that can correspond to either FIG. 35 or FIG. 36.

FIG. 32 shows the lifter pin 226 in a position that prevents the carriage 150 from rotating when a user attempts to shut the lever 104 with the door 102 open. FIG. 33 shows the lifter pin 226 in a position that allows the carriage 150 to rotate in response to a user closing the lever 104 when the door 102 is closed.

When the door 102 is open as shown in FIG. 32, the lifter pin 226 sticks out of a hole (see FIGS. 2-4 for a clear view of the end of the lifter pin 226) to ensure that the carriage 150 is locked and is prevented from rotation in direction 608 as shown in FIG. 34. As shown in FIG. 34, the pawl 154 is located in a groove of the notches 268 which prevents the carriage 150 from rotating to the position shown in FIG. 36. That is, the pawl 154 has locked the carriage 150. When the door 102 is open as shown in FIG. 32, the pawl 154 is engaged with the notches 268 as shown in FIG. 34. Because the door 102 is open, the lifter pin 226 is not pushing on the lift 156 through the lifter spring 228. This prevents the lever 104 from being actuated toward the closed position because the carriage 150 is coupled to the gears 212, which in turn is mechanically coupled to the main shaft 118. This feature prevents the user from actuating the lever 104 closed while the door 102 is open. Closing the door 102 actuates the pawl 154 out of the notches 268 (via the lifter pin 226).

FIG. 33 shows the same cross-sectional view as in FIG. 32 but with the door 102 closed which thereby actuates the lifter pin 226 away from the door 102 to compress the lifter spring 228 which actuates the lift 156. That is, as shown in FIG. 33, when the door 102 is shut, the door 102 presses on an end of the lifter pin 226 (see FIGS. 2-4) which actuates the lifter pin 226 in a direction that is illustrated by an arrow 604 in FIG. 33. The lifter-pin collar 230 is rigidly coupled to the lifter pin 226 and thus both the lifter-pin collar 230 and the lifter pin 226 move in the direction of the arrow 604 when the door 102 is shut to the position shown in FIG. 33.

Figure 36:
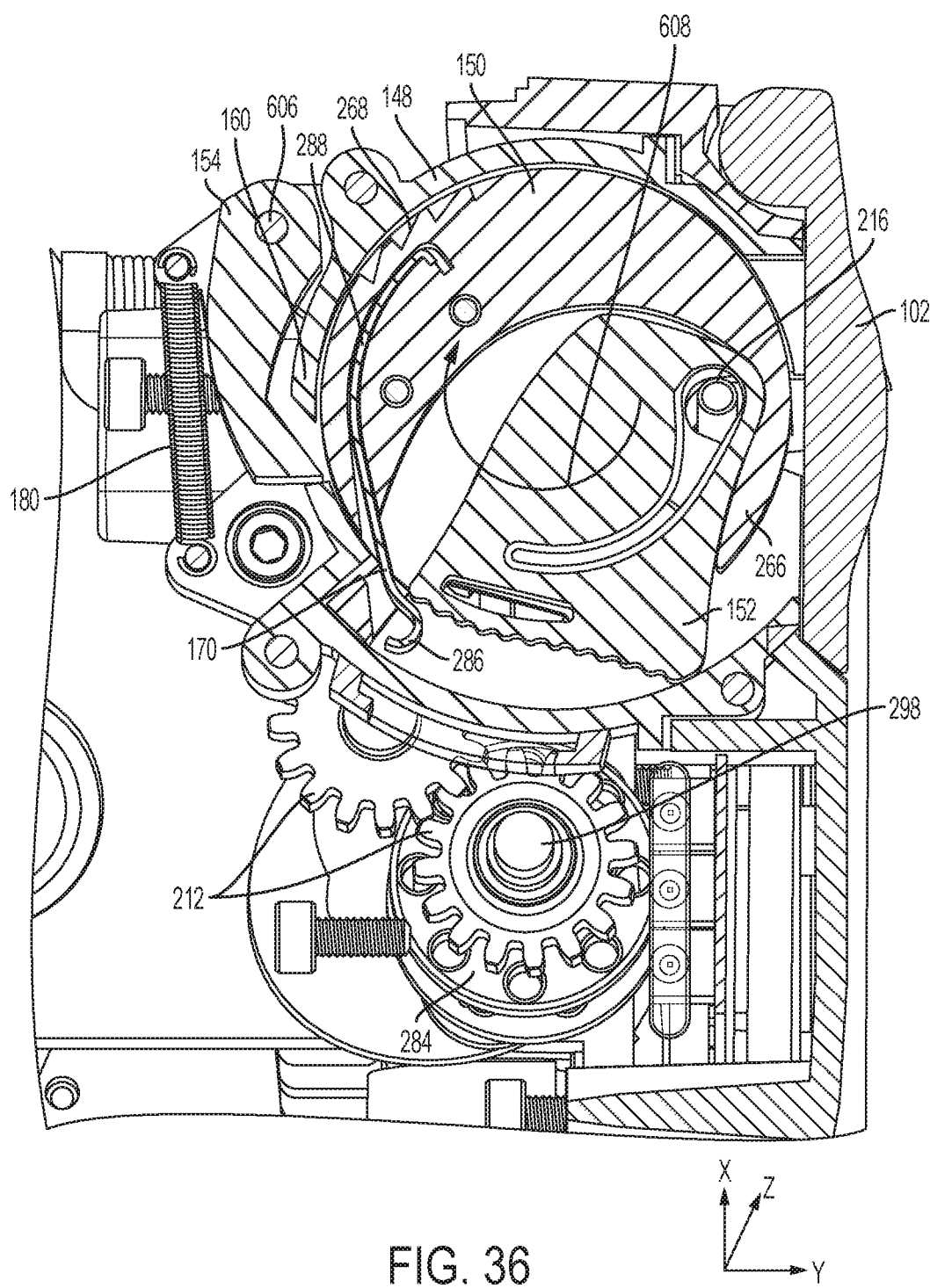
FIG. 36 shows the same cross-sectional view as in FIG. 35 but with the carriage in a rotated position which is caused by closure of the lever in accordance with an embodiment of the present disclosure.

As previously mentioned, the door 102 impinges on the end (see FIGS. 2-4) of the lifter pin 226 when the door 102 is shut thereby actuating the lifter pin 226 in the direction of arrow 604 as shown in FIGS. 32-33. As the lifter pin 226 actuates away from the door 102, the lifter-pin collar 230 also moves away from the door 102 to thereby compress a lifter spring 228 against the lift 156. Compression of the lifter spring 228 applies a force against the lifter pin 226 which actuates the lift 156 away from the door 102 because the lift 156 is coupled to a pawl 154 as shown in FIGS. 34-36. The pawl 154 is pivotably coupled to the carriage assembly 160 via a pawl pivot 606.

When the door 102 is open as shown in FIG. 32, the lifter pin 226 is actuated away from the lift 156 such that the pawl 154 engages with the notches 268 as is shown in FIG. 34. FIG. 34 shows a cross-sectional view of the peristaltic pump 100 of FIG. 1 to show a cross-sectional view of the carriage assembly 160 with the door 102 open and the lever 104 open. As shown in FIG. 33, when the lift 156 is actuated away from the carriage 150 by closing the door 102, the pawl 154 is also actuated away from the carriage 150 as is shown in FIG. 35 by compression of the lifter spring 228 against the lift 156 coupled to the pawl 154. FIG. 35 shows the same cross-sectional view as in FIG. 34 but the door 102 is closed which actuates the pawl 154 out of the notches 268.

That is, actuation of the lift 156 away from the carriage 150 actuates the pawl 154 such that the carriage 150 can freely rotate. When the pawl 154 is lifted by the lift 156, the pawl 154 cannot engage with the notches 268 of the carriage 150 as shown in FIG. 35 and therefore the carriage 150 can freely rotate. When the pawl 154 is engaged with the notches 268 as shown in FIG. 34 of the carriage 150, the carriage 150 cannot rotate to the position shown in FIG. 36. The carriage 150 can rotate in the direction 608 shown as the clockwise arrow in FIGS. 34 and 35 into the position shown in FIG. 36 when the lever 104 is closed. FIG. 36 shows the same cross-sectional view as in FIG. 35 but with the carriage 150 in a rotated position which is caused by closure of the lever 104.

As shown in FIG. 34, the slide-clamp retainer 170 includes a retainer hook 286 and a spring body 288. The slide-clamp retainer 170 allows the slide clamp 152 to be snap-fitted in the carriage 150 and also provides resistance when pulling the slide clamp 152 out of the carriage 150.

Figure 37:
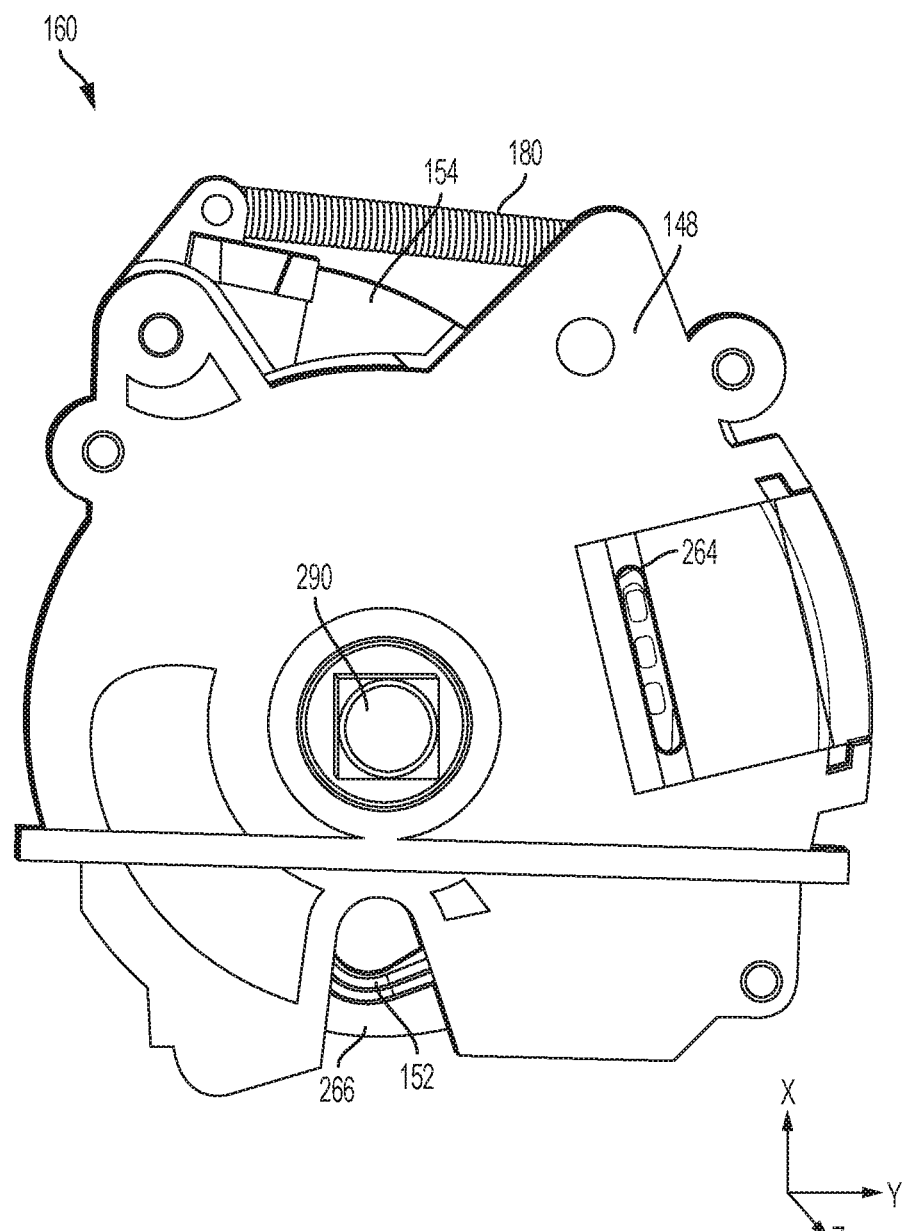
FIG. 37 shows the carriage assembly of the peristaltic pump of FIG. 1 from a bottom side of the carriage in accordance with an embodiment of the present disclosure.
Figure 38:
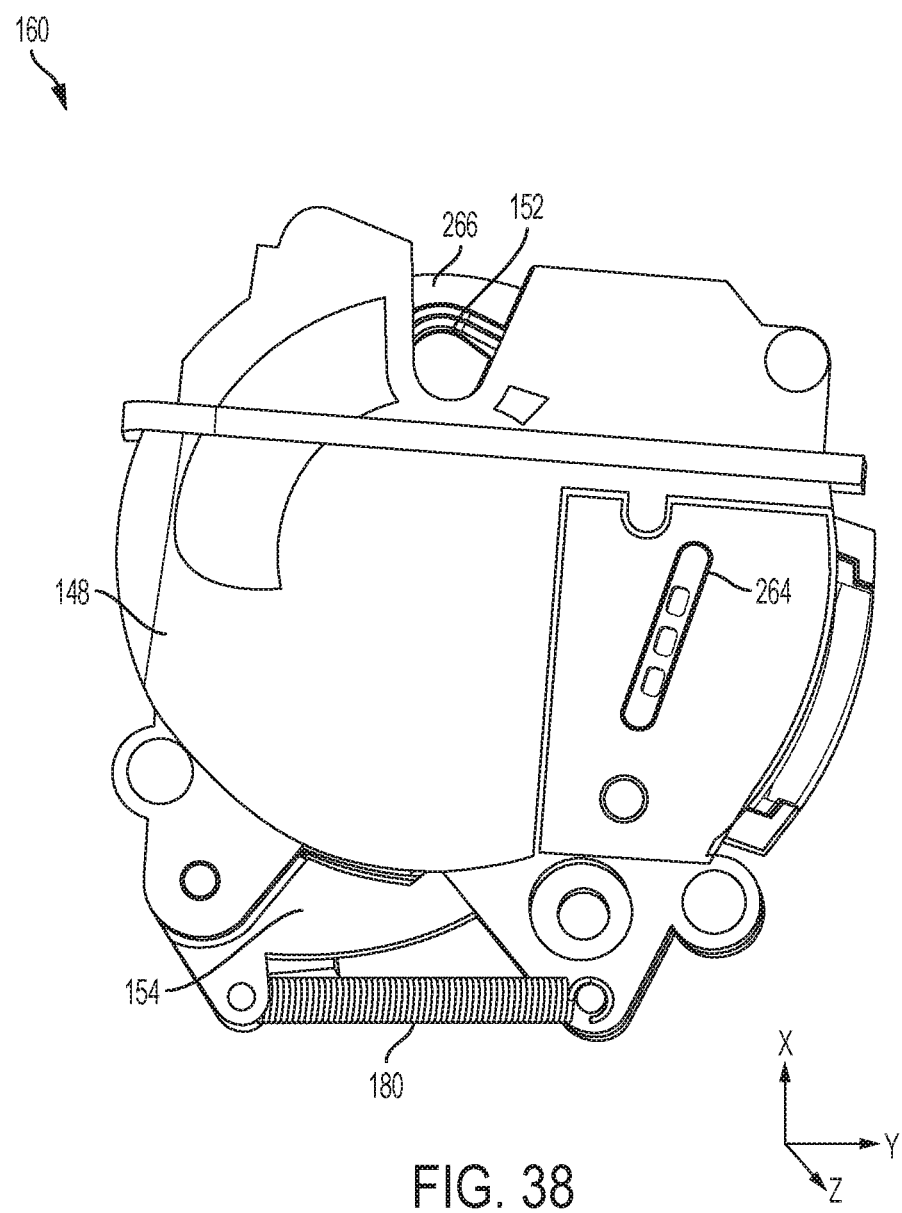
FIG. 38 shows the carriage assembly of the peristaltic pump of FIG. 1 from a top side of the carriage in accordance with an embodiment of the present disclosure.

FIG. 37 shows the carriage assembly 160 of the peristaltic pump 100 of FIG. 1 from a bottom side of the carriage 150, and FIG. 38 shows the carriage assembly 160 of the peristaltic pump 100 of FIG. 1 from a top side of the carriage 150. FIG. 37 shows the gear connector 290 that mechanically couples the carriage 150 to the main shaft 118. The carriage assembly 160 includes a carriage housing 148, a pawl 154, a pawl spring 180, the gear connector 290, and a window 264. The window 264 allows light (e.g., generated by an LED) to shine through the window 264. A sensor on the other side of the window 264 can sense which portions of the window 264 are blocked and/or which positions of the window 264 has light shining therethrough. Slide-clamp ID holes 294 on a slide clamp 152 can indicate a binary number which can be used to identify the slide clamp 152 and/or the set the slide clamp 152 is attached to. As shown in FIG. 37, when the carriage 150 is in the closed position, a cover 266 blocks the entrance to the carriage assembly 160 (also see FIG. 37).

Figure 39:
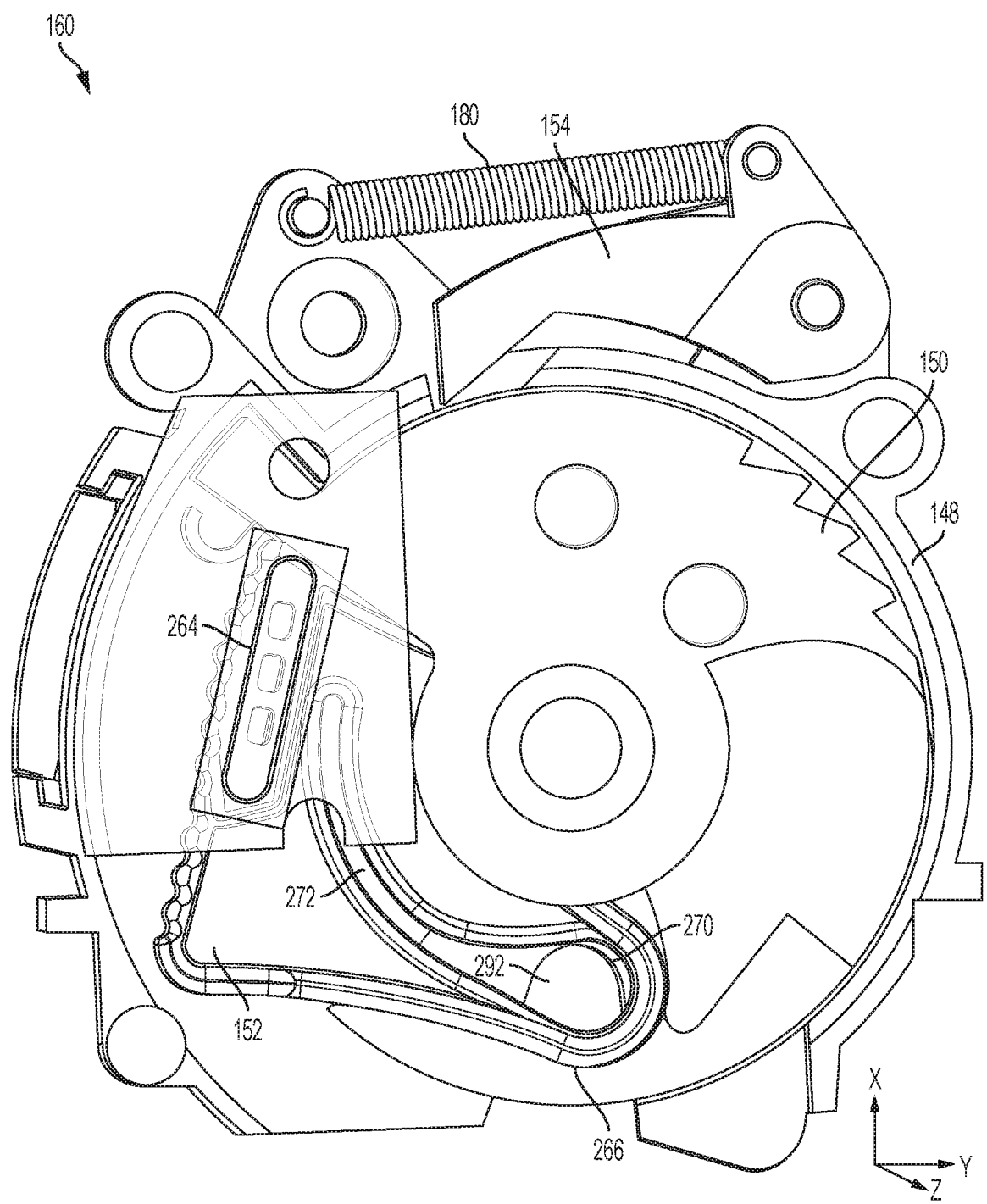
FIG. 39 shows the carriage assembly of the peristaltic pump of FIG. 1 from a bottom side of the carriage assembly with the bottom portion of the carriage housing removed for clarity in accordance with an embodiment of the present disclosure.

FIG. 39 shows the carriage assembly 160 of the peristaltic pump 100 of FIG. 1 from a bottom side of the carriage assembly 160 with the bottom portion of the carriage housing 148 removed for clarity. As shown, the cover 266 can be easily seen as blocking the entrance of the carriage assembly 160, which in turn prevents insertion of anything into the carriage 150 while the carriage 150 is rotated to the closed position. The flowing portion 270 of the slide clamp 152 is over the carriage-assembly hole 292 which allows fluid to flow through the tube 216. When the carriage 150 is in the open position, the carriage-assembly hole 292 holds the tube 216 such that the tube 216 is positioned between the occluding portion 272 of the slide clamp 152. This requires the slide clamp 152 to be loaded and unloaded into the carriage 150 by the user only when the slide clamp 152 is occluding the tube 216.

Figure 40:
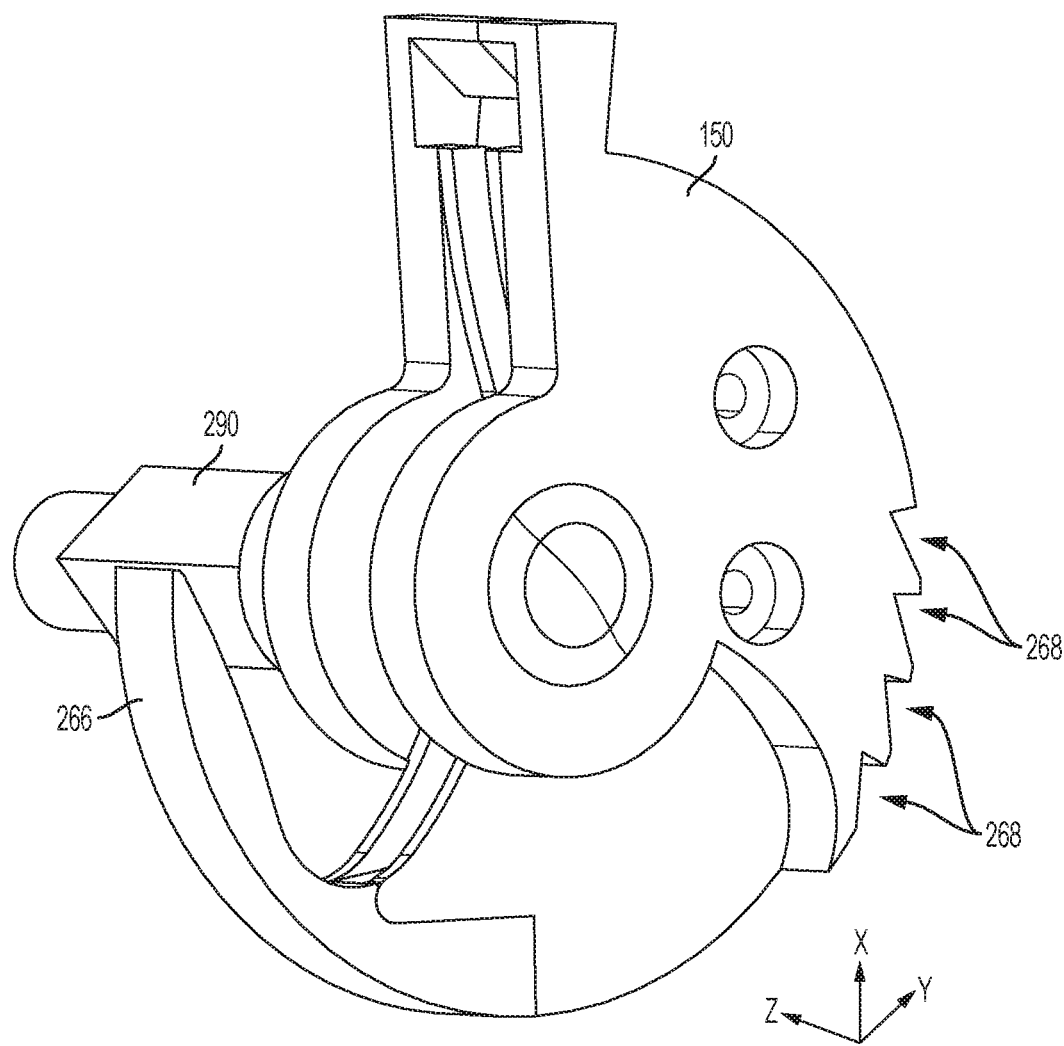
FIGS. 40 and 41 show views of the carriage of the peristaltic pump of FIG. 1 in accordance with an embodiment of the present disclosure.
Figure 41:
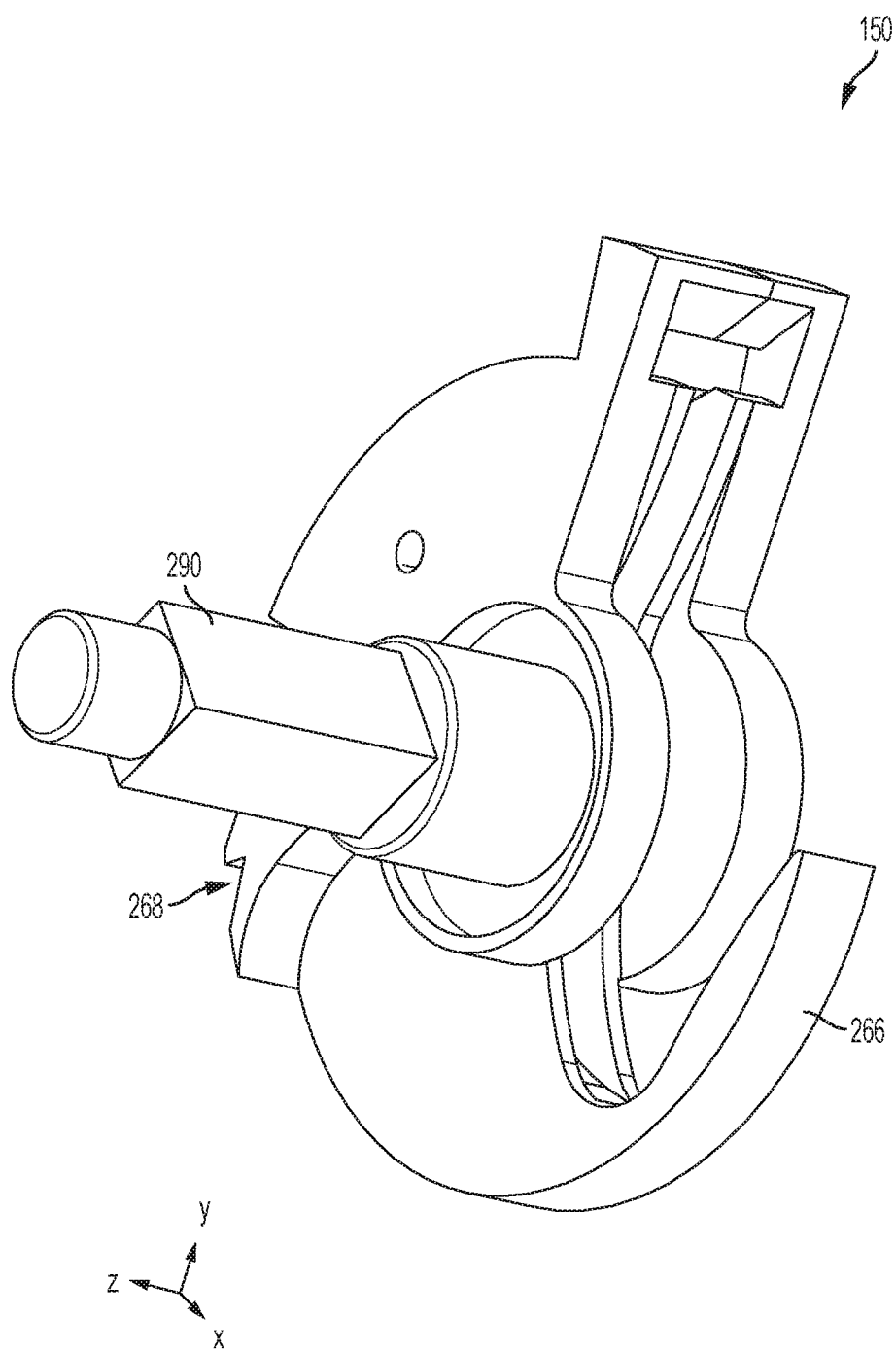

After the slide clamp 152 is secured within the carriage 150 and the door 102 is shut, actuation of the lever 104 to the closed position rotates the carriage 150 such that the carriage-assembly hole 292 holds the tube 216 such that the tube 216 can reside within the flowing portion 270 of the slide clamp 152. When the tube 216 is positioned within the flowing portion 270, fluid may easily flow through the tube 216. FIGS. 40 and 41 show views of the carriage 150 of the peristaltic pump 100 of FIG. 1. The notches 268 are easily seen as is the cover 266.

Figure 42:
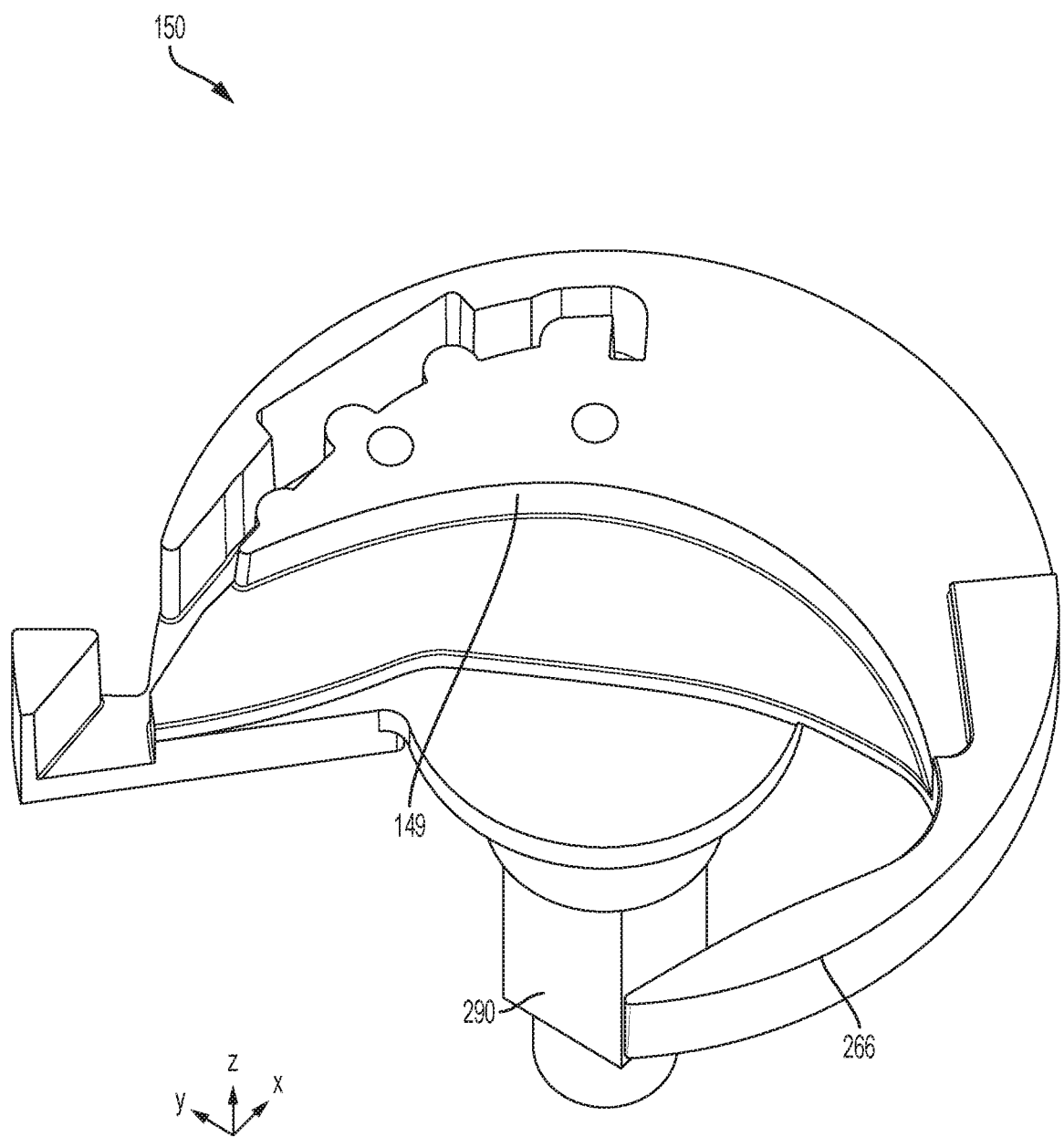
FIG. 42 shows the carriage of the peristaltic pump of FIG. 1 with the top portion removed in accordance with an embodiment of the present disclosure.
Figure 43:
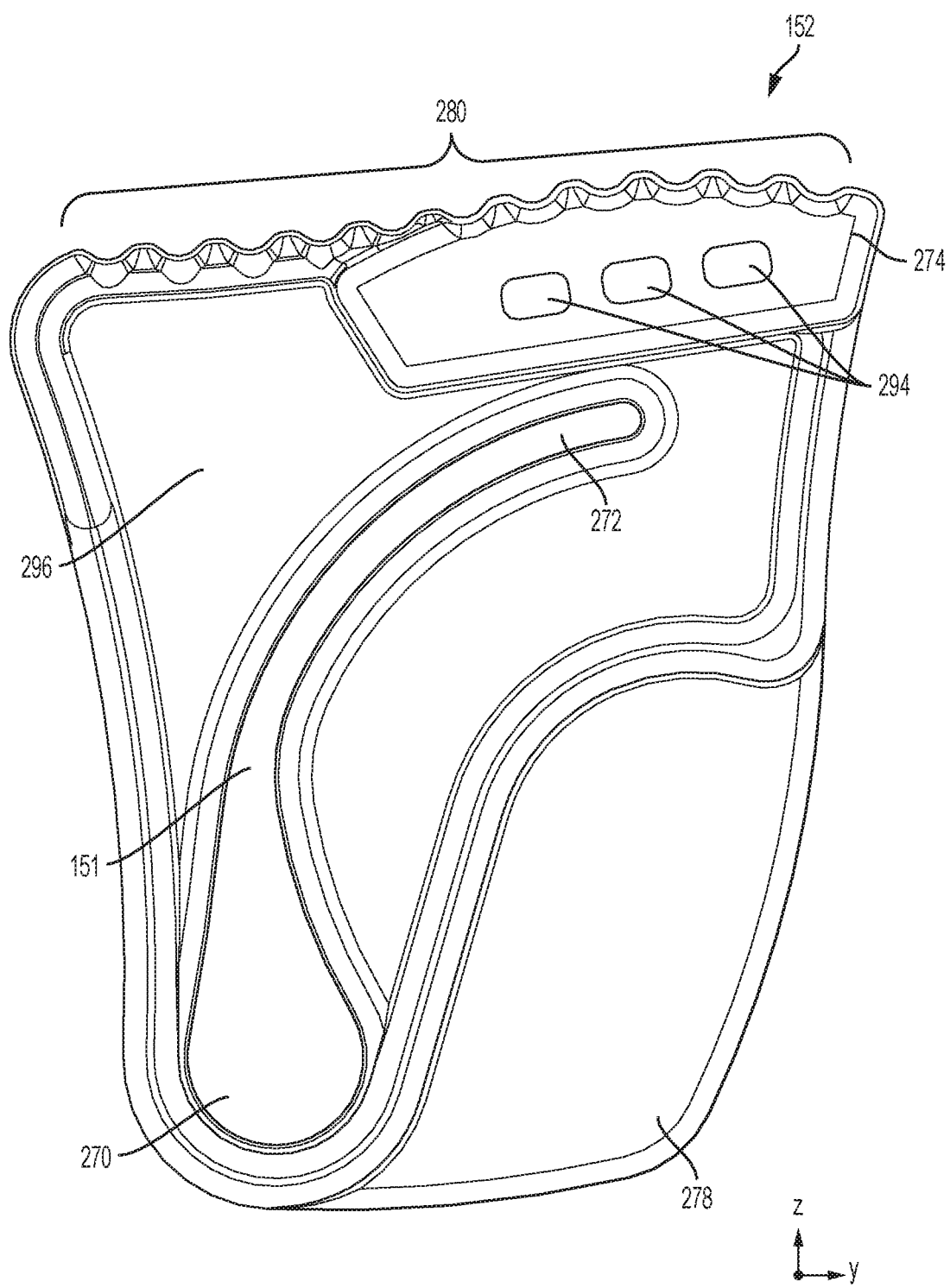
FIGS. 43-48 show several views of the slide clamp that can be inserted into the carriage of the peristaltic pump of FIG. 1 in accordance with an embodiment of the present disclosure.
Figure 44:
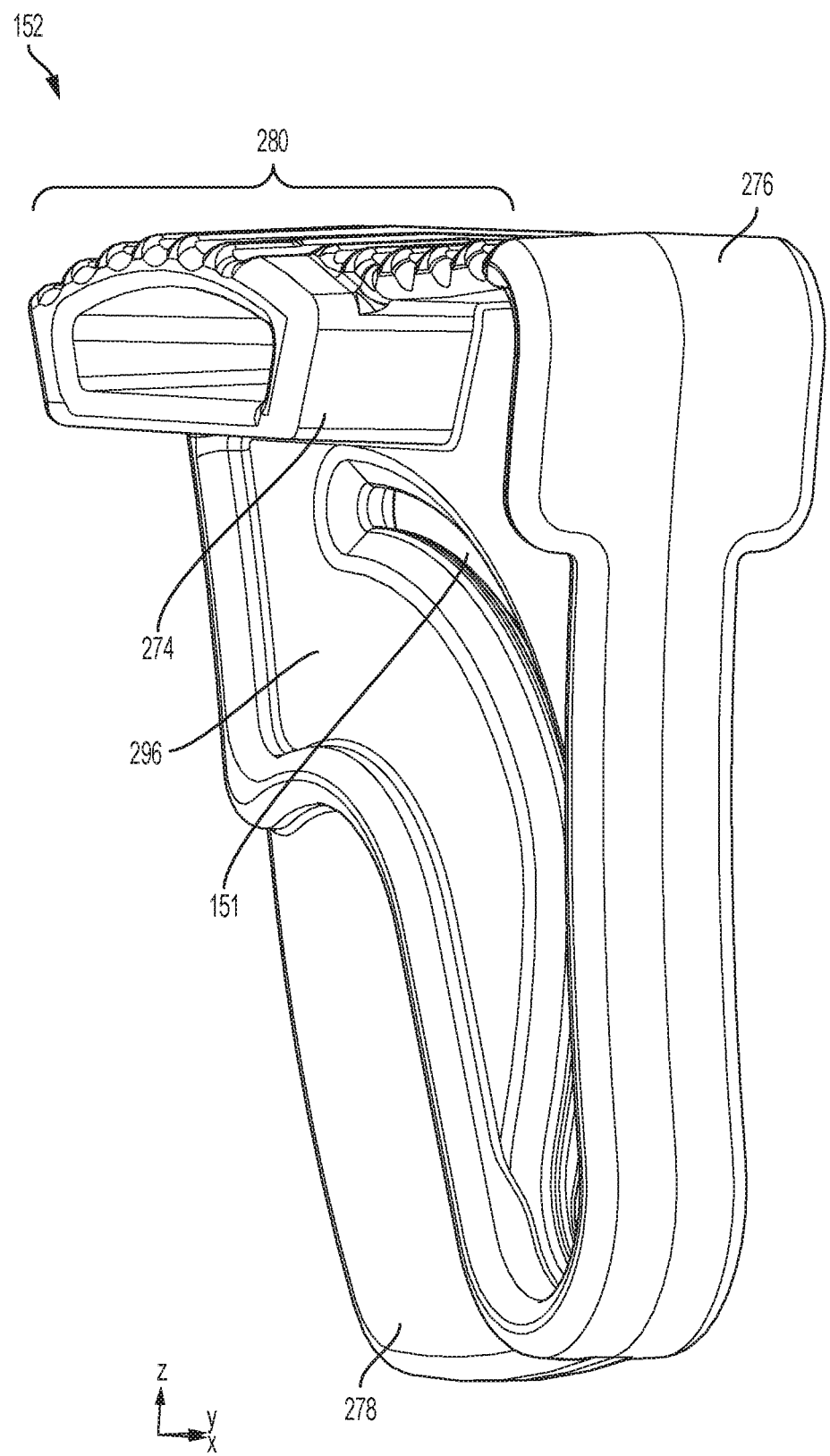
Figure 45:
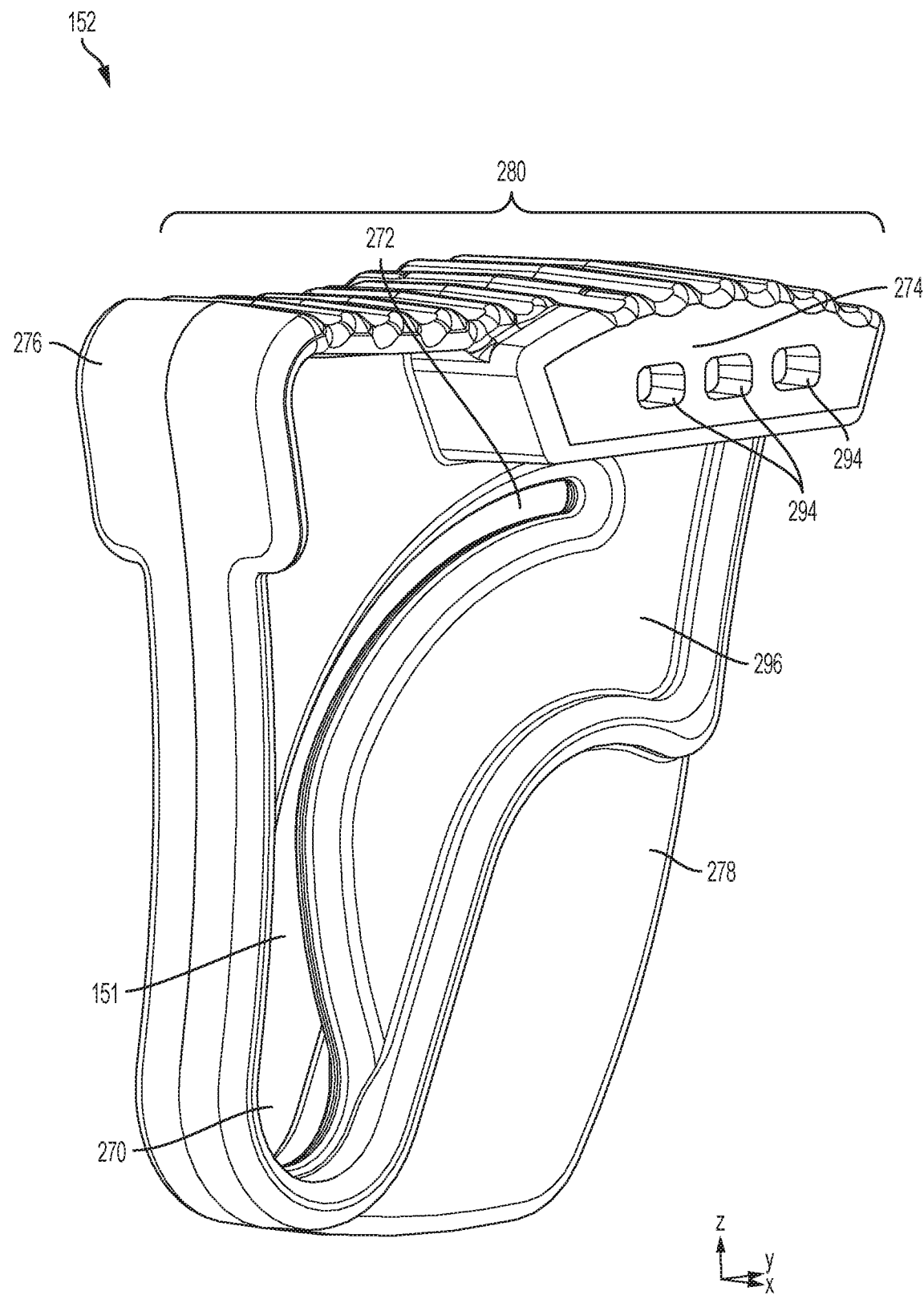
Figure 46:
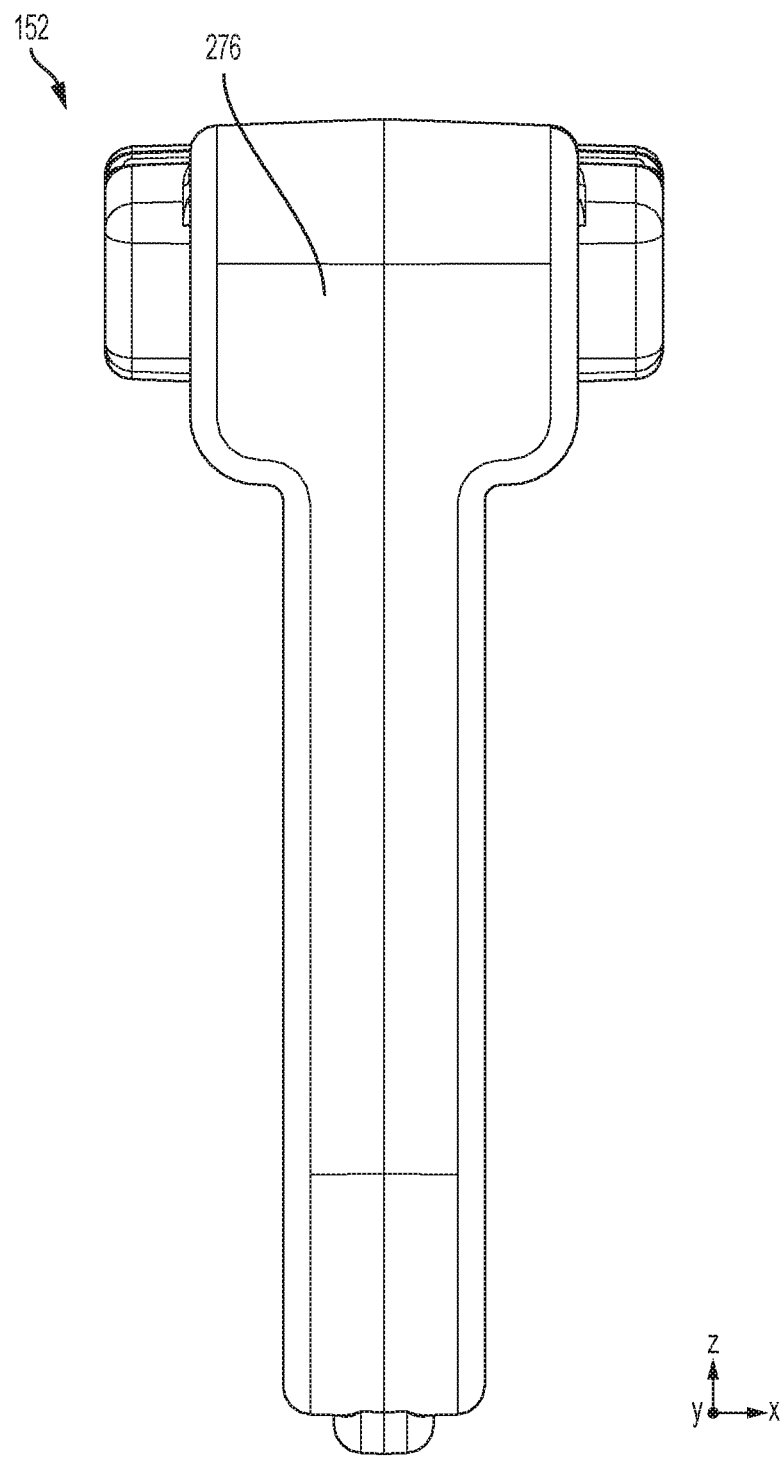
Figure 47:
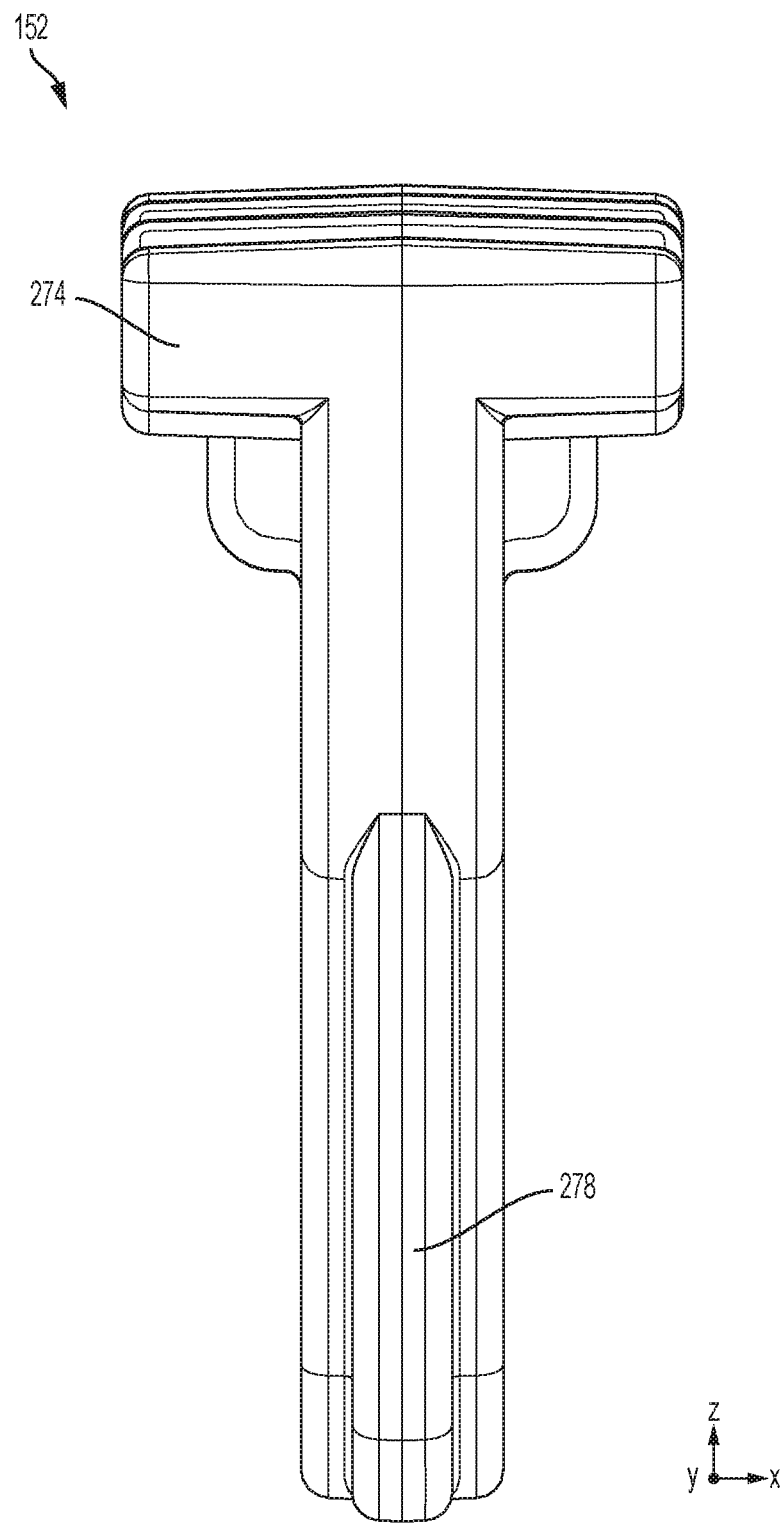
Figure 48:
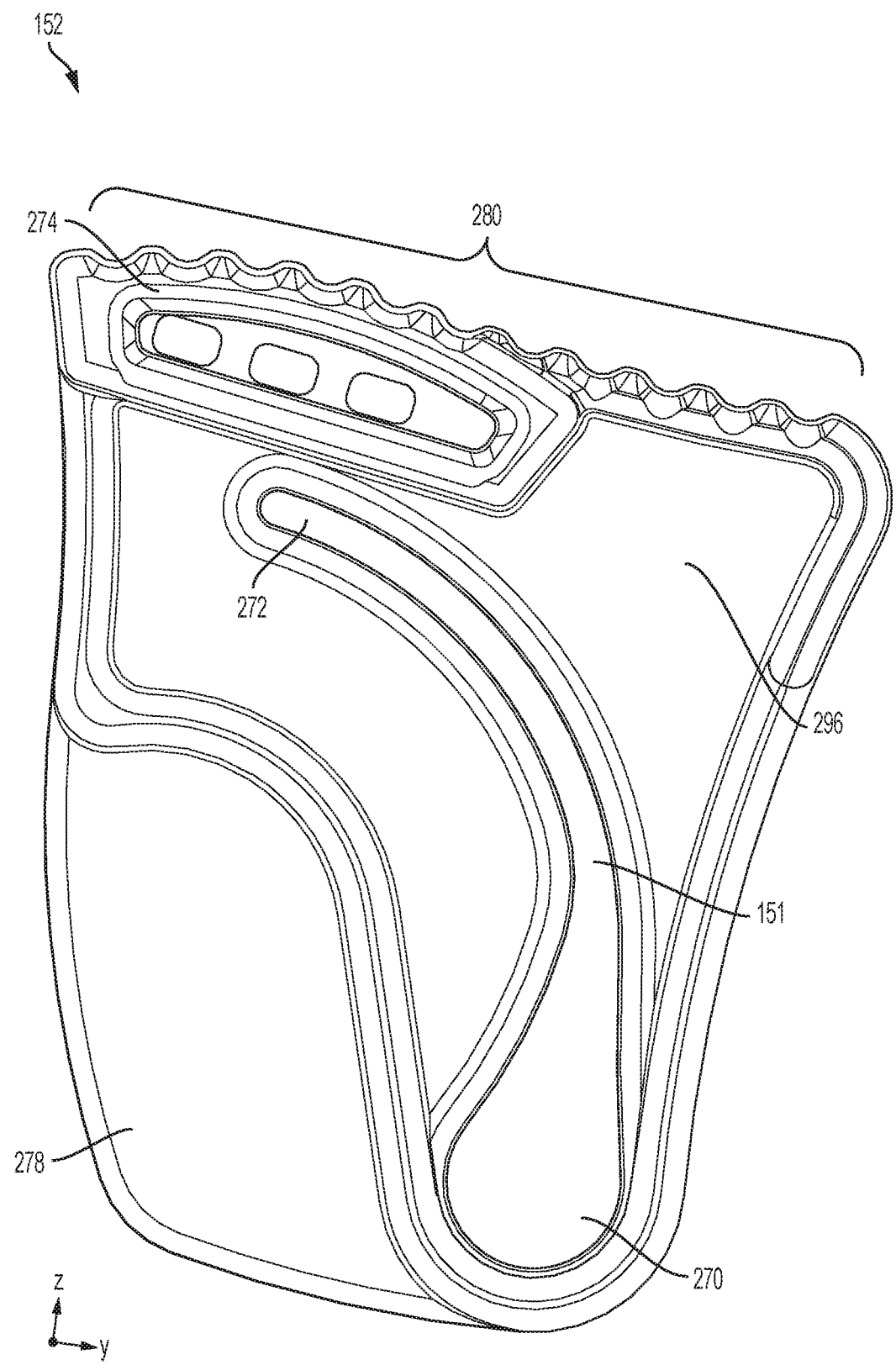

FIG. 42 shows the carriage 150 with the top portion removed to illustrate a guide surface 149 of the carriage 150. The guide surface 149 is configured to allow the stabilizer 278 of the slide clamp 152 to translate insertion force applied to the thumb rest 280 into sliding of the tube 216 within a arcuate slot 151 of the slide clamp 152 which is described in greater detail below.

FIGS. 43-48 show several views of the slide clamp 152 that can be inserted into the carriage 150 of the peristaltic pump 100 100 100 of FIG. 1. The slide clamp 152 includes a body 296 defining an arcuate slot 151 that receives a tube 216 therein. The arcuate slot 151 includes an occluding portion 272 and a flowing portion 270. The slide clamp 152 also includes a stabilizer 278. The stabilizer 278 facilitates insertion of the slide clamp 152 into the carriage 150. A thumb rest 280 is shown that provides a frictional area for a person to press the slide clamp 152 into the carriage 150. As is easily seen in FIG. 43, the thumb rest 280 includes an extension 274. Within the extension 274 are the slide-clamp ID holes 294 for the light to identify the slide clamp 152. The slide-clamp ID holes 294 are easily seen in FIG. 43. The back 276 is easily seen in FIG. 45.

FIGS. 49-53 show a sequence of events to illustrate the slide clamp 152 of FIGS. 43-48 being inserted in the carriage assembly 160 of the peristaltic pump 100 of FIG. 1. The carriage 150 as shown in FIGS. 49-53 is shown with the top removed for easy viewing of the interaction of the stabilizer 278 and the guide surface 149. The stabilizer 278 and the guide surface 149 interact with each other in order to prevent the slide clamp 152 from being inserted into the carriage at an angle that would pinch the tube 216.

Initially, prior to insertion of a slide clamp 152 of an administration set, a user may place the tube 216 anywhere within the arcuate slot 151. If the user places the tube 216 within the end of the occluding portion 272 of the arcuate slot 151, the carriage 150 can receive the slide clamp 152 with the tube 216 being occluded without moving or repositioning the tube 216 within the arcuate slot 151.

However, if the user has the tube 216 positioned in the flowing portion 270 or partially between the flowing portion 270 and the end of the occluding portion 272, the carriage assembly 160 will reposition the tube 216 to the end of the occluding portion 272 as the slide clamp 152 is inserted into the carriage 150.

FIG. 49 shows the initial insertion of the slide clamp 152 where the tube 216 is in the flowing portion 270. As can be seen in the sequence of events from FIG. 49 to FIG. 53, as the slide clamp 152 is inserted, the tube 216 slides into the end of the occluding portion 272 as shown in FIG. 34. During this process, the stabilizer 278 and the guide surface 149 interact with each other to prevent the tube 216 from getting pinched or damaged from forces orthogonal to the center line of the arcuate slot 151.

That is, as a user pushes on the thumb rest 280, the guide surface 149 causes the slide clamp 152 to be guided to the fully-inserted position in the carriage 150 as shown in FIG. 53 while adjusting the angle of the slide clamp 152 to translate forces on the thumb rest 280 to the tube 216 so that the tube 216 experiences a force substantiality parallel with the center line of the arcuate slot 151. The stabilizer 278 is guided by the guide surface 149 because the stabilizer 278 will abut the guide surface 149 if the user attempts to rotate the slide clamp 152 counterclockwise (from the perspective shown in FIGS. 49-53) while attempting to insert the slide clamp 152. Thus, the stabilizer 278 of the slide clamp 152 prevents the tube 216 from becoming pinched or damaged by the interface between the carriage 150 and the slide clamp 152. The stabilizer 278 and the guide surface 149 mitigate the force of the user pressing on the slide clamp 152 from being translated on the tube 216 to push the tube orthogonal with the center line of the arcuate slot 151 which would cause the tube 216 to become pinched because the tube 216 would be trapped within the channel defined by the hole 106 (see FIG. 2) if the tube 216 was forced to move orthogonally to the center line of the arcuate slot 151.

Figure 54:
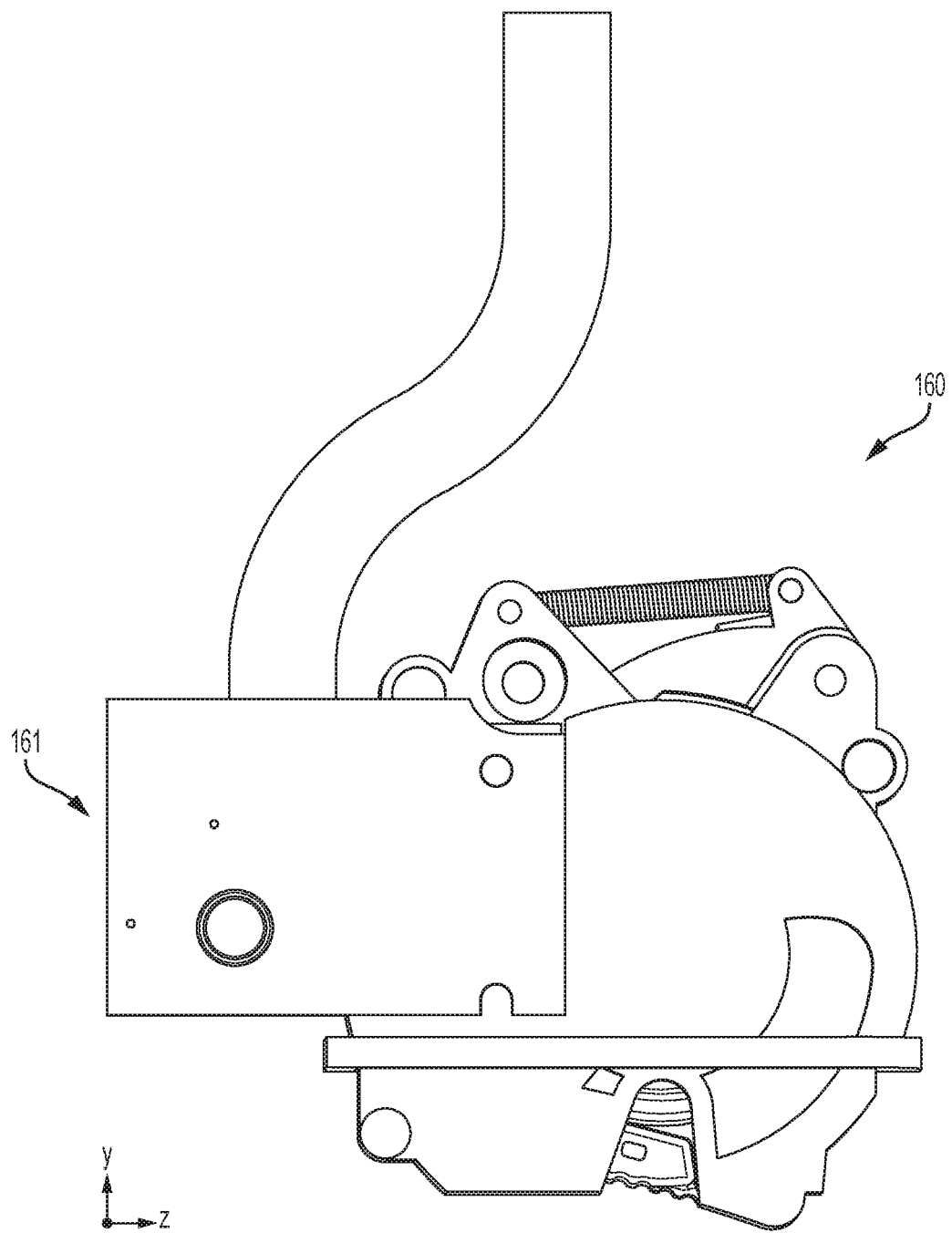
FIG. 54 shows the carriage assembly from the top side with a sensor board coupled thereto of the peristaltic pump of FIG. 1 in accordance with an embodiment of the present disclosure.
Figure 55:
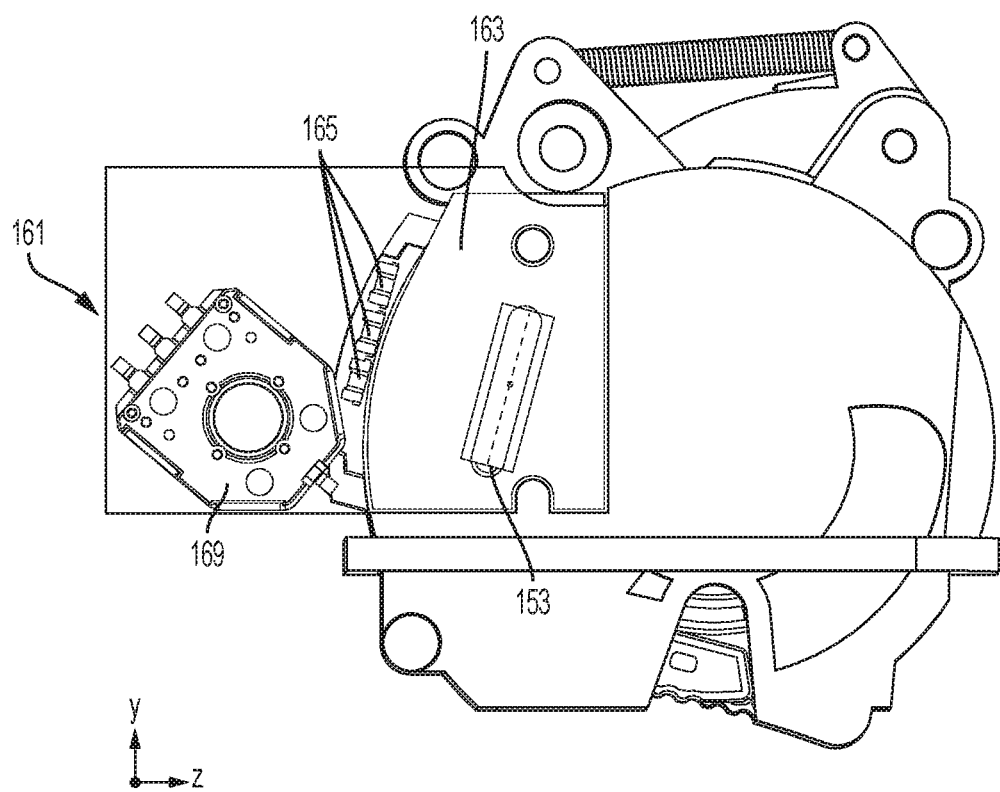
FIG. 55 shows the same view as FIG. 54 but with the sensor board shown as being transparent to show LEDs and the corresponding slide-clamp ID sensor in accordance with an embodiment of the present disclosure.
Figure 56:
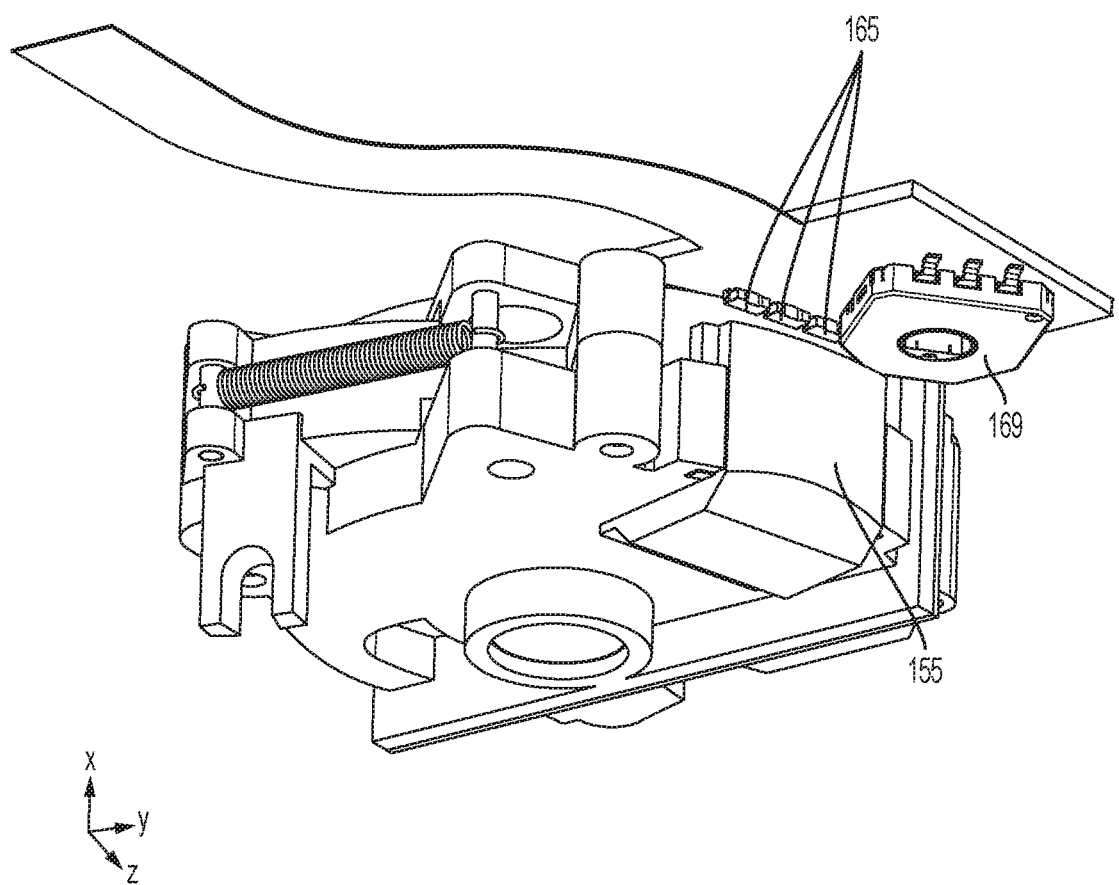
FIG. 56 shows the carriage assembly from an angled bottom view to more clearly see the LEDs of the slide-clamp ID sensor and a light pipe for the LEDs in accordance with an embodiment to the present disclosure.

FIG. 54 shows the carriage assembly 160 from the top side with a sensor board 161 coupled thereto of the peristaltic pump 100 of FIG. 1. FIG. 55 shows the same view as FIG. 54 but with the sensor board 161 shown as being transparent to show a group of LEDs 165 which are part of a slide-clamp ID sensor 163. The slide-clamp ID sensor 163 includes the LEDs 165 that are used to generate light, which may be visible light, non-visible light, infrared light, near infrared light, ultraviolet light, narrow-band light, wide-band light, within an optical portion of the electromagnetic spectrum, or some suitable combination thereof. The slide-clamp ID sensor 163 also includes an optical sensor 153, which may be a linear array of light sensitive elements, e.g., 128 grayscale detectors. Also, as is easily seen in FIG. 56, the slide-clamp ID sensor 163 includes a light pipe 155.

Figure 57:
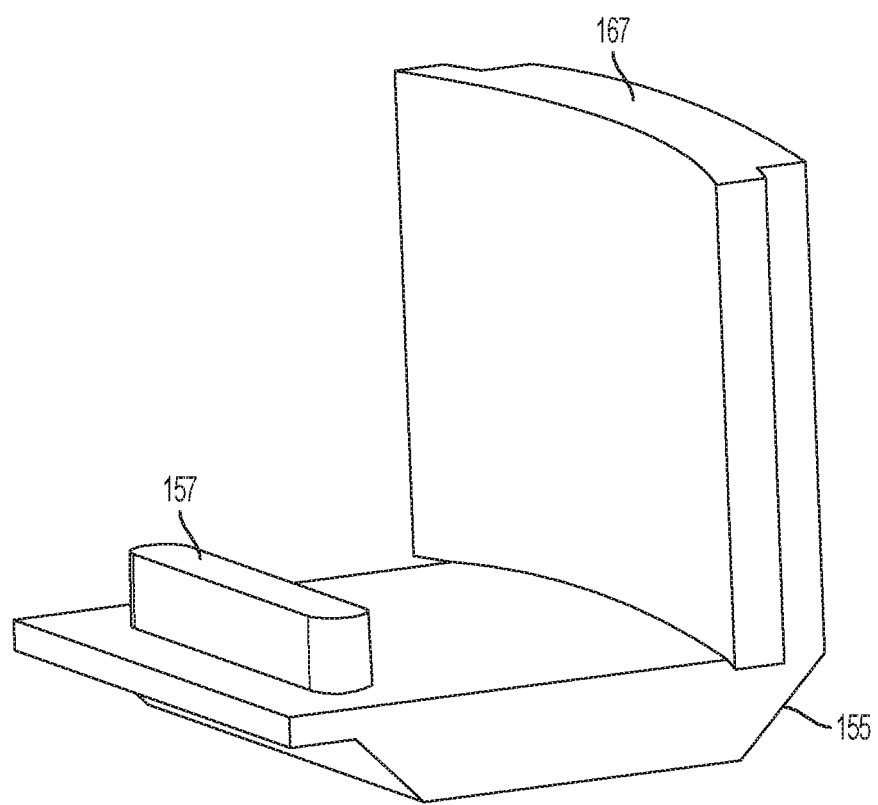
FIG. 57 shows the light pipe used in the carriage assembly of the peristaltic pump of FIG. 1 in accordance with an embodiment of the present disclosure.

The LEDs 165 emit light that is transmitted within the light pipe 155 to route light to the side of the carriage assembly 160 opposite to the side that the sensor board 161 is coupled to. FIG. 57 shows the light pipe 155 including a receiver aperture 167 that receives light from the LEDs 165 (see FIG. 56) and a transmission aperture 157 that transmits light through a window 264 of the carriage assembly 160 on the bottom side of the carriage assembly 160 (see FIG. 37 for the window 264 on the bottom side). The light is transmitted through any of the slide-clamp ID holes 294 of the extension 274 (see FIG. 43) when the slide clamp 152 is in the carriage 150 and the carriage 150 is positioned in the lever-closed position (as shown in FIG. 39) when the lever 104 is closed.

Referring again to FIGS. 55 and 56, as is easily seen, using the light pipe 155 allows a single sensor board 161 to house the LEDs 165 and the optical sensor 153. The sensor board 161 also includes a rotation sensor 169 that may be a rotary encoder coupled to an end of the upper shaft 298 (see FIG. 11).

Figure 58:
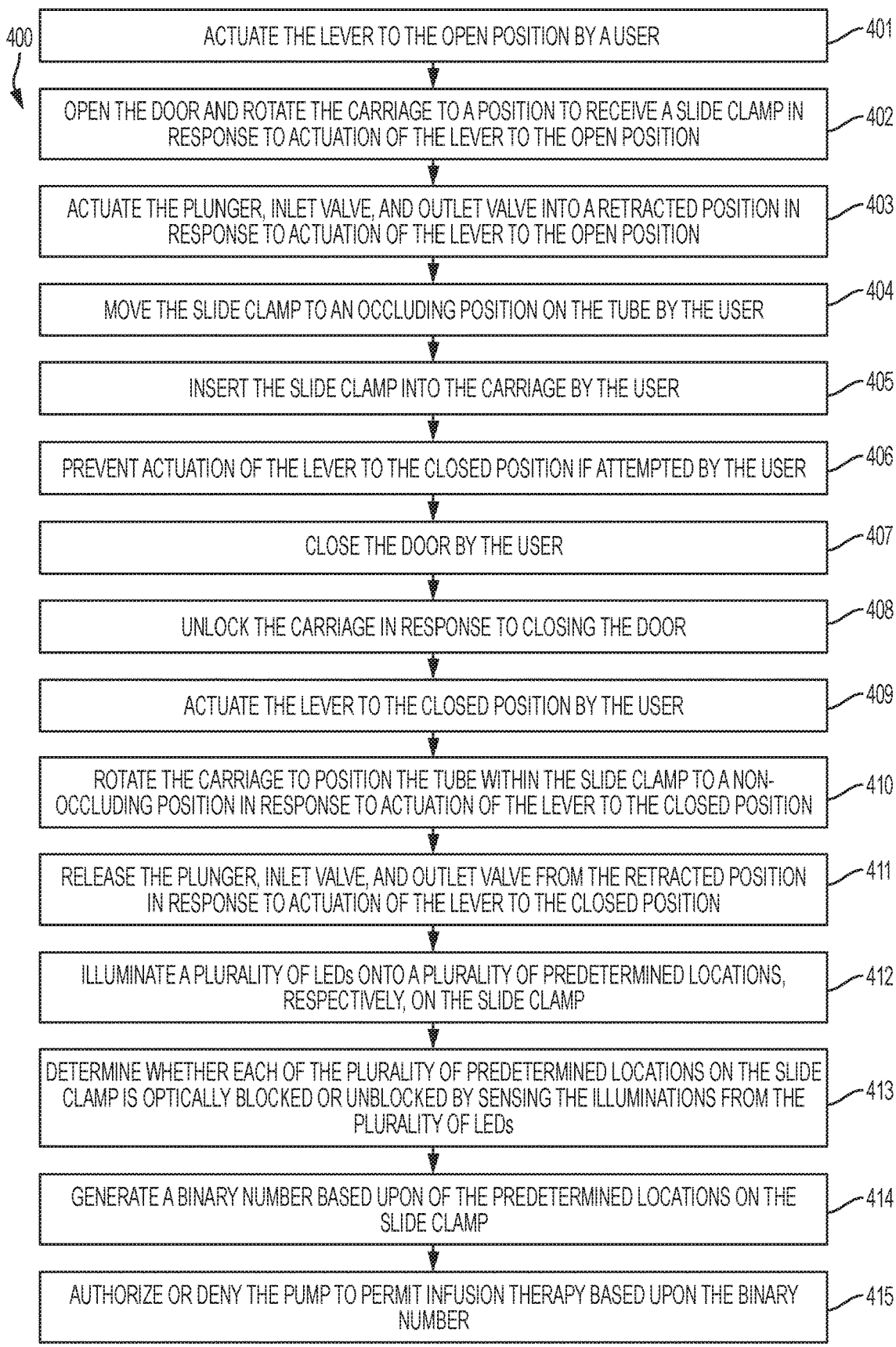
FIG. 58 shows a flow-chart diagram to illustrate a method of using the peristaltic pump of FIG. 1 in accordance with an embodiment of the present disclosure.

FIG. 58 shows a flow-chart diagram to illustrate a method 400 of using the peristaltic pump 100 of FIG. 1. The method 400 may include acts 401-415. Act 401 actuates the lever 104 to the open position by a user. That is, if the lever 104 was previously closed, the user can actuate the lever 104 open, which will open the door 102 as described above and is illustrated as Act 402 in the method. Act 402 opens the door 102 and rotates the carriage 150 to a position to receive a slide clamp 152 in response to actuation of the lever 104 to the open position (see FIG. 34). In this position, if the carriage 150 already includes a slide clamp 152 (e.g., from a previous therapy), the user can remove the slide clamp 152 and replace it with a new slide clamp 152 because in Act 402, the carriage 150 was rotated to a position where a user can remove or insert the slide clamp 152. Act 403 actuates the spring-biased plunger 116, the inlet valve 198, and the outlet valve 200 into a retracted position in response to actuation of the lever 104 to the open position. This facilitates easy insertion of the tube 216 into the raceway 168 without being impeded by one or more of the spring-biase plunger 116, the inlet valve 198, and/or the outlet valve 200.

Act 404 moves the slide clamp 152 to an occluding position on the tube 216 by the user. Act 404 is optional because during Act 405 the user will insert the slide clamp 152 into the carriage 150 and, as described above with reference to FIGS. 49-53, the tube 216 may be moved to the occluding position within the arcuate slot 151 automatically during slide clamp 152 insertion into the carriage 150.

Act 406 prevents actuation of the lever 104 to the closed position if attempted by the user while the door 102 remains open. Act 407 closes the door 102 by the user. Act 408 unlocks the carriage 150 in response to closing the door 102. Act 409 actuates the lever 104 to the closed position by the user. Act 410 rotates the carriage 150 to position the tube 216 within the slide clamp 152 to a non-occluding position in response to actuation of the lever 104 to the closed position. Act 411 releases the spring-biased plunger 116, inlet valve 198, and the outlet valve 200 from the retracted position in response to actuation of the lever 104 to the closed position. That is, the lift cam 120 or (or 302) will no longer interact with the spring-biased plunger 116, inlet valve 198, and outlet valve 200. Act 412 illuminates a plurality of LEDs 165 onto a plurality of predetermined locations on the slide clamp 152, such as on the slide-clamp ID holes 294. Act 413 determine whether each of the plurality of predetermined locations on the slide clamp 152 is optically blocked or unblocked by sensing the illuminations from the plurality of LEDs 165. Act 414 generates a binary number based upon of the predetermined locations on the slide clamp 152. Act 415 authorizes or denies the pump 100 to permit infusion therapy based upon the binary number.

Figure 59:
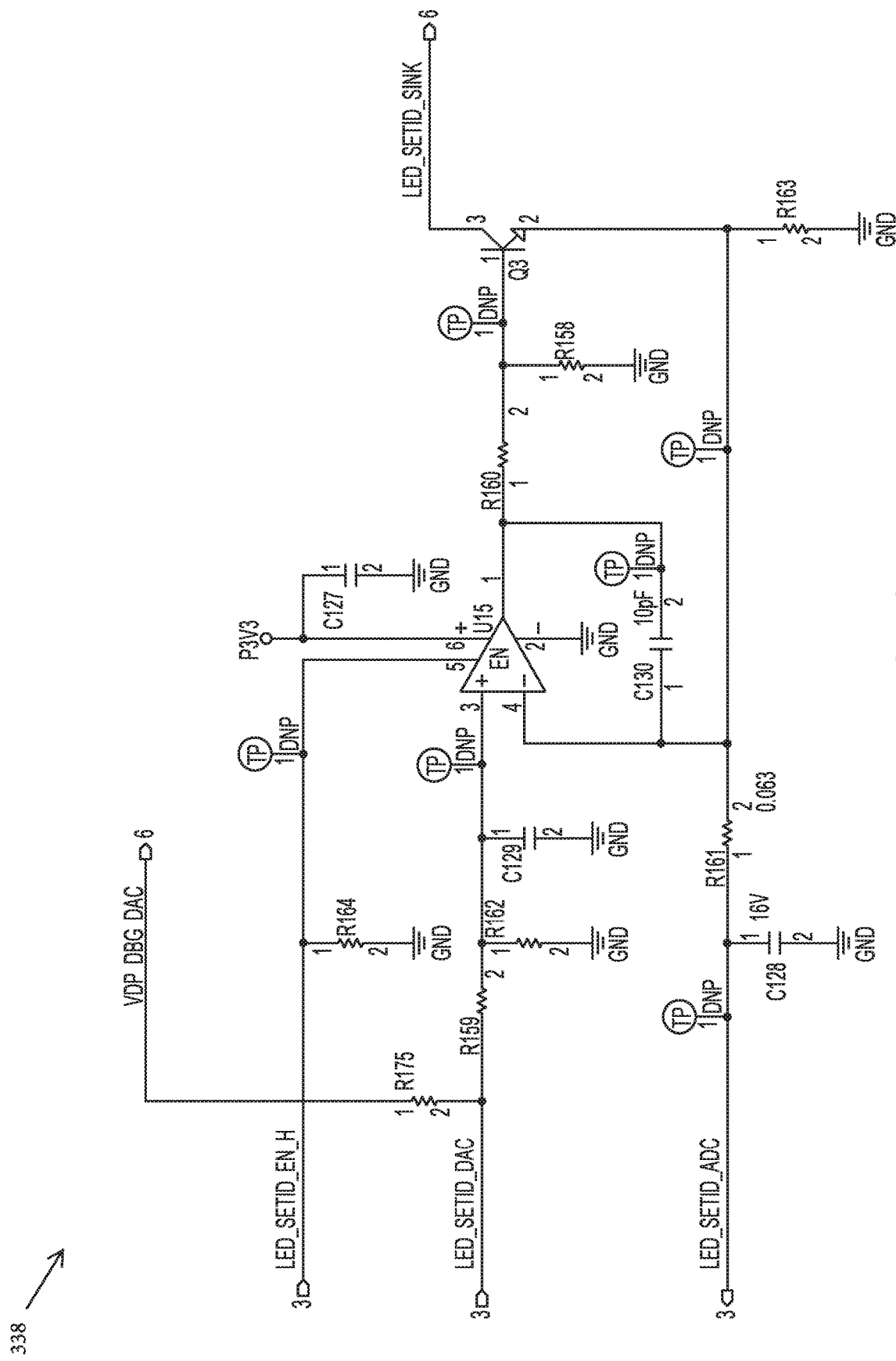
FIG. 59 shows a circuit of the peristaltic pump of FIG. 1 for driving the LEDs of the slide-clamp ID sensor in accordance with an embodiment of the present disclosure.

FIG. 59 shows a driver circuit 338 of the peristaltic pump 100 of FIG. 1 for driving the LEDs 165 of the slide-clamp ID sensor 163. The driver circuit includes an op-amp U15 which is arranged in a negative feedback loop to a drive transistor Q3. The op-amp U15 drives its output such that a target voltage is achieved. This target voltage controls the base of the transistor Q3 which in turn causes the transistor Q3 to control for a constant current through resistor R163. This causes the current flowing from terminal 3 to terminal 2 of the transistor Q3 is be substantially constant.

Figure 60:
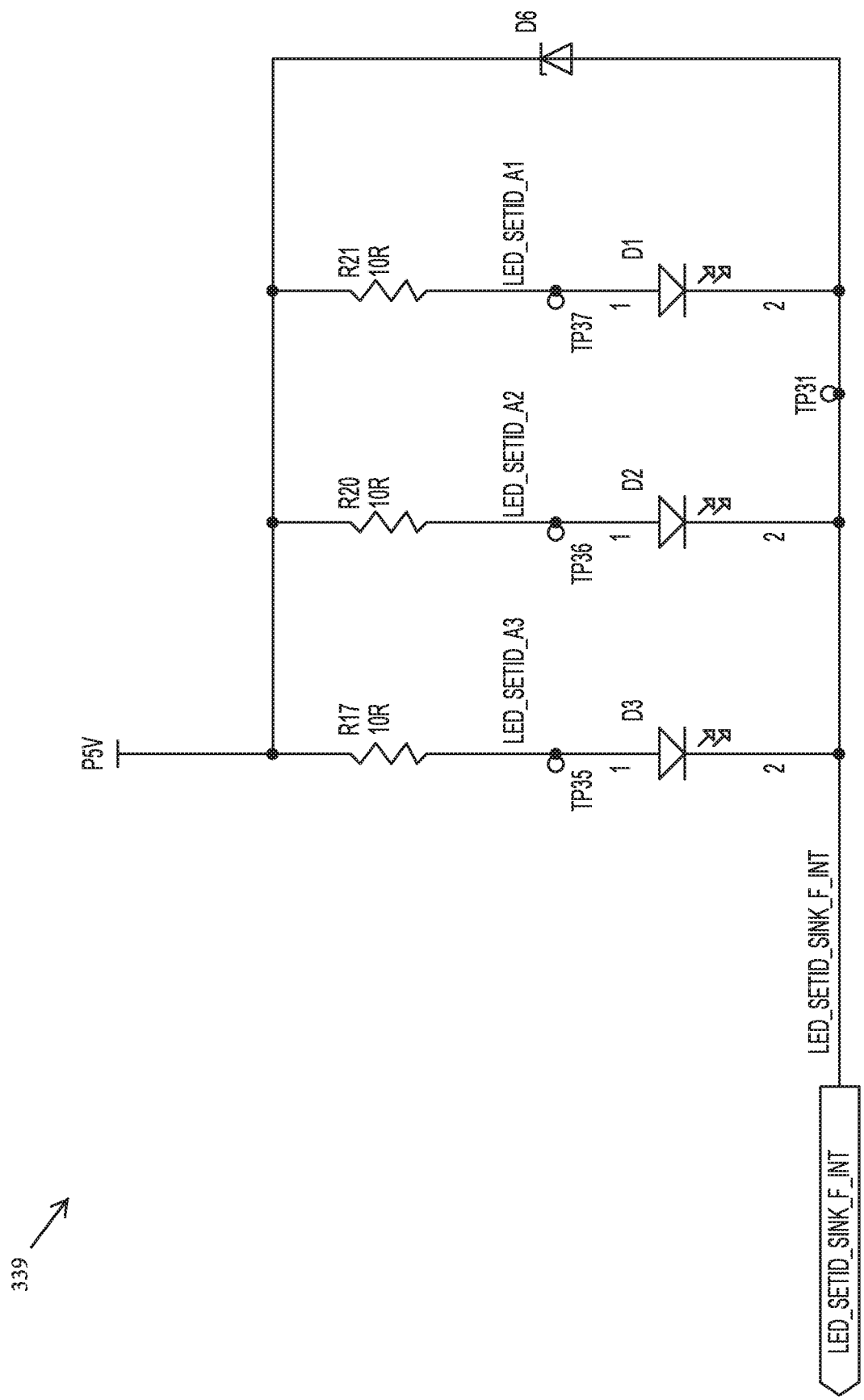
FIG. 60 shows a circuit of the peristaltic pump of FIG. 1 showing the arrangement of the LEDs of the slide-clamp ID sensor in accordance with an embodiment of the present disclosure.

FIG. 60 shows an LED circuit 339 of the peristaltic pump 100 of FIG. 1 showing the arrangement of the LEDs 165 of the slide-clamp ID sensor 163. The LED_SETID_SINK_F_INT pin is coupled to the output of the circuit of FIG. 59 which includes the same label. The constant current causes the LEDs D1, D2, D3 to generate optical light which is directed through the light pipe 155. The LEDs D1, D2, D3 may be the LEDs 165 shown in FIG. 55-56.

Figure 61:
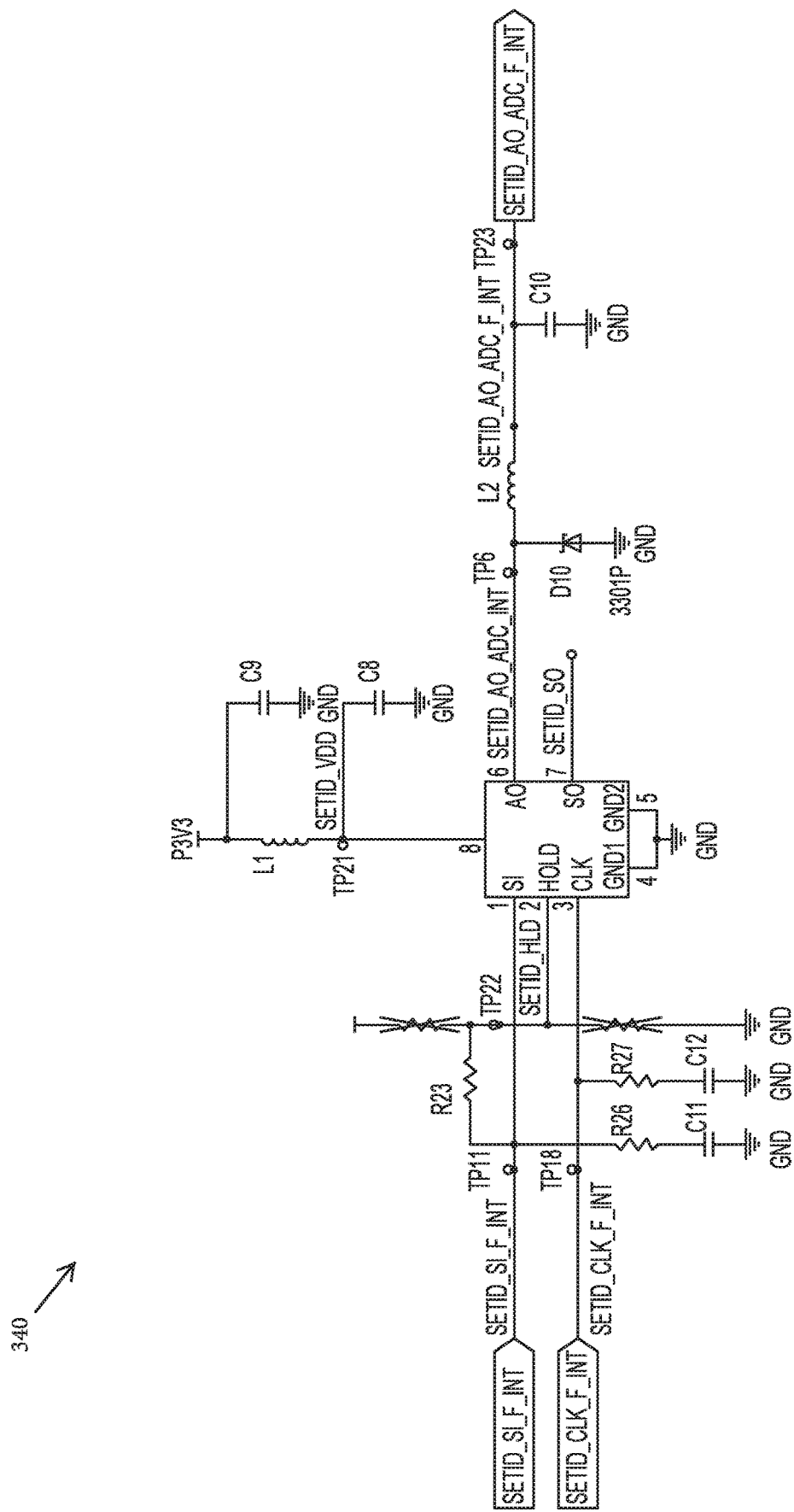
FIG. 61 shows a circuit of the peristaltic pump of FIG. 1 for sensing light received after light from the LEDs has passed through the slide-clamp ID holes of the extension of the slide clamp in accordance with an embodiment of the present disclosure.

FIG. 61 shows an optical-sensor circuit 340 of the peristaltic pump 100 of FIG. 1 for sensing light received after light from the LEDs 165 has passed through the slide-clamp id holes 294 of the extension 274 of the slide clamp 152. The optical sensor circuit of FIG. 61 uses a linear detector shown as IC U3. In some embodiments of the present disclosure, the IC U3 may be part number TSL1401CCS manufactured by ams AG of Tobelbader Strasse 308141, Premstaetten, Austria. However, any suitable optical sensor 153 may be used including, but not limited to, other linear optical sensors. The IC U3 may be the optical sensor 153 shown in FIG. 55. Output of the IC U3 is sent to a processor via pin 6 of the IC U3 after being processed, e.g., by an analog-to-digital converter (not shown) that in some specific embodiments, is integrated into the processor. However, the analog-to-digital converter may be a separate integrated circuit from the processor.

Figure 62:
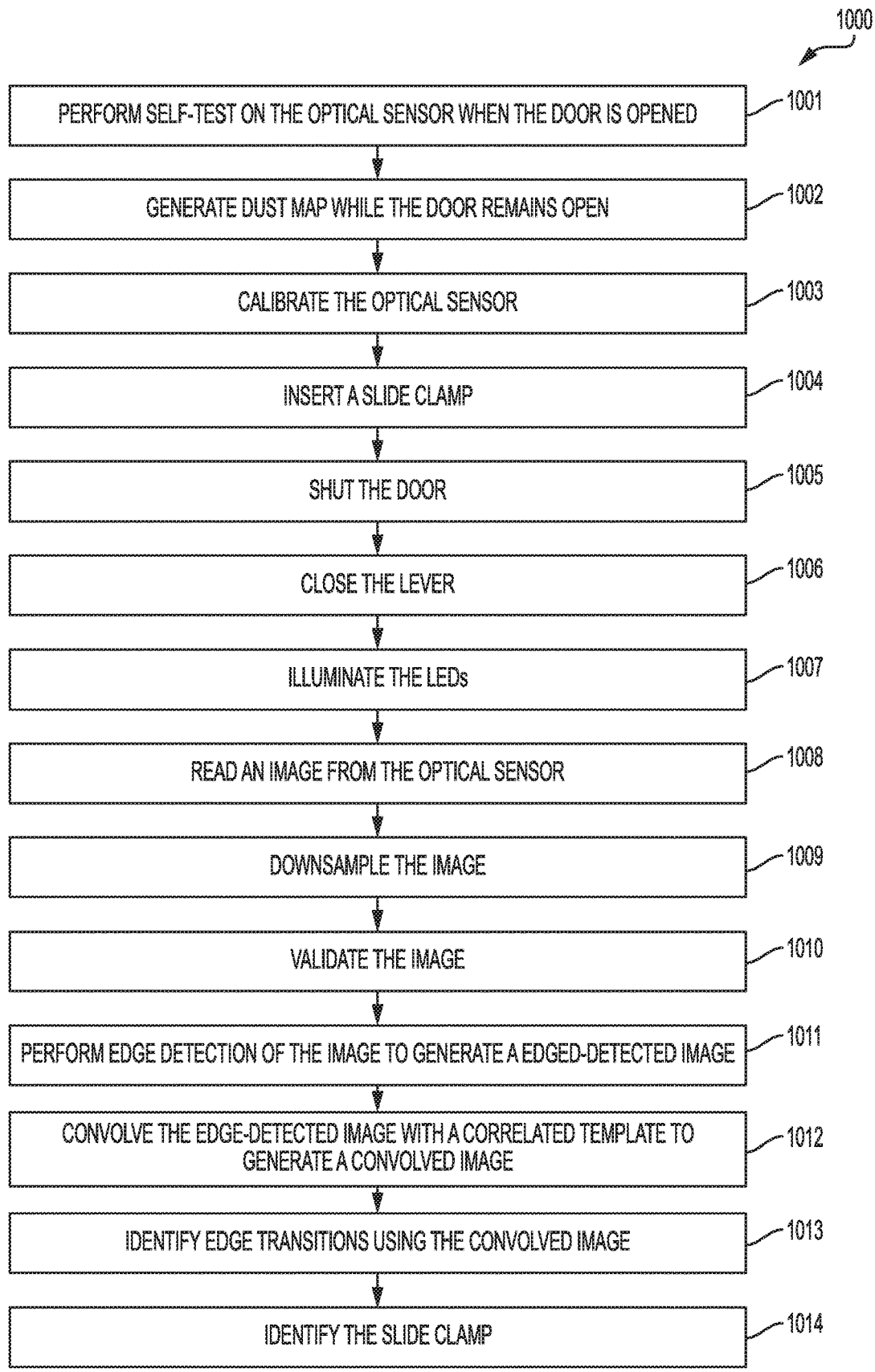
FIG. 62 shows a flow chart diagram illustrating a method of using data from the light sensor shown in FIG. 61 to identify a slide clamp in accordance with an embodiment of the present disclosure.

FIG. 62 shows a flow chart diagram 1000 illustrating a method of using data from the light sensor shown in FIG. 61 to identify a slide clamp 152. The holes or absence of holes on the slide clamp 152 may include 10 locations that correspond to 10 bits such that 10 different codes can be identified each of which corresponds to an infusion-set model number connected to the slide clamp 152. The 10 codes can have a hamming distance of four relative to each other. And if any code is shifted to the left or right, the shifted code will have a hamming distance of three when the shift is less than 3 and a hamming distance of two when the shift is greater than or equal to 3. The codes may have an even number of ones and zeroes, e.g., 6/4 or 8/2. The codes may have at least six transitions from 1 to 0 or from 0 to 1.

The method includes Acts 1001-1014. Act 1001 performs a self-test on the optical sensor when the door is opened. The optical sensor may be 128 pixels wide and each bit may be no less than 11 pixels wide. Act 1002 generates a dust map while the door remains open. Act 1003 calibrates the optical sensor. Act 1004 inserts a slide clamp. Act 1005 shuts the door. Act 1006 closes the lever. Act 1007 illuminates the LEDs. Act 1008 reads an image from the optical sensor. A PI controller may control the exposure so that a mean image intensity is at or close to a mid-range value or other predetermined value. Act 1009 downsamples the image. For example, each grayscale pixel in the image may be downsampled from 12 bits to 8 bits. Act 1010 validates the image. For example, variance and mean values must be within predetermined ranges to be validated. Act 1011 performs edge detection of the image to generate an edged-detected image. The edge detection may be performed using a modified Prewitt kernel with a kernel function of {−1, −2, −3, 0, 3, 2, 1}. Act 1012 convolves the edge-detected image with a correlated template to generate a convolved image. Act 1013 identifies edge transitions using the convolved image. An area of the highest intensity may be considered to be a center of a bit. Thereafter, a location is based upon fixed distances to the left and/or right where values are expected to be. That is, bit indices are used to sample the original image with a threshold value to determine whether a location is a '1' or '0'. Each value is an average of five pixels centered around the sample point, in some specific embodiments. Act 1014 identifies the slide clamp. A lookup table may be used to correspond values with infusion set part numbers.

Referring generally to the drawings, FIGS. 63-96 show an alternative embodiment of the peristaltic pump 100 of FIG. 1 where an alternative lift cam 121, an alternative mechanical linkage between the shaft and carriage 150, and an alternative door catch 308 are used and is labeled generally as peristaltic pump 300.

Figure 63:
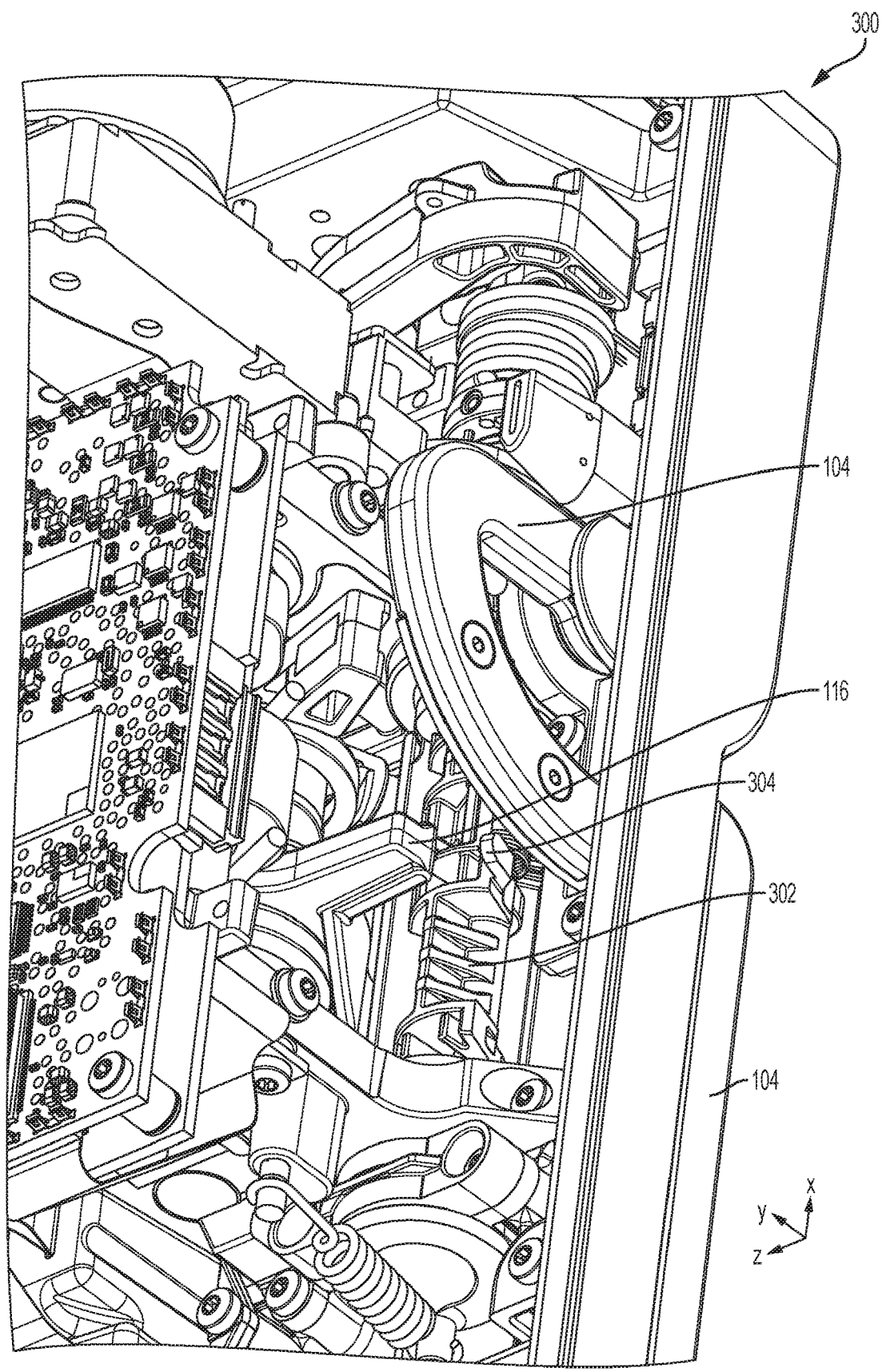
FIG. 63 shows an alternative embodiment of the peristaltic pump of FIG. 1 where an alternative lift cam, an alternative mechanical linkage between the shaft and carriage, and an alternative door catch are used in accordance with an embodiment of the present disclosure.
Figure 64:
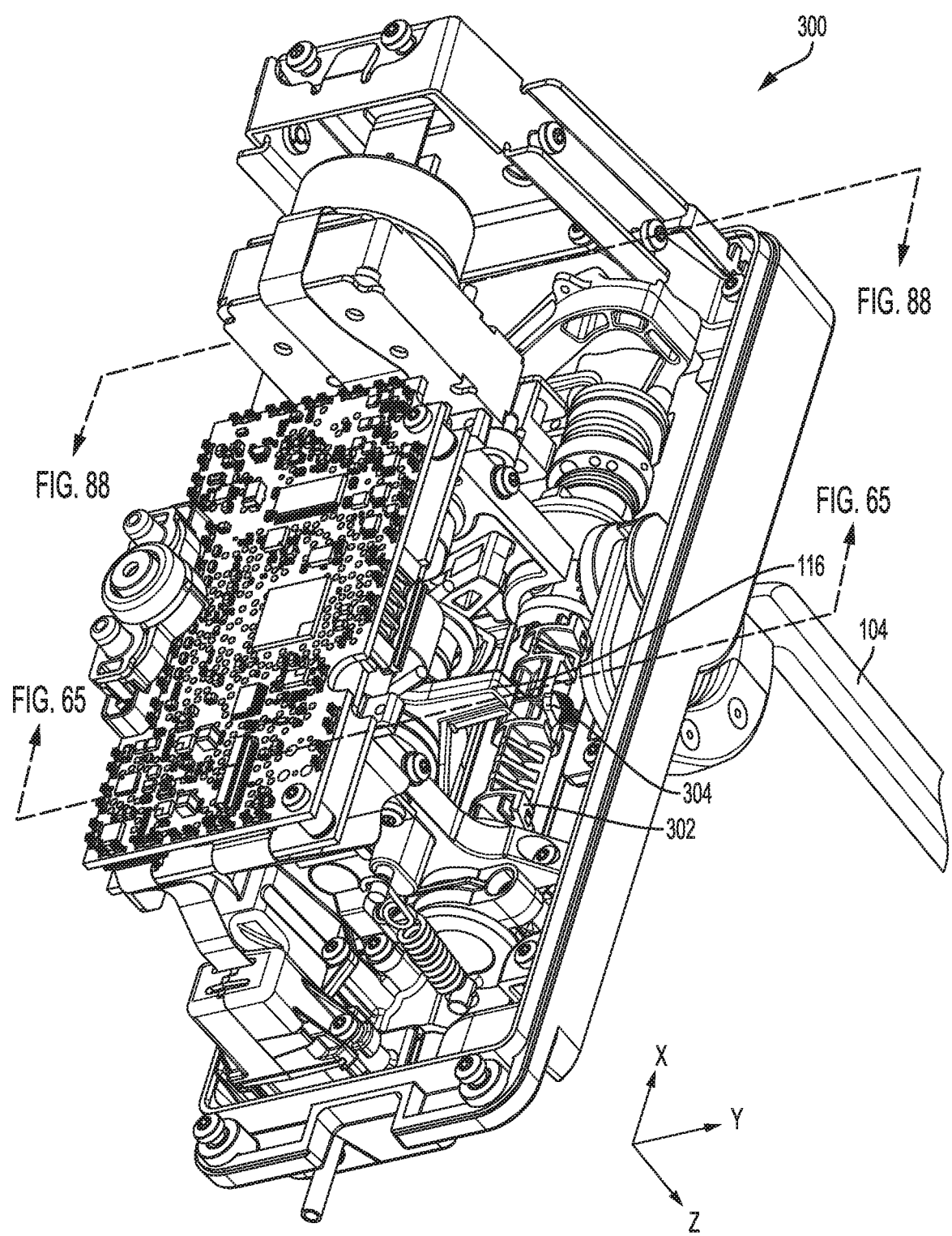
FIG. 64 shows another view of the peristaltic pump of FIG. 63 to illustrate the operation of the lift cam in accordance with an embodiment of the present disclosure.
Figure 65:
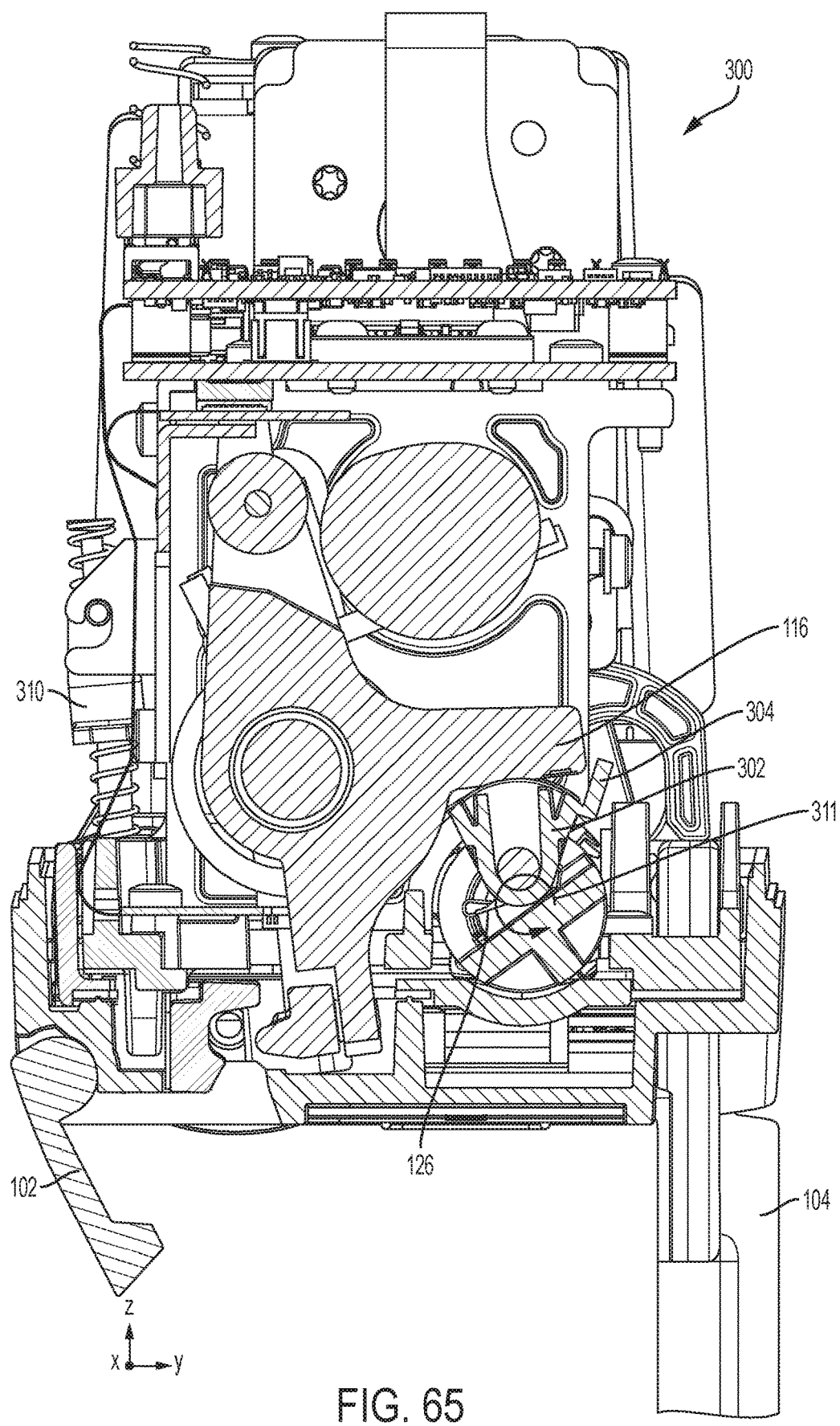
FIG. 65 shows a cross-sectional view of the lift cam of the peristaltic pump of FIG. 63 when the lever is in the open position accordance with an embodiment of the present disclosure.
Figure 66:
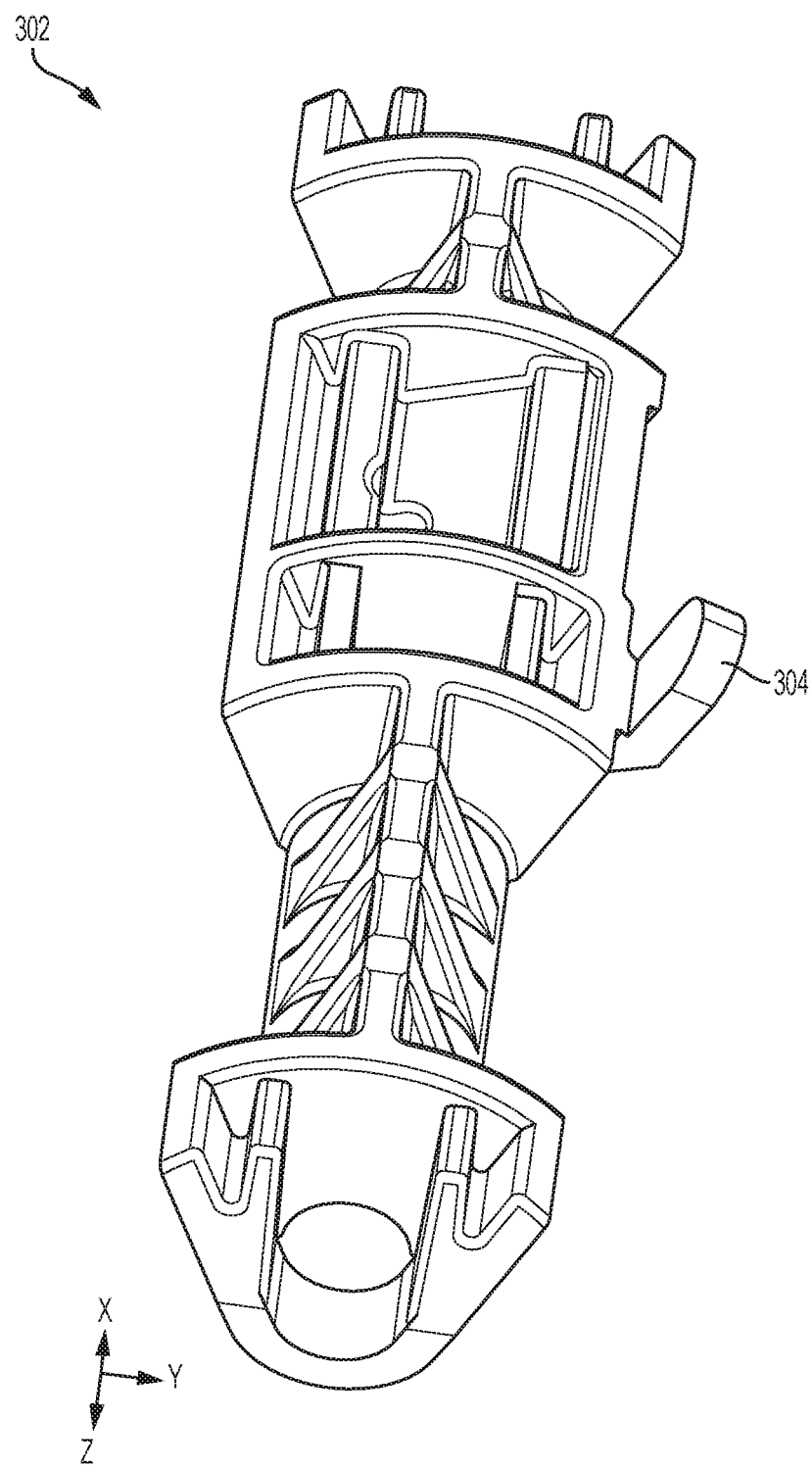
FIGS. 66-72 show the lift cam of the peristaltic pump of FIG. 63 from various viewing angles in accordance with an embodiment of the present disclosure.
Figure 67:
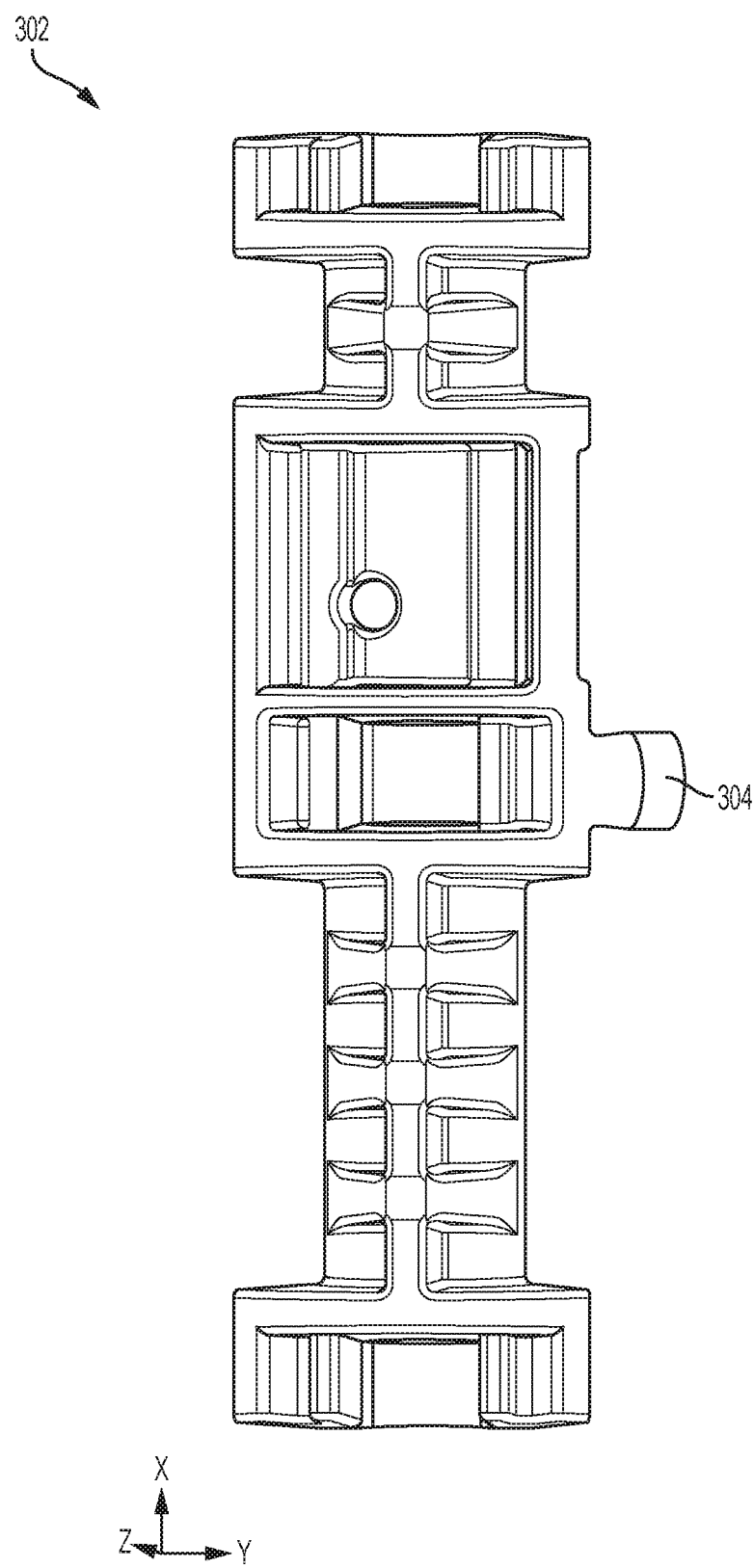
Figure 68:
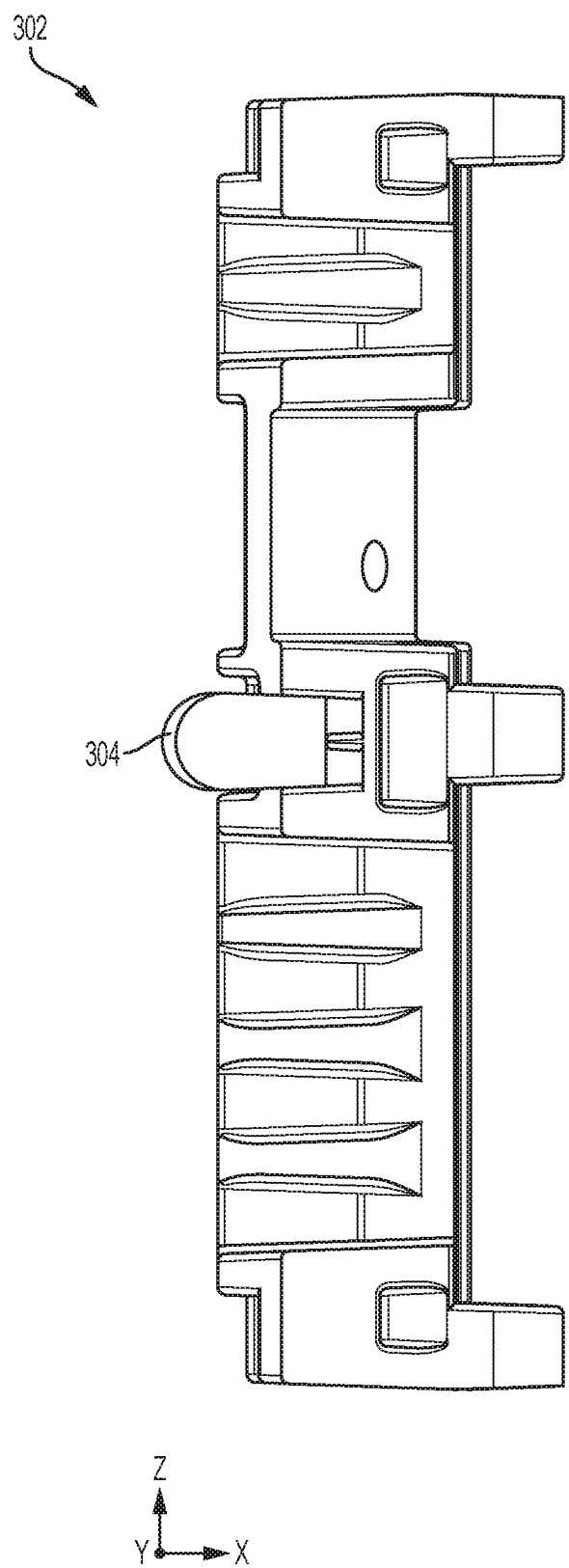
Figure 69:
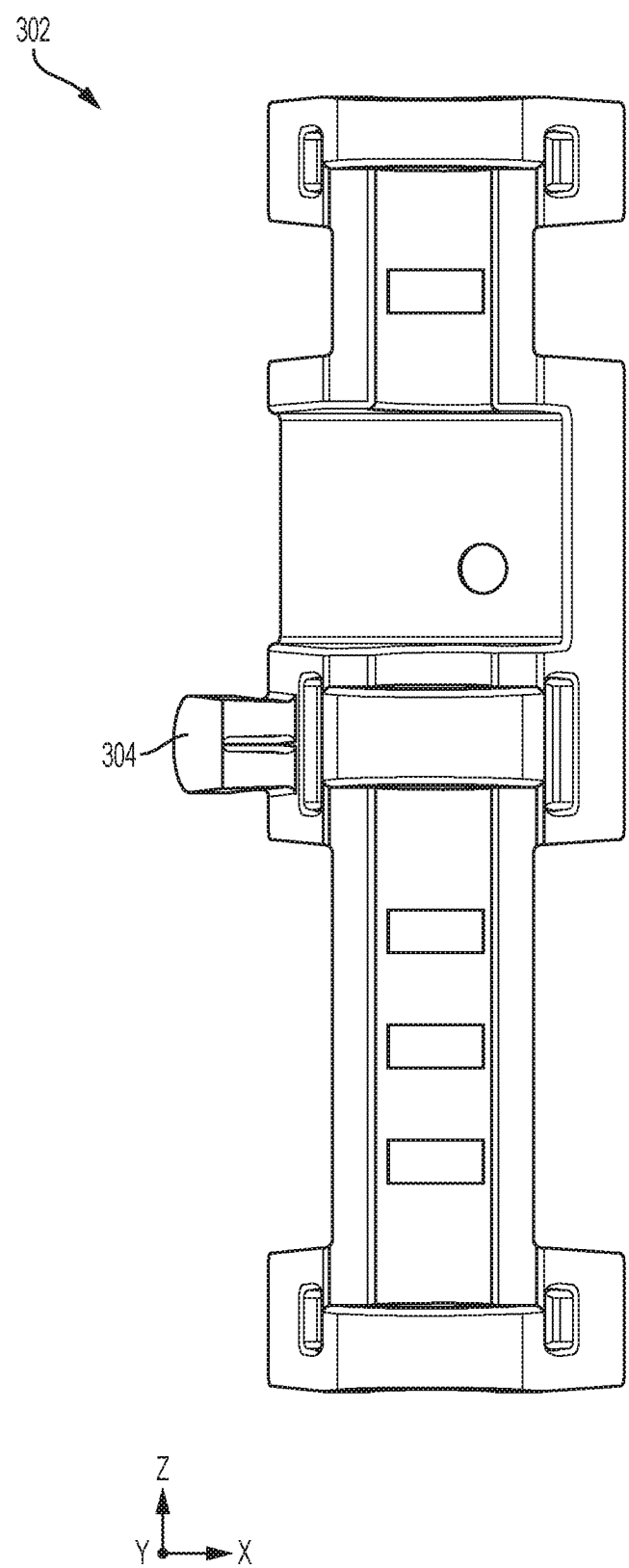
Figure 70:
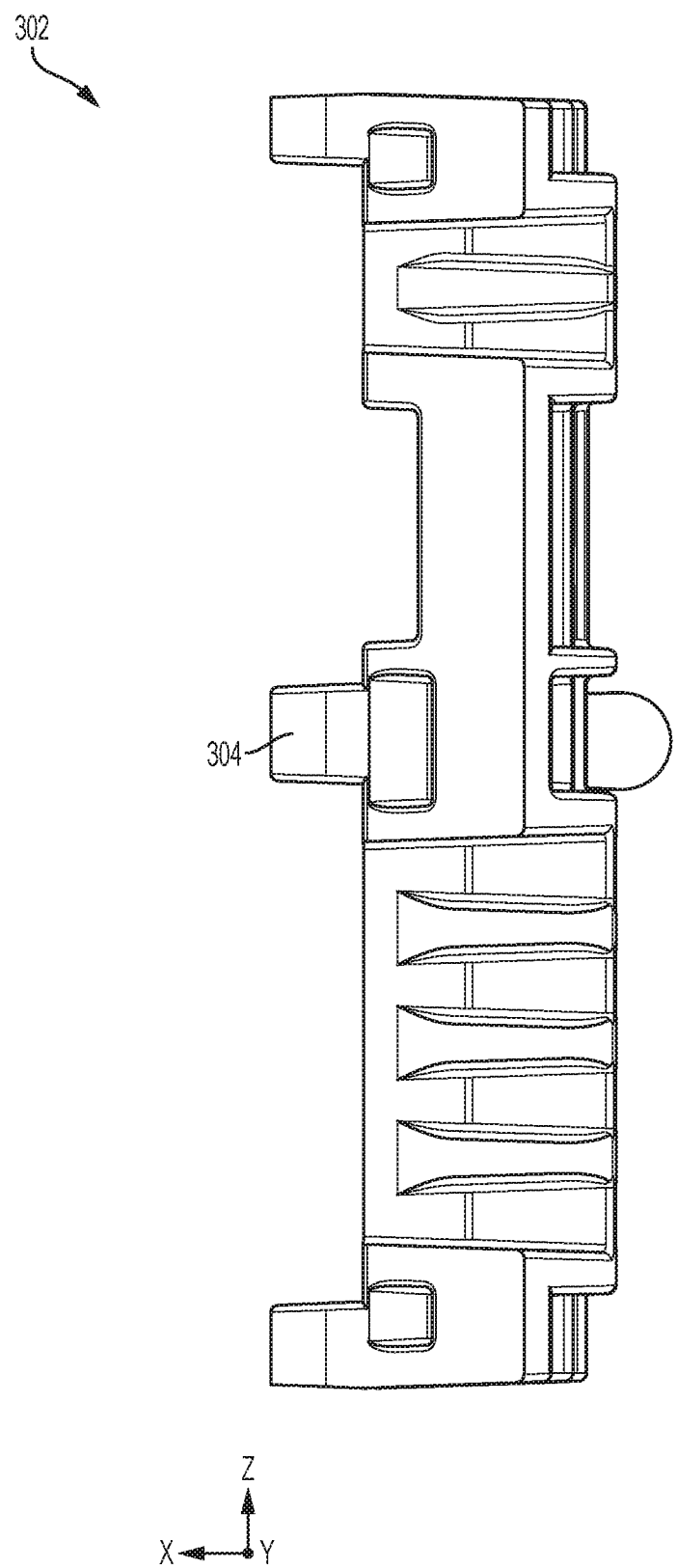
Figure 71:
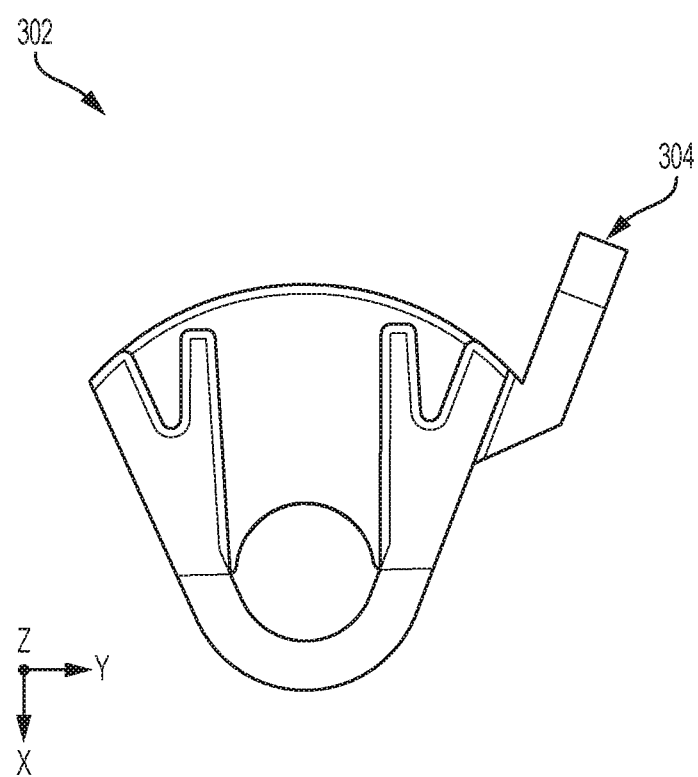
Figure 72:
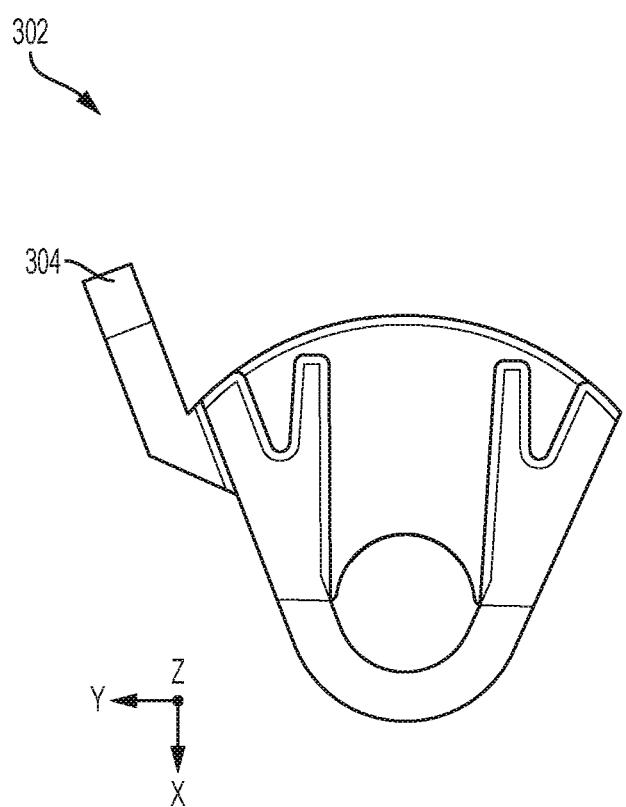

FIG. 63 shows a rear view of the peristaltic pump 300 with the rear cover removed. A lift cam 302 is shown and includes a flange 304. The flange 304 limits the movement of the lift cam 302 toward the spring-biased plunger 116. FIG. 64 shows another view of the peristaltic pump 300 of FIG. 63 to illustrate the operation of the lift cam 120 by showing the lever 104 in the open position. The lift cam 302 is rotated into a lifting position, but, as is shown in FIG. 64, the flange 304 prevents the lift cam 302 from slipping under the spring-biased plunger 116. FIG. 65 shows a cross-sectional view of the lift cam 120 of the peristaltic pump 300 of FIG. 63 when the lever 104 is in the open position. As shown in FIG. 65, the flange 304 prevents the lift cam 302 from slipping beyond a predetermined rotational angle. The lift cam 302 is biased by a cam-lifter torsion spring 126 in the direction of arrow 311. FIGS. 66-72 show the lift cam 120 of the peristaltic pump 300 of FIG. 63 from various viewing angles.

Figure 73:
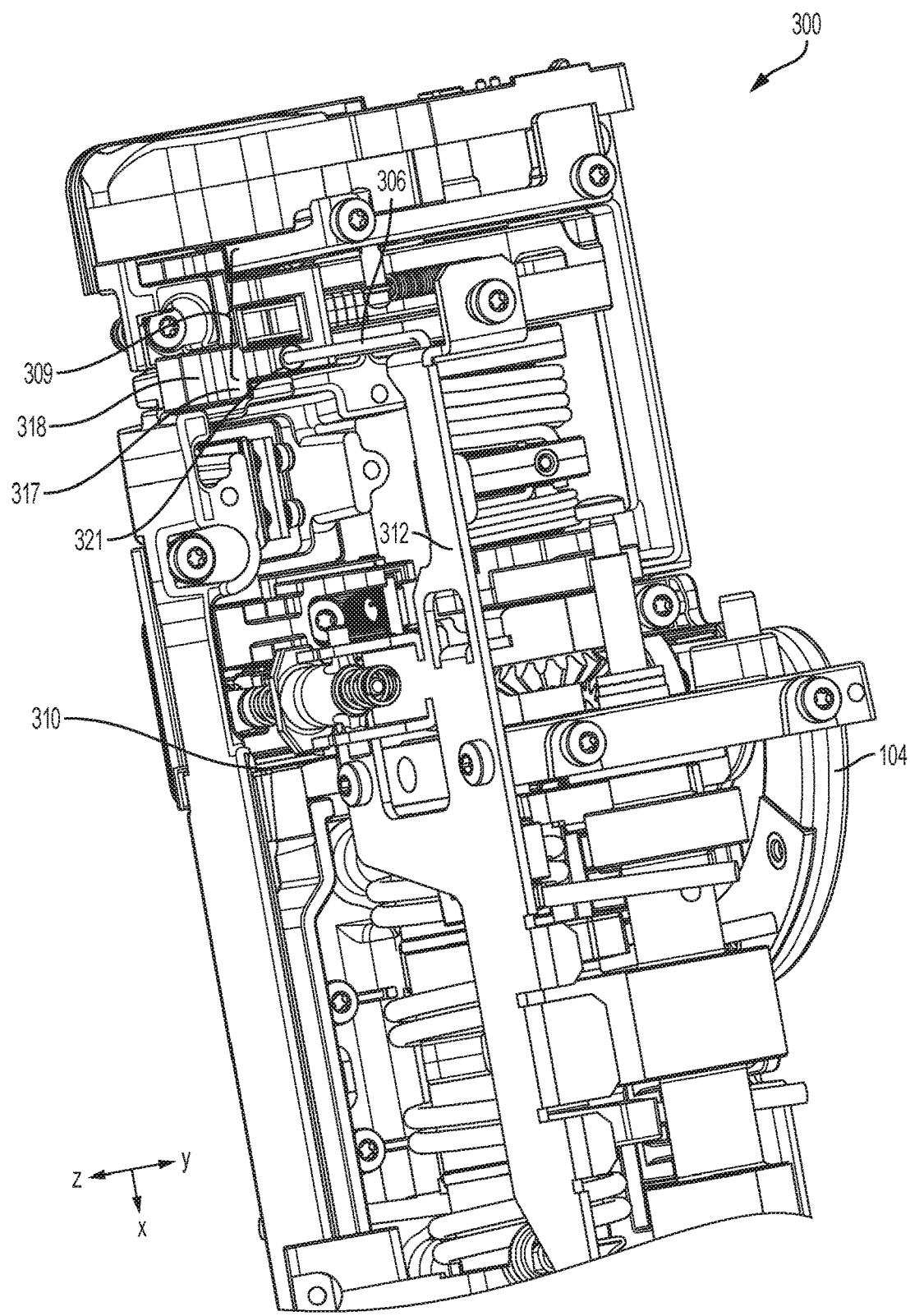
FIG. 73 shows the peristaltic pump of FIG. 63 from a back view to show a linkage bar between the door catch and a linear ratchet in accordance with an embodiment of the present disclosure.
Figure 74:
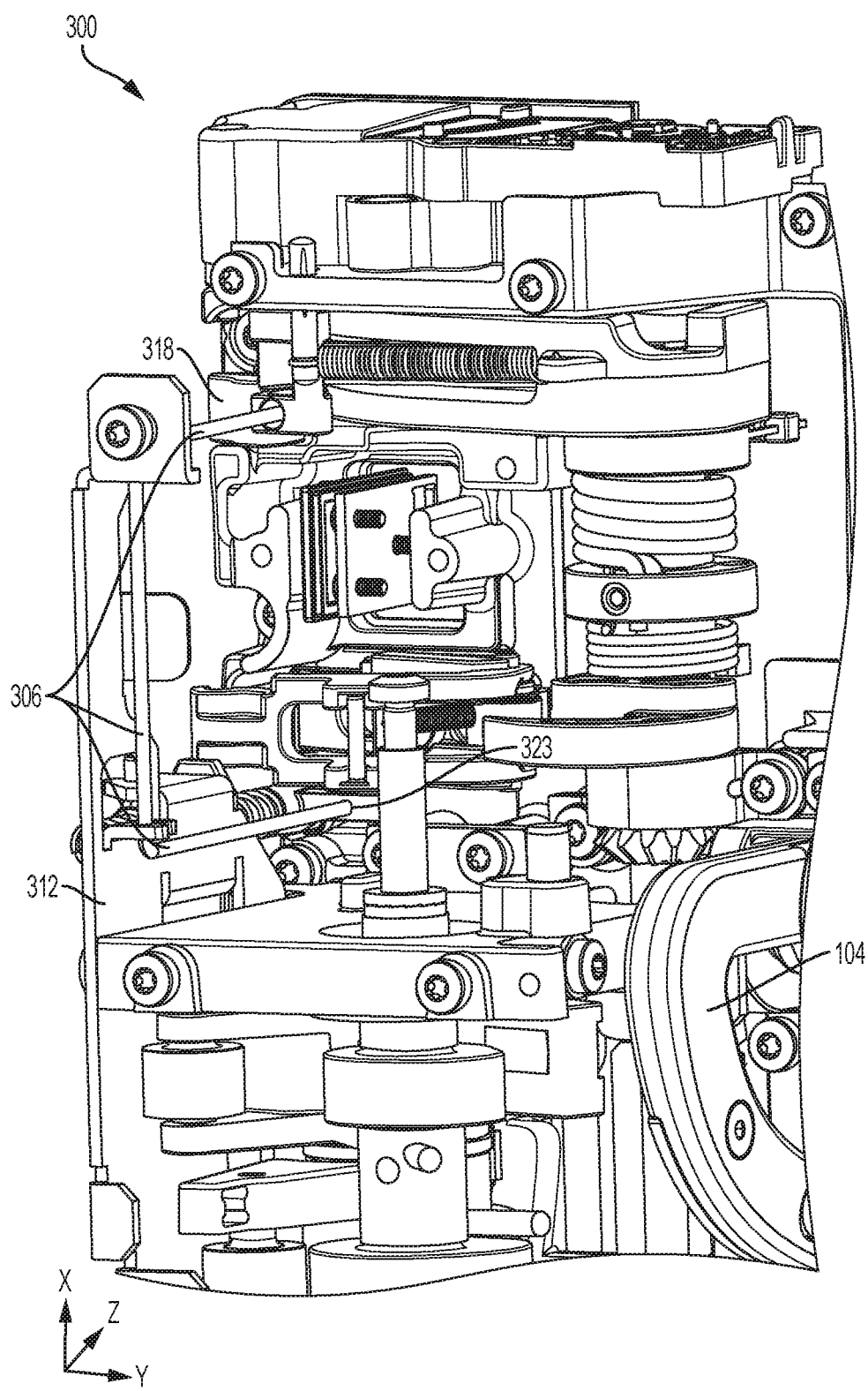
FIG. 74 shows the peristaltic pump of FIG. 63 to provide another view of the linkage bar between the door catch and a linear ratchet in accordance with an embodiment of the present disclosure.

FIG. 73 shows the peristaltic pump 300 of FIG. 63 from a back view to show a door-catch linkage bar 306 between the door catch 308 and a linear ratchet 309. A door-catch spring 310 is coupled to the door-catch linkage bar 306 and the linear ratchet 309. The door-catch linkage bar 306 can rock back-and-forth because it is pivotally coupled to a frame 312. The door-catch spring 310 operates using an over-center action as described above which makes the door catch 308 bi-stable. FIG. 74 shows the peristaltic pump 300 of FIG. 63 to provide another view of the door-catch linkage bar 306 between the door catch 114 and a linear ratchet 309. As is shown in FIG. 74, a central span of the door-catch linkage bar 306 is rotateably coupled to the frame 312 so that actuation of the door catch 308 causes the linear ratchet 309 to change states. The linear ratchet 309 can be in a ratcheting state or in a non-ratcheting state. In the ratcheting state, the linear ratchet 309 can act as a lock to prevent rotation of the carriage 150. That is, the linear ratchet 309 in the peristaltic pump 300 performs the locking action that is performed by the pawl 154 in the peristaltic pump 100 of FIG. 1. The linear ratchet 309 also includes a pawl 318 that locks the main shaft 118 via a carriage linkage bar 335 rather than directly acting on the carriage 150.

Figure 75:
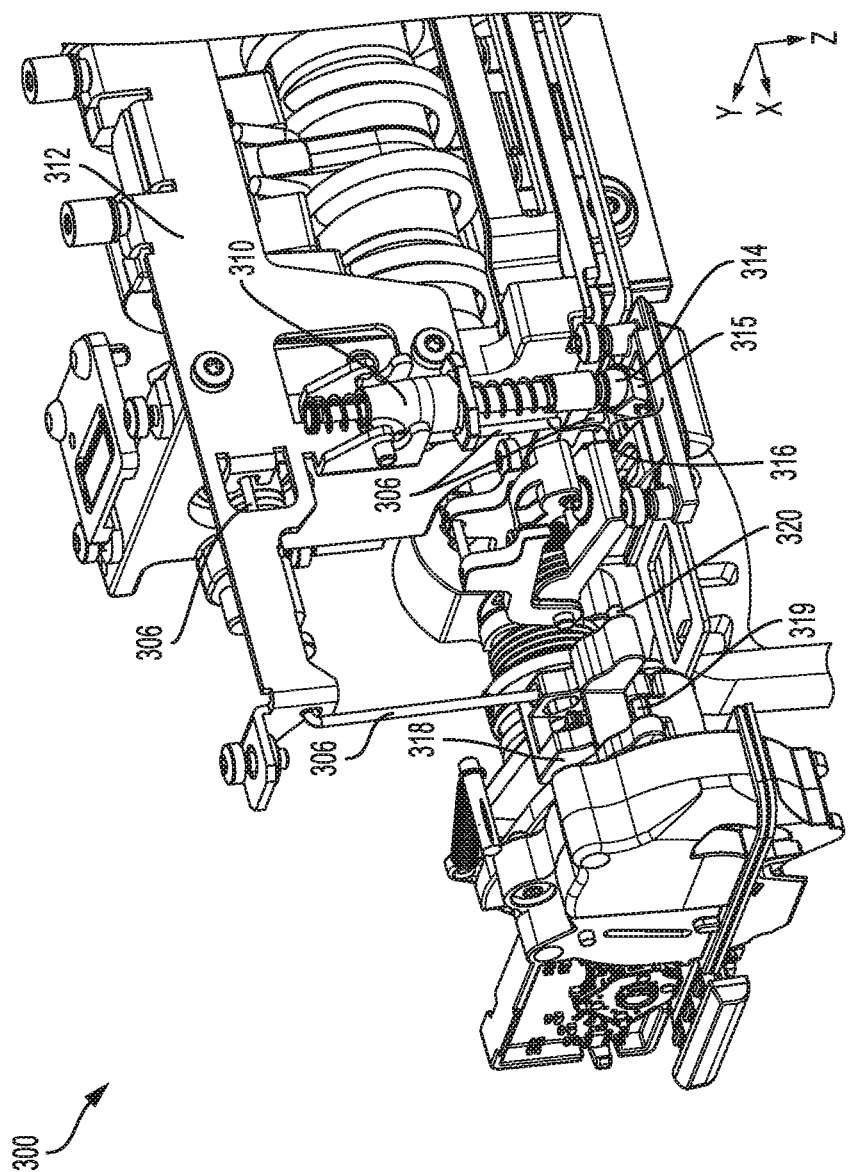
FIG. 75 shows a close-up view of the interface of the over-center spring and the door catch with the linkage bar of the peristaltic pump of FIG. 63 with door-catch in the door open position and the lever open.
Figure 76:
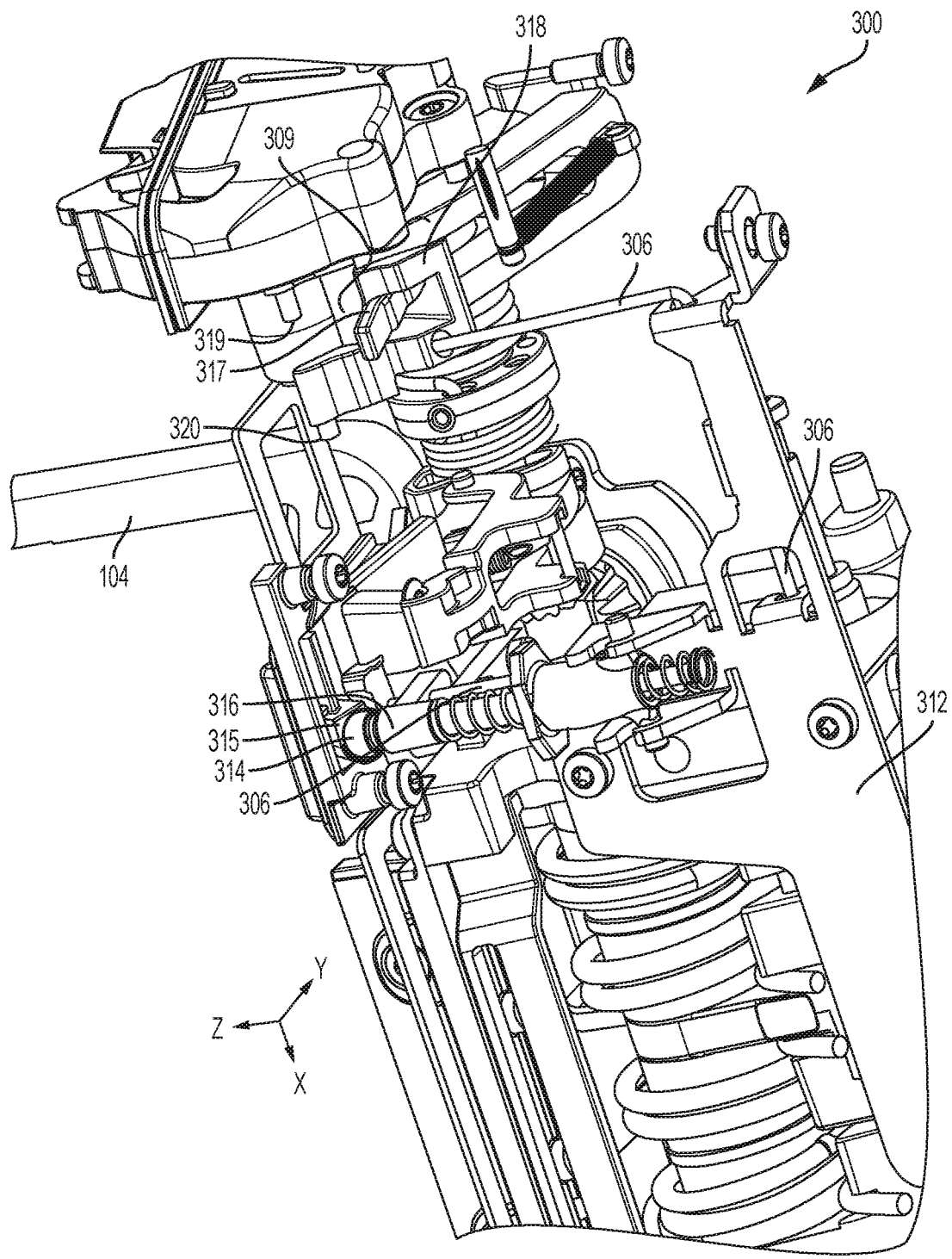
FIG. 76 shows the same close-up view of FIG. 75 but with the door catch in the door shut position in accordance with an embodiment of the present disclosure.
Figure 77:
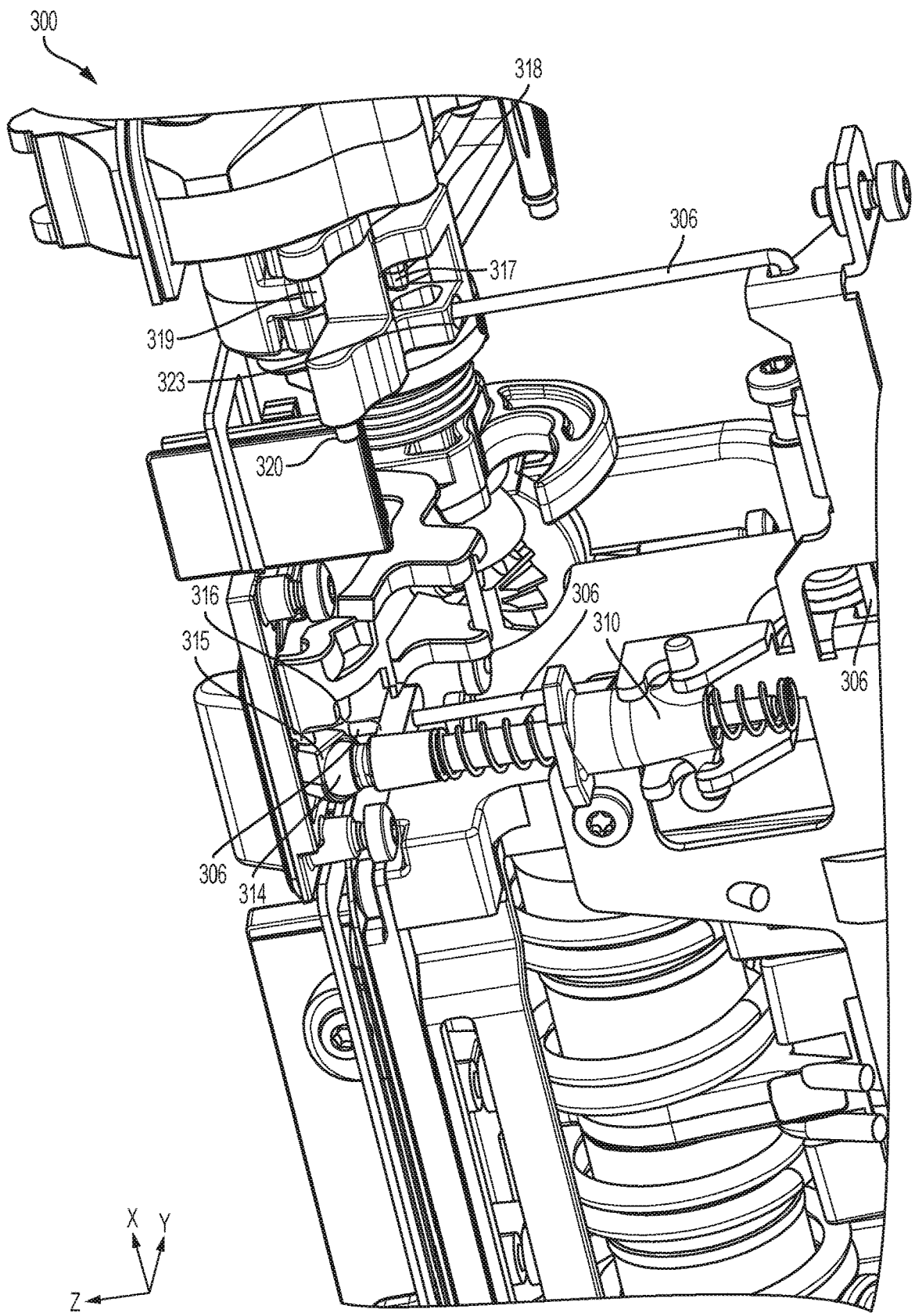
FIG. 77 shows the same close-up view of FIG. 75 but with the door catch in the door shut position and the lever in the closed position in accordance with an embodiment of the present disclosure.
Figure 78:
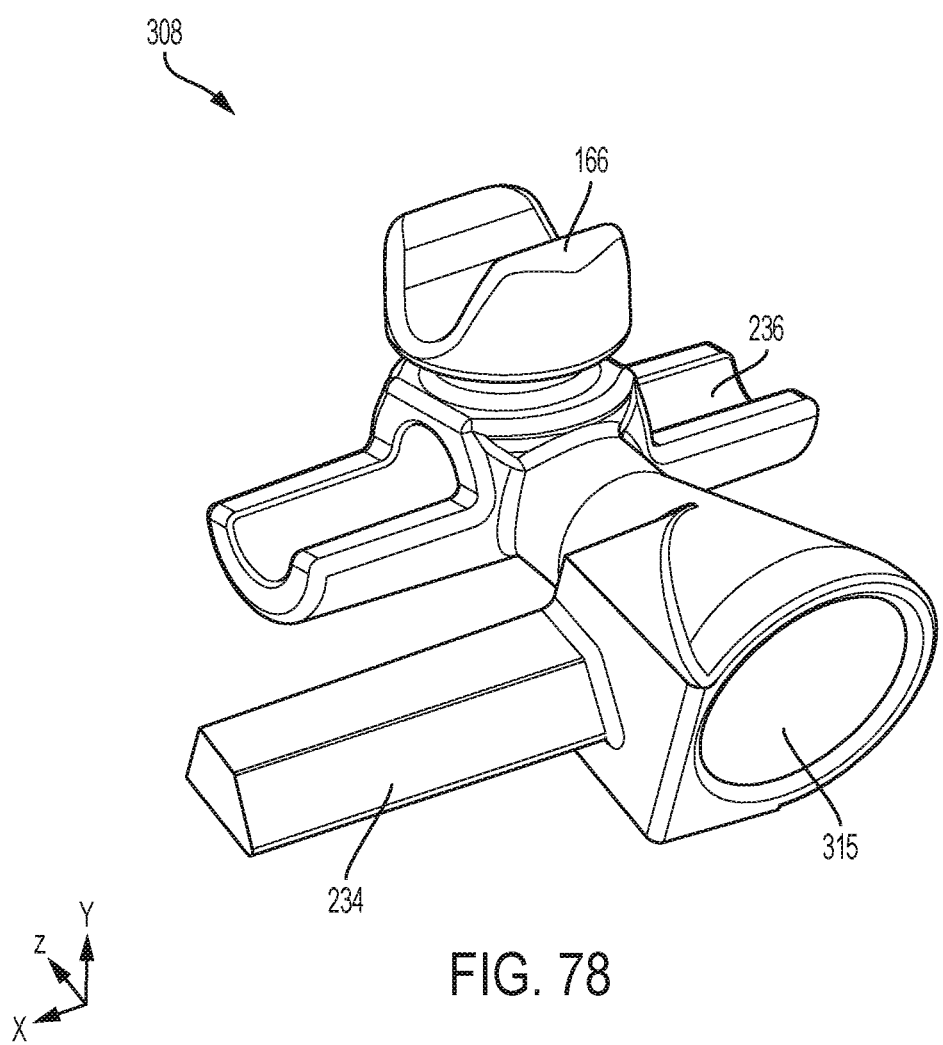
FIG. 78-84 show several views of the door catch of the peristaltic pump of FIG. 63 in accordance with an embodiment of the present disclosure.
Figure 79:
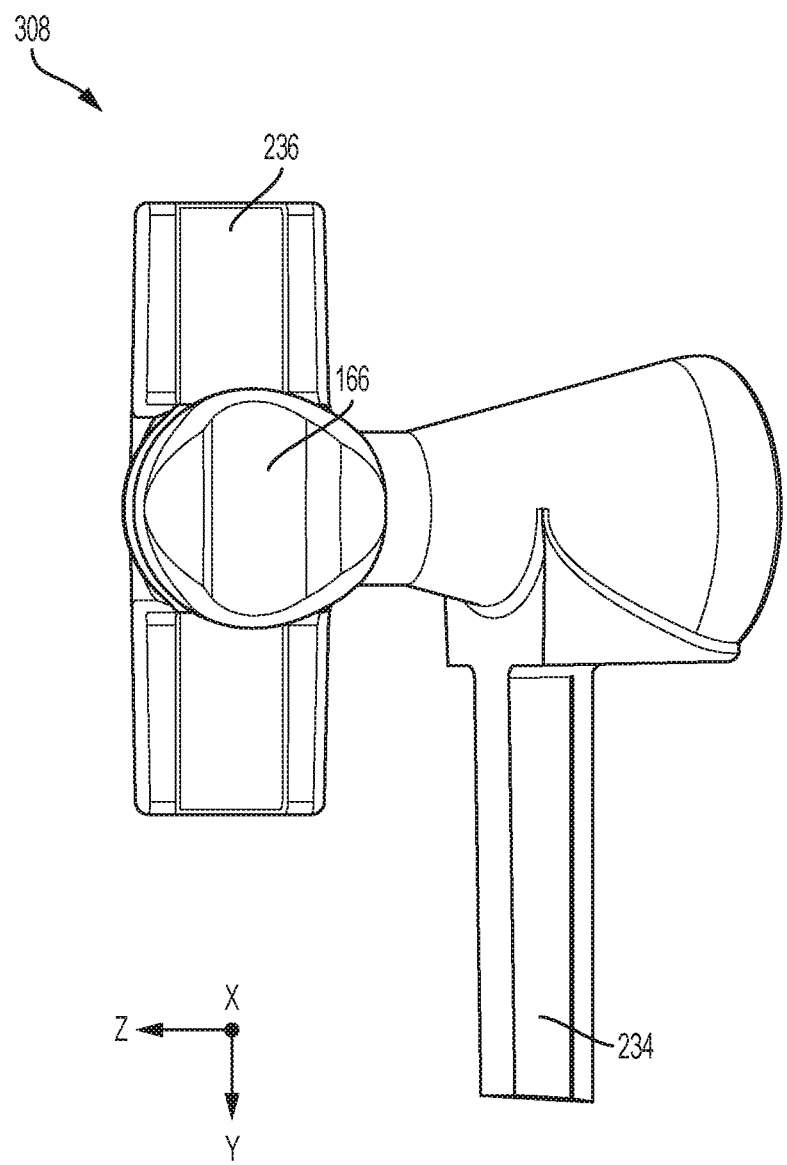
Figure 80:
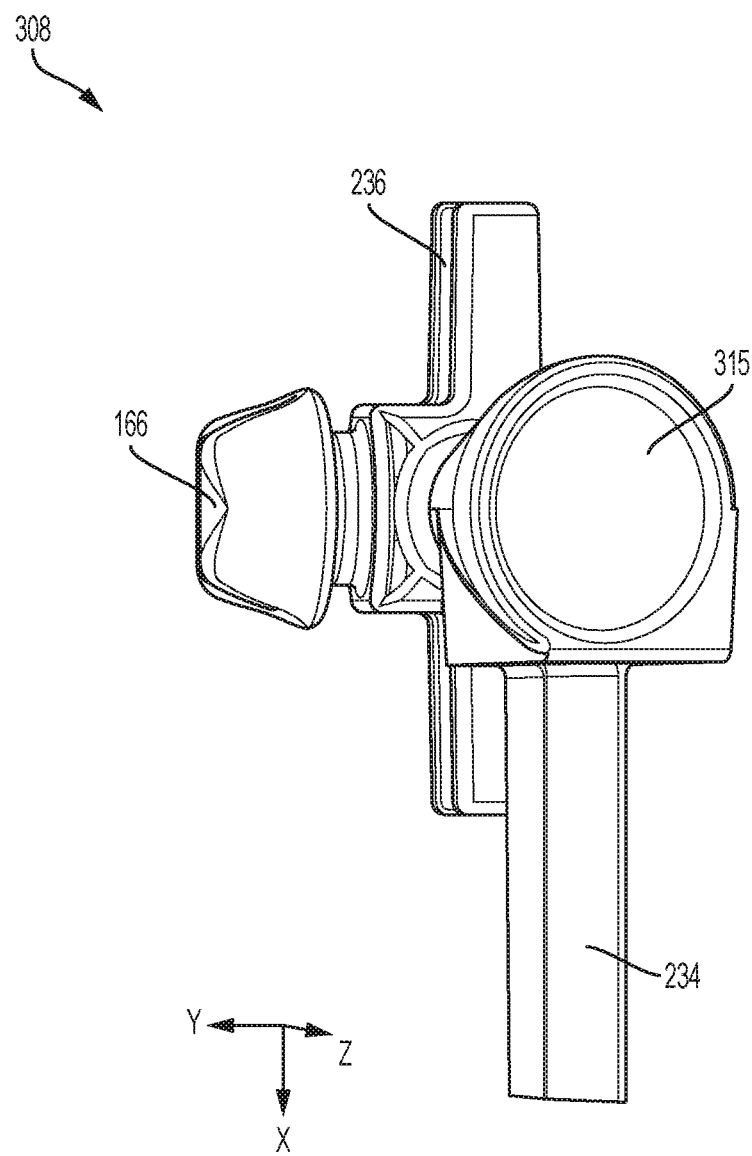
Figure 81:
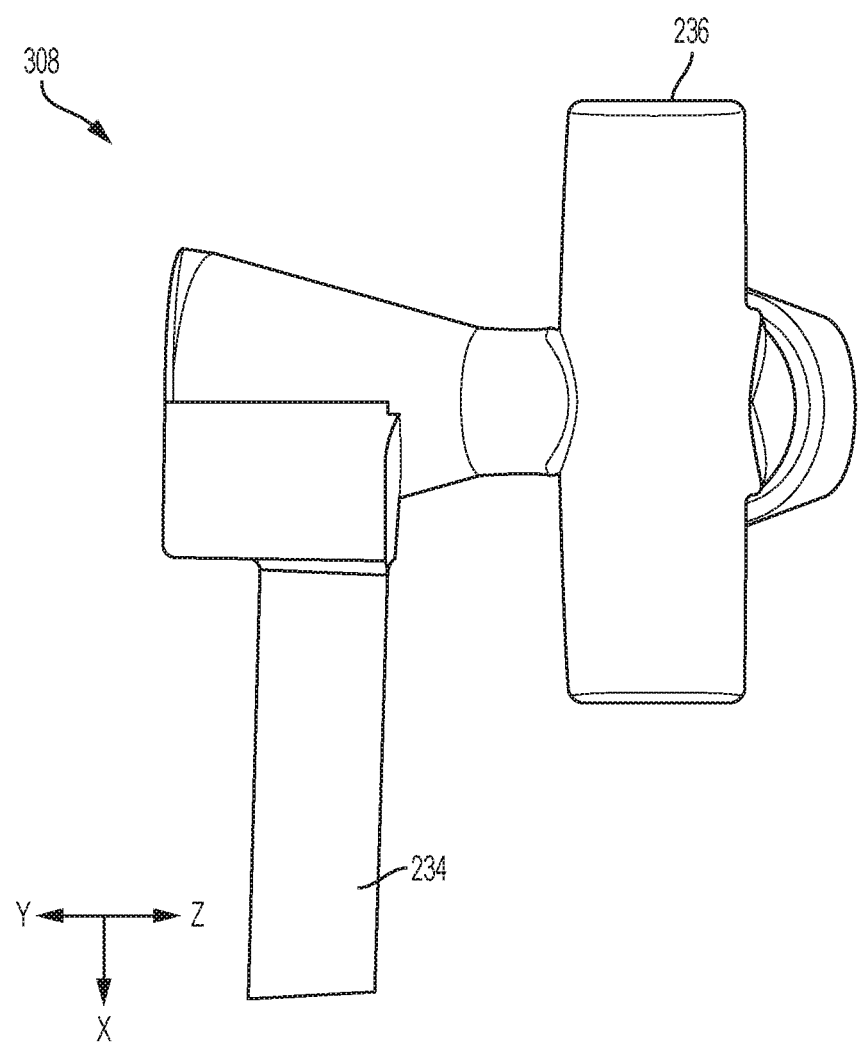
Figure 82:
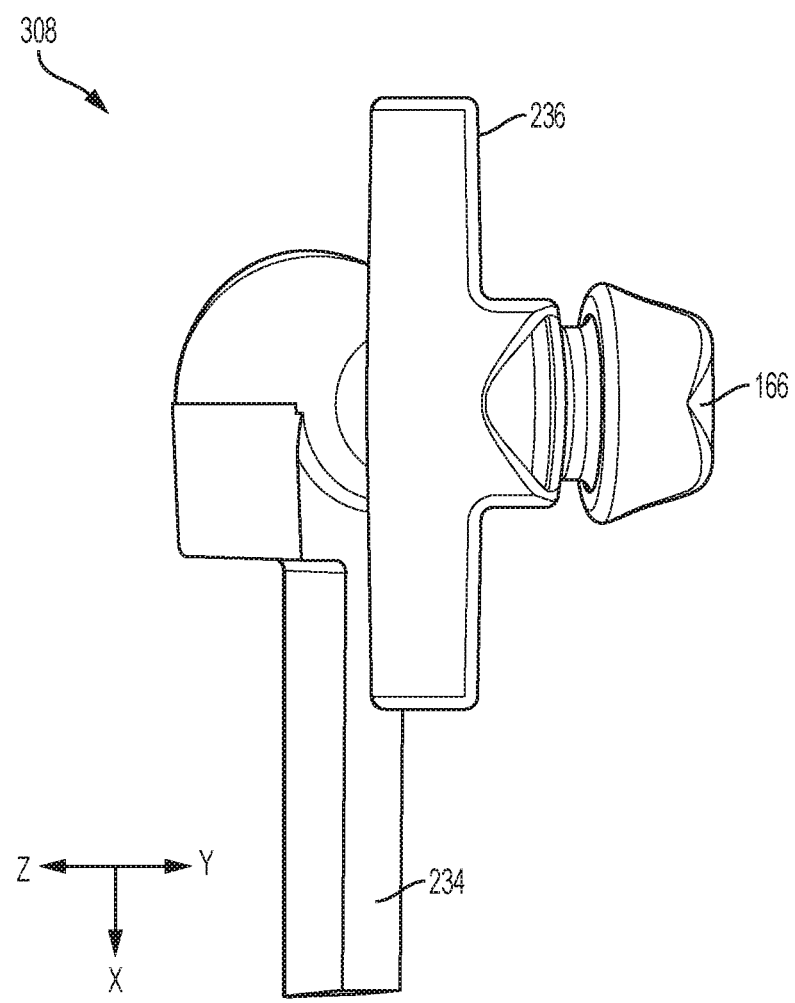
Figure 83:
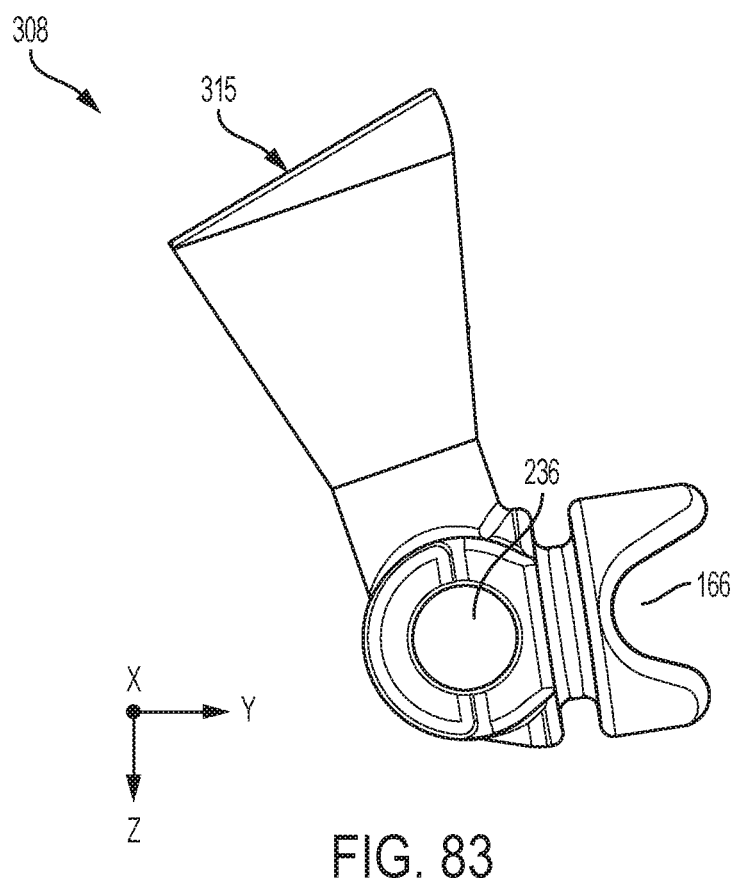
Figure 84:
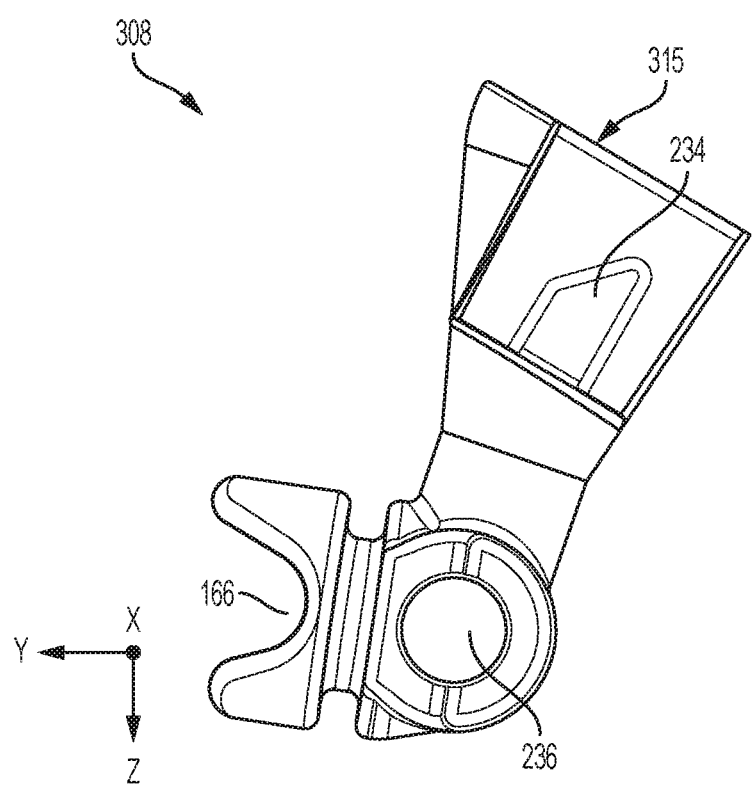

FIG. 75 shows a close-up view of the interface of the door-catch spring 310 and the door catch 308. FIG. 75 also shows the door-catch linkage bar 306 of the peristaltic pump 300 of FIG. 63 with a door catch 308 in the door 102 open position and the lever 104 in the open position. As can be seen, the door-catch spring 310 includes a ball 314 that interfaces with a socket 315 to form a ball-and-socket joint 316. When the door 102 is open, the door catch 308 can be in a position such that the door-catch linkage bar 306 has actuated the linear ratchet 309 to a ratcheting state. In the ratcheting state, the linear ratchet 309 prevents the main shaft 118 from rotating when a user attempts to close the lever 104 thereby preventing the user from closing the lever 104 while the door 102 remains open. FIG. 76 shows the same close-up view of FIG. 75 but with the door catch 308 in the door-shut position and the lever 104 in the open position. When a user shuts the door 102, it actuates the door catch 308, which actuates the door-catch spring 310, which actuates the door-catch linkage bar 306 which places the linear ratchet 309 in the non-ratcheting state. That is, the lever 104 can now be shut by the user because the door 102 is closed. FIG. 77 shows the same close-up view of FIG. 76 but after the lever 104 was actuated to the closed position. The lever 104 could be shut because the linear ratchet 309 was in the non-locking position when the lever 104 was actuated closed as described above FIG. 78-84 show several views of the door catch 308 including the socket 315 that receives the ball 314 from the door-catch spring 310. The door catch 308 of FIGS. 78-84 operates in the same manner as the door catch 308 shown in FIG. 25; however, the door catch 308 has a socket 315 to connect to an the door-catch spring 310 rather than a door-catch anchor 232 as shown in FIG. 25. The door catch 308 includes a door catch 114 The door catch 308 includes a pin catch 166, a door-catch hold 234, and a channel 236 to allow the door catch 308 to pivot.

Figure 85:
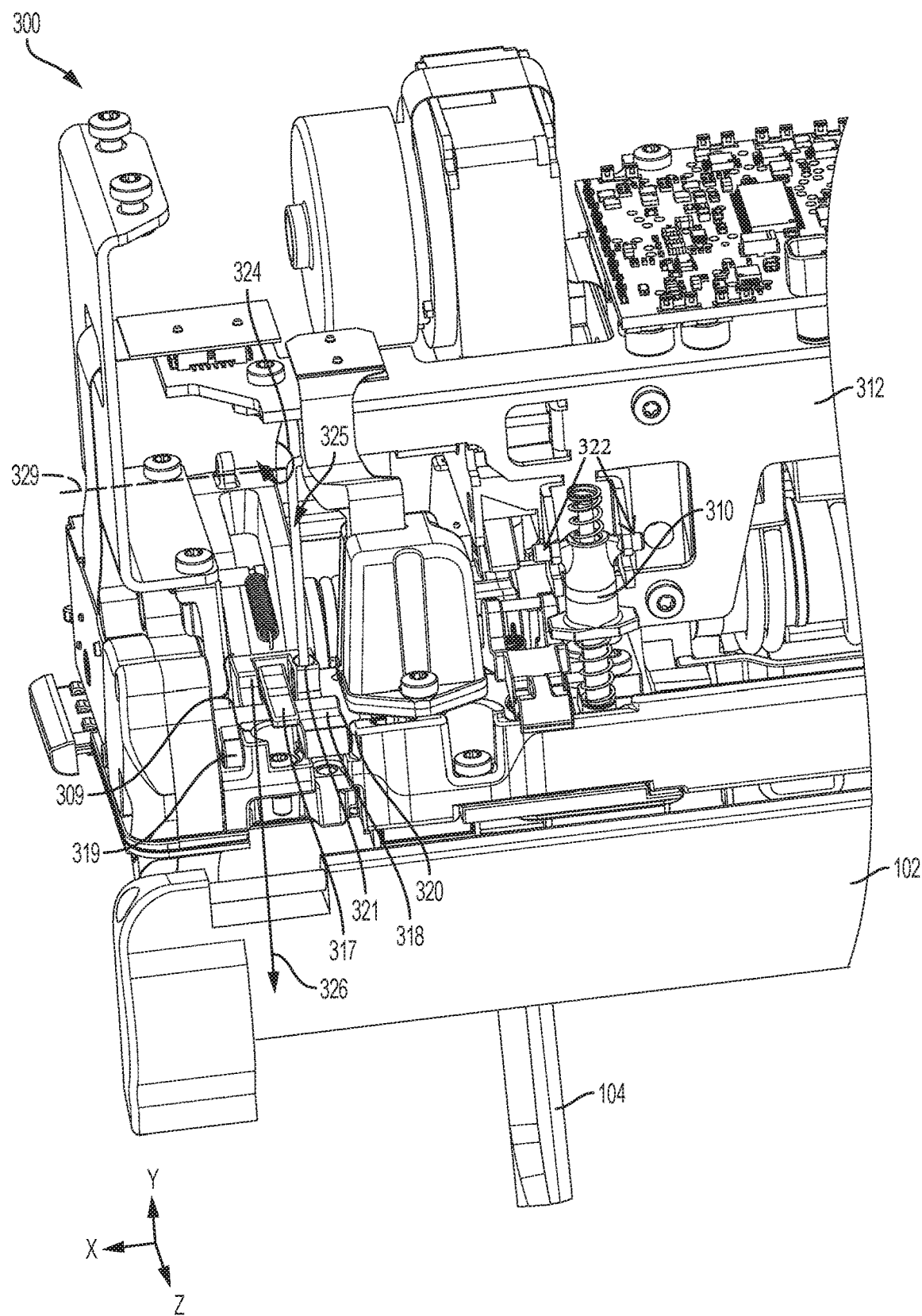
FIG. 85 shows a close-up view of the linear ratchet when the door is open and the lever is open in accordance with an embodiment of the present disclosure.

FIG. 85 shows a close-up view of the linear ratchet 309 when the door 102 is open and the lever 104 is open. The linear ratchet 309 includes a toothed linkage bar 317 and a pawl 318 that can be rotated along pivots 319, 320 so that the pawl 318 can engage or disengage with the toothed linkage bar 317. The pawl 318 is coupled to the linkage bar 325 through a pawl hole 321. The linkage bar 325 may slide through the pawl hole 321.

The pawl 318 includes a pivotable end that is coupled to the pivots 319, 320 and is configured to so that the an engagement end, such as a tooth 341 (see FIGS. 90-92) can pivot to engage the toothed linkage bar 317 or disengage the toothed linkage bar 317. The door-catch linkage bar 306 can rotate around an axis 329. Because the door-catch linkage bar 306 is in sliding engagement with the pawl hole 321 movement of the door-catch linkage bar 306 around an axis 329 can raise or lower the tooth 341 of the pawl 318 to engage or disengage the toothed linkage bar 317.

Figure 86:
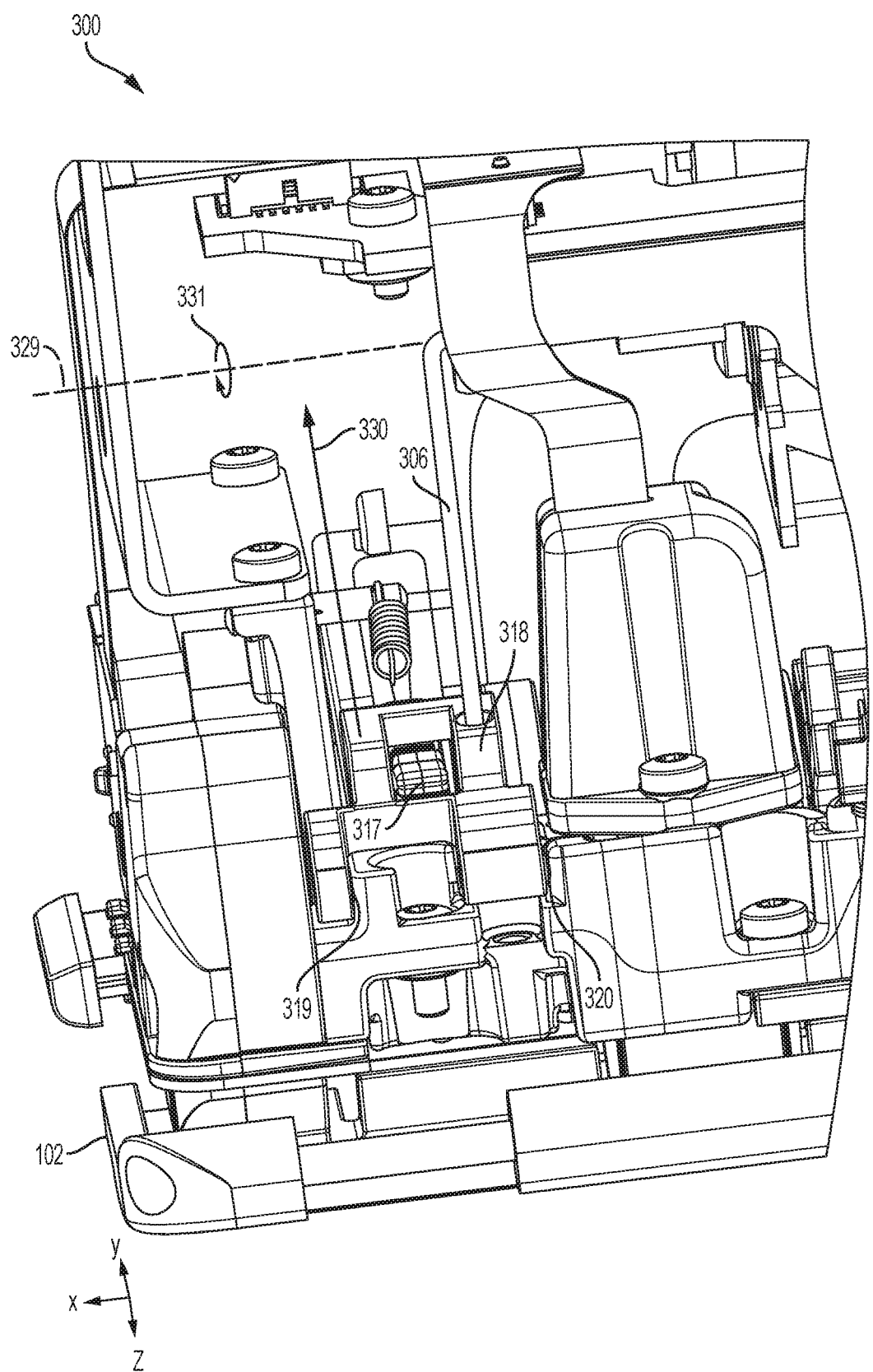
FIG. 86 shows a close-up view of the linear ratchet when the door is closed and the lever is open in accordance with an embodiment of the present disclosure.
Figure 87:
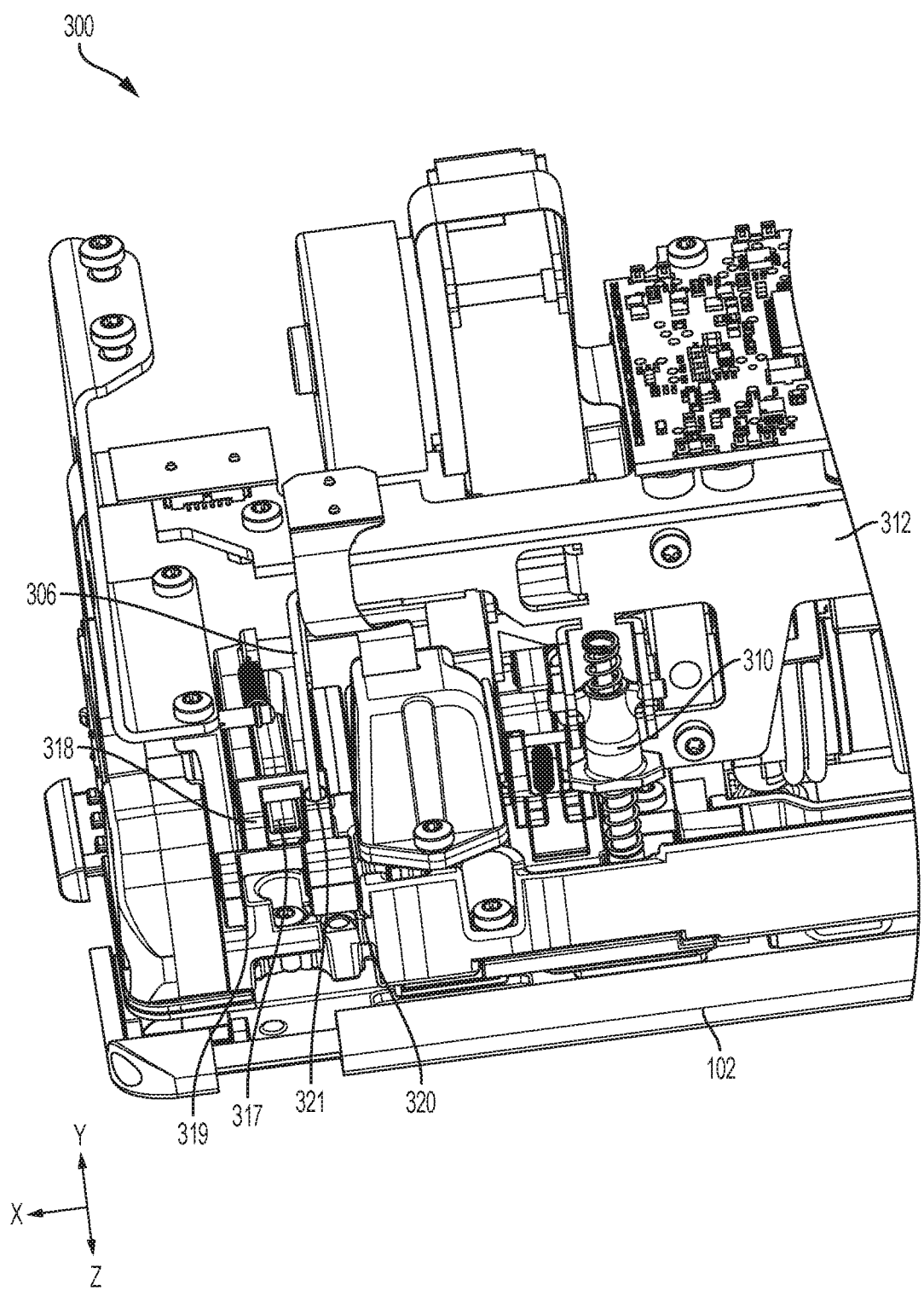
FIG. 87 shows a close-up view of the linear ratchet when the door is closed and the lever is closed in accordance with an embodiment of the present disclosure.

As shown in FIG. 85, the door catch 114 is in the open door 102 position which actuates the door-catch spring 310 to pivot along spring pivots 322. Because the door-catch spring 310 is coupled to the door-catch linkage bar 306 via a door-catch spring hole 323 (see FIG. 77), when the door-catch spring 310 is actuated to the door-open position, the linkage bar 325 is rotated along arrow 324 which in turn actuates the linkage bar 325 coupled to the pawl 318. The tooth 341 of the pawl 318 is actuated in direction of the arrow 326. This latching state of the pawl 318 means the pawl 318 is pivoted such that an tooth 341 of the pawl 318 engages with the toothed linkage bar 317 to prevent the user from closing the lever. That is, when the tooth 341 engages with the toothed linkage bar 317, the linear ratchet 309 is in the locking state FIG. 86 shows a close-up view of the linear ratchet 309 when the door 102 is closed and the lever 104 is open. The tooth 341 of the pawl 318 has actuated in the direction of arrow 330 by rotation of the door-catch linkage bar 306 in the direction indicated by arrow 331. Actuation of the tooth 341 of the pawl 318 away from the toothed linkage bar 317 thereby disengages the pawl 318 from the toothed linkage bar 317 thereby making the linear ratchet 309 to be in the non-latching state. A user can close the lever 104 when the linear ratchet 309 is in the non-latching state as shown in FIG. 87. That is, FIG. 87 shows a close-up view of the linear ratchet 309 when the door 102 is closed and the lever 104 is also closed.

Figure 88:
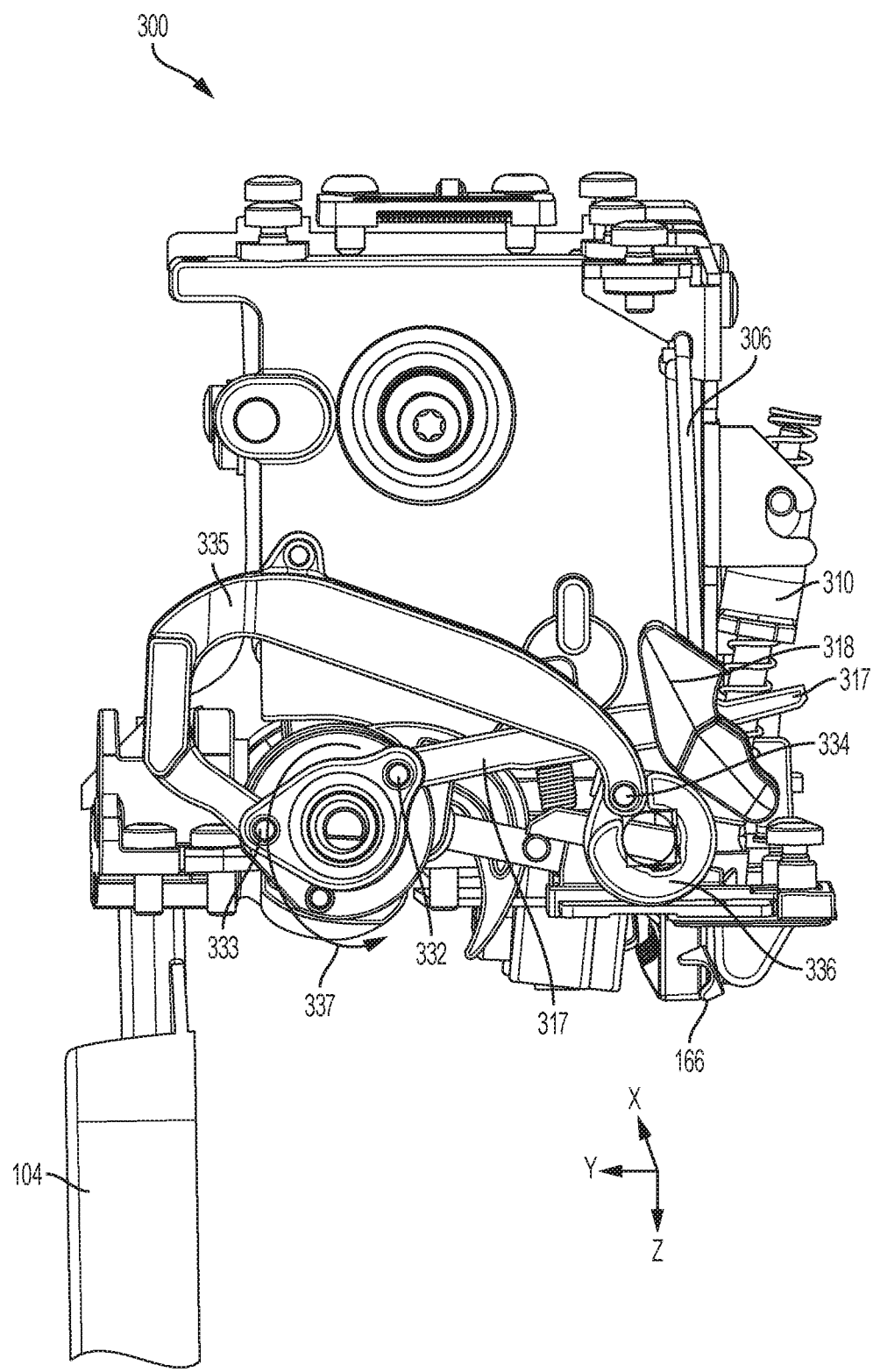
FIGS. 88-89 show the peristaltic pump of FIG. 63 with some parts removed to illustrate the mechanical linkage between the shaft and the carriage where the door-catch, the door, and the lever are in the open position in accordance with an embodiment of the present disclosure.
Figure 89:
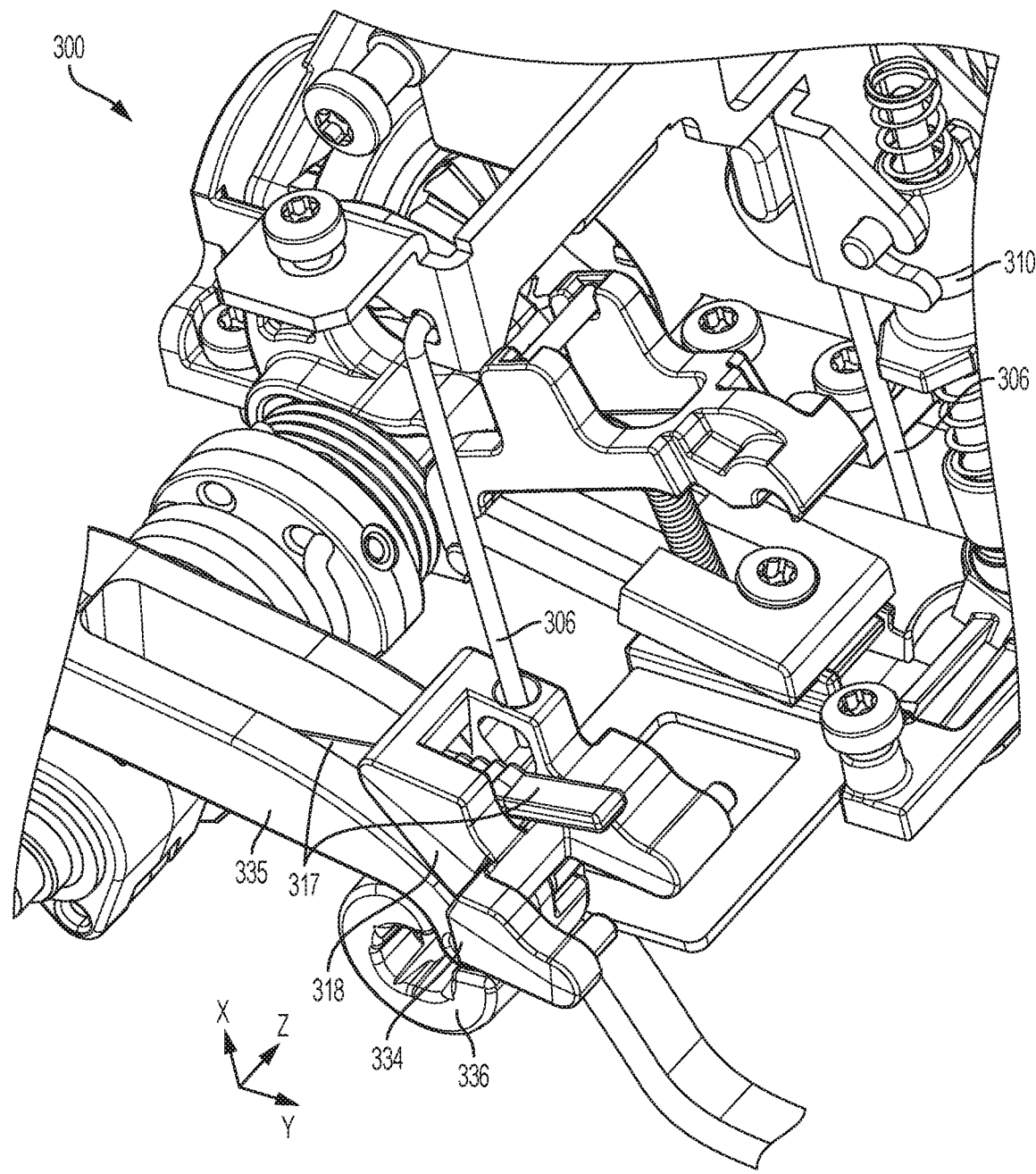

FIGS. 88-89 show the peristaltic pump 300 of FIG. 63 with some parts removed to illustrate the mechanical linkage between the main shaft and the carriage 150 where the door catch 308, the door 102, and the lever 104 are in the open position. The mechanical linkage includes the toothed linkage bar 317 that is coupled to the main shaft 118 via a first pin pivot 332. The toothed linkage bar 317 is only connected at one end (i.e., via the first pin pivot 332). The mechanical linkage also includes a carriage linkage bar 335 where one end is connected to the main shaft 118 via a second pin pivot 333 and to a carriage-shaft collar 336 via a third pin pivot 334.

As previously mentioned, when the door catch 114 is in the door-open position, the tooth 341 of the pawl 318 engages with the toothed linkage bar 317. As can be seen in FIG. 88, in this position, the toothed linkage bar 317 cannot be actuated toward the main shaft 118 when a user attempts to close the lever 104 because the main shaft 118 is prevented from being rotated in direction 337 because the toothed linkage bar 317 is locked by the pawl 318. This prevents the user from closing the lever 104 prior to the door 102 being closed.

Figure 90:
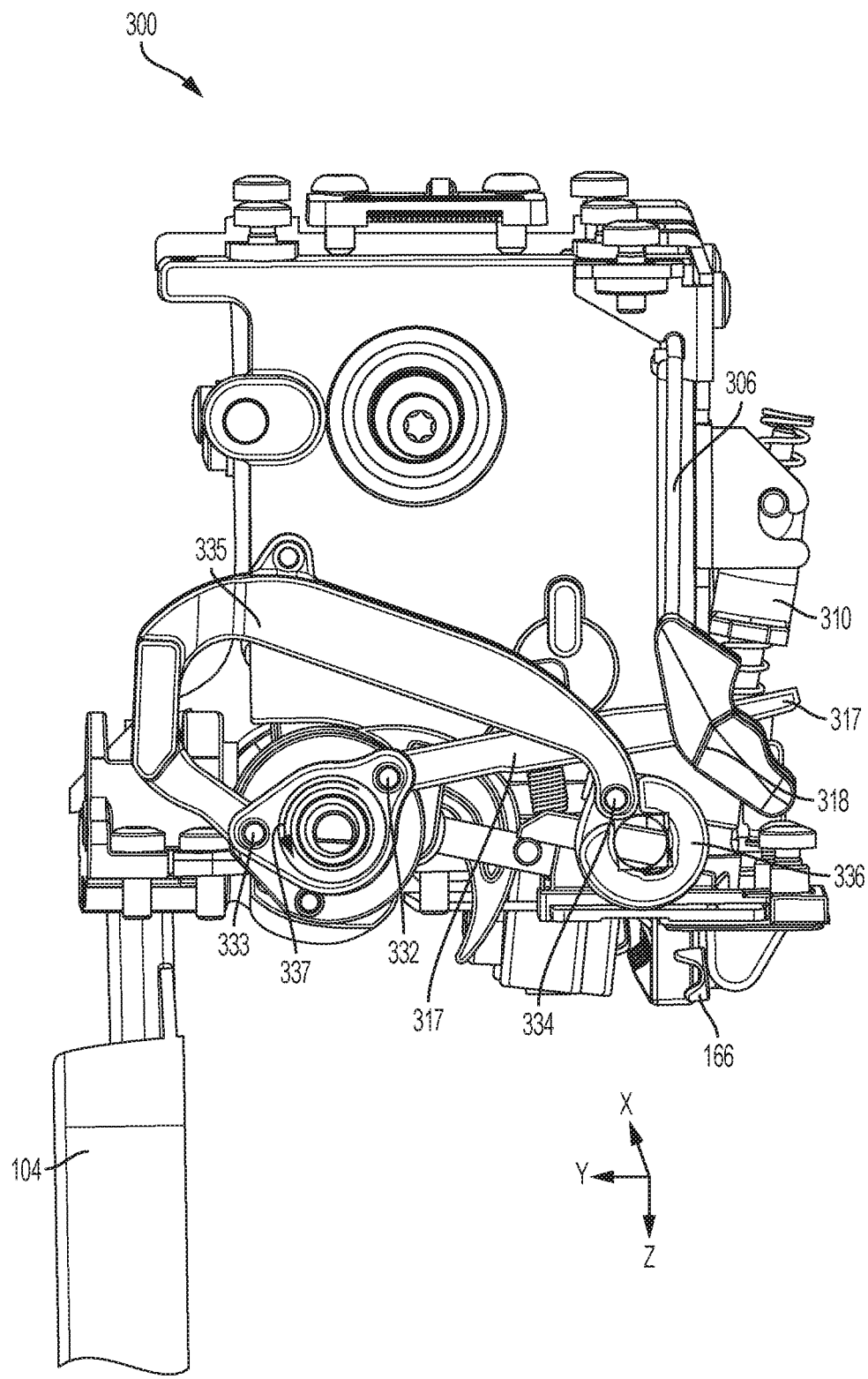
FIGS. 90-91 show the peristaltic pump of FIG. 63 with some parts removed to illustrate the mechanical linkage between the shaft and the carriage where the door and the door catch are in the closed position and the lever is in open position in accordance with an embodiment of the present disclosure.
Figure 91:
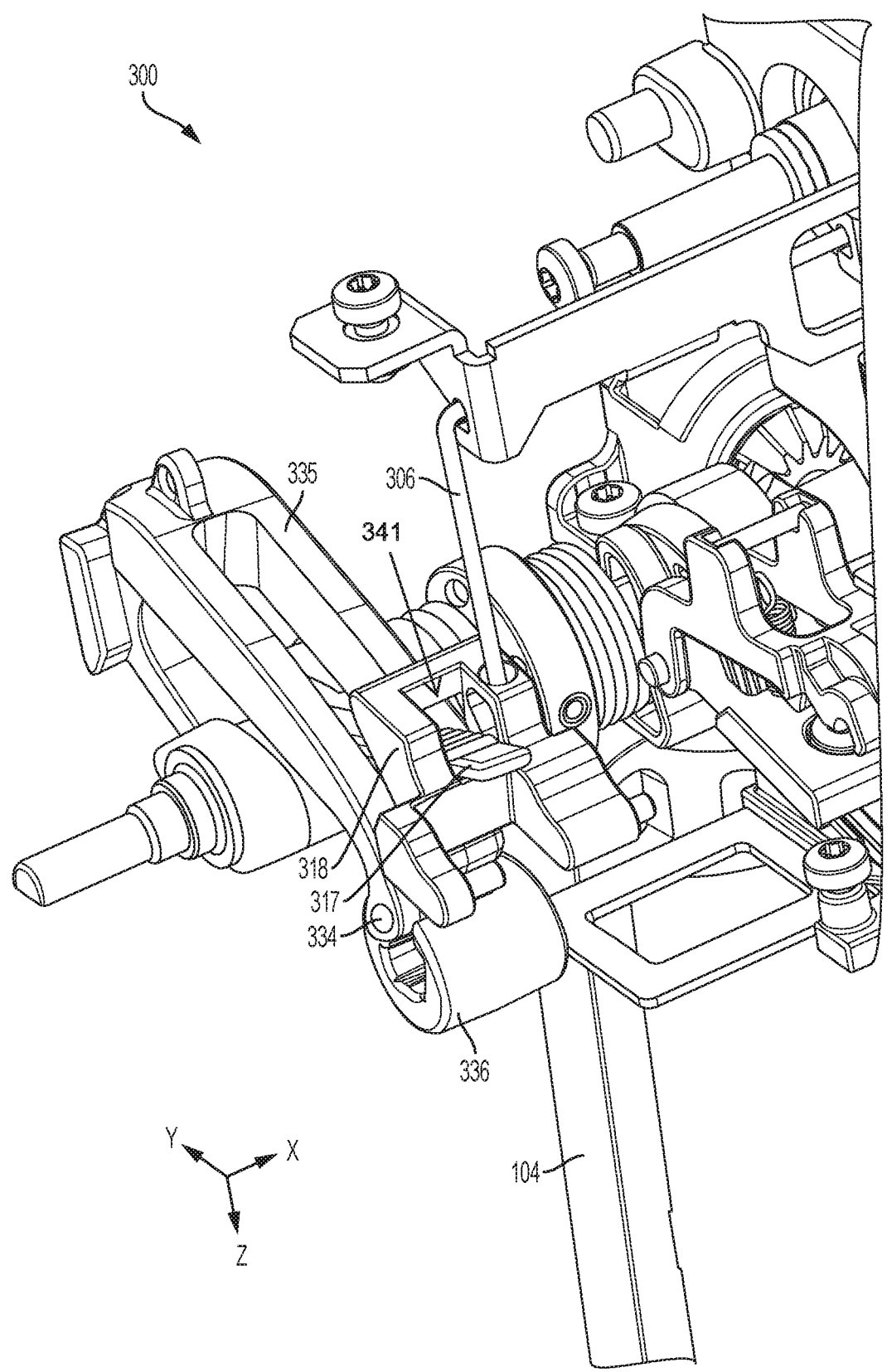

FIGS. 90-91 show the peristaltic pump 300 of FIG. 63 with some parts removed to illustrate the mechanical linkage between the shaft and the carriage 150 where the door 102 and the door catch 308 are in the closed position and the lever 104 is in open position. As can be seen, the tooth 341 of the pawl 318 has been actuated away from the toothed linkage bar 317 thereby allowing the toothed linkage bar 317 to retract toward the main shaft 118. Thus, a user can now actuate the lever 104 to the closed position.

Figure 92:
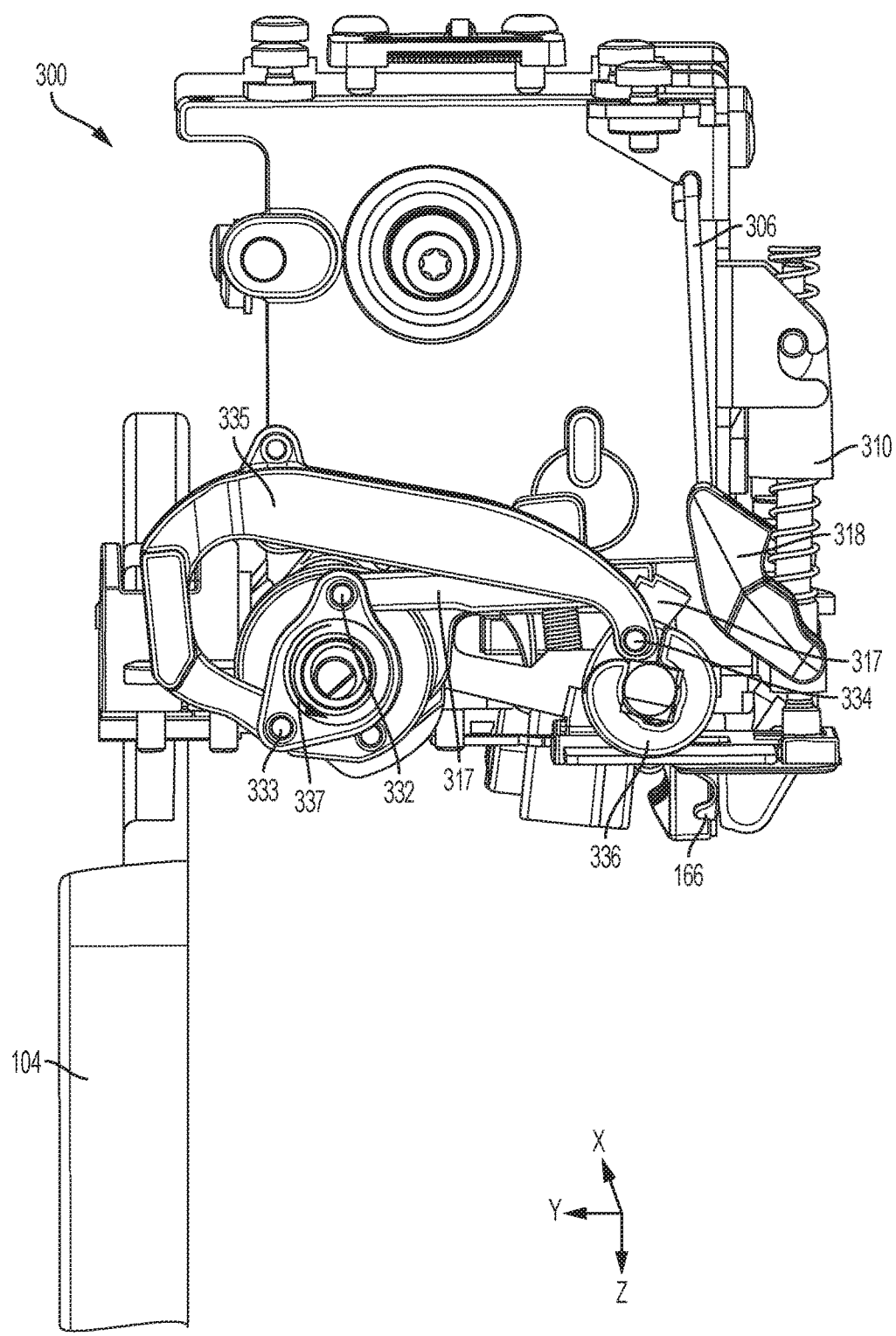
FIG. 92 shows the peristaltic pump of FIG. 63 with some parts removed to illustrate the mechanical linkage between the shaft and the carriage where the door and the door catch are in the closed position while the lever is between the open and closed position in accordance with an embodiment of the present disclosure.
Figure 93:
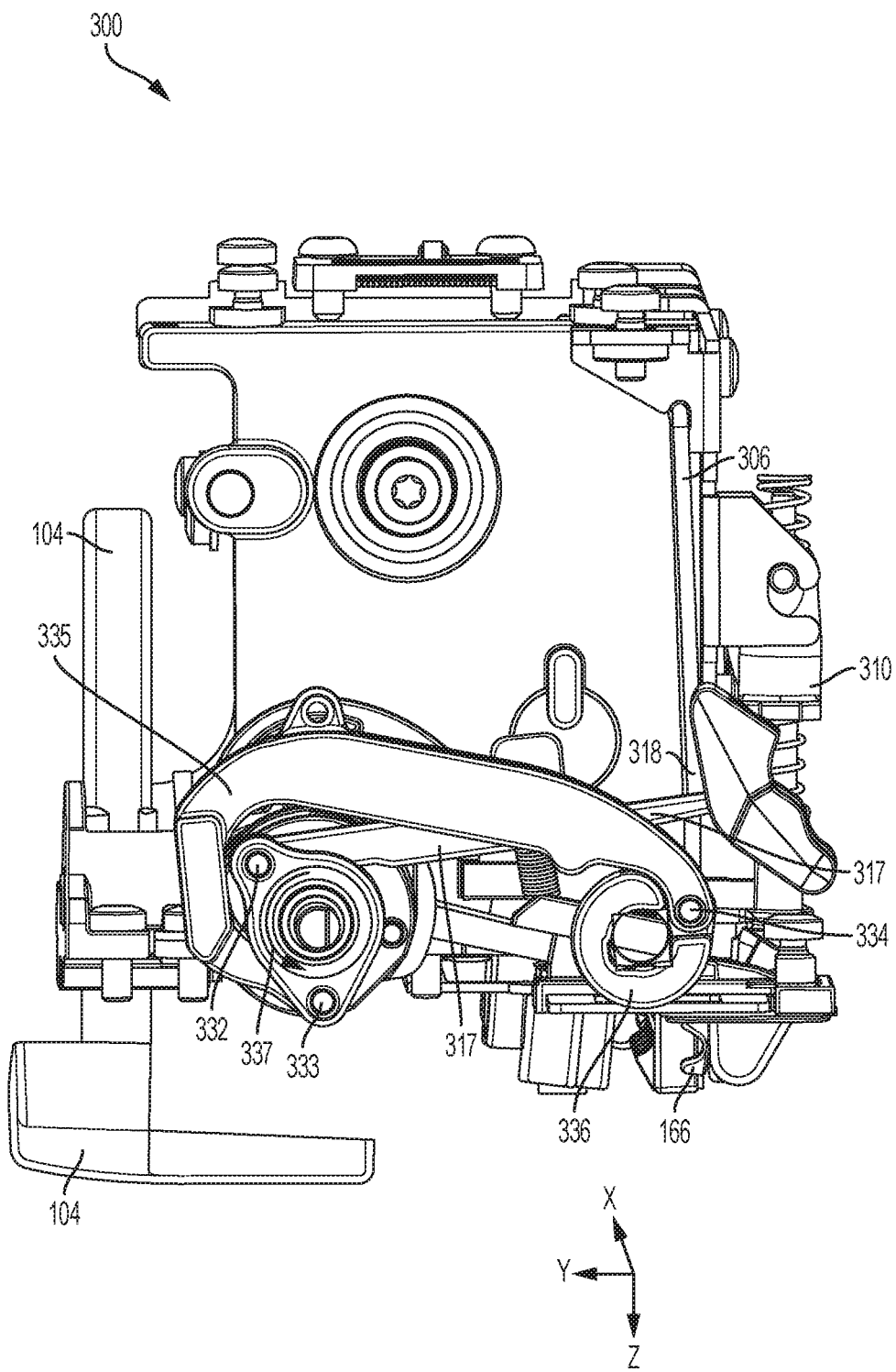
FIG. 93 shows the peristaltic pump of FIG. 63 with some parts removed to illustrate the mechanical linkage between the shaft and the carriage where the door, the door catch, and the lever are in the closed position in accordance with an embodiment of the present disclosure.

FIG. 92 shows the peristaltic pump 300 of FIG. 63 with some parts removed to illustrate the mechanical linkage between the shaft and the carriage 150 where the door 102 and the door catch 114 are in the closed position while the lever 104 is between the open and closed position. Because the main shaft 118 has partially rotated in direction 337 by actuation of the lever 104, the carriage linkage bar 335 has pulled on the carriage-shaft collar 336 such that it is rotated along with the carriage 150 attached thereto. FIG. 93 shows the peristaltic pump 300 of FIG. 63 when the lever 104 has been closed. As can be seen, the carriage-shaft collar 336 has been fully rotated such that the carriage 150 is now in the position as shown in FIG. 36.

Figure 94:
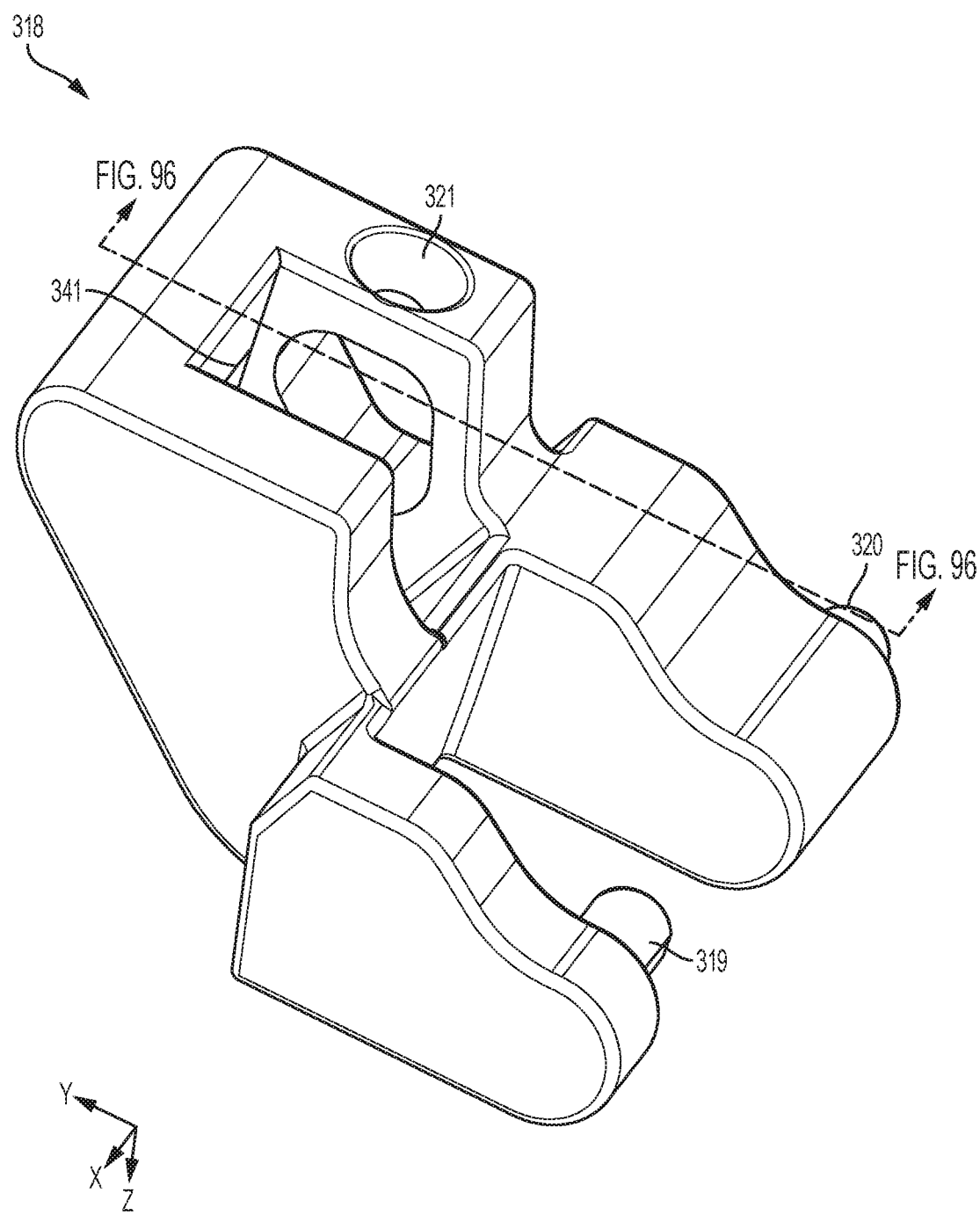
FIGS. 94-96 show the pawl of the peristaltic pump of FIG. 63 from several views in accordance with an embodiment of the present disclosure.
Figure 95:
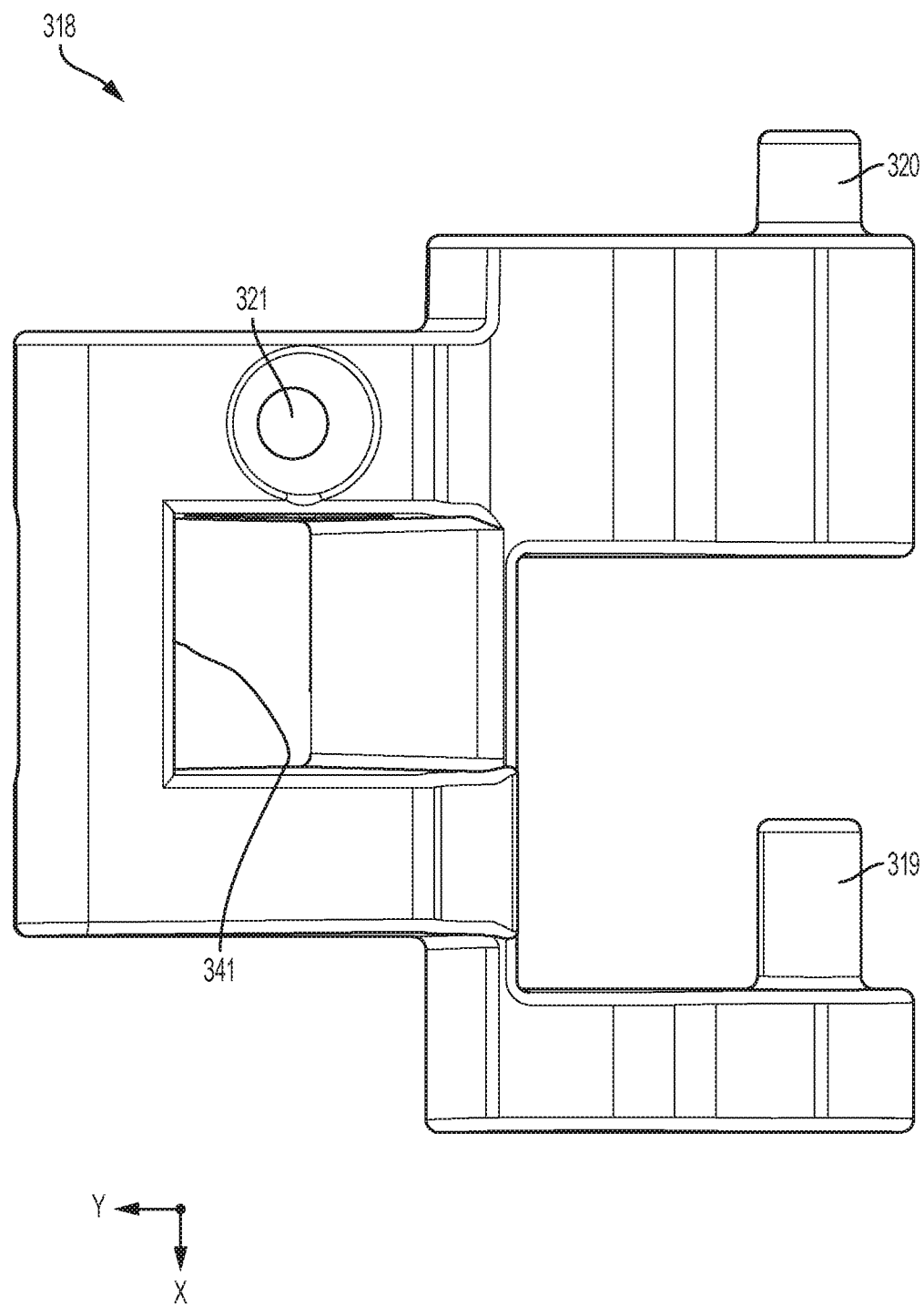
Figure 96:
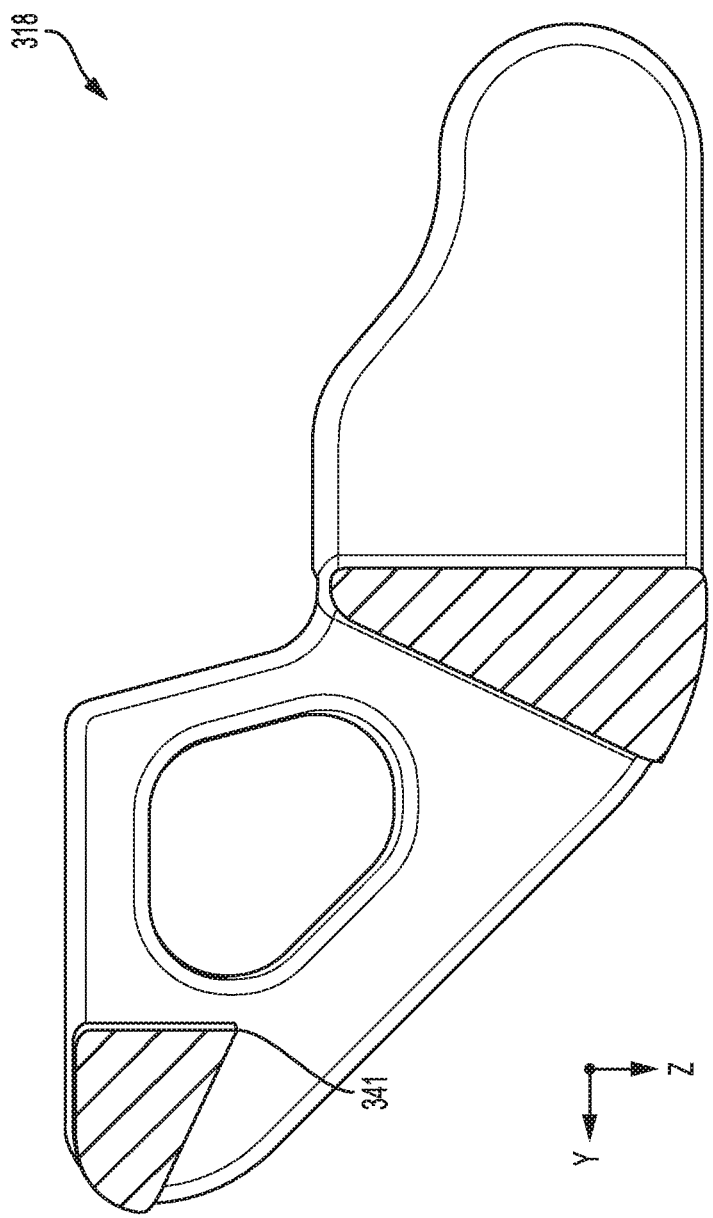

FIG. 94-96 show the pawl 318 of the peristaltic pump 300 of FIG. 63 from several views. FIG. 96 shows a cross-sectional view of the pawl 318 along the view indicated in FIG. 94. In FIG. 96, a tooth 341 is shown that engages with the teeth of the toothed linkage bar 317 shown above in FIGS. 73-93.

Figure 97:
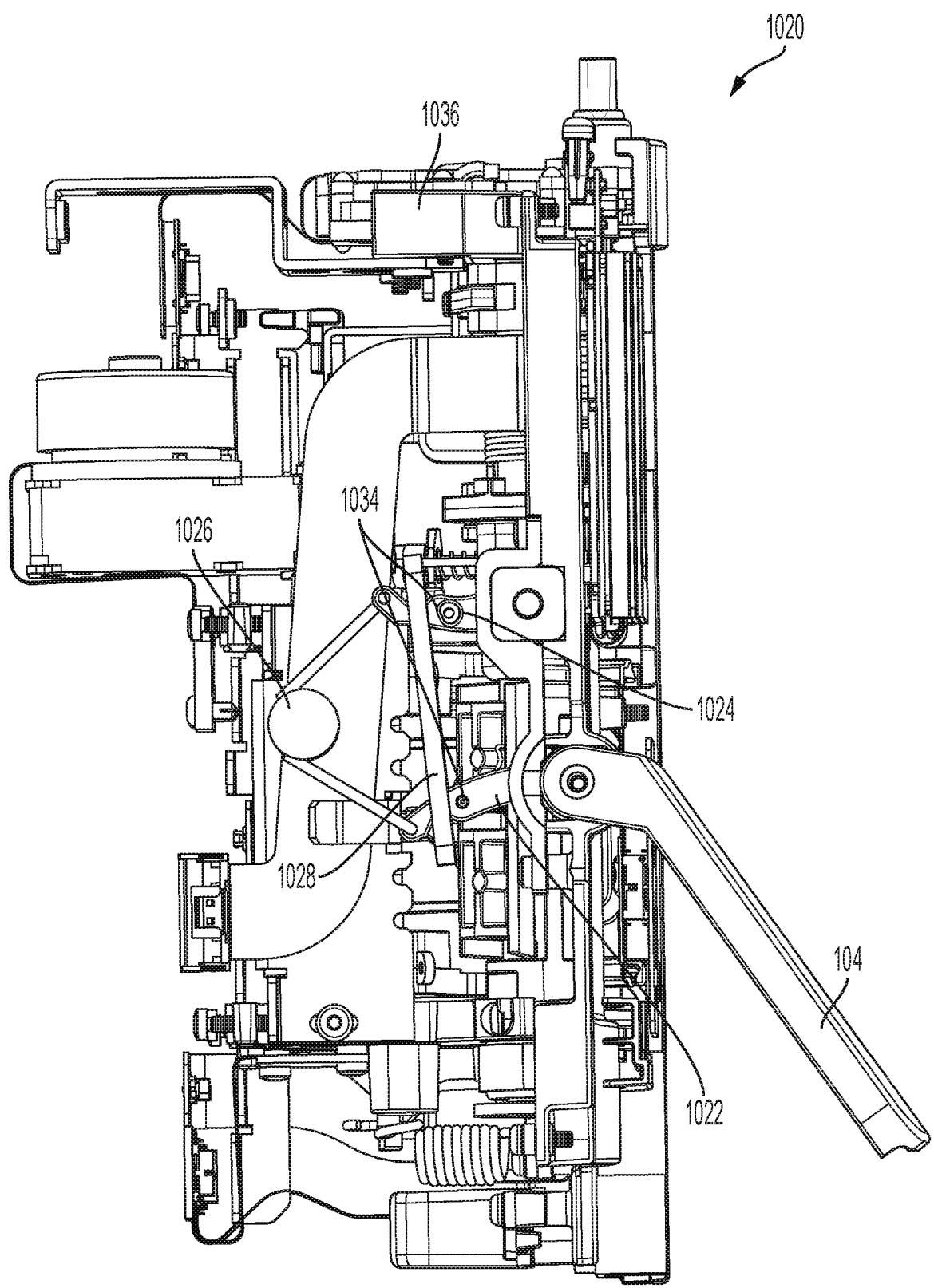
FIGS. 97-98 show an alternative embodiment of the peristaltic pump of FIG. 1 where an alternative mechanical assembly between the lever and the main shaft is used and an alternative carriage is used in accordance with an embodiment of the present disclosure.
Figure 98:
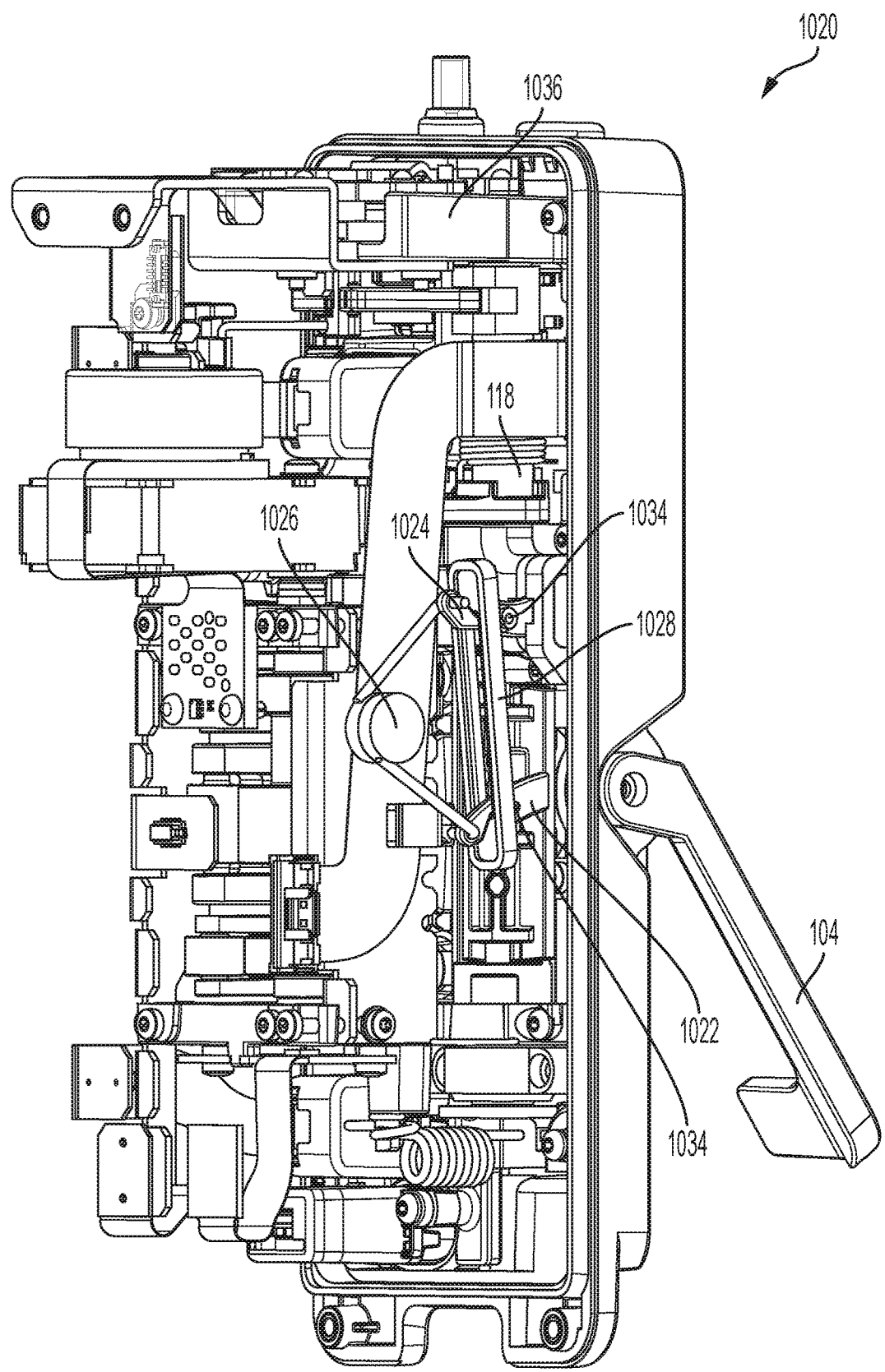

FIGS. 97-98 shows an alternative embodiment of the peristaltic pump 1020 where an alternative mechanical assembly 1021 between the lever 104 and the main shaft 118 is used. FIGS. 97-98 also shows an embodiment of the peristaltic pump 1020 where an alternative carriage 1036 is used. The peristaltic pump 1020 provides resilience between the lever 104 and a main shaft 118 via a spring 1026. The spring 1026 is a torsion spring, in some specific embodiments.

As shown in FIG. 97, when in operation the spring 1026 provides resilience such that the spring 1026, via its ends, urges the first linkage 1022 and the second linkage 1024 outward toward the ends of the track 1028. When the ends of the spring 1026 remain at the ends of the track 1028, the track 1028 moves when the lever 104 is actuated which moves the second linkage 1024. That is, the first linkage 1022 and the second linkage 1024 remain at a predetermined distance from each other at a respective end of the track 1028 when the spring 1026 maintains the first linkage 1022 and the second linkage 1024 at a maximal distance between each other in the track 1028. However, if the door is open, the main shaft 118 (see FIG. 98) cannot be rotated because it is effectively locked. Therefore, the spring 1026 can become compressed as described below. The guides 1034 are configured to guide the linkages 1022, 1024 along the track 1028. Each of the linkages 1022, 1024 includes guides 1034 to keep the linkages 1022, 1024 disposed on a predetermined position on the track 1028.

Figure 99:
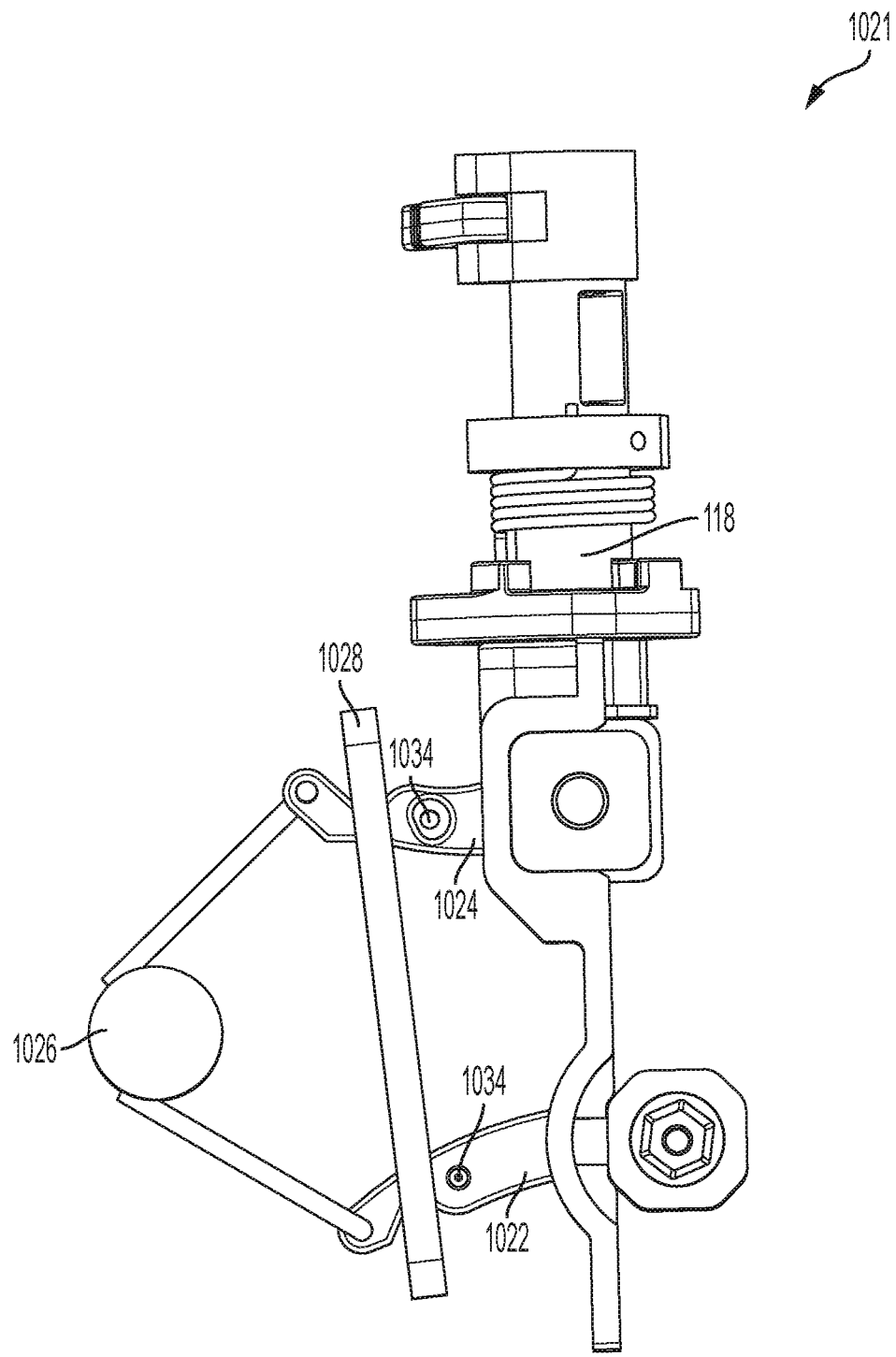
FIGS. 99-101 show portions of the alternative mechanical assembly of the peristaltic pump of FIGS. 97-98 in accordance with an embodiment of the present disclosure.

Referring now to FIG. 99, when the lever 104 is actuated, the first linkage 1022 applies a force to the spring 1026; but, when the second linkage 1024 is locked (because, for example, the carriage is locked because the door 102 is open), the first linkage 1022 approaches the second linkage 1024 as guided by the track 1028 as the spring 1026 compresses. Eventually, the first linkage 1022 will engage with the second linkage 1024, in which case, the lever 104 will be stopped by a hard stop.

Figure 100:
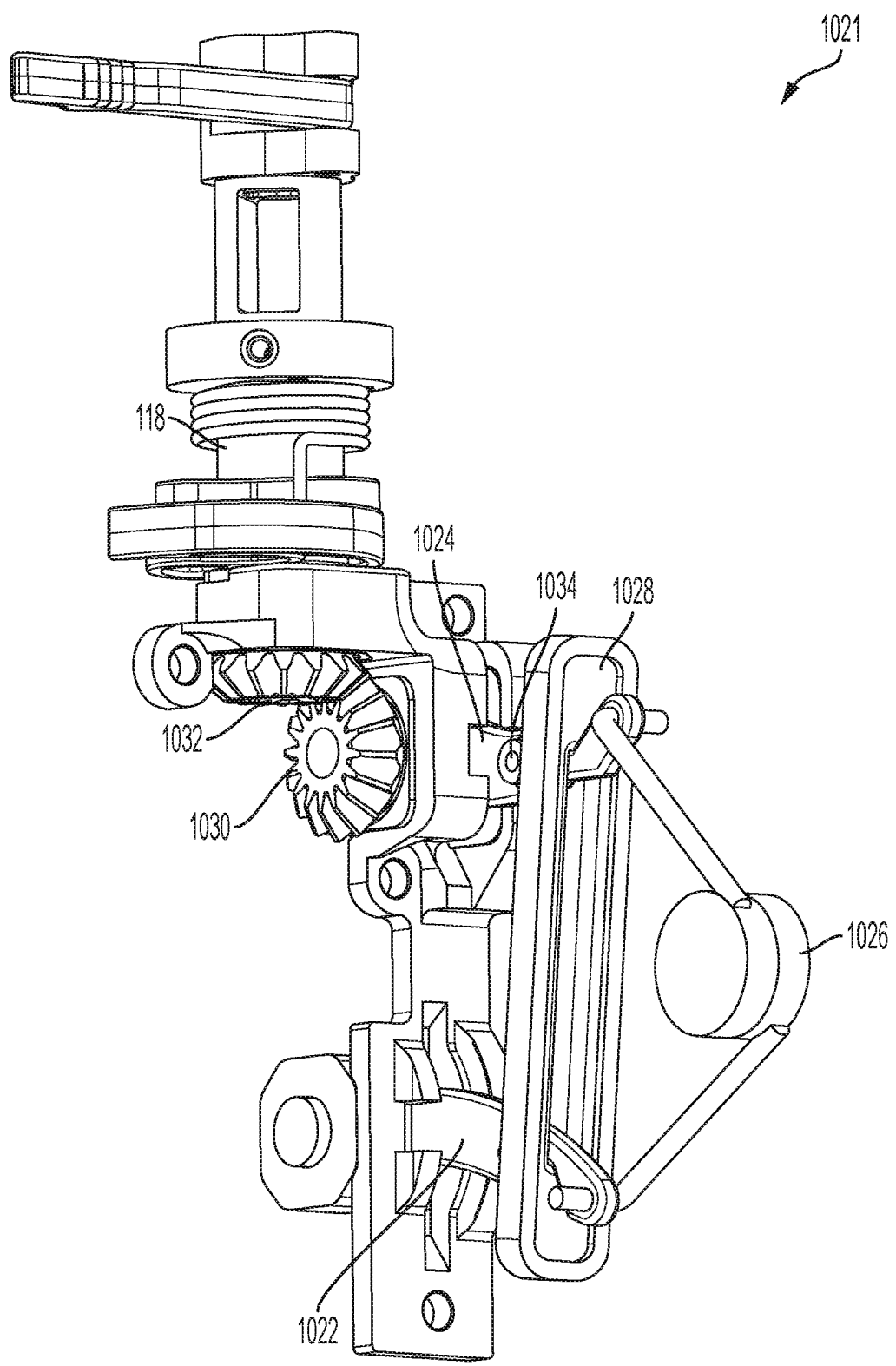
Figure 101:
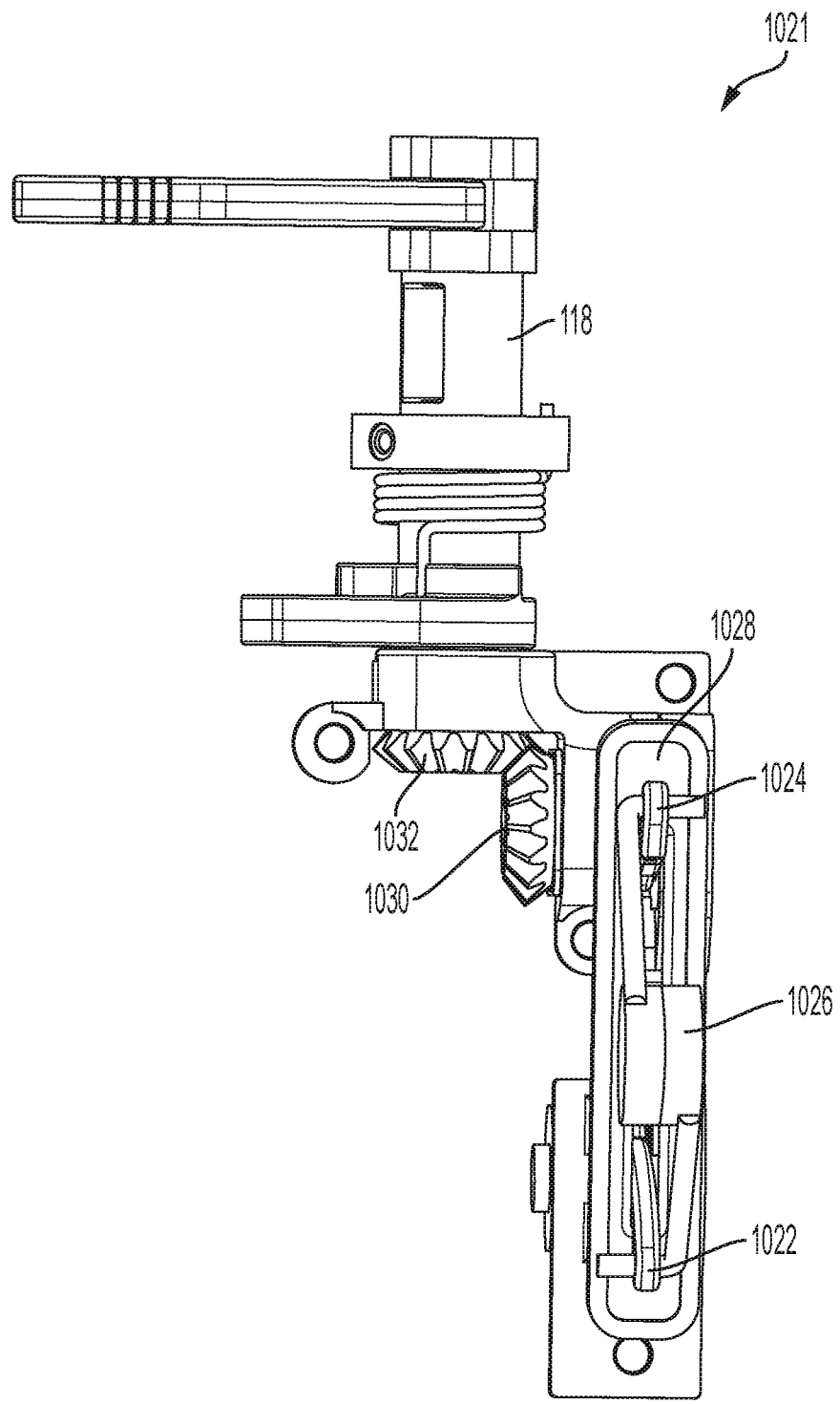

The lever 104 can pivot to actuate a first linkage 1022. When the main shaft 118 is not locked, this actuation also actuates the second linkage 1024. As shown in FIGS. 100-101, actuating the second linkage 1024 rotates the first bevel gear 1030, which in turn rotates a second bevel gear 1032. The second bevel gear 1032 is attached to the main shaft 118. The lower portion of the shaft may extend from the second bevel gear 1032 by being attached to the second bevel gear 1032 thereto (not shown in FIGS. 100-101). The first linkage 1022 slides along the track 1028 when the main shaft 118 is unable to rotate thereby compressing the spring 1026. Additionally or alternatively, the second linkage 1024 slides along the track when the main shaft 118 is unable to rotate.

FIGS. 102-105 show several views a slide-clamp assembly 1038 in accordance with an embodiment of the present disclosure. The slide-clamp assembly 1038 includes a top housing 1040 and a bottom housing 1042. A tube 1046 is coupled to the slide-clamp assembly 1038 via a tube coupling 1044. The slide-clamp assembly 1038 can occlude fluid flow through the tube 1046 or can allow fluid to flow freely therethrough.

Figure 103:
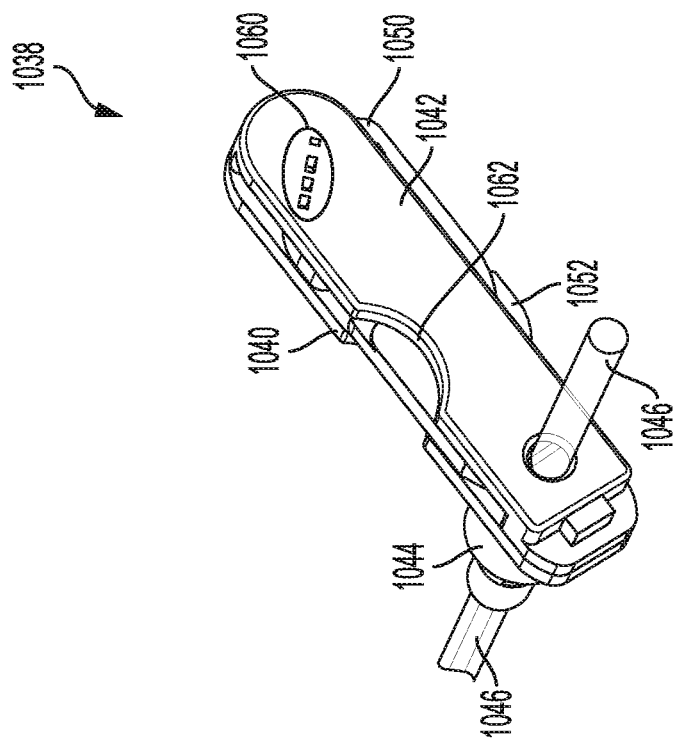
FIGS. 102-105 show several views a slide-clamp assembly in accordance with an embodiment of the present disclosure.
Figure 102:
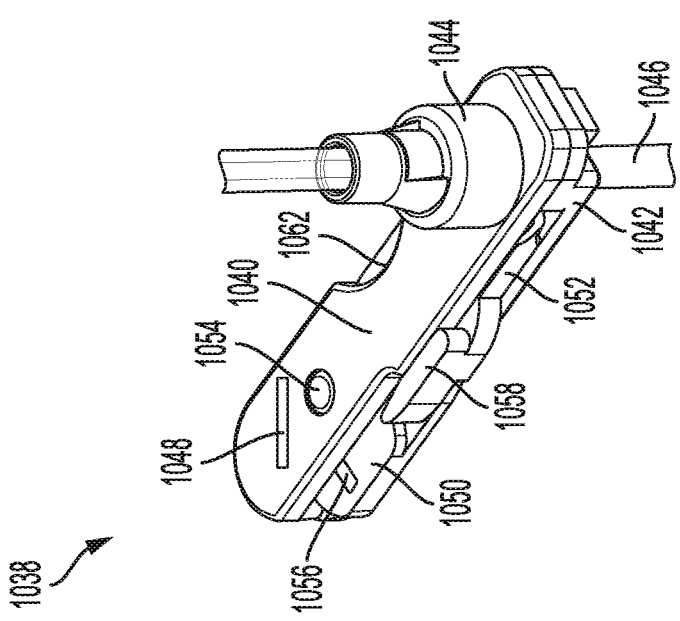
Figure 105:
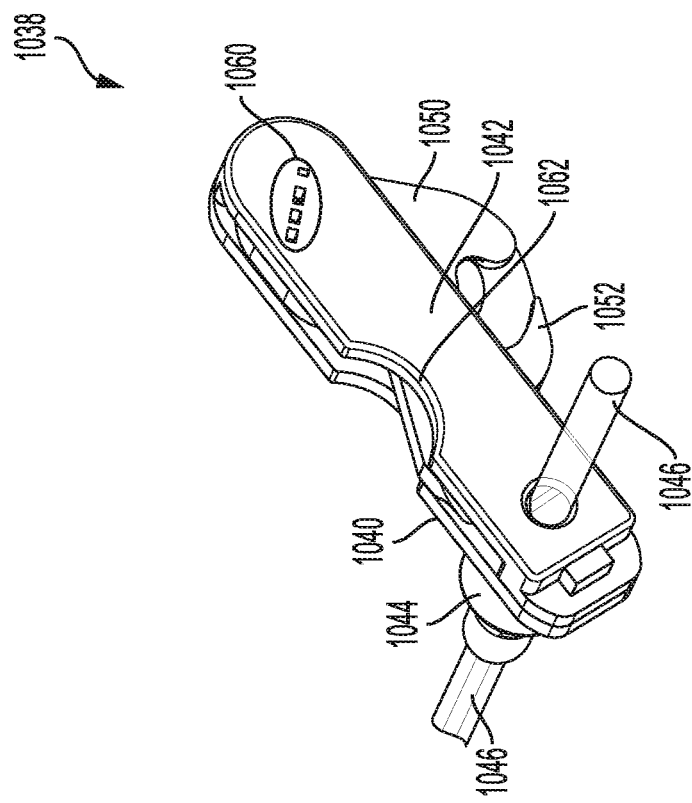
Figure 104:
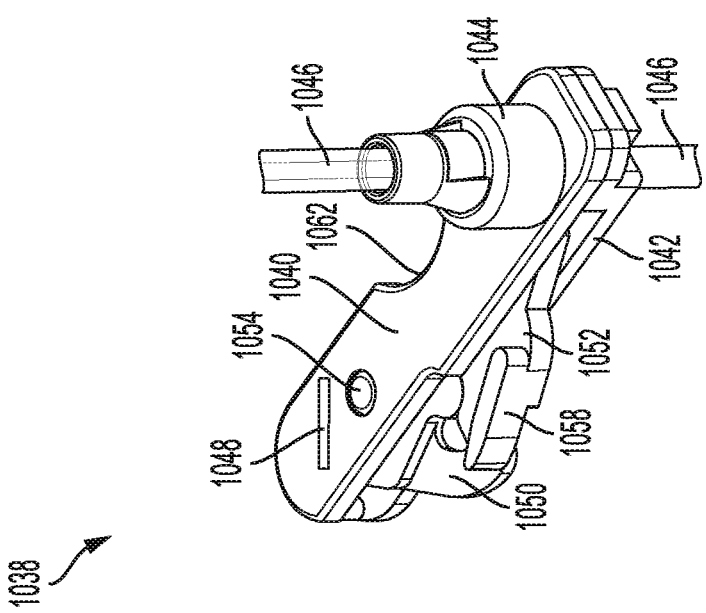

Non-occluded and occluded fluid flow may be effected through the tube 1046 via actuation of a first link 1052 and a second link 1050. FIGS. 102-103 show the slide-clamp assembly 1038 in the occluding position and FIGS. 104-105 show the slide-clamp assembly 1038 in the non-occluding position. When the slide-clamp assembly 1038 is in the occluding position, as shown in FIGS. 102-103, a user can press on the first link 1052 via a finger groove 1062 to actuate the second link 1050 and first link 1052 to the non-occluding position as shown in FIGS. 104-105. Likewise, when the slide-clamp assembly 1038 is in the non-occluding position as shown in FIGS. 104-105, a user can press on a flange 1058 to actuate the second link 1050 and first link 1052 to the occluding position as shown in FIGS. 102-103.

Figure 106:
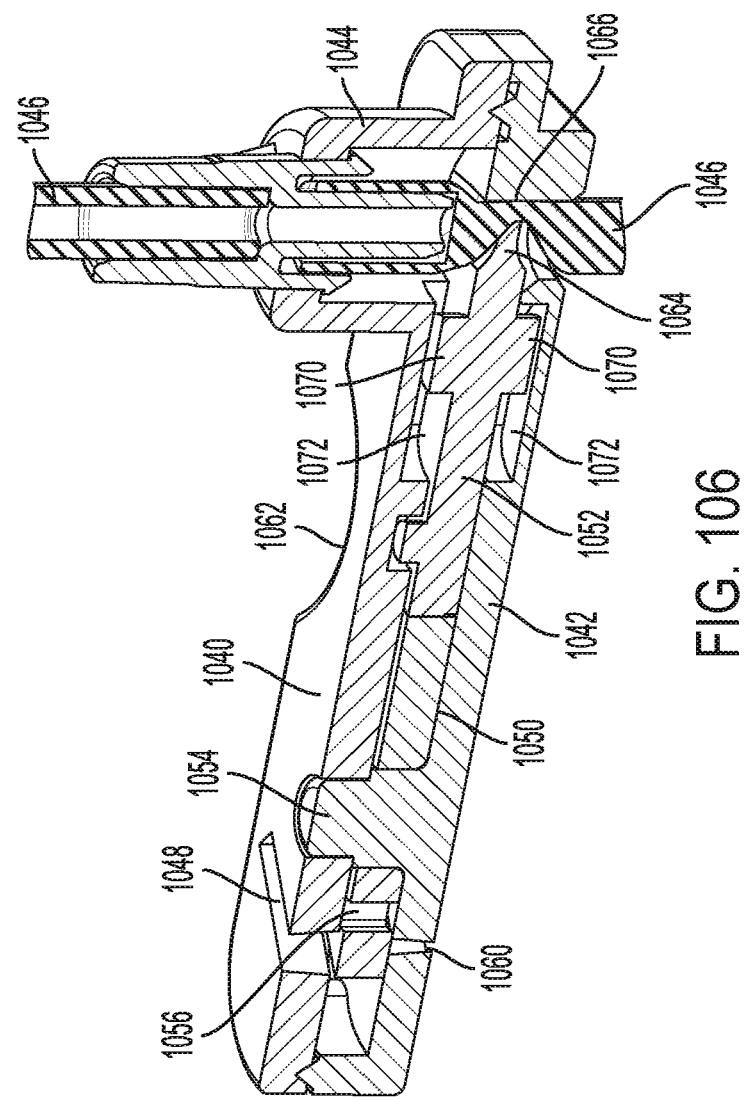
FIG. 106 shows a cross-sectional view of the slide-clamp assembly of FIGS. 102-105 in accordance with an embodiment of the present disclosure.

The slide-clamp assembly 1038 also includes a housing aperture 1048 which can be used to sense the configuration of an identification aperture 1060, can be used to determine if the slide-clamp assembly 1038 is loaded properly or improperly, and can be used to determine the configuration of the slide-clamp assembly 1038 (e.g., the occluding vs. non-occluding position, etc.). The identification may take place as is described herein using optical recognition of a pattern of the identification aperture 1060. FIG. 106 shows a cross-sectional view of the slide-clamp assembly 1038, which shows a pivot post 1054 about which the second link 1050 can pivot. When the first link 1052 and the second link 1050 are in the occluding position, as shown in FIG. 106, a plunger 1064 occludes a tube 1046 by wedging the tube 1046 between the plunger 1064 and a backstop 1066. A shutter aperture 1056 is shown which blocks or allow light to pass through depending whether or not the slide-clamp assembly 1038 is in the occluding position or the non-occluding position.

Figure 109:
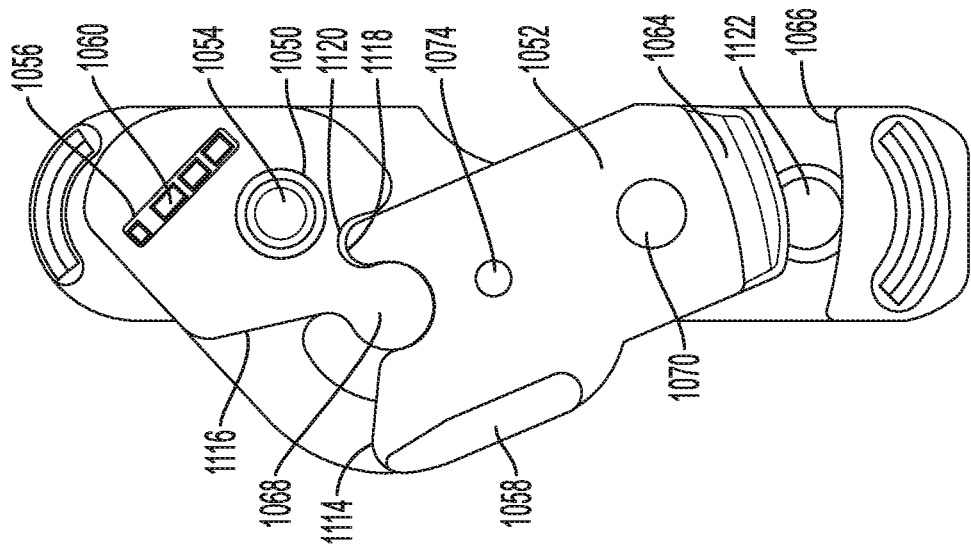
Figure 108:
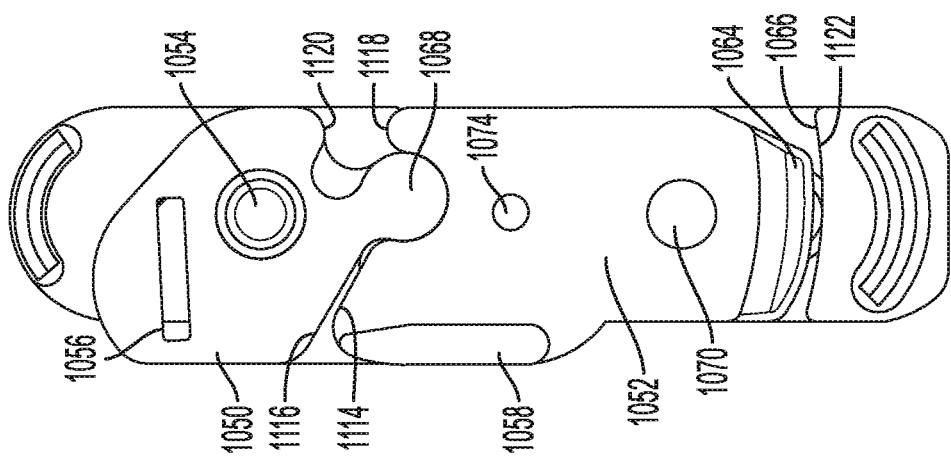
Figure 114:
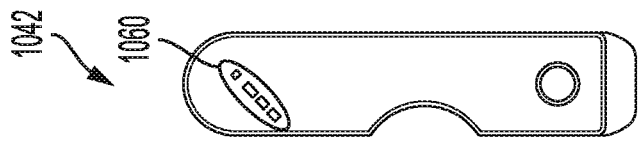
FIGS. 110-114 show several views of the bottom housing of the slide-clamp assembly of FIGS. 102-105 in accordance with an embodiment of the present disclosure.
Figure 113:
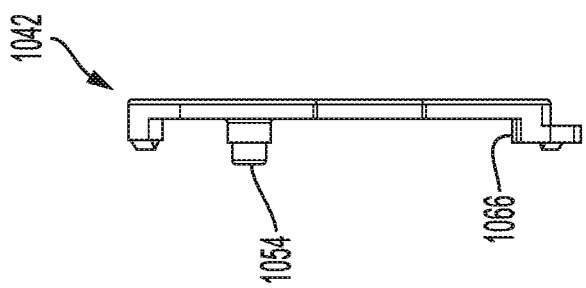
Figure 112:
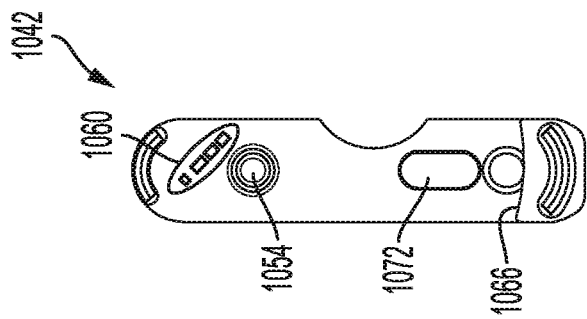
Figure 110:
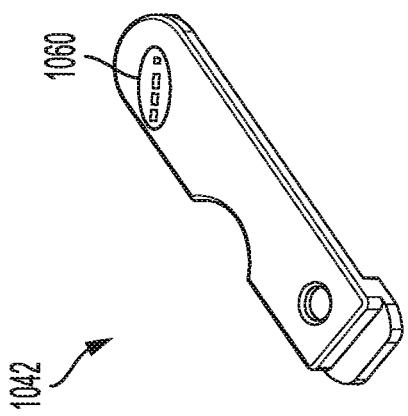
Figure 111:
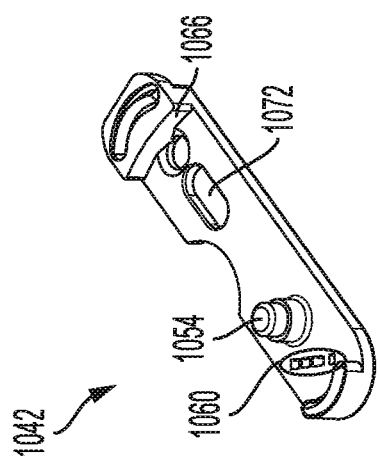
Figure 124:
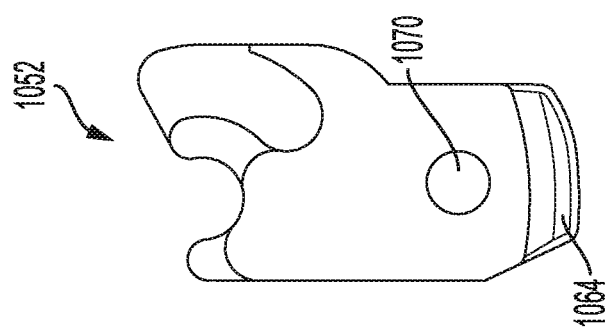
FIGS. 120-124 show several views of a first link of the slide-clamp assembly of FIGS. 102-105 having a plunger in according with an embodiment of the present disclosure.
Figure 123:
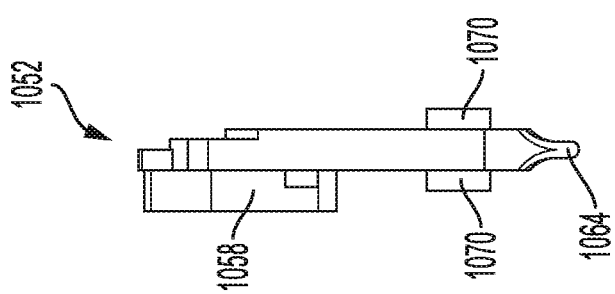
Figure 122:
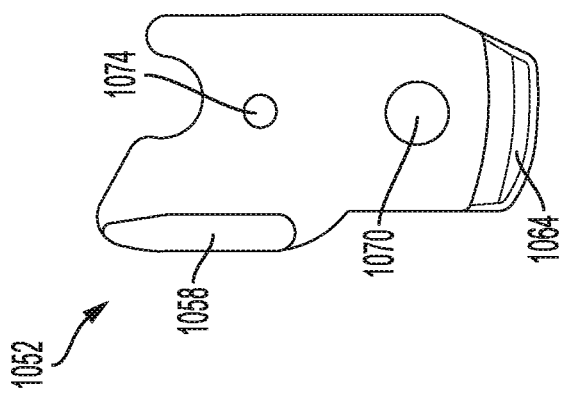
Figure 120:
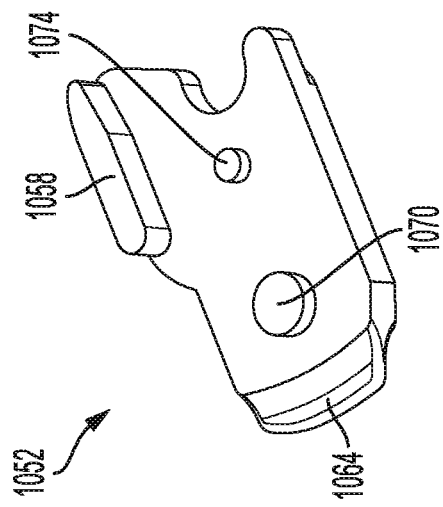
Figure 121:
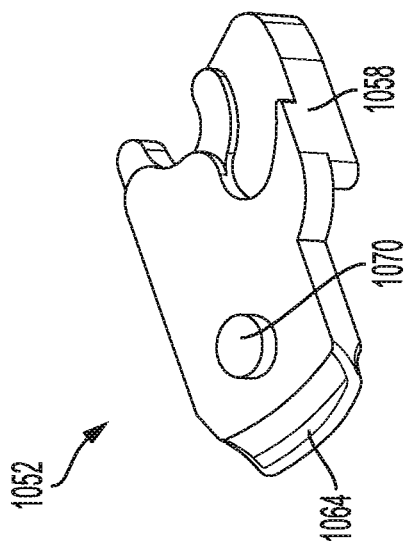
Figure 129:
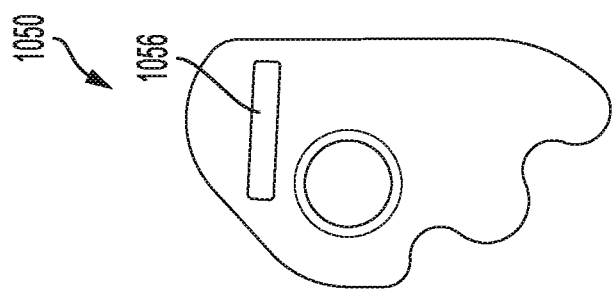
FIGS. 125-129 show several views of a second link of the slide-clamp assembly of FIGS. 102-105 in accordance with an embodiment of the present disclosure.
Figure 128:
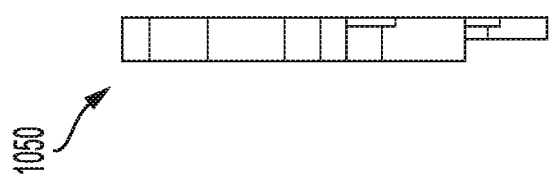
Figure 127:
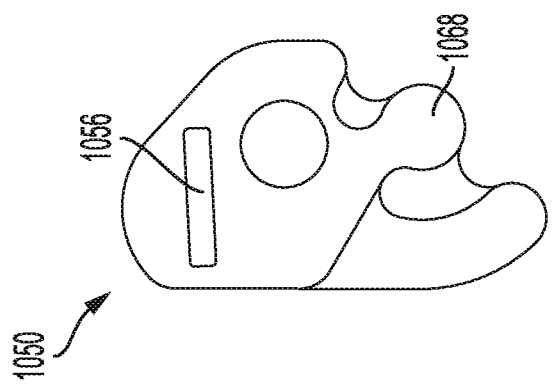
Figure 125:
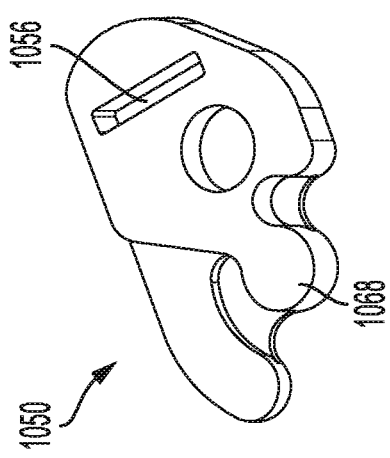
Figure 126:
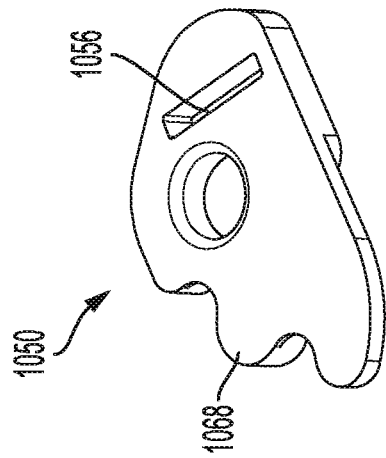
Figure 133:
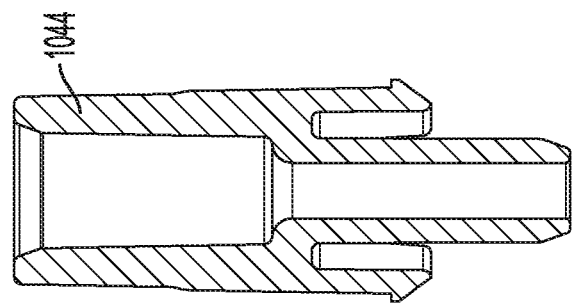
FIGS. 130-133 show several views of a tube coupling of the slide-clamp assembly of FIGS. 102-105 in accordance with an embodiment of the present disclosure.
Figure 132:
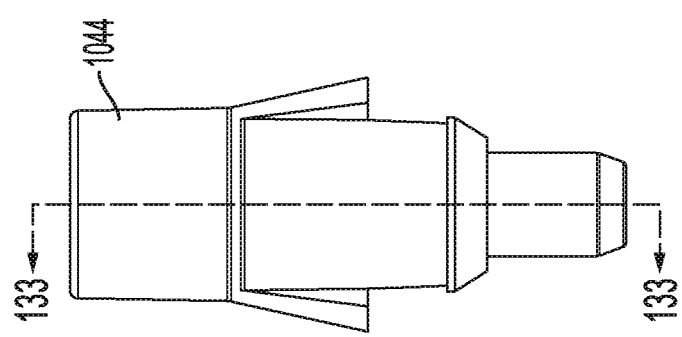
Figure 130:
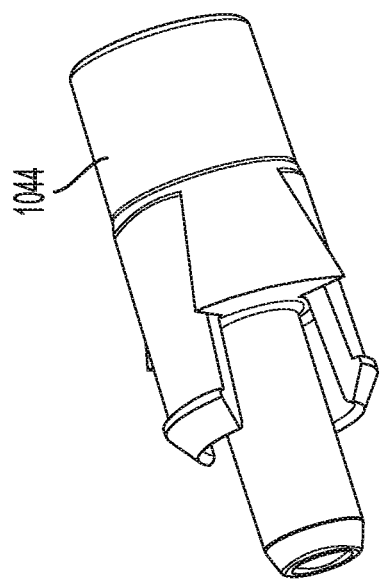
Figure 131:
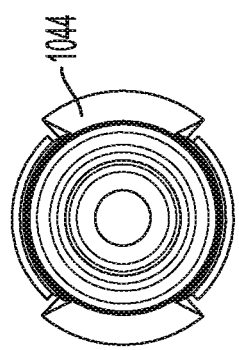

The second link 1050 pivots around the pivot post 1054. The first link 1052 is coupled to the second link 1050 via a ball-and-socket joint 1068 (see FIG. 107). As the first link 1052 is actuated, it is guided within a track 1072 by guides 1070. FIG. 108 shows the slide-clamp assembly 1038 with the top housing 1040 removed while in the occluding position and FIG. 109 shows the slide-clamp assembly 1038 with the top housing 1040 while in the non-occluding position. As is shown in FIG. 108, when the first link 1052 is in the occluding position, the plunger 1064 is closer to the backstop 1066 and when the second link 1050 is in the non-occluding position, the plunger 1064 is a predetermined distance from the backstop 1066. The second link 1050 and the first link 1052 are coupled together via a ball-and-socket joint 1068. The guides 1070 positions the first link 1052 such that rotation of the second link 1050 along the pivot post 1054 translates to linear motion of the guides 1070 along the track 1072 as shown in FIGS. 110-114. FIGS. 108-109 also illustrate how the position of the shutter aperture 1056 is positioned in different locations based upon the position of the second link 1050. FIGS. 110-114 show several views of the bottom housing 1042 of the slide-clamp assembly 1038 including the track 1072. Please note the identification aperture 1060 where identification of the slide-clamp assembly 1038 can be made, as described herein.

The first link 1052 includes a first contacting surface 1114 and a third contacting surface 1118. The second link 1050 includes a second contacting surface 1116 and a fourth contacting surface 1120. As shown in FIG. 108, when the slide-clamp assembly 1038 is in the occluding position, the first contacting surface 1114 contacts the second contacting surface 1116. As shown in FIG. 109, when the slide-clamp assembly 1038 is in the non-occluding position, the third contacting surface 1118 contacts the fourth contacting surface 1120. In some embodiments, a secondary guide 1074 can limit the movement of the first link 1052 via limiting the range of motion the secondary guide 1074 can travel within a secondary track 1076 (see FIG. 119). Referring again to FIGS. 108-109, in some specific embodiments of the present disclosure, the compliance of the tube 1046 may make the slide-clamp assembly 1038 bi-stable, with one stable configuration being the occluding position as shown in FIG. 108 and the other stable configuration being the non-occluding configuration as shown in FIG. 109 (a hole 1122 is shown in FIGS. 108 and 109 where the tube 1046 is positioned (see FIG. 107). In alternative embodiments, a spring or springs may be used to urge the second link 1050 and first link 1052 into the two bi-stable configurations.

FIGS. 115-119 show several views of the top housing 1040 of the slide-clamp assembly 1038. A track 1072 is shown which can guide the movement of first link 1052 via a secondary guide 1074 (see FIGS. 108 and 109 in conjunction with FIGS. 115-119). FIGS. 120-124 show several views of a first link 1052 of the slide-clamp assembly 1038 having the plunger 1064 and FIGS. 125-129 show several views of a second link 1050 of the slide-clamp assembly 1038. FIGS. 130-133 show several views of a tube coupling 1044 of the slide-clamp assembly 1038.

FIGS. 134-138 show the slide-clamp assembly 1038 being inserted into a carriage 1036. In FIG. 134, the slide-clamp assembly 1038 is in the non-occluding configuration. As the slide-clamp assembly 1038 is inserted into the alternative carriage 1036, a cooperating surface 1094 interacts with the second link 1050 to actuate both the second link 1050 and the first link 1052 to place the slide-clamp assembly 1038 in the occluding position illustrated in FIGS. 135-136. As shown in FIG. 136, the slide-clamp assembly 1038 will be actuated into the occluding position prior to insertion into the alternative carriage 1036. Thus, in some embodiments of the present disclosure, the peristaltic pump 1020 is configured to only receive a slide-clamp assembly 1038 in the occluding position; And, if the slide-clamp assembly 1038 is not in the occluding position prior to insertion, the peristaltic pump 1020 will actuate the slide-clamp assembly 1038 into the occluding position prior to being received (in some specific embodiments, before being partially received and in others, before or during being fully received).

FIG. 137 shows the slide-clamp assembly 1038 fully inserted where the gripper finger 1086 engages with the flange 1058. Also shown, is a tube shutter 1078 that actuates when the slide-clamp assembly 1038 engages with it. A shaft coupler 1080 is coupled to a shaft of the peristaltic pump 1020. The shaft coupler 1080 may be coupled directly to the main shaft 118, to the main shaft 118 via one or more gears or linkages, through another shaft, or through any other mechanical mechanism known to one of ordinary skill in the relevant art.

Figure 140:
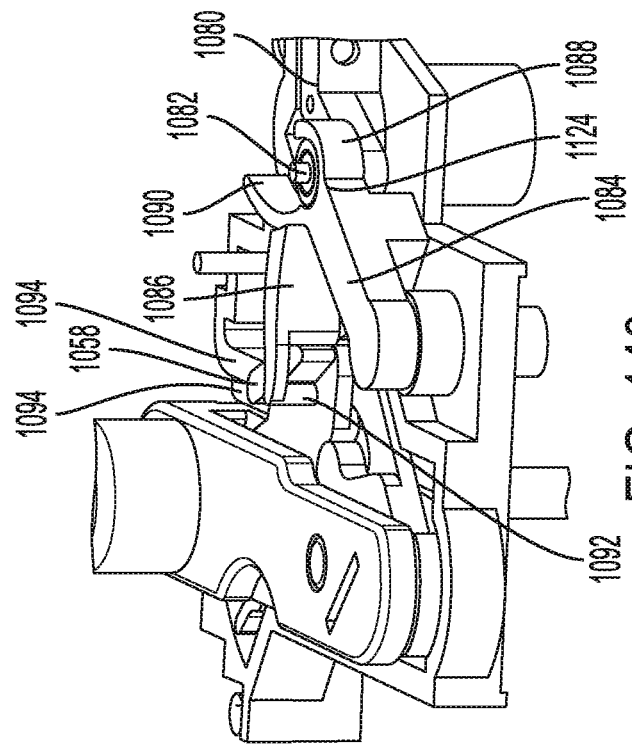
FIG. 140 shows a perspective view of the internal mechanism of the carriage when the end effector is engaged with a flange of the slide-clamp assembly of FIGS. 102-105 in accordance with an embodiment of the present disclosure.
Figure 139:
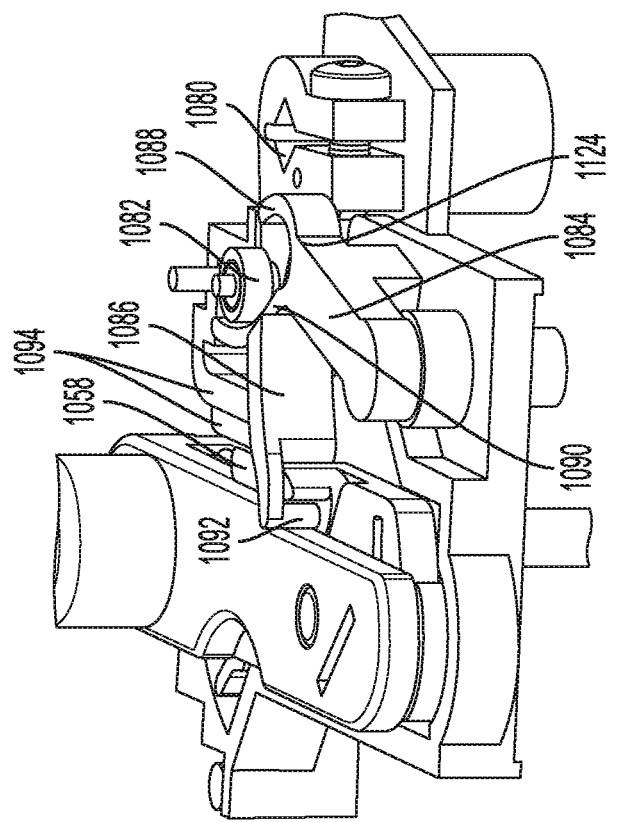
FIG. 139 shows a perspective view of the internal mechanism of the carriage when the end effector is engaged with a flange of the slide-clamp assembly of FIGS. 102-105 in accordance with an embodiment of the present disclosure.

When the slide-clamp assembly 1038 is fully inserted into the carriage 1036, a user can actuate the lever 104 thereby causing the shaft coupler 1080 to rotate along with a pin 1082. An interlock arm 1084 includes a second finger 1088 and a first finger 1090 such that actuation of the pin 1082 into a catch well 1124 causes actuation of the interlock arm 1084, which actuates a gripper finger 1086. Because the gripper finger 1086 engages with the flange 1058, actuation of the gripper finger 1086 actuates the first link 1052 and the second link 1050 into the non-occluding position by pulling the flange 1058 in a direction away from the slide-clamp assembly 1038. FIG. 139 shows a perspective view of the internal mechanism of the carriage 1036 when the end effector 1092 is engaged with a flange 1058 of the slide-clamp assembly 1038 and FIG. 140 shows a perspective view of the internal mechanism of the carriage 1036 when the end effector 1092 is engaged with a flange 1058 of the slide-clamp assembly 1038 in the non-occluding position. The end effector 1092 may apply a force on the flange 1058 to actuate the slide-clamp assembly to the non-occluding position as shown in FIG. 140. In some embodiment of the present disclosure, the first finger 1090 and the second finger 1088 may be integrated together as a single structure, e.g., and may form a loop around the pin 1082. The pin 1082 may be a protraction, a roller wheel, a roller bearing, a cam, a rolling cam, a wheel, a slidable protrusion, or any suitable device known to one of ordinary skill in the relevant art.

Figure 142:
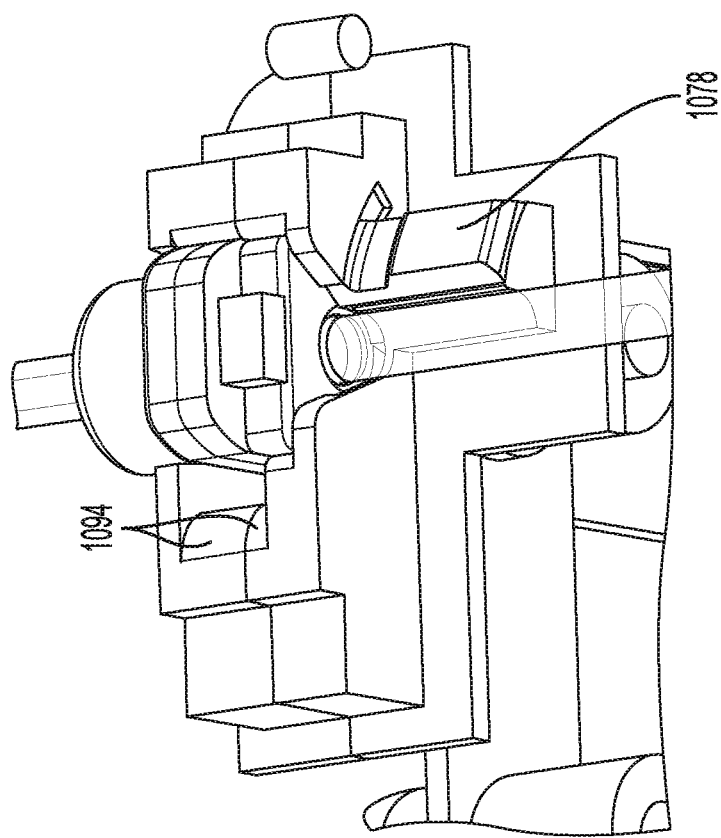
FIG. 142 shows the front of the carriage orifice with a cooperating surface when the slide-clamp assembly has been inserted and a tube shutter retracted in accordance with an embodiment of the present disclosure
Figure 141:
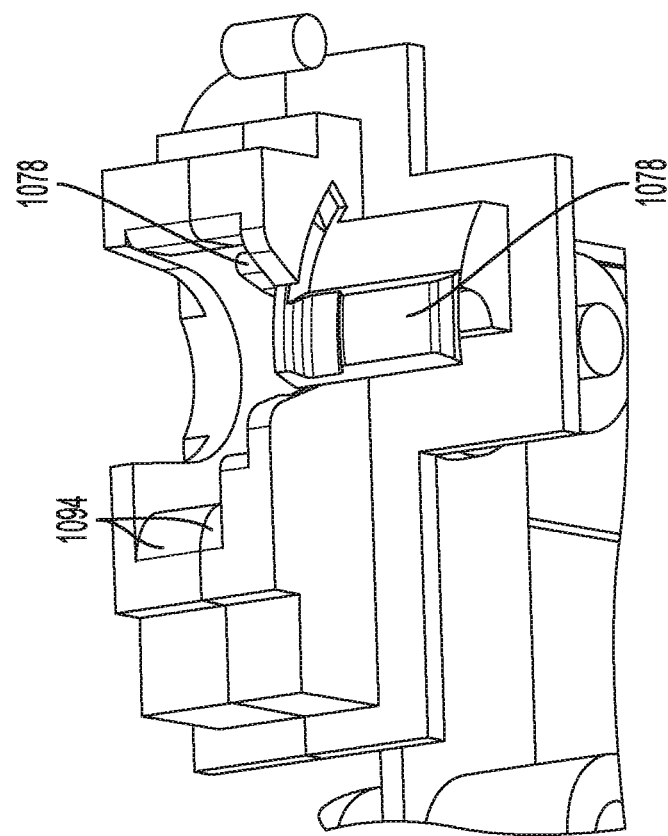
FIG. 141 shows the front of the carriage orifice with a cooperating surface in accordance with an embodiment of the present disclosure.

FIGS. 134-138 also show the actuation of the tube shutter 1078, FIG. 141 shows the front of the carriage orifice with a cooperating surface 1094 and a tube shutter 1078. FIG. 142 shows the front of the carriage orifice when the slide-clamp assembly 1038 has been inserted and the tube shutter 1078 has been opened.

In some embodiments of the present disclosure, the shaft coupler 1080 can rotate in FIG. 138 (clockwise as seen in FIG. 138) to actuate the slide-clamp assembly 1038 to the occluding position when the end effector 1092 of the gripper finger is suitably shaped and configured. In yet an additional embodiment of the present disclosure, when a user pulls the slide-clamp assembly 1038 out of the carriage in FIG. 138, the walls of the carriage actuate the first and second links 1050, 1052 to the occluding position.

FIGS. 143-146 show several views of another embodiment of the slide-clamp assembly 1038. The slide-clamp assembly 1038 of FIGS. 143-146 is similar to the slide-clamp assembly 1038 of FIGS. 102-105 described supra; however, alternative features are described herein or are readily apparent to one of ordinary skill in the relevant art.

Figure 144:
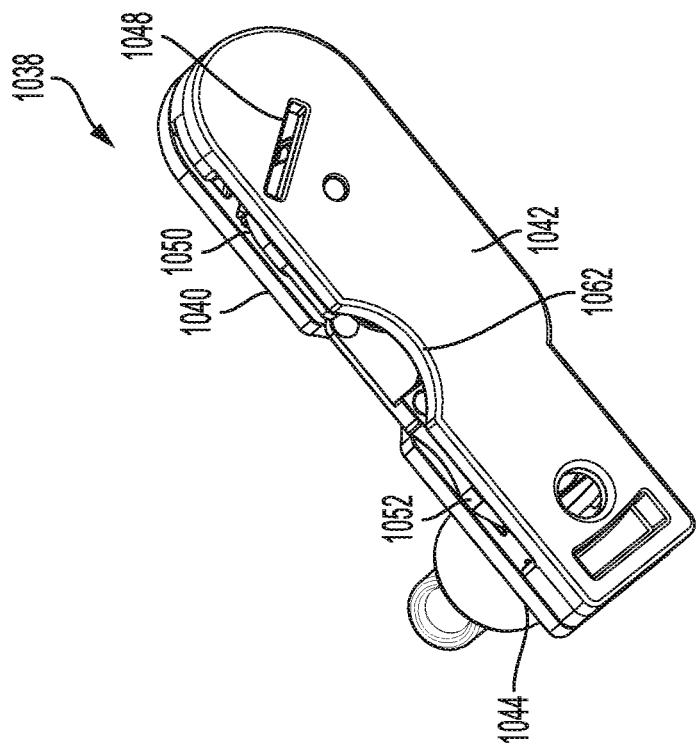
FIGS. 143-146 show several views a slide-clamp assembly in accordance with an embodiment of the present disclosure.
Figure 143:
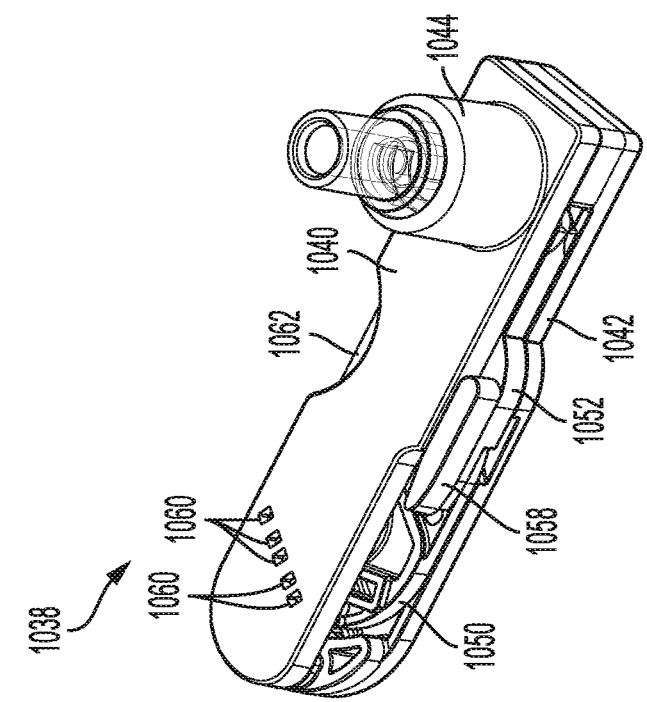
Figure 146:
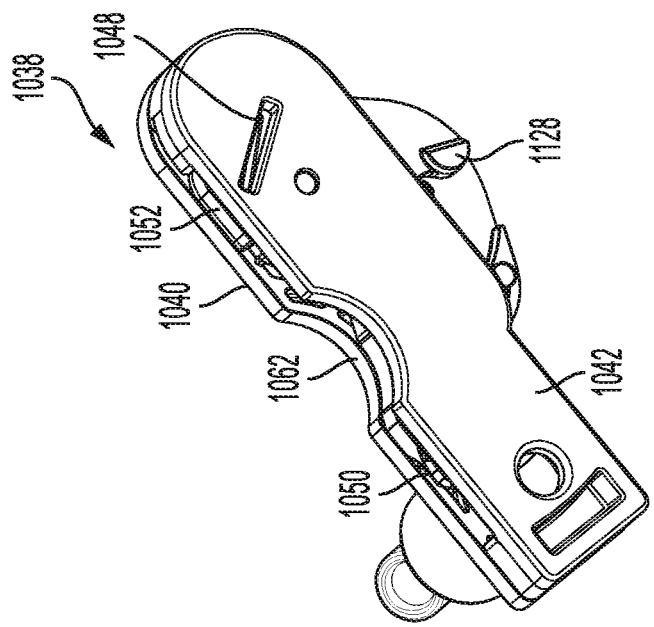
Figure 145:
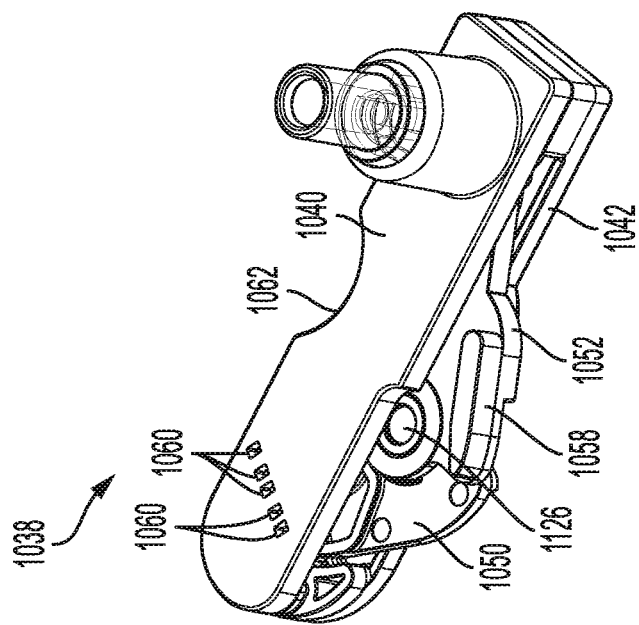

As shown in FIG. 143, the identification aperture 1060 is on the top housing 1040. FIG. 144 shows the housing aperture 1048 on the bottom housing 1042. Non-occluded and occluded fluid flow may be effected through the tube 1046 via actuation of a first link 1052 and second link 1050. FIGS. 143-144 shows the slide-clamp assembly 1038 in an occluding position, and FIGS. 145-146 show the slide-clamp assembly 1038 in the non-occluding position. When the slide-clamp assembly 1038 is in the occluding position, as shown in FIGS. 143-144, a user can press on the first link 1052 via a finger groove 1062 to actuate the second link 1050 and first link 1052 to the non-occluding position as shown in FIGS. 145 and 146. Likewise, when the slide-clamp assembly 1038 is in the non-occluding position as shown in FIGS. 145-146, a user can press on a flange 1058 to actuate the second link 1050 and first link 1052 to the occluding position as shown in FIGS. 143-144.

Figure 147:
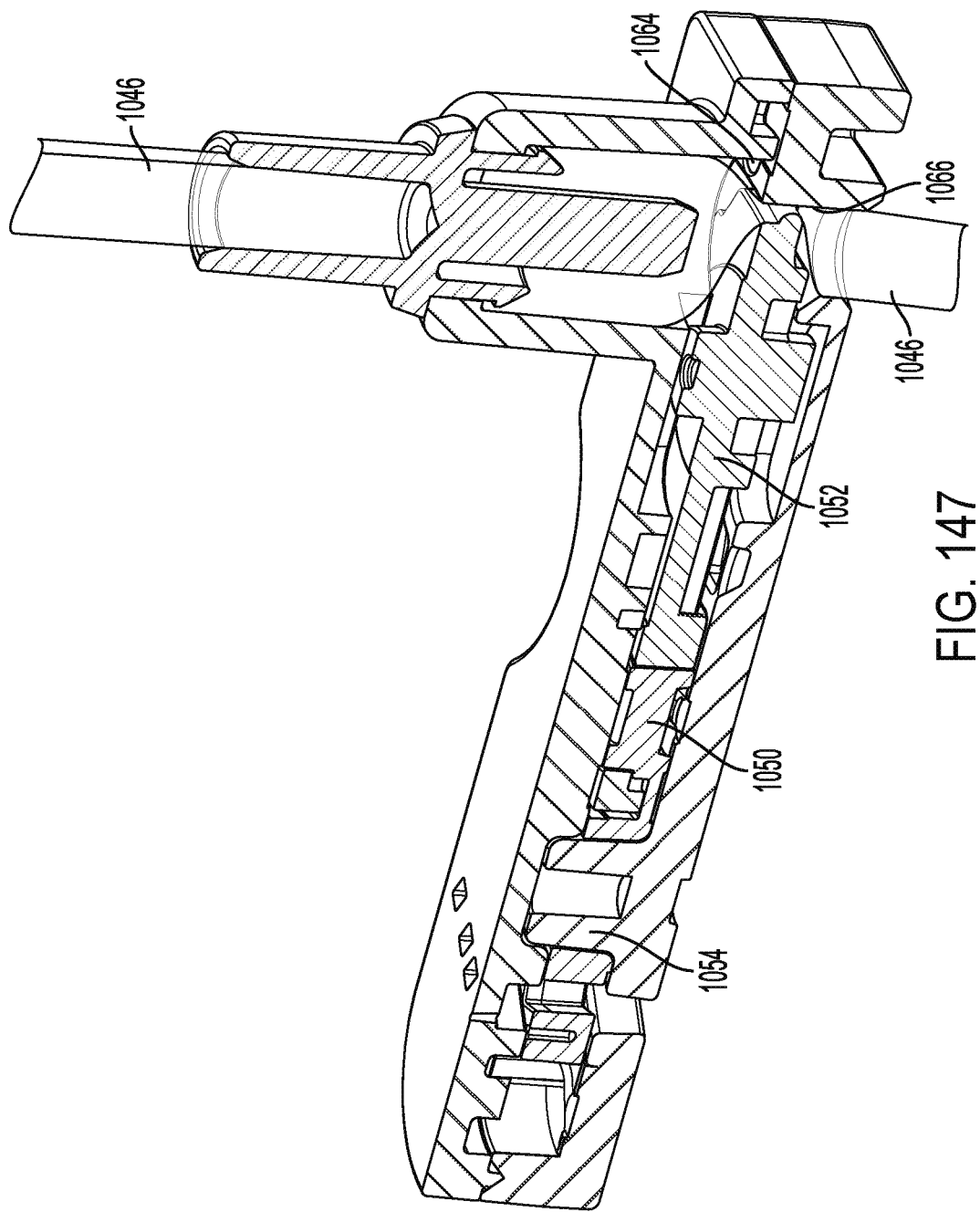
FIG. 147 shows a cross-sectional view of the slide-clamp assembly of FIGS. 143-146 in accordance with an embodiment of the present disclosure.
Figure 166:
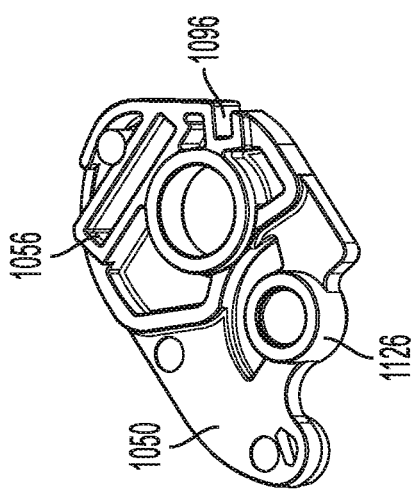
Figure 167:
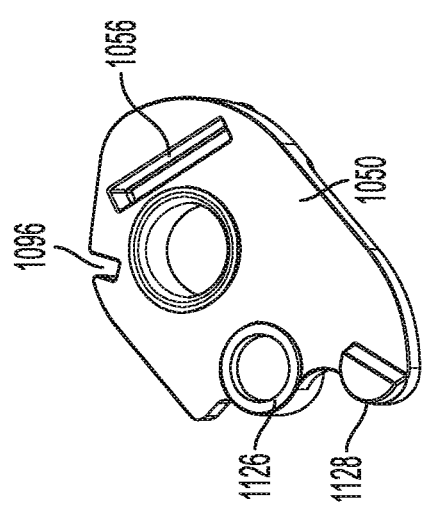

The slide-clamp assembly 1038 also includes a housing aperture 1048 which can be used to sense the configuration of an identification aperture 1060, can be used to determine if the slide-clamp assembly 1038 is loaded properly or improperly, and can be used to determine the configuration of the slide-clamp assembly 1038 (e.g., the occluding vs. non-occluding position, etc.) using an optical sensor as described herein. FIG. 147 shows a cross-sectional view of the slide-clamp assembly 1038, which shows a pivot post 1054 about which the second link 1050 can pivot. When the first link 1052 and the second link 1050 are in the occluding position, as shown in FIG. 166, a plunger 1064 occludes the tube 1046 by wedging the tube 1046 between the plunger 1064 and a backstop 1066.

Figure 148:
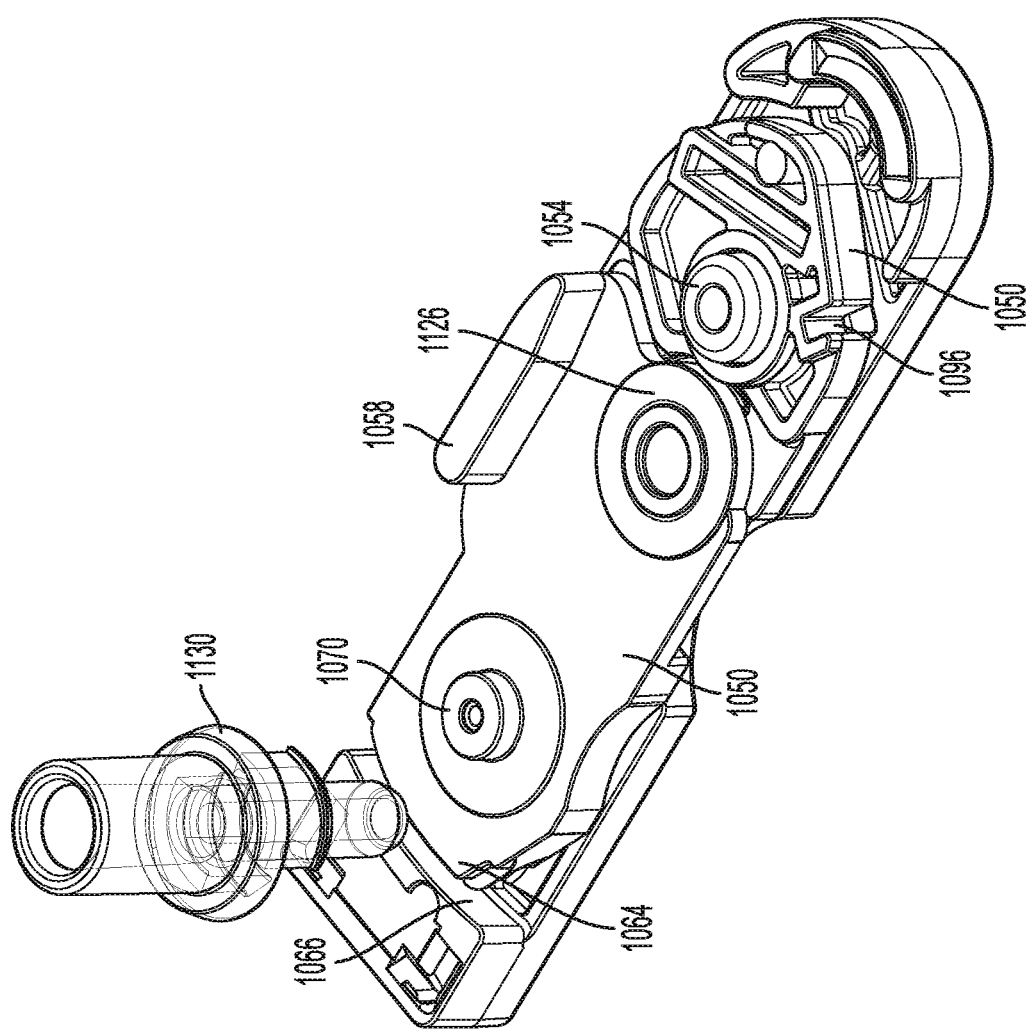
FIGS. 148-150 show several views of the slide-clamp assembly of FIGS. 143-146 with the top housing removed in accordance with an embodiment of the present disclosure.
Figure 150:
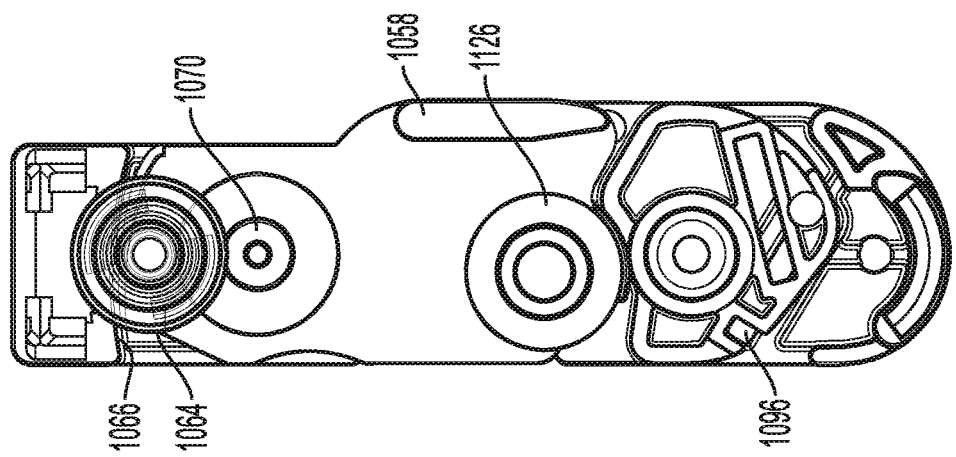
Figure 149:
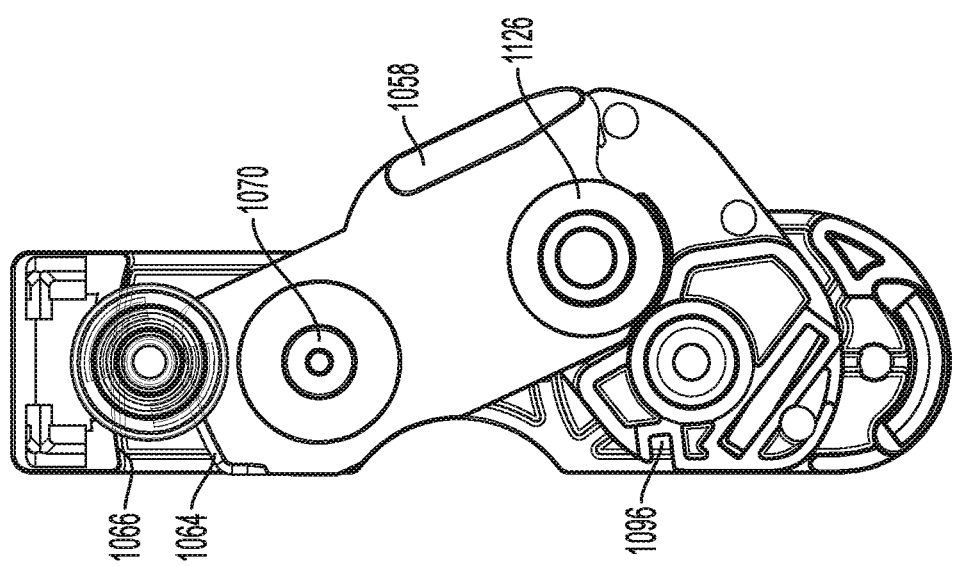
Figure 155:
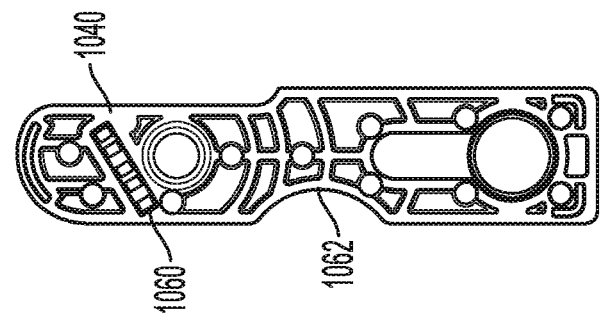
FIGS. 151-155 show several views of the top housing of the slide-clamp assembly of FIGS. 143-146 in accordance with an embodiment of the present disclosure.
Figure 154:
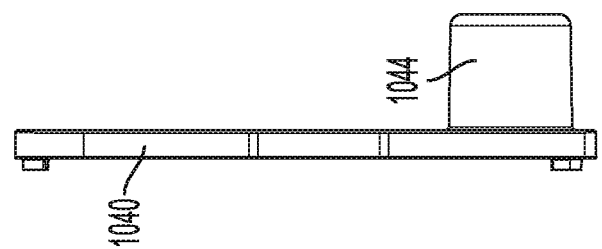
Figure 153:
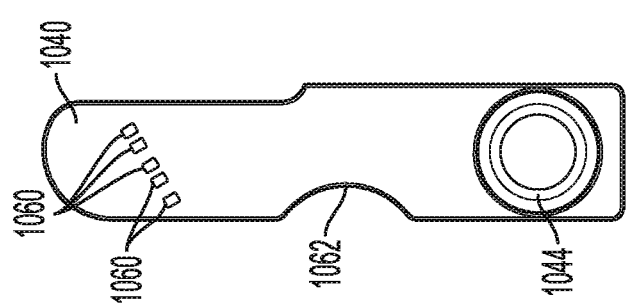
Figure 151:
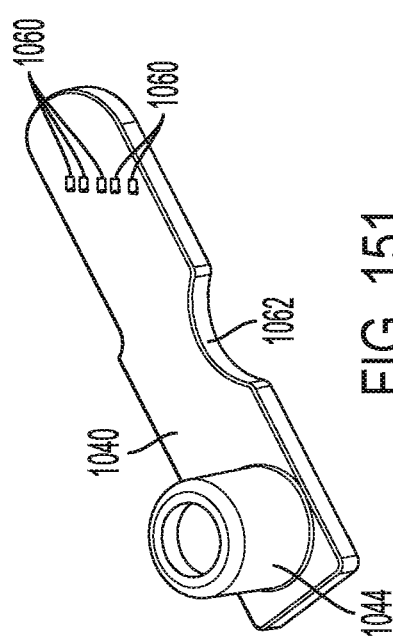
Figure 152:
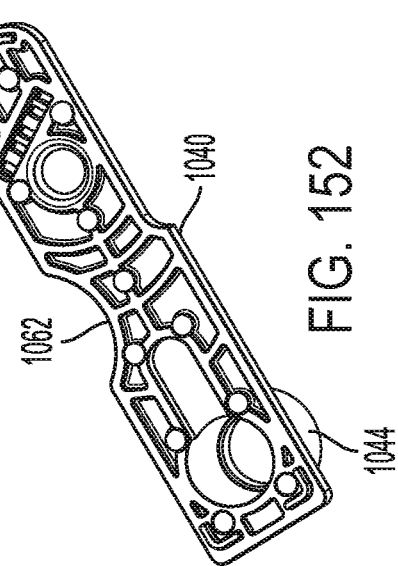
Figure 160:
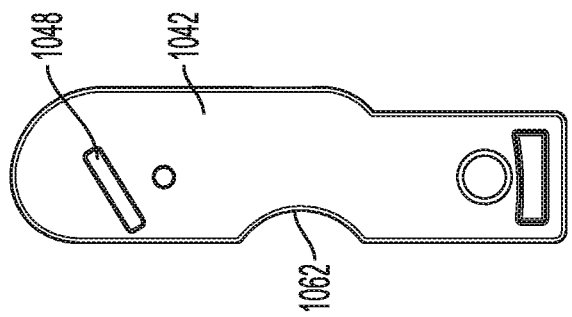
FIGS. 156-160 show several views of the bottom housing of the slide-clamp assembly of FIGS. 143-146 in accordance with an embodiment of the present disclosure.
Figure 159:
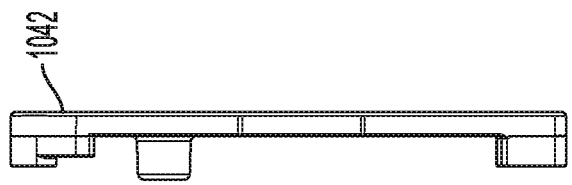

The second link 1050 pivots around the pivot post 1054. The first link 1052 is coupled to the second link 1050 via a hinge 1126. As the first link 1052 is actuated, it is guided within a track 1072 by guides 1070. FIG. 148 shows the slide-clamp assembly 1038 with the top housing 1040 removed while in the occluding position and FIG. 149 shows the slide-clamp assembly 1038 with the top housing 1040 while in the non-occluding position. As is shown in FIG. 150, when the first link 1052 is in the occluding position, the plunger 1064 is closer to the backstop 1066 and when the second link 1050 is in the non-occluding position as shown in FIG. 149, the plunger 1064 is a predetermined distance from the backstop 1066. The second link 1050 and the first link 1052 are coupled together via a ball-and-socket joint 1068. The guides 1070 positions the first link 1052 such that rotation of the second link 1050 along the pivot post 1054 translates to linear motion of the guides 1070 along the track 1072.

In some embodiments, the slide-clamp assembly 1038 includes a notch 1096 configured to use optical recognition to determine when the slide-clamp assembly 1038 is in the occluding or non-occluding position. As shown in FIG. 150, the notch 1096 aligns with the housing aperture 1048 such that the optical recognition determines that the slide-clamp assembly 1038 is inserted into the carriage 1036 and is in the occluding position.

Figure 158:
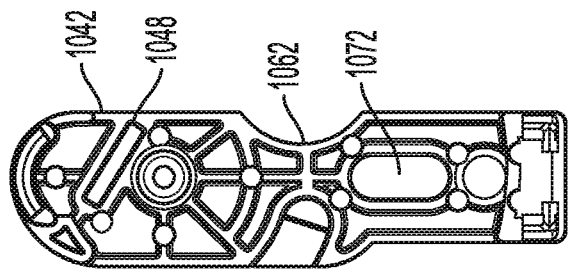
Figure 156:
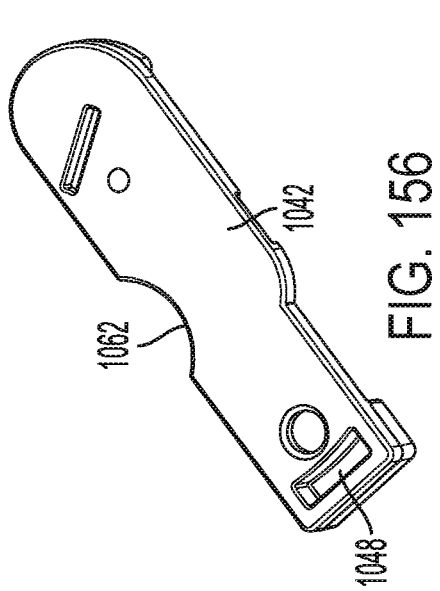
Figure 157:
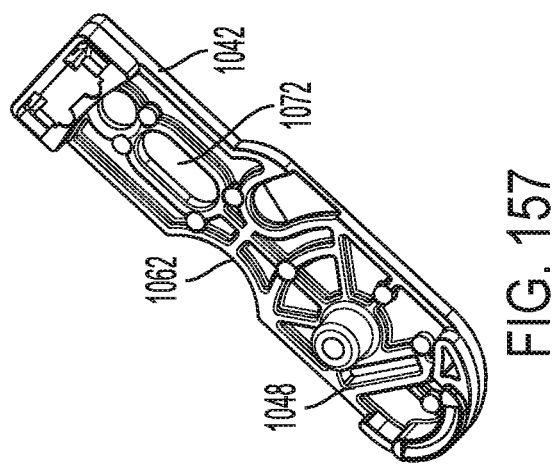
Figure 165:
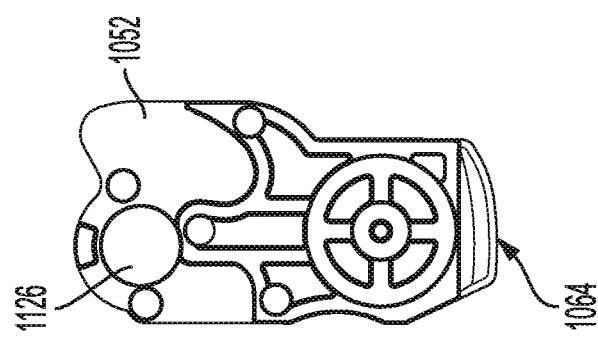
FIGS. 161-165 show several views of a first link of the slide-clamp assembly of FIGS. 143-146 having a plunger in according with an embodiment of the present disclosure.
Figure 164:
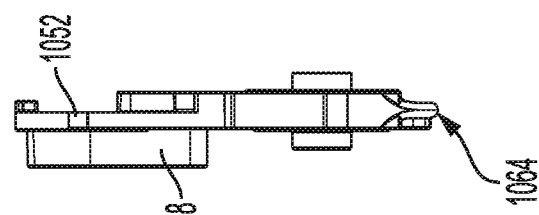
Figure 163:
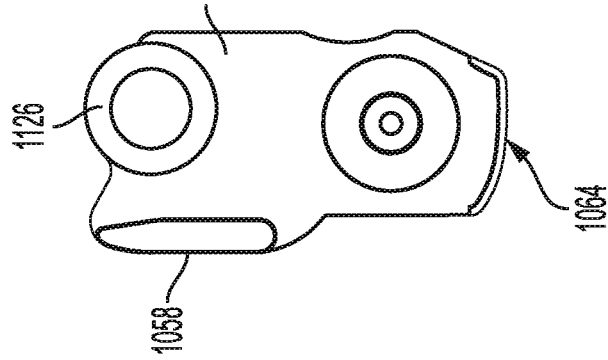
Figure 161:
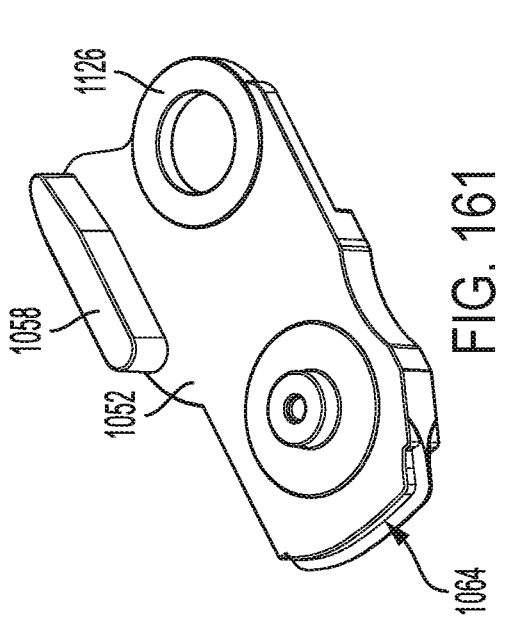
Figure 162:
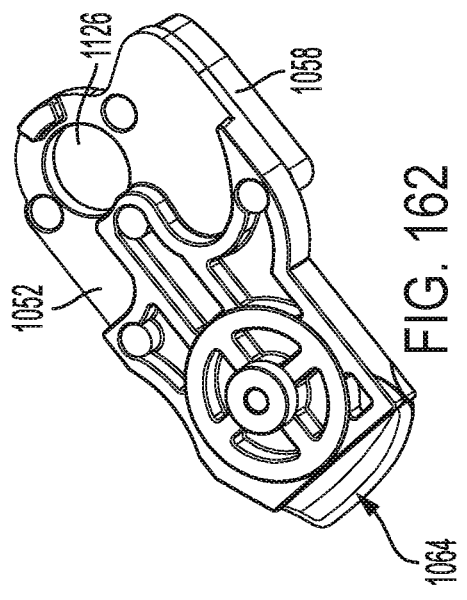
Figure 170:
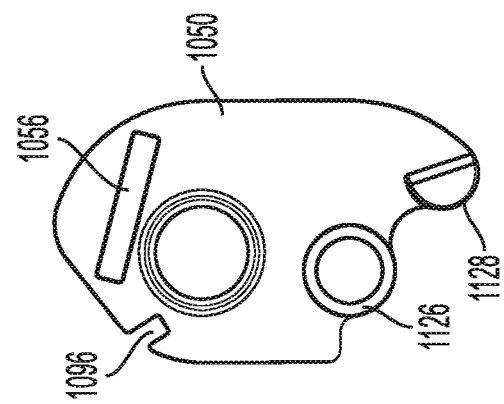
FIGS. 166-170 show several views of a second link of the slide-clamp assembly of FIGS. 143-146 in accordance with an embodiment of the present disclosure.
Figure 169:
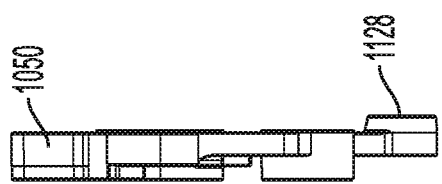
Figure 168:
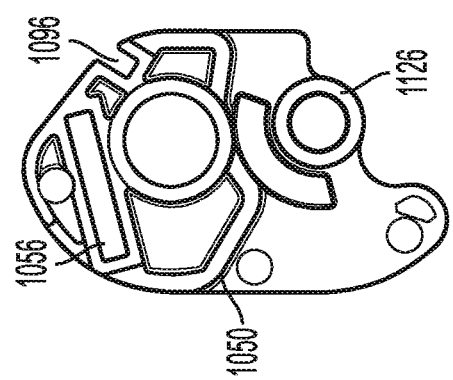

FIGS. 151-155 show several views of the top housing 1040 of the slide-clamp assembly 1038. The tube coupling 1044 is integrated with top housing 1040 in the embodiment shown in FIGS. 151-155. In some embodiments, a tube 1046 may include a snap-fit adapter 1130 (see FIGS. 148) configured to interface with the tube coupling 1044 of FIGS. 151-155. FIGS. 156-160 show several views of the bottom housing 1042 of the slide-clamp assembly 1038 of FIGS. 143-146. As shown in FIGS. 157-158, the bottom housing 1042 includes a secondary track 1076. The secondary track 1076 is configured such that a flange 1128 of a second link 1050 serves a guide and stops movement of the second link 1050 in one (or both) directions of actuation as is readily apparent by one of ordinary skill in the art. FIGS. 161-165 show several views of a first link 1052 of the slide-clamp assembly 1038 having a plunger 1064 and FIGS. 166-170 show several views of the second link 1050 of the slide-clamp assembly 1038 of FIGS. 143-146.

Figure 172:
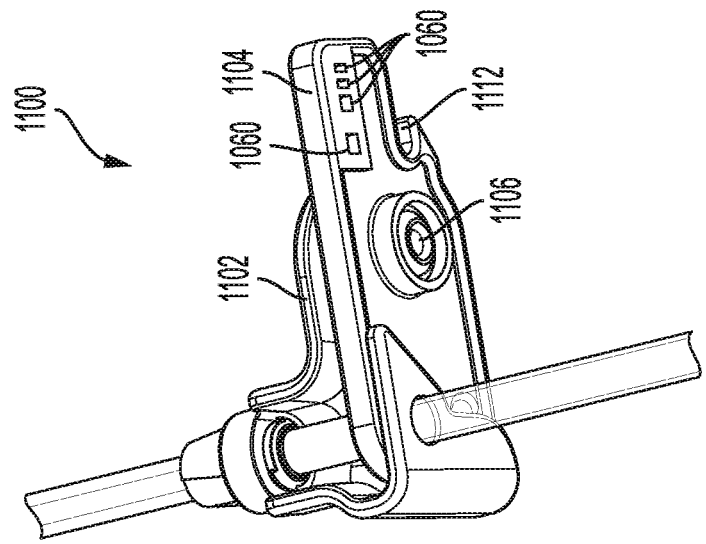
FIGS. 171-174 show several views of a pinching slide-clamp assembly having a slide clamp with an arcuate slot in accordance with an embodiment of the present disclosure.
Figure 171:
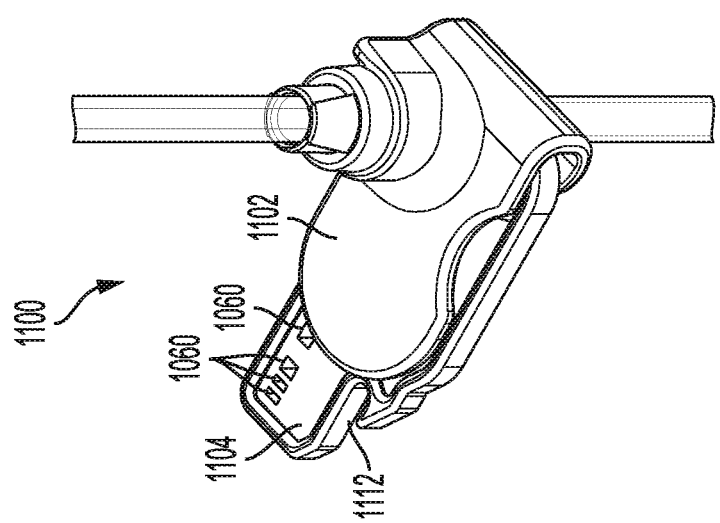
Figure 174:
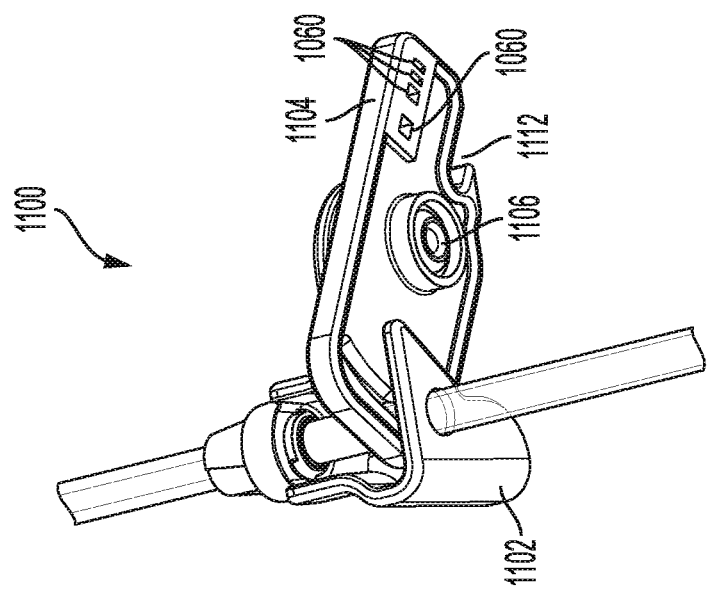
Figure 173:
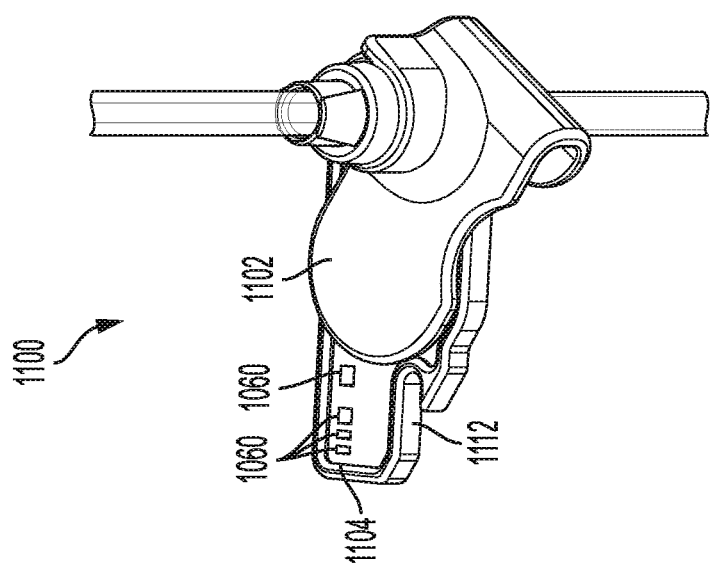
Figure 177:
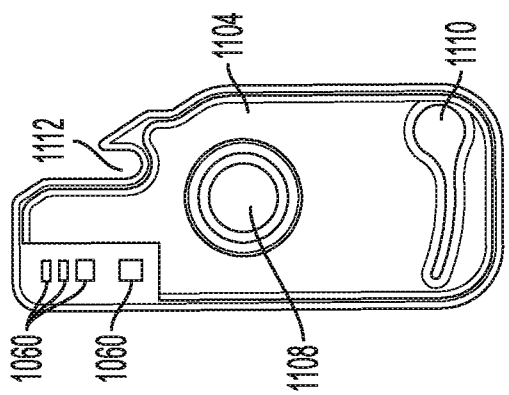
FIGS. 175-178 show several views of the slide clamp of the pinching slide-clamp assembly of FIGS. 171-174 in accordance with an embodiment of the present disclosure.
Figure 176:
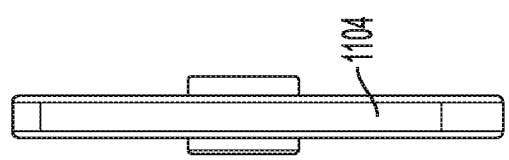
Figure 178:
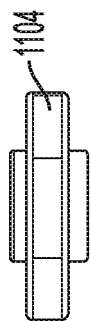
Figure 175:
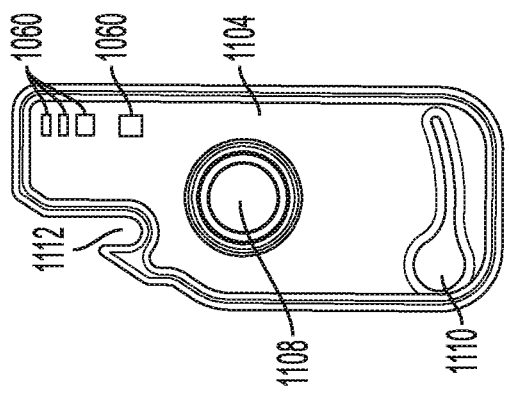

FIGS. 171-174 shows several views of a pinching slide-clamp assembly 1100 having a slide clamp 1104 with an arcuate slot 1110 FIGS. 171-172 show the pinching slide-clamp assembly 1100 when the slide clamp 1104 is in the occluding position. The slide clamp 1104 can pivot around a pivot post 1054. FIGS. 173-174 show the pinching slide-clamp assembly 1100 in the non-occluding position. A user can actuate the slide clamp 1104 to transition the pinching slide-clamp assembly 1100 to one of the occluding position or the non-occluding position.

Figure 180:
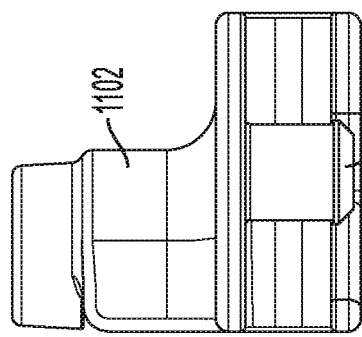
FIGS. 179-181 show several views of the housing of the pinching slide-clamp assembly of FIGS. 171-174 in accordance with an embodiment of the present disclosure.
Figure 181:
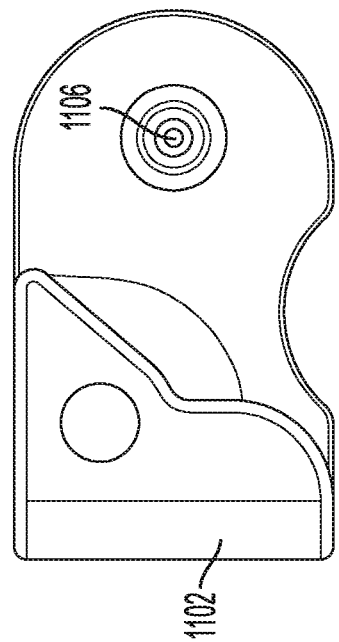
Figure 179:
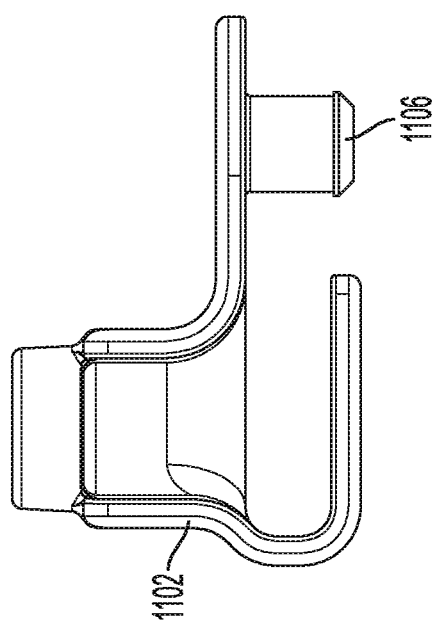

FIGS. 175-178 show several views of the slide clamp 1104 of the pinching slide-clamp assembly 1100. A tube 1046 can be placed within an arcuate slot 1110 between a narrow portion or a wider portion based upon a pivot of the slide clamp 1104 relative to a housing 1102 via the pivot hole 1108. As shown in FIGS. 175-178, the slide clamp 1104 includes a notch 1096 that can be engaged by an end effector 1092 of a gripper finger 1086. FIGS. 179-181 show several views of the housing 1102 of the pinching slide-clamp assembly 1100. The housing 1102 may be on a top side of the slide clamp 1104, a bottom side of slide clamp 1104, surrounding both, and in some embodiments, integrated together in a single piece that partially surrounds the slide clamp 1104. The pivot hole 1108 of the slide clamp 1104 engages with the pivot post 1106 to pivot relative to each other.

Figure 184:
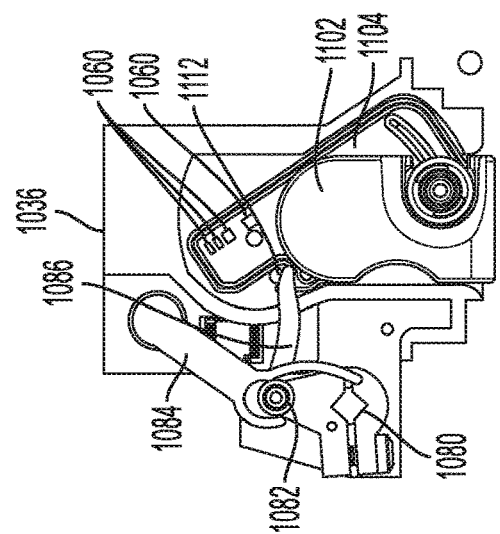
FIGS. 182-184 show the pinching slide-clamp assembly of FIGS. 171-174 being inserted into a carriage in accordance with an embodiment of the present disclosure.
Figure 183:
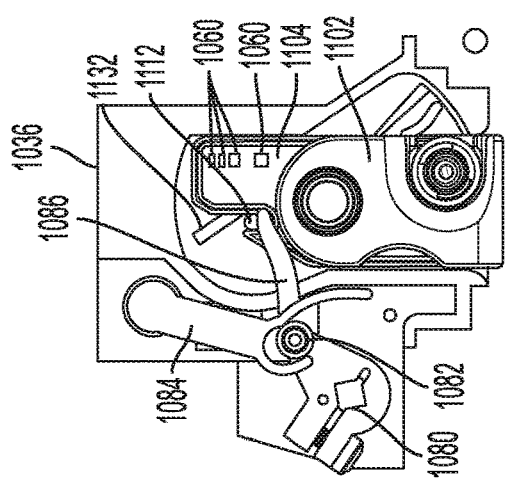
Figure 182:
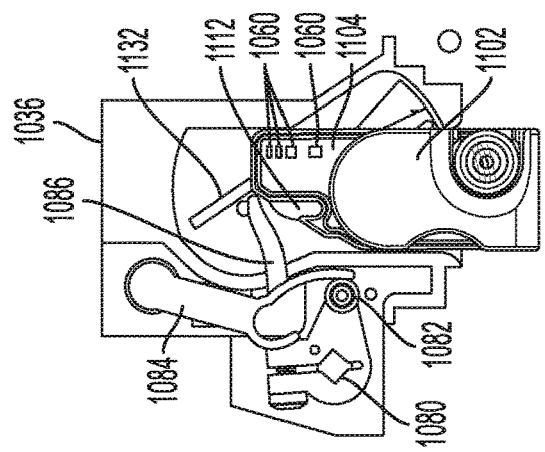
Figure 186:
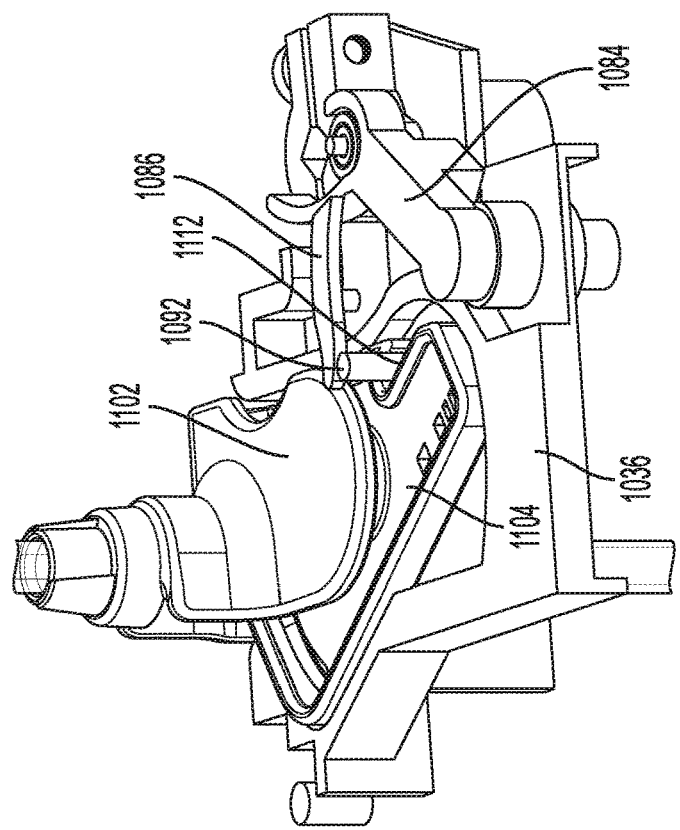
FIG. 186 shows a perspective view of the internal mechanism of the carriage when the end effector is engaged with a flange of the pinching slide-clamp assembly of FIGS. 171-174 in accordance with an embodiment of the present disclosure.
Figure 185:
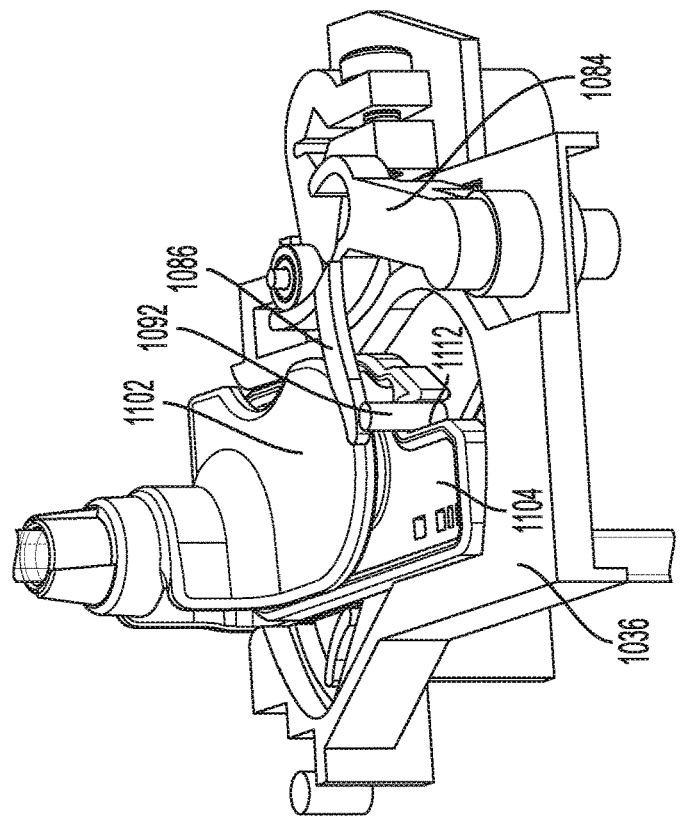
FIG. 185 shows a perspective view of the internal mechanism of the carriage when the end effector is engaged with a flange of the pinching slide-clamp assembly of FIGS. 171-174 in accordance with an embodiment of the present disclosure.

FIGS. 182-184 show the pinching slide-clamp assembly 1100 being inserted into a carriage 1036. As shown in FIG. 182, when the pinching slide-clamp assembly 1100 is inserted, an a notch 1112 approaches and can engage with the end effector 1092 of the gripper finger 1086. As shown in FIG. 182, the alternative carriage 1036 also includes an optical sensor 1132. FIG. 183 shows the pinching slide-clamp assembly 1100 fully inserted, but with the slide clamp 1104 in the occluding position. FIG. 184 shows the gripper finger 1086 actuating the slide clamp 1104 into the non-occluding position to treat a patient. The identification aperture 1060 is now aligned such that the pinching slide-clamp assembly 1100 can be identified. A shutter can also be used as part of the alternative carriage 1036 with the pinching slide-clamp assembly 1100.

In some embodiments of the present disclosure, the shaft coupler 1080 can rotate in FIG. 184 (clockwise as seen in FIG. 184) to actuate the pinching slide-clamp assembly 1100 to the occluding position when the end effector 1092 of the gripper finger is suitably shaped and configured. In yet an additional embodiment of the present disclosure, when a user pulls the pinching slide-clamp assembly 1100 out of the carriage in FIG. 184, the walls of the carriage actuate the slide clamp 1104 to the occluding position.

Figure 187:
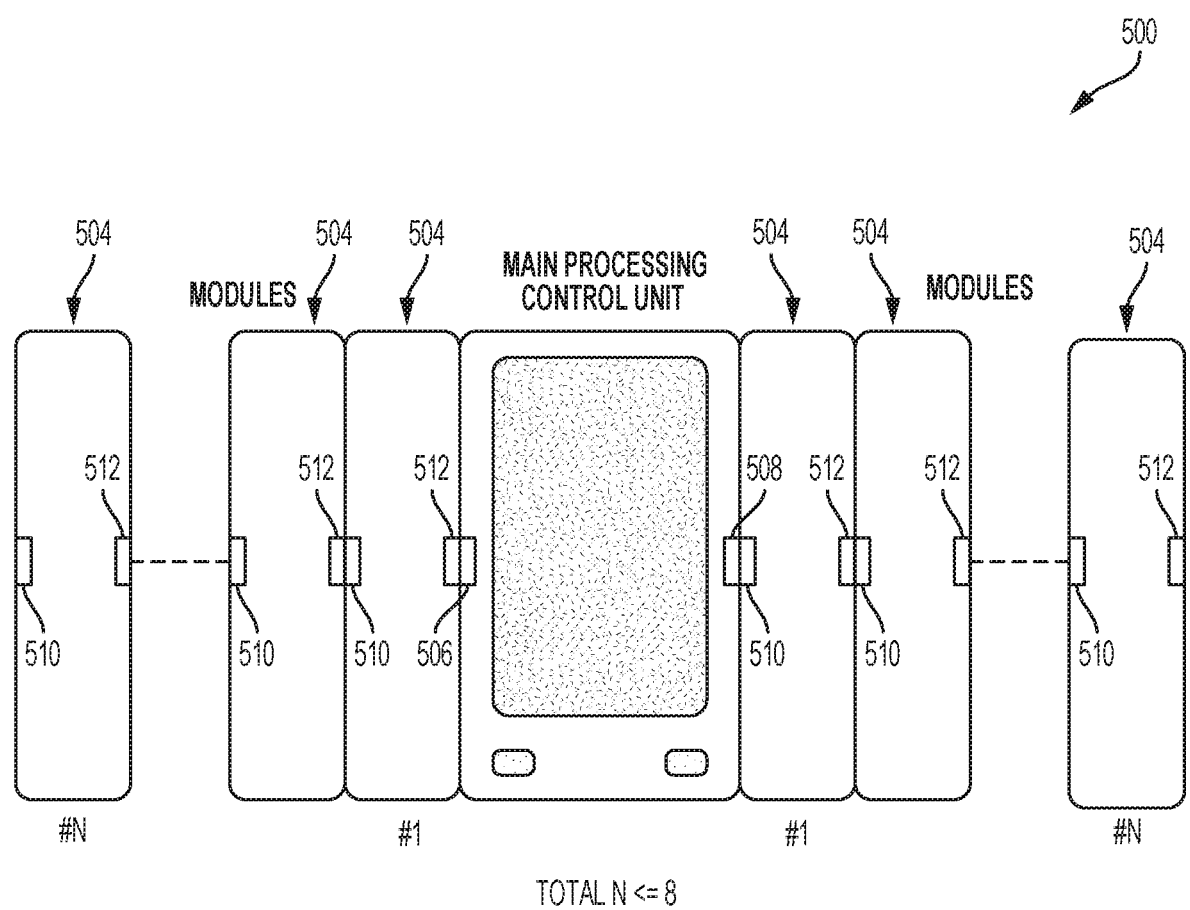
FIG. 187 shows a block diagram of a modular pump system having a central unit and a plurality of medical device assemblies coupled together in accordance with an embodiment of the present disclosure.

FIG. 187 shows a block 138 diagram of a modular pump system 500 having a central unit 502 and a plurality of medical-device assemblies 504 coupled together. One or more of the medical-device assemblies 504 may be the peristaltic pump 100 or 300 shown and described herein. Additionally or alternatively, the medical-device assemblies 504 may include syringe pumps 100, battery packs, micropumps, or other medical devices.

The central unit 502 provides power to the medical-device assemblies 504. The central unit 502 includes a left central-unit connector 506 and a right central-unit connector 508. The left central-unit connector 506 and the right central-unit connector 508 each may include a power pin, a communications pin, and one or more ground pins. The central unit 502 provides power to the connected medical-device assemblies 504 through the left central-unit connector 506 when activated and/or the right central-unit connector 508 when activated.

All of the medical-device assemblies 504 includes a left medical-device connector 510 and a right medical-device connector 512 which allow the medical-device assemblies 504 to be connected to the modular pump system 500 from the left side or the right side to receive power and communicate using a common bus. Additionally, the connected medical-device assemblies 504 may be configured to connect the power from the central unit 502 to power a connected medical-device assembly 504 downstream. For example, a medical-device assembly 504 connected just to the right of the central unit 502 may be configured to subsequently power another medical-device assembly 504 connected to it on the right.

Figure 188:
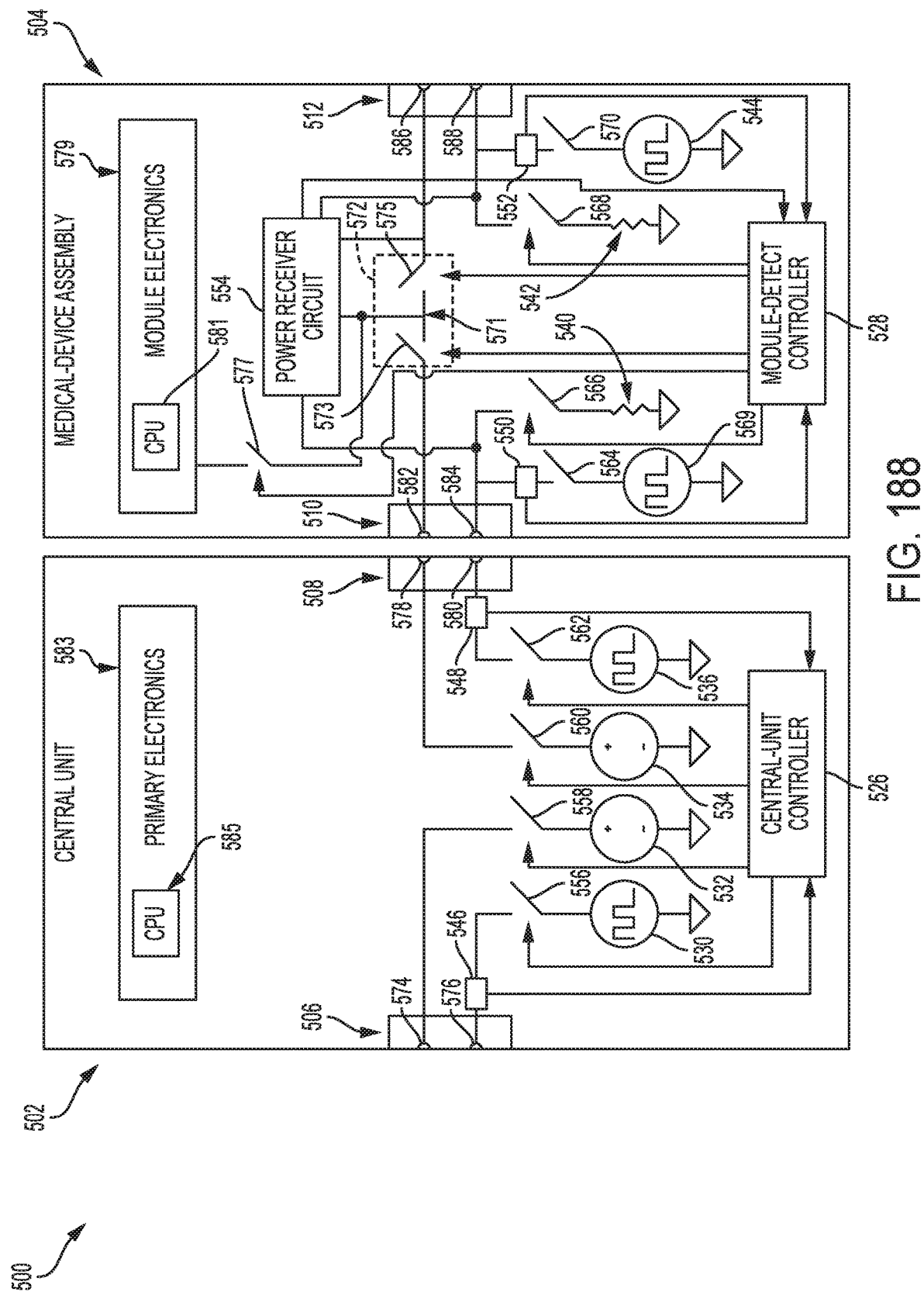
FIG. 188 shows a block diagram of a modular pump system to illustrate the power circuity of the system in accordance with an embodiment of the present disclosure.

FIG. 188 shows a block diagram of a modular pump system 500 to illustrate the power circuitry of the modular pump system 500. The modular pump system 500 includes a central unit 502 and one or more medical-device assemblies 504. Although one medical-device assembly 504 is shown in FIG. 188, one or more medical-device assemblies 504 may be attached to the right of the medical-device assembly 504 shown in FIG. 188 and/or to the left of the central unit 502. Also, medical-device assemblies 504 may be serially coupled together such as is shown in FIG. 187 to the left or right side of the central unit 502.

The central unit 502 includes primary electronics 583 including a CPU 585. The primary electronics 583 includes addition functions beyond the power circuitry illustrated in FIG. 188. The medical-device assembly 504 includes module electronics 579 that includes a CPU 581. The module electronics 579 includes an electric motor for pumping fluid, power circuits, and other electronics.

The modular pump system 500 is configured such that each of the medical-device assemblies 504 can be coupled to either a right central-unit connector 508 of the central unit 502, a left central-unit connector 506 of the central unit 502, a left medical-device connector 510 or a right medical-device connector 512 of another medical-device assembly 504 (not shown in FIG. 188) to establish sufficient communication prior to receiving power through a power pin. For example, the right power pin 578 is not powered until after the medical-device assembly 504 is connected to the right central-unit connector 508 via left medical-device connector 510; Initially, the medical device assembly 504 can power itself sufficiently using the signal received via the communications pin 584. The medical device assembly 504 can request power by using the signal received via a communications pin 584 to power the medical device assembly suitably to passively request power from the device (e.g., the central unit or a medical-device assembly 504) through the communications pin 584. Power can thereafter be received via the left power pin 582 by the medical-device assembly 504 from the central unit 502 when using the system as shown in FIG. 188.

When the central unit 502 is powered up, the central-unit controller 526 may turn on a left signal switch 556 to apply a signal generated by the left signal generating circuit 530 to a left communications pin 576 of a left medical-device connector 510. Also after power up, the central-unit controller 526 may switch the right signal switch 562 into the on position to apply a signal from the right signal generating circuit 536 to the right communications pin 580 of the right central-unit connector 508. In additional embodiments of the present disclosure, the left signal generating circuit 530 and the right signal generating circuit 536 may be combined into a single circuit that generates a single signal for application to the left communications pin 576 and to the right communications pin 580. Additionally or alternatively, enable/disable circuits may be used in place of switches 556, 562, respectively, where the central-unit controller 526 can signal to enable or disable the signal generating circuits 530, 536.

The central-unit controller 526 is coupled to a left load-detect circuit 546 and a right load-detect circuit 548. The left load-detect circuit 546 is configured to detect a passive indication of a request for power of a left connected medical-device assembly 504 (none is shown in FIG. 188). The right load-detect circuit 548 is configured to detect a passive indication of a request for power of a right connected medical-device assembly 504 (one is shown in FIG. 188). The central-unit controller 526 keeps the left power switch 558 open until a request for power by a left connected medical-device assembly 504 has been received and likewise keeps the right power switch 560 open until a request for power by a right connected medical-device assembly 504 has been received. The left load-detect circuit 546 and the right load-detect circuit 548 may be current sense circuits in some embodiments. However, any circuit known to one of ordinary skill in the art may be used to detect a passive indication of a request for power. In some embodiments of the present disclosure, the passive indication of a request for power may be a change in impedance, e.g., a coupling of a resistor to the communications pin 584. Load detection may be done by monitoring current, voltage, frequency response, decay rate, an RC constant, the like, or some combination thereof.

As previously mentioned, the right load-detect circuit 548 may in some embodiments be a current sensor. Thus, if the signal from the right signal generating circuit 536 is a voltage waveform (e.g., a square waveform), the current of the right signal generating circuit 536 may be monitored by the right load-detect circuit 548 to determine if an impedance change (e.g., a decreased resistance) has occurred on the load impedance as detected by the right load-detect circuit 548.

As previously mentioned, after power up, the central-unit controller 526 switches the right signal switch 562 into the on position to apply a signal from the right signal generating circuit 536 to the right communications pin 580 of the right central-unit connector 508. When the medical-device assembly 504 is initially coupled to the central unit 502, a signal is received from the right signal generating circuit 536 through the right communications pin 580 of the right central-unit connector 508 via the left communications pin 584 of the left medical-device connector 510. The signal is used by the power receiver circuit 554 to initially power the power receiver circuit 554. That is, energy harvesting, such as a rectifier, a charge pump, etc., may be used by the power receiver circuit 554 to power itself.

The power receiver circuit 554 powers the module-detect controller 528. Upon determination by the module-detect controller 528 that a signal is present on the left communications pin 584, the module-detect controller 528 signals the left load switch 566 to close so that the left resistor 540 is now coupled to the left communications pin 584. That is, the left load switch 566 is closed thereby connecting the left resistor 540 to the left communications pin 584. This change in impedance is detected by the right load-detect circuit 548 of the central unit 502 which is communicated to the central-unit controller 526. The central-unit controller 526 takes this change in impedance to be a passive request for power. Therefore, the central-unit controller 526 switches the right power switch 560 ON so that the right power circuit 534 supplies power to the right power pin 578 through the right central-unit connector 508 via the left power pin 582 of the left medical-device connector 510. Then a switch 573 can be closed to provide power to the cross-bar bus 571 which is receivable by the power receiver circuit 554. The power is received by the power receiver circuit 554 which is then used to power the module electronics 579 by closing the switch 577. The power receiver circuit 554 can use its power to power the module-detect controller 528. In some embodiments, the switch 577 may be replaced by a diode or other circuitry to allow power to flow to the module electronics 579 anytime power is supplied to the crossbar bus 571.

After the module-detect controller 528 determines that power is being supplied from the left power pin 582, the module-detect controller 528 can configure the right side of the medical-device assembly 504 to accept another medical-device assembly 504 on its right as seen from FIG. 188 and in this example. The module-detect controller 528 may set the frequency of the right signal generating circuit 536 to half of the frequency it receives via the right signal generating circuit 536 of the central unit 502. Thereafter, the module-detect controller 528 closes the right signal switch 570 and monitors the right communications pin 588 load by monitoring the right load-detect circuit 552. Please note that load-detect circuit 550 performs the same function, but on the other side of the medical-device assembly 504. If or when the module-detect controller 528 detects a passive request for power, the module-detect controller 528 may close a right cross-bar switch 575 of a crossbar 572 so that power is supplied downstream, i.e., to the right from the view of FIG. 188. Also a right resistor 542 is coupled to a right load switch 568 that are used to passively request power, e.g., when the medical-device assembly 504 is connected to the other side of the central unit 502 from what is shown in FIG. 188.

Because the central-unit controller 526 generates a fixed frequency by the signal generating circuits 530, 536, and each medical-device assembly 504 reduces the frequency sent downstream by half, each of the medical-device assemblies 504 coupled to the modular pump system 500 can determine its position relative to the central unit 502 by monitoring the frequency of the signal coming in on respective communications pin 584, 588 because the frequency of the signals generated by 530 and 536 are predetermined and known by all of the medical-device assemblies 504. For example, the frequency values of the signals generated by 530 and 536 may be stored in non-volatile memory within the module electronics 579. Also, the side on which the medical-device assembly 504 initially receives the signal via a communication pin 584, 588 may be used by the module-detect controller 528 to know on which side of the central unit 502 it resides and by monitoring the frequency of the signal initially incoming, the medical-device assembly 504 will know how many other medical-device assemblies 504 (if any) reside between it and the central unit 502. Thus, a medical-device assembly's 504 position may be used as a bus-communications address to communicate with other medical-device assemblies and/or with the central unit 502, e.g., using on-off keying modulated signal carrying a Controller Area Network ("CAN")-protocol signal.

Figure 189:
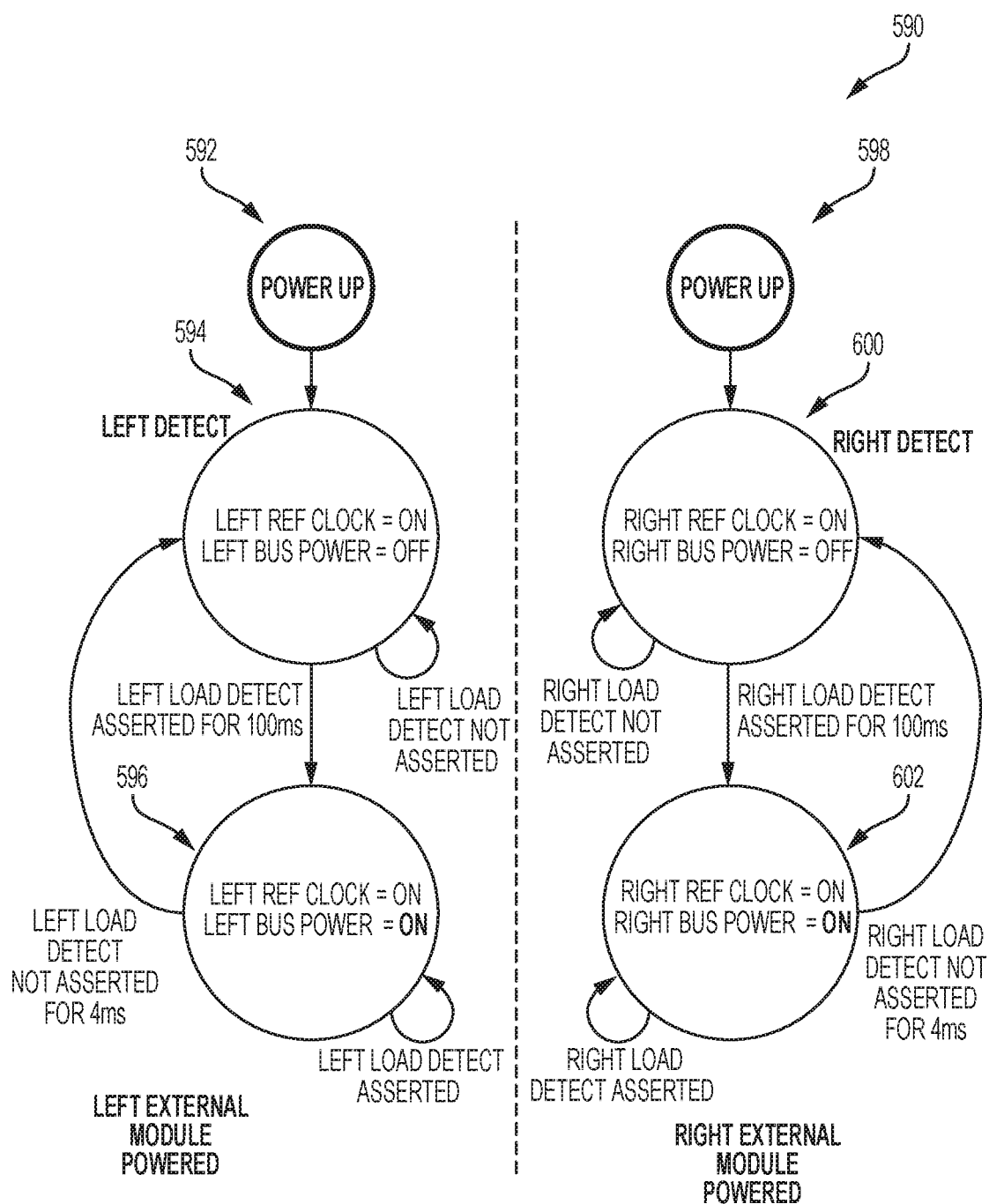
FIG. 189 shows a state diagram of the central unit power circuitry in accordance with an embodiment of the present disclosure.

FIG. 189 shows a power-on state diagram 590 of the central unit 502 power circuitry shown in FIGS. 97-98. A state 592, a state 594, and a state 596 illustrate the left power circuitry of the central unit 502 which can provide power to an attached medical-device assembly 504 through the left central-unit connector 506. A state 598, a state 600, and a state 602 illustrate the right power circuitry of the central unit 502 which can power an attached medical-device assembly 504 through the right central-unit connector 508. Please note that the two sides of power-on state diagram 590 can occur in parallel, and, in some embodiments, out of sync with each other.

In state 592, designated as POWER UP, the circuitry of the central unit 502 is powered up, for example, when a user turns on a power switch and/or plugs the central unit 502 into an A/C outlet. Thereafter, state 594 is entered into, which is designated as LEFT DETECT. In state 594, a left reference clock (e.g., signal generating circuit 530 of FIG. 188) will be turned on (e.g., the switch 556 is closed) and a left bus power (e.g., the left power circuit 532) will remain off (e.g., switch 558 remains open). The left reference clock may be created and/or controlled by a signal generating circuit 530 that is coupled to a left communications pin 576 of the left central-unit connector 506. The left bus power is a left power circuit 532 that can send power to a left power pin 574 of the left central-unit connector 506. As described in greater detail below, the left reference clock signal is monitored via left load-detect circuit 546 to sense if an impedance change indicates a passive indication of a request for power of a left connected medical-device assembly 504. For example, a left connected medical-device assembly 504 can change a resistance, e.g., by grounding (e.g., sinking) a resistor, to the communications pin 588 of the right medical-device connector 512 that is coupled to the left communications pin 576 of the left central-unit connector 506 to indicate a request for power.

As shown in FIG. 189, state 594 will continue to transition to itself as long as the passive request for power is not detected as indicated by the LEFT LOAD DETECT NOT ASSERTED transition. In state 594, if the left signal detects a load for 100 milliseconds, it is interpreted as a passive request for power, after which, the state 594 transitions to the state 596. This transition is indicated by the "LEFT LOAD DETECT ASSERTED FOR 100 ms" transition in the state diagram 590. In state 596, the central unit 502 switches to a left power-on mode and applies power to the left power pin 574 of the left central-unit connector 506 (indicated as LEFT BUS POWER=ON). The central unit 502 will continue to apply power as long as the passive request for power is detected; this is illustrated as "LEFT LOAD DETECT ASSERTED" transition in the state diagram 590. The LEFT BUS POWER=ON may signify that the left power switch 558 is closed to connect the left power circuit 532 to the left power pin 574 of the left central-unit connector 506.

The right side of the power-on state diagram 590 operates in a similar manner as the left side of the power-on state diagram 590. The two sides of the power-on state diagram 590 may operate independently and/or in parallel. As shown in FIG. 189, state 598, state 600, and state 602 illustrate the right power circuitry of the central unit 502 which can provide power to an attached medical-device assembly 504 through the right central-unit connector 508.

In state 598, designated as POWER UP, the circuitry is powered up, for example, when a user turns on a power switch and/or plugs the central unit 502 into an A/C outlet. Thereafter, the state 600 is entered into, which is designated as RIGHT DETECT. In the state 600, a right reference clock (e.g., signal generating circuit 536 of FIG. 188) will be turned on and a right bus power (e.g., the right power circuit 534) will remain off or unconnected via the right power switch 560. The right reference clock may be created and/or controlled by a signal generating circuit 536 that is coupled to a communications pin 588 of the right central-unit connector 508. The right bus power is a right power circuit 534 that can send power to a right power pin 578 of the right connector 508. The right reference clock signal is monitored via right load-detect circuit 548 to sense if an impedance change indicates a passive indication of a request for power of a right connected medical-device assembly 504. For example, a right connected medical-device assembly 504 can apply a resistance, e.g., by grounding a resistor, to the communications pin 580 of the left medical-device connector 510 that is coupled to the right communications pin 580 of the right central-unit connector 508 to indicate a passive request for power.

As shown in FIG. 189, the state 600 will continue to transition to itself as long as the passive request for power is not detected and is indicated by the "RIGHT LOAD DETECT NOT ASSERTED" transition. In the state 600, if the right signal detects a load for 100 milliseconds, it is interpreted as a passive request for power, after which, the state 600 transitions to the state 602. This transition is indicated by the "RIGHT LOAD DETECT ASSERTED FOR 100 ms" transition in the state diagram 590. In the state 602, a central-unit switchable power circuit switches to a power-on mode and applies power to a power pin of the right central unit connector 508 (indicated as RIGHT BUS POWER=ON). The right power circuit 534 will continue to apply power as long as the passive request for power is detected and is designated as RIGHT LOAD DETECT ASSERTED in the state diagram 590. The RIGHT BUS POWER=ON may signify that the right power switch 560 is closed to connect the right power circuit 534 to the right power pin 578 of the right central-unit connector 508.

Figure 190:
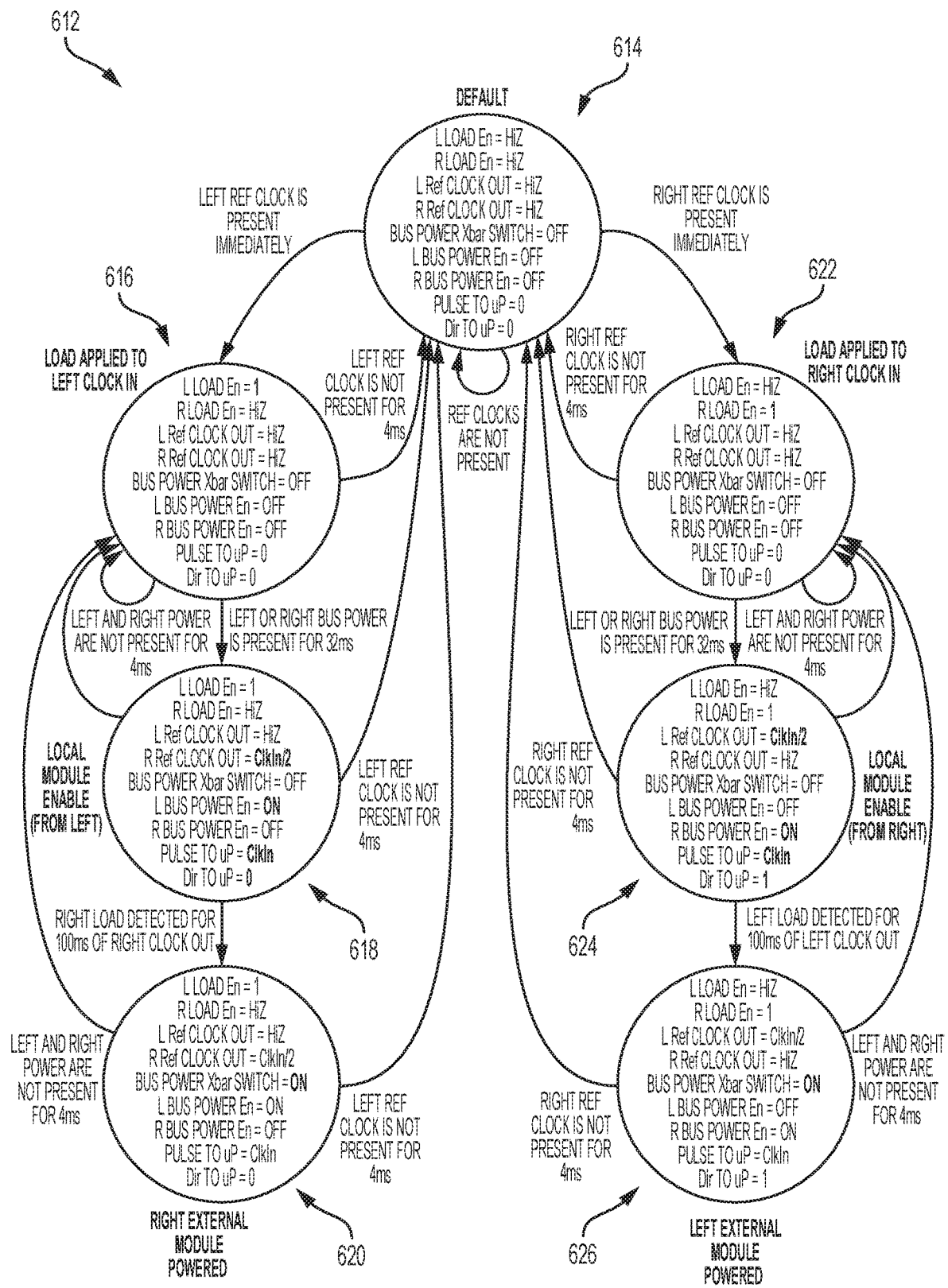
FIG. 190 shows a state diagram of the medical device assembly power circuitry in accordance with an embodiment of the present disclosure.

FIG. 190 shows a state diagram 612 of the medical device assembly 504 power circuitry. The state diagram 612 includes states 614, 616, 618, 620, 622, 624, and 626. Within each state of the state diagram 612, Table 1 defines the output values as follows:

TABLE 1

| Label | Description | Possible Values | Correspondence to FIG. 188 |
| --- | --- | --- | --- |
| L LOAD En | Controls whether a resistive load is coupled to a left communications pin. | HiZ (high impedance) or 1 (resistor connected) | Signal from Module-detect controller 528 to left load switch 566. |
| R LOAD En | Controls whether a resistor is coupled to a right communications pin. | HiZ (high impedance) or 1 (resistor connected) | Signal from Module-detect controller 528 to right load switch 568. |
| L Ref CLOCK OUT | Controls a left clock signal to a left communications pin. | HiZ (high impedance) Clkin/2 (outputs a signal one-half of the frequency received via a communications pin | Signal from Module-detect controller 528 to the left signal switch 564 and frequency selection of the right power pin 578 by the module-detect controller 528. |
| R Ref CLOCK OUT | Controls a right clock signal to a right communications pin. | HiZ (high impedance) Clkin/2 (outputs a signal one-half of the frequency received via a communications pin | Signal from Module-detect controller 528 to right signal switch 570 and frequency selection of the signal generator 544 by the module-detect controller 528. |

TABLE 1-continued

| Label | Description | Possible Values | Correspondence to FIG. 188 |
|---|---|---|---|
| BUS POWER Xbar SWITCH | Controls whether both power pins are coupled to the cross-bar bus. | Off (both power pins are not coupled to the cross-bar bus). On (both power pins are coupled to the cross-bar bus). | Signal from Module-detect controller 528 to crossbar 572 closes switches 573, 575 |
| L BUS POWER En | Controls whether the left cross-bar switch couples the left power pin to the cross-bar bus. | Off (power not applied from the left power pin to the cross-bar bus) On (power is applied from the left power pin to the cross-bar bus) Turns on power to device electronics in some embodiments. | Signal from Module-detect controller 528 to the left cross-bar switch 573. |
| R BUS POWER En | Controls whether the right cross-bar switch couples the right power pin to the cross-bar bus. | Off (power not applied from the right power pin to the cross-bar bus) On (power is applied from the right power pin to the cross-bar bus) Turns on power to device electronics in some embodiments. | Signal from Module-detect controller 528 to the right cross-bar switch 575. |
| PULSE TO uP | A signal to the processor to indicate a presence of a received communications signal. | ClkIn (signals to the processor that a clock has been received). 0 (signals to the processor that a clock has not been received. | Signal from Module-detect controller 528 to CPU. |
| Dir TO uP | A signal to the processor to indicate the direction, e.g., left or right, the communications signal comes from. | 0 (Clock signal received from module coupled to the left connector) 1 (Clock signal received from module coupled to the right connector) May be ignored if no pulse signal is present. | Signal from Module-detect controller 528 to CPU. |

Initially, state 614 is entered into. In state 614, the medical device assembly 504 is a state where it is detached from all power sources, such as when it is resting within a cabinet. States 616, 618, and 620 correspond to the left side of the medical device assembly 504 being connected to a central unit 502 or another medical-device assembly 504 on its left side. Likewise, states 622, 624, and 626 correspond to the medical device assembly 504 being connected to a central unit 502 or another medical-device assembly 504 on its right side.

The transition "LEF REF CLOCK IS PRESENT IMMEDIATELY" from state 614 to state 616 occurs when the left connector 510 detects a signal from the left communications pin 584. In state 616, the "L LOAD En" is set to "1", which means that the left resistor 540 is coupled to the left communications pin 584 (e.g., by closing the switch 566). The state 616 will continue to transition back to itself if no power is detected from either the left side from the left power pin 582 or the right side from the right power pin 586 after 4 ms, as indicated by the "LEFT AND RIGHT POWER ARE NOT PRESENT FOR 4 ms" transition. However, if the left clock signal is not detected via the left communications pin 584 for at least 4 ms, the medical-device assembly 504 transitions from state 616 to 614 by the transition labeled as "LEFT REF CLOCK IS NOT PRESENT FOR 4 ms".

When the power is received from the left power pin for at least 32 ms, state 616 transitions to state 618 as indicated by the "LEFT OR RIGHT BUS POWER IS PRESENT FOR 32 ms". In state 618, the "L BUS POWER En" is set to ON, which would close the left cross-bar switch 573 thereby sending power to the common bus 571. In some embodiments, the switch 577 is closed at state 618 to send power to the module electronics 579. Also in state 618, the "R Ref Clock Out" turns on the right clock at half the frequency received via the left communications pin 584. That is, the switch 570 is closed while signal generator 544 generates a square wave that is one-half the frequency received via the left communications pin 584. Also, the "Pulse to uP" CkIn signal is sent to the CPU 581 (connection not explicitly shown in FIG. 188, but it may be a wired connection) so that the CPU 581 knows that a clock signal has been received via the left communications pin 584. The "Dir To uP" signal is set to 0, which is sent to the CPU 581 so that the CPU 581 can determine which direction the signal is received from. In this exemplary embodiment, the 0 value indicates that the signal is coming from the left communications pin 584; however, the particular logic values used may be changed.

If the left clock is not present for 4 ms, the medical-device assemblies 504 transitions from state 618 to state 614 via transition labeled "LEFT REF CLOCK IS NOT PRESENT FOR 4 ms". If neither the left power pin or the right power pin is powered up for 4 ms, the medical-device assemblies 504 transition from state 618 to state 616. If a passive request for power is detected via the right communications pin of the medical-device assemblies 504, the medical-device assemblies 504 transitions from state 618 to state 620 when the load is detected for 100 ms via the right clock output. The transition is labeled "RIGHT LOAD DETECTED FOR 100 ms OF RIGHT CLOCK OUT", which corresponds to the case in which the BUS POWER XbarSWITH is turned ON, which means that both of switches 573 and 575 are closed thereby allowing power to flow from the left power pin to the right power pin.

At state 620, if the left and right power pins are ever not receiving power for 4 ms, then the medical-device assembly 504 transition from state 620 to state 616 via the transition labeled "LEFT AND RIGHT POWER ARE NOT PRESENT FOR 4 ms". If, at state 620, the left reference clock is not present for 4 ms, the medical-device assemblies 504 transitions from state 620 to state 614 via the transition labeled "LEFT REF CLOCK IS NOT PRESENT FOR 4 ms".

Referring again to FIG. 190, the right branch from state 614 will now be described. The transition "RIGHT REF CLOCK IS PRESENT IMMEDIATELY" from state 614 to state 622 occurs when the right connector 512 detects a signal from the right communications pin 588. In state 622, the "R LOAD En" is set to "1", which means that the right resistor 542 is coupled to the right communications pin 588 (e.g., by closing the switch 568). The state 622 will continue to transition back to itself if no power is detected from either the left side from the left power pin 582 or the right side from the right power pin 586 after 4 ms, as indicated by the "LEFT AND RIGHT POWER ARE NOT PRESENT FOR 4 ms" transition. However, if the right clock signal is not detected via the right communications pin 588 for at least 4 ms, the medical-device assembly 504 transitions from state 622 to 614 by the transition labeled as "RIGHT REF CLOCK IS NOT PRESENT FOR 4 ms".

When the power is received from the right power pin for at least 32 ms, state 616 transitions to state 624 as indicated by the transition label "LEFT OR RIGHT BUS POWER IS PRESENT FOR 32 ms". In state 624, the "R BUS POWER En" is set to ON, which would close the right cross-bar switch 575 thereby sending power to the common bus 571. In some embodiments, the switch 577 is closed at state 624 to send power to the module electronics 579. Also in state 624, the "L Ref Clock Out" turns on the left clock at half the frequency received via the right communications pin 588. That is, the switch 564 is closed while signal generator 569 generates a square wave that is one-half the frequency received via the right communications pin 588. Also, the "Pulse to uP" CkIn signal is sent to the CPU 581 (connection not explicitly shown in FIG. 188, but it may be a wired connection) so that the CPU 581 knows the a clock signal has been received via the left communications pin 584. The "Dir To uP" signal is set to 1, which is sent to the CPU 581 so that the CPU 581 can determine which direction the signal is received from. In this exemplary embodiment, the 1 value indicate that the signal is coming from the right communications pin 588; however, the particular logic values used may be changed.

If the left clock is not present for 4 ms, the medical-device assemblies 504 transitions from state 624 to state 614 via transition labeled "RIGHT REF CLOCK IS NOT PRESENT FOR 4 ms". If neither the left power pin or the right power pin is powered up for 4 ms, the medical-device assemblies 504 transition from state 624 to state 622. If a passive request for power is detected via the left communications pin of the medical-device assemblies 504, the medical-device assemblies 504 transitions from state 624 to state 626 when the load is detected for 100 ms via the left communication pin. The transition is labeled "LEFT LOAD DETECTED FOR 100 ms OF RIGHT CLOCK OUT", which corresponds to the case in which the BUS POWER XbarSWITH is turned ON, which means the both of switches 573 and 575 are closed thereby allowing power to flow from the left power pin to the right power pin. At state 626, if the left and right power pins are ever not receiving power for 4 ms, then medical-device assemblies 504 transition from state 626 to state 622 via the transition labeled "LEFT AND RIGHT POWER ARE NOT PRESENT FOR 4 ms". If, at state 626, the right reference clock is not present for 4 ms, the medical-device assemblies 504 transitions from state 626 to state 614 via the transition labeled "RIGHT REF CLOCK IS NOT PRESENT FOR 4 ms".

Figure 191A:
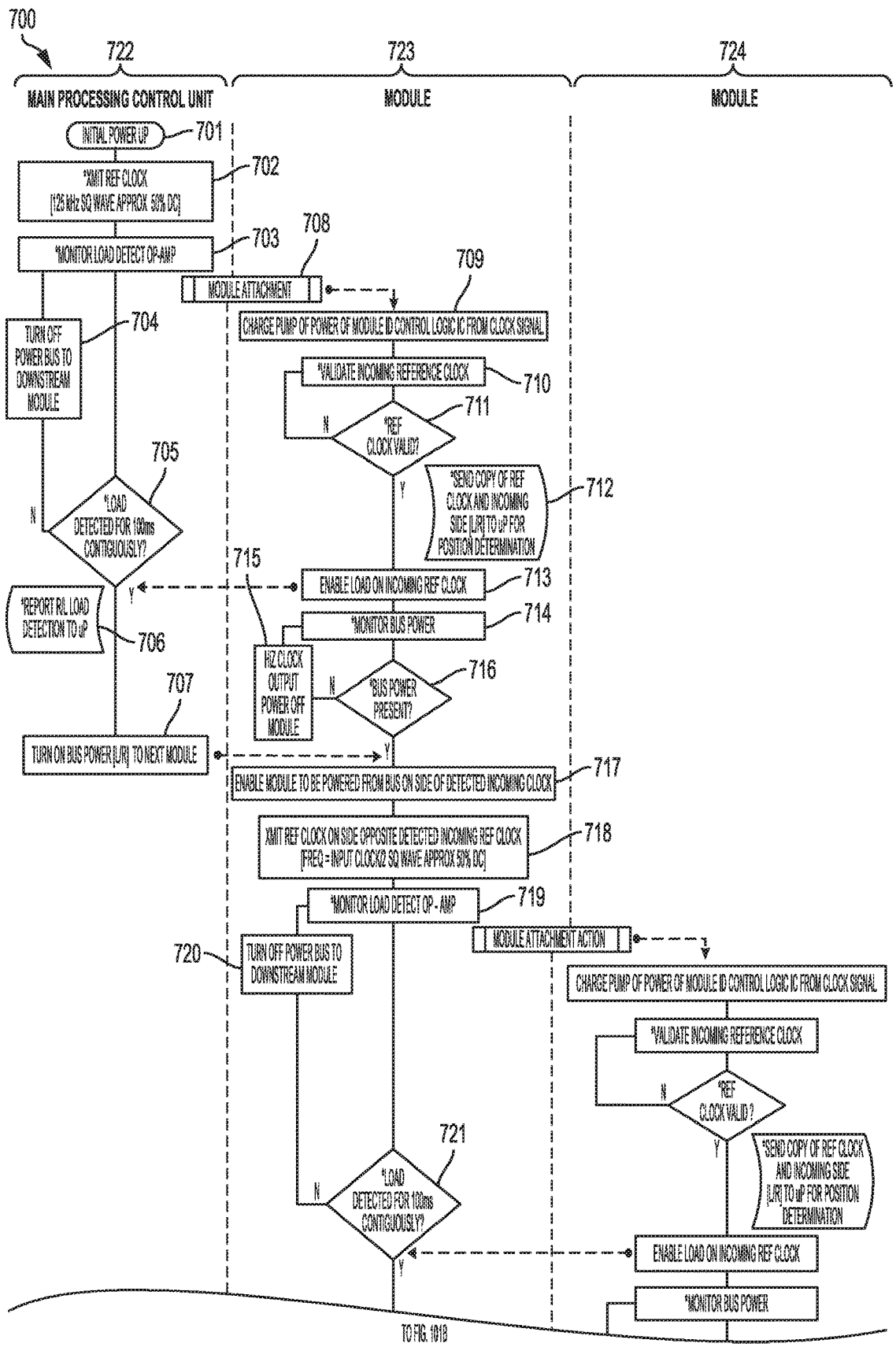
FIGS. 191A-191B show a timing diagram of the modular pump system as two medical device assemblies are coupled to the central unit to illustrate the powering-up sequence of the system in accordance with an embodiment of the present disclosure.
Figure 191B:
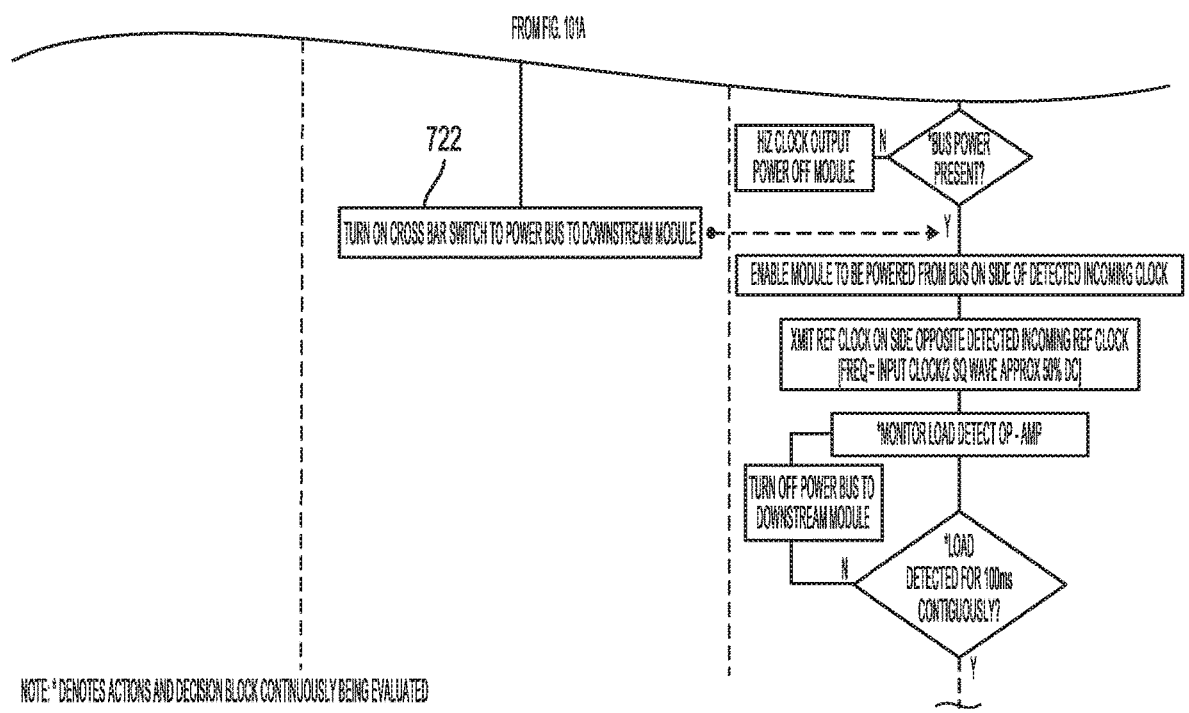

FIGS. 191A-191B show a timing diagram 700 of the modular pump system 500 as two medical device assemblies 504 are coupled to the central unit 502 to illustrate the powering-up sequence of the system. The timing diagram 700 shows a central unit 722, which may be the same as the central unit 502 described herein, and the timing diagram 700 shows two medical device assemblies 723, 724 which may be the same as the medical device assembly 504 described herein.

At 701, the central unit 722 has an initial power up. At 702 the reference clock generates a square wave and couples it to a communication pin of the module 723 after the module is attached at 708. At 703, a passible indication of a request for power is determined by using an operational amplifier to detect impedance on the communications pin. If a load is not detected at 100 ms at 705, then at 704 the power applied to a right power pin is turned off (if already on). If it is detected, then at 706, a detected load is communication to the microprocessor and the right power bus is turned on as to supply power to the right power pin at 707.

The timing diagram 700 also shows the operation of the medical-device assembly 723 when it is coupled to the central unit 722. The attachment is shown as 708. At 709, the medical-device assembly 723 uses the signal received from the central unit 722 and harvests it using a charge pump. If the clock is validated 710 (e.g., a predetermined number of signals determines it is a clock having the proper characteristics), then 710 transitions through 711 to 713,otherwise, 710 transitions to 711 and back to 710. For example, the first few samples of a square wave may be ignored so that transient signals generated by a users' touch does not cause a false positive for a passive request for power. Additionally or alternatively, a clock may start on the rising edge of a waveform and a predetermined amount of time may be required to pass where the clock is above a predetermined threshold until the square wave is considered valid; one of ordinary skill in the art will appreciate variations including the use of positive logic, negative logic, or inverted logic to implement this touch-detect feature. In some specific embodiments, a predetermined number of valid pulses must be detected until the signal is considered to be valid. At 712, a copy of the reference signal clock and incoming side of the signal is sent to the processor so that it can determine its position within the system 500.

At 713, a load is applied to the communications pin and then, the assembly 723 transitions to 714 where it waits for power via the power pin. That is, 714 transitions from 716 to 715 until power is received after which the assembly 723 transitions to 717. At 717, the module is powered from the power bus.

At 718, a signal is turned on the opposite side connected to the central unit 722 for application to the communications pin that is opposite to the central unit 722. At 719, an op-amp monitors the load on the communications pin and if a load is not detected for 100 ms continuously, then it will turn off the power bus at 720 and transitions back to 719. Otherwise, 721 transitions from 722 to turn on the crossbar to dower downstream to the to the assembly 724. The assembly 724 operates in the same way as the assembly 723 and as indicated by the timing diagram 700. Please note that the assembly 723, 724 operate the same way regardless as to whether a central unit 722 is applying the signal or another assembly 504 is apply8ing the power (however the frequency changes of the clock to indicate relative position is used).

Figure 192A:
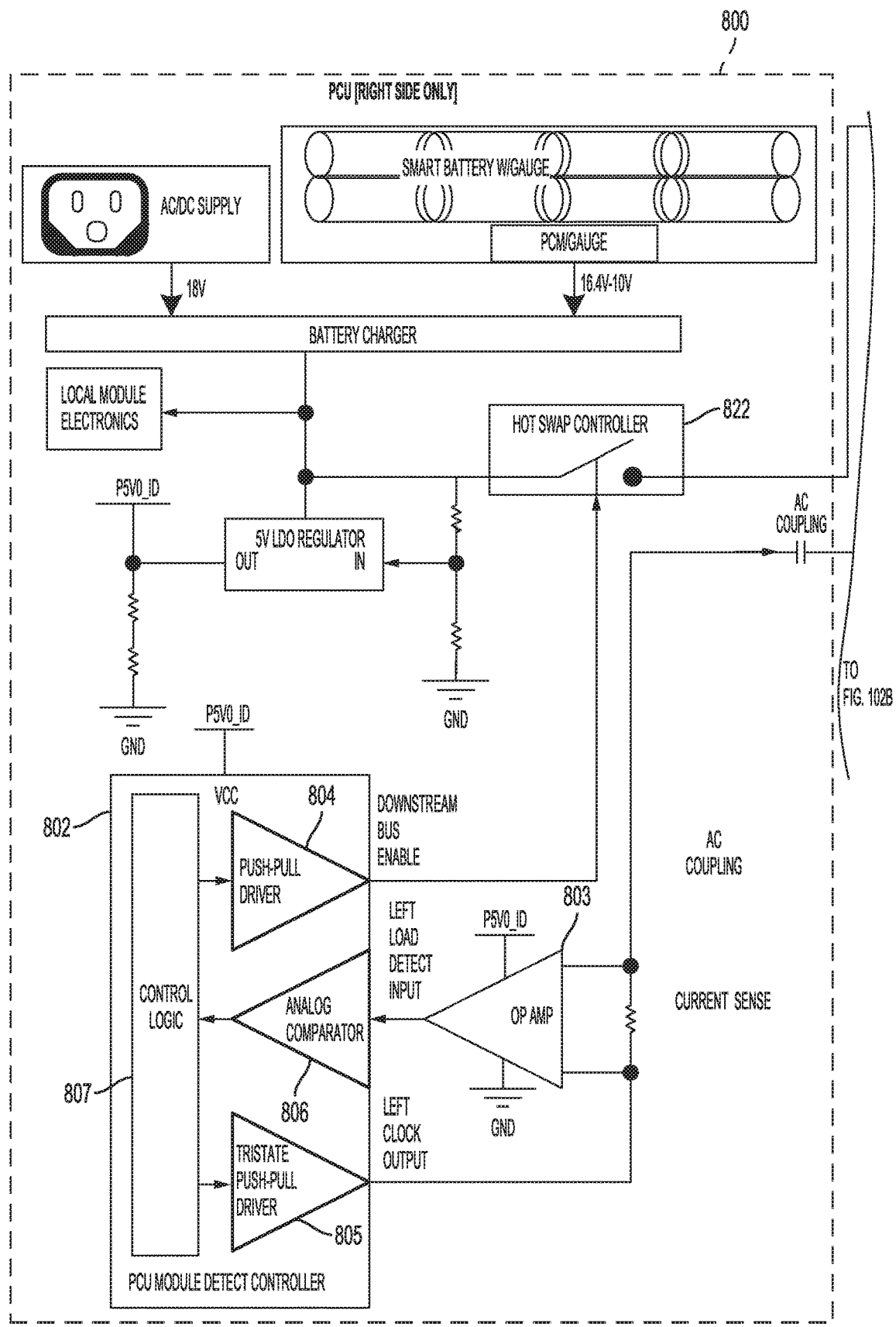
FIGS. 192A-192C show a block diagram of a modular pump system in accordance with an embodiment of the present disclosure.
Figure 192B:
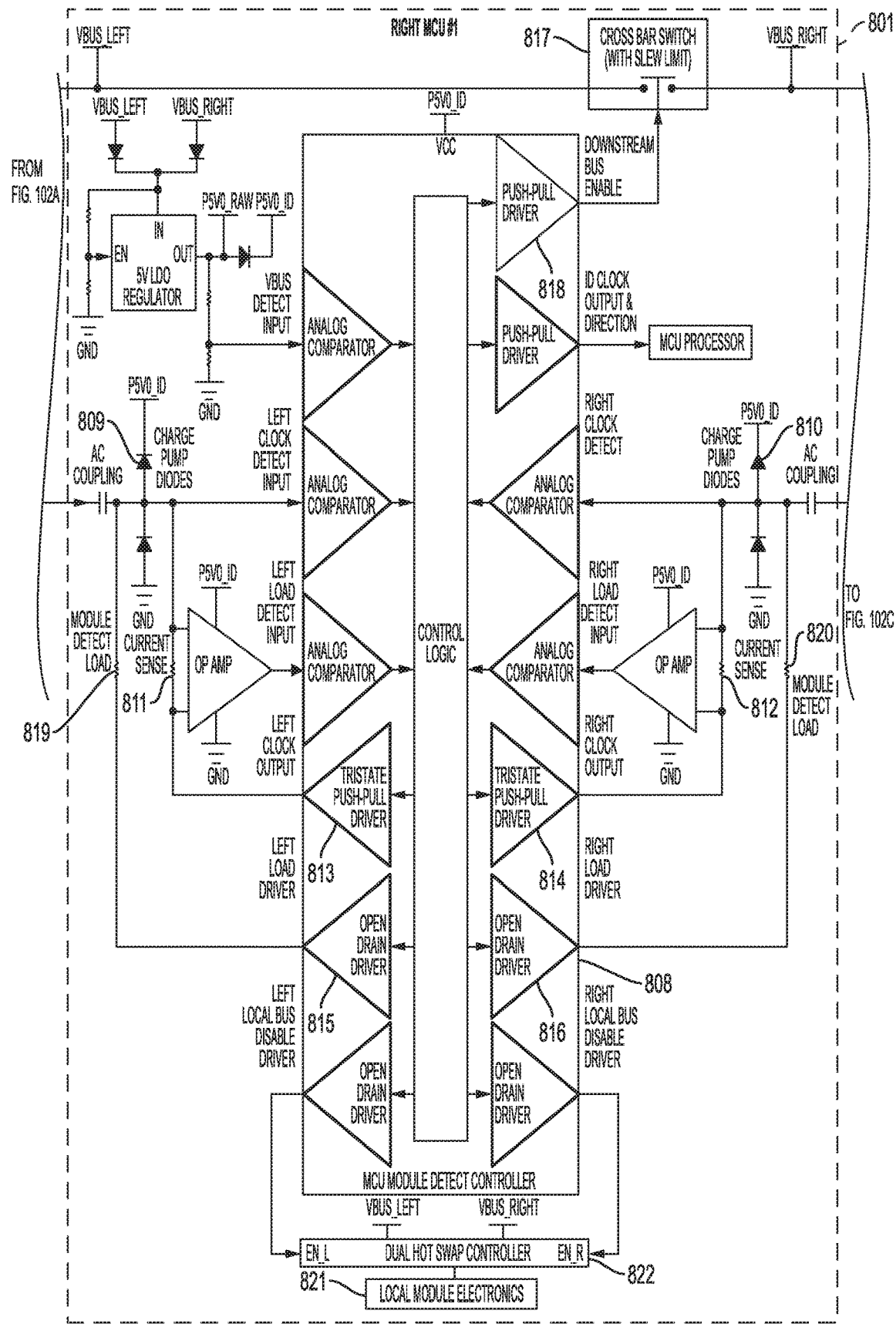
Figure 192C:
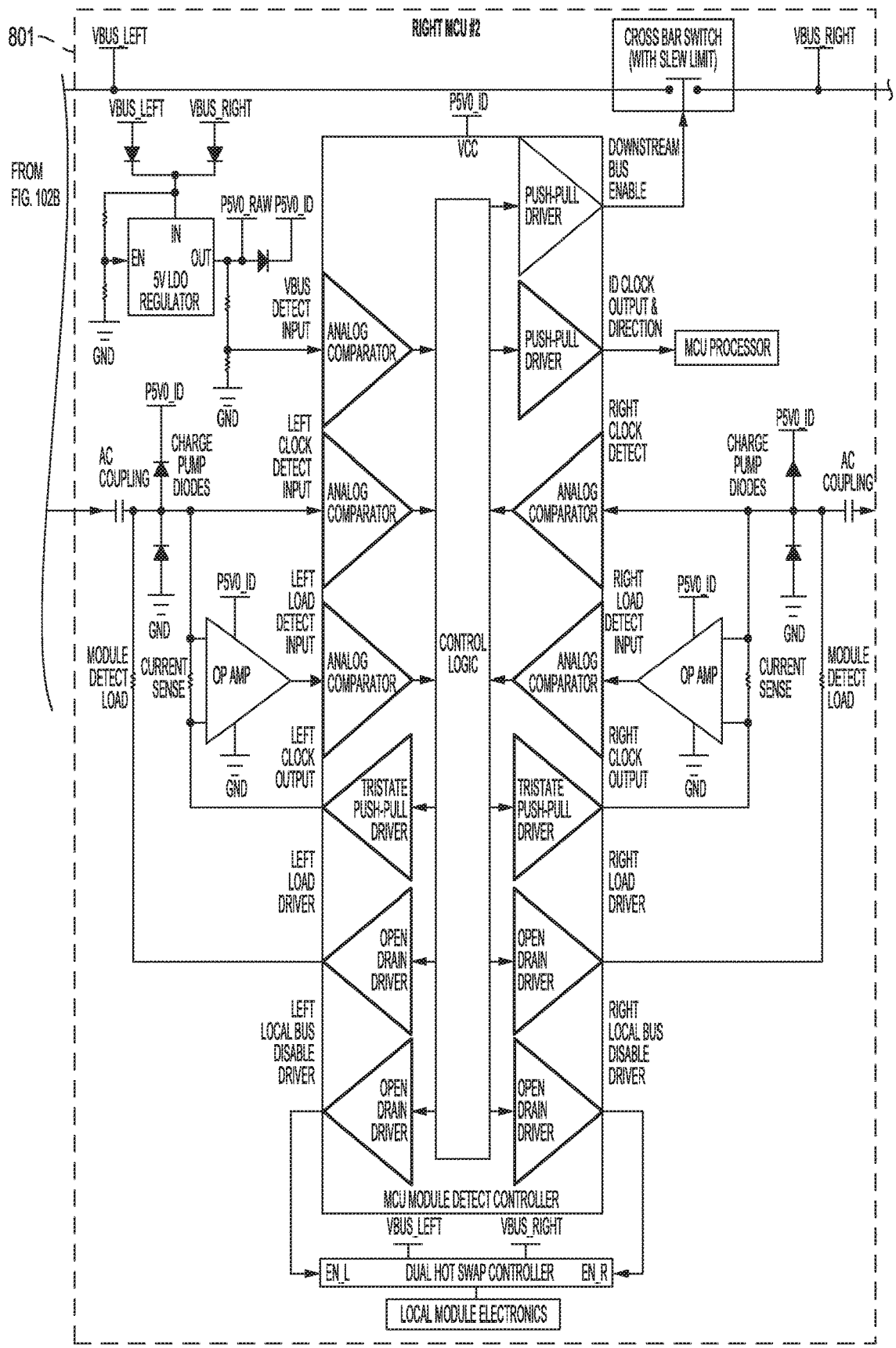

FIGS. 192A-192C show a block diagram of a modular pump system 500 including a central unit 800, and medical-device assemblies 801. The central unit 800 includes a dual hot swap controller 822 to apply power to a power pin, which is controlled by a controller 802 via a driver 804. The controller generates a clock signal via driver 805 which then uses the current sensor 803 to determine changes in impedance as described above. An analog comparator 806 communicates the output of the current sensor 803 (op-amp design) to the control logic 807. The controller 802 uses the state diagrams described above and/or the timing diagrams described above.

The assembly 801 (shown in FIG. 192B and another one is shown in FIG. 192C) includes a controller 808. The controller 808 controls the cross-bar switch 817 via a driver 818. The controller 808 can be powered via left charge pump diodes 809 or right charge pump diodes 810. A clock may be generated to apply to the left communications pin via driver 813 or a right communications pin via driver 814. A left current sense 811 detects changes in impedances of the left communications pin and the right current sense 812 detects changes in impedance as the clock is applied to the right communications pin.

A driver 815 controls whether or not a load 819 is coupled to the left communications pin while a driver 816 controls whether or not a load 820 is applied to the right communications pin. A dual hot swap controller 822 allows power to be applied to the module electronics 821 via a left power pin or right power pin.

FIGS. 103A-103J shows circuitry of the modular pump system 500 to illustrate the assembly ID circuitry, e.g., that may be used with the modular pump system described herein.

Figure 193A:
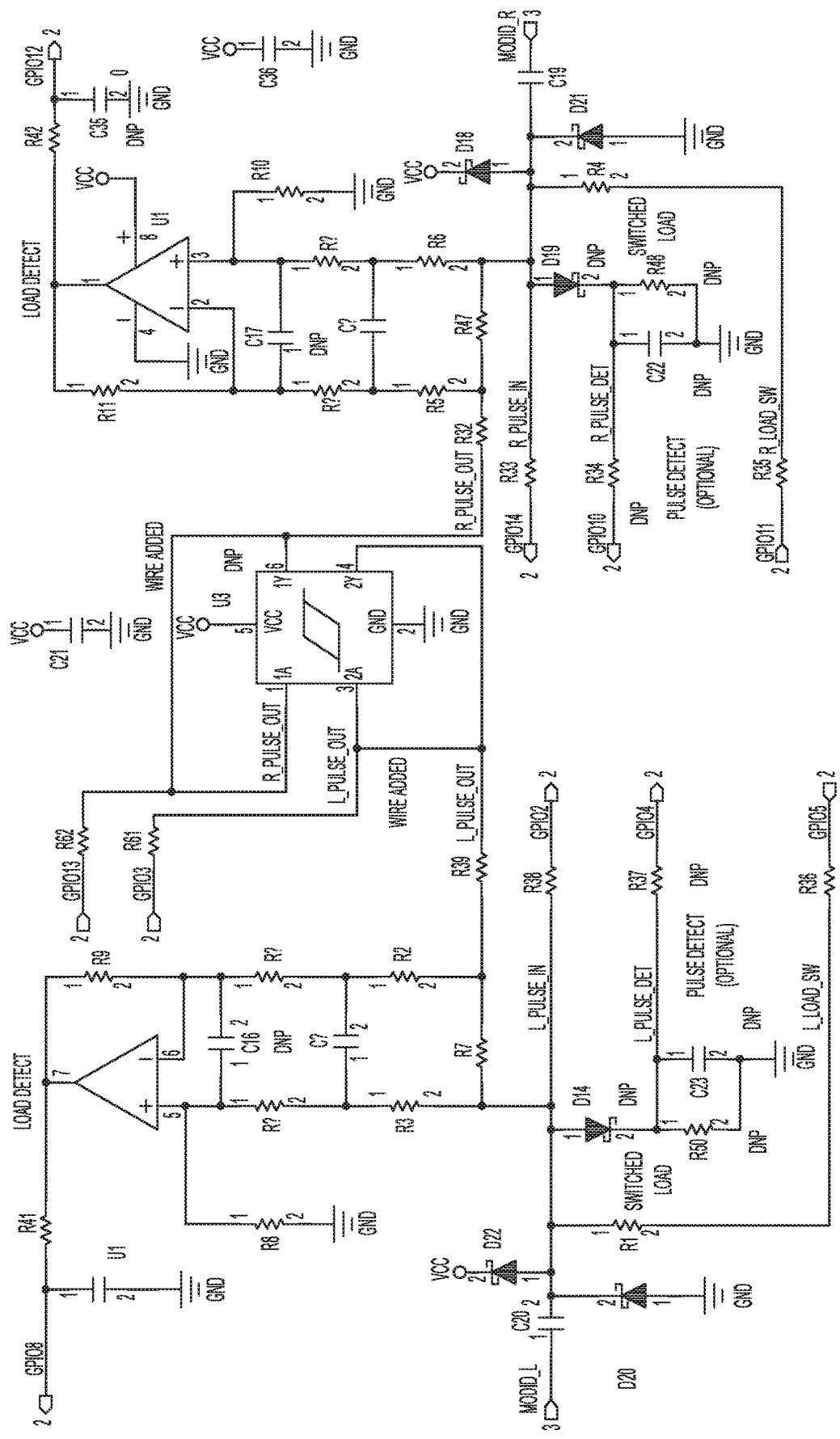
FIGS. 193A-193J show a circuit of the modular pump system in accordance with an embodiment of the present disclosure.

FIG. 193A shows a buffer circuit to buffer the output signal as applied to a communications pin. U3 may be a part number SN74LVC2G17DBVR manufactured by Texas Instruments of 12500 TI Blvd., Dallas, Tex. 75243.

Figure 193B:
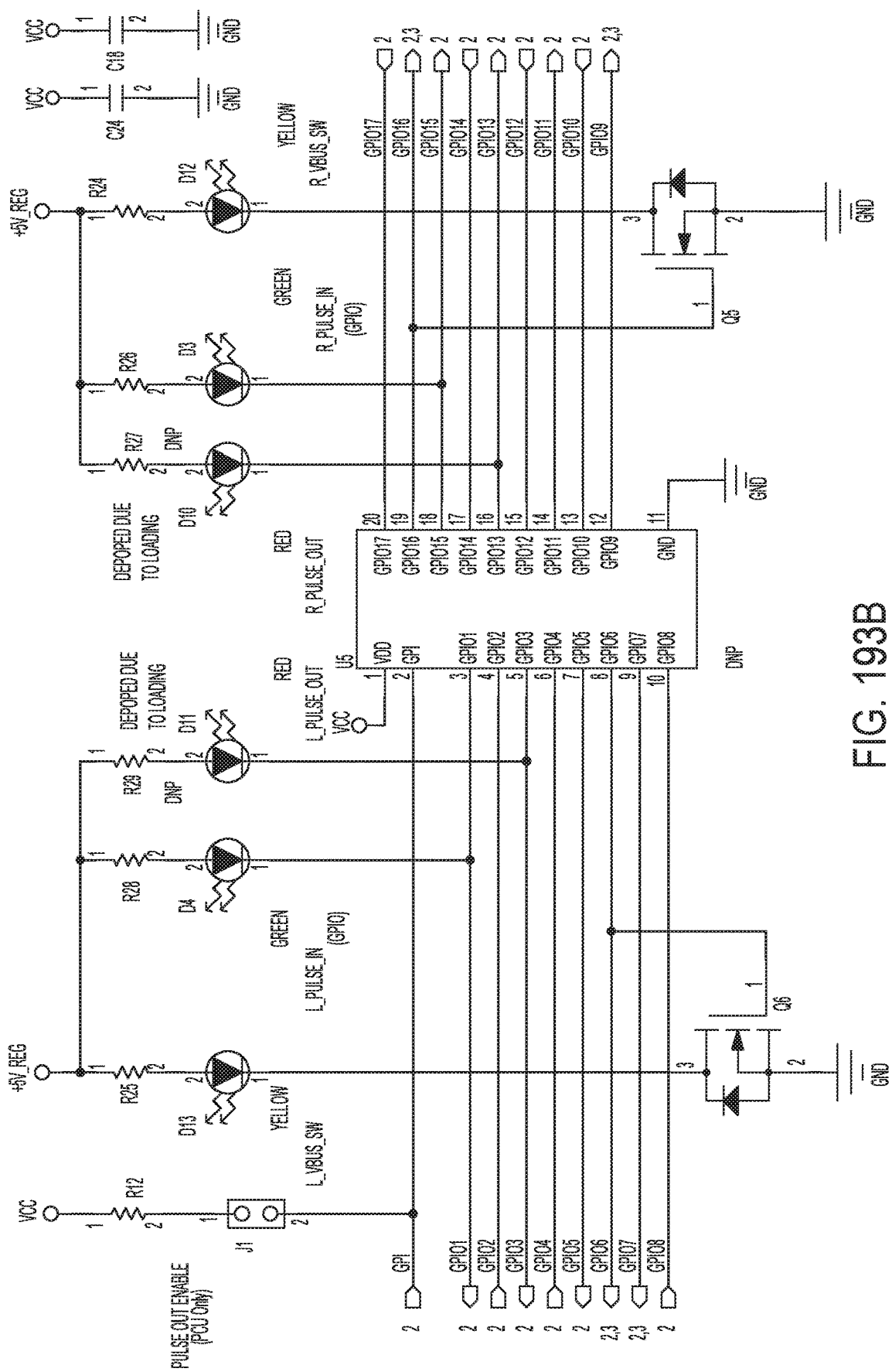
Figure 193C:
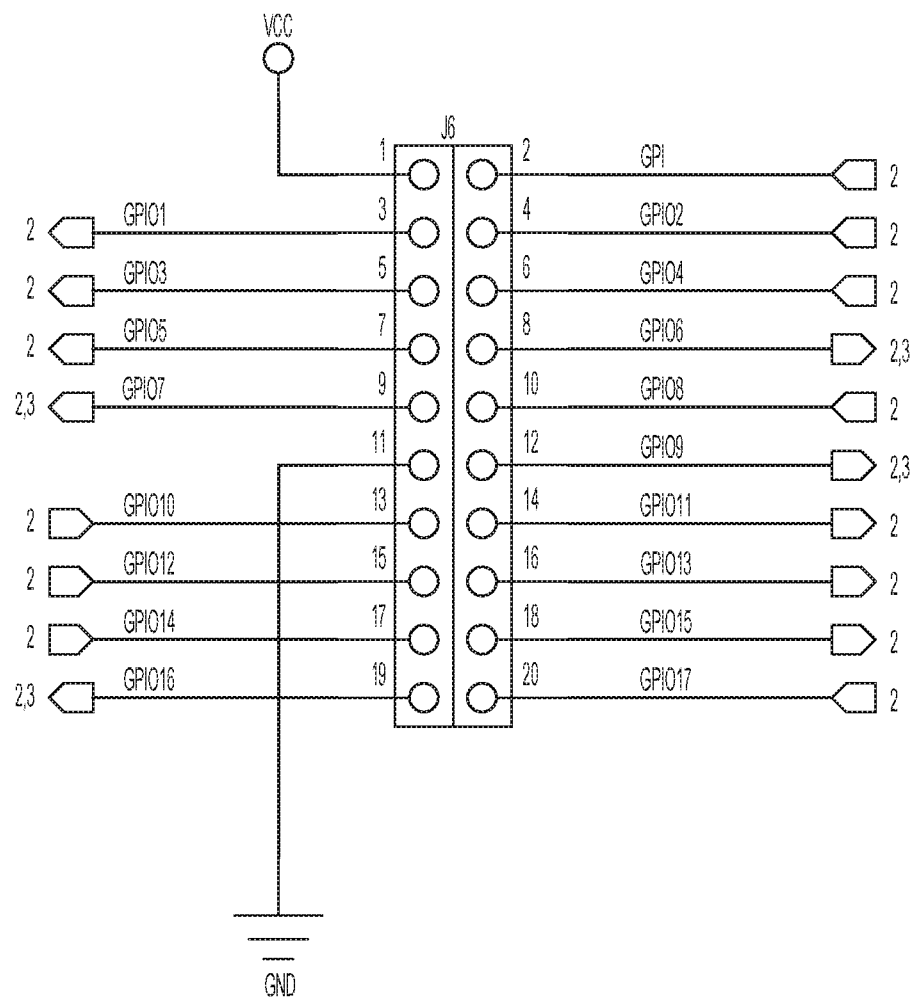
Figure 193D:
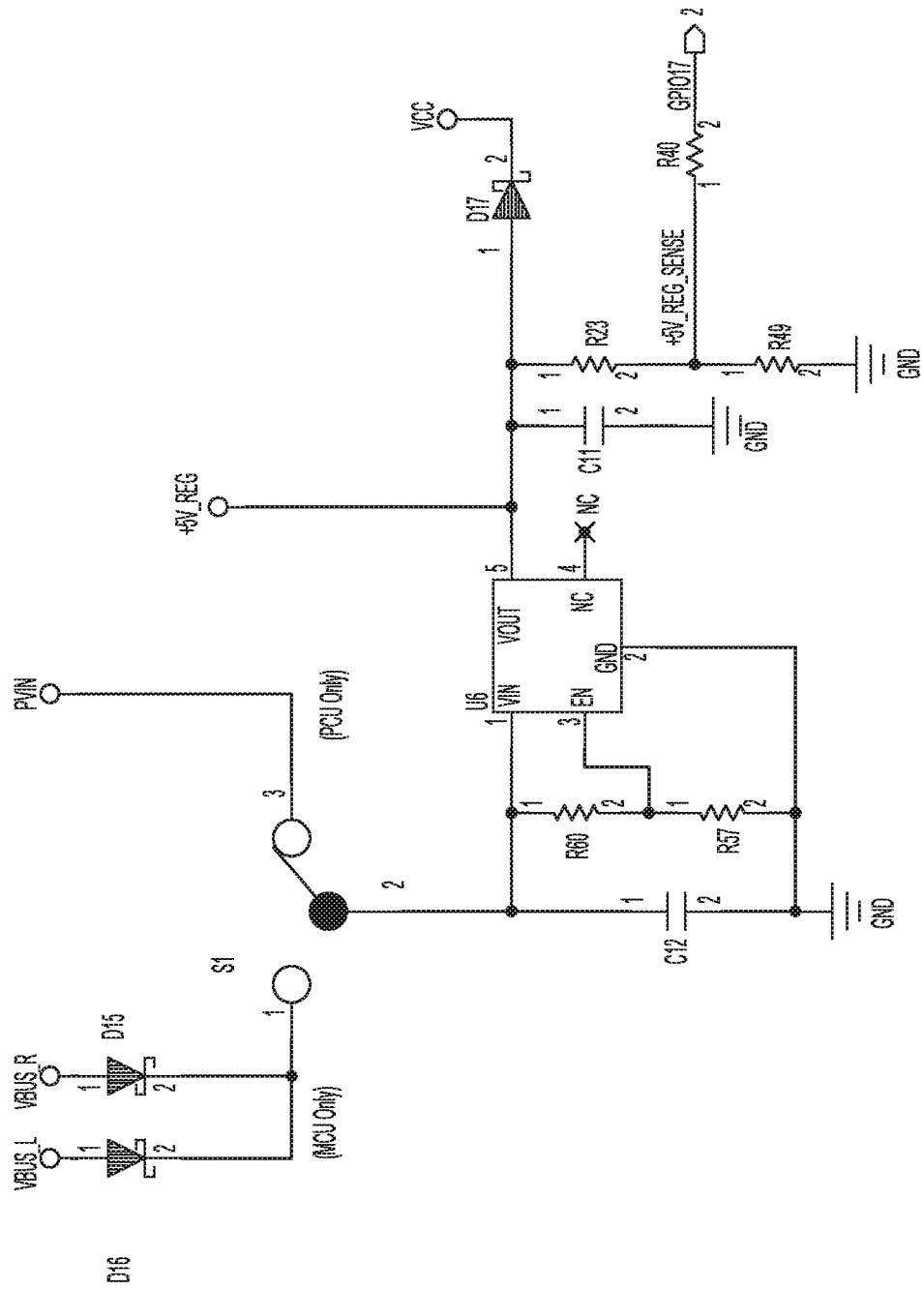
Figure 193E:
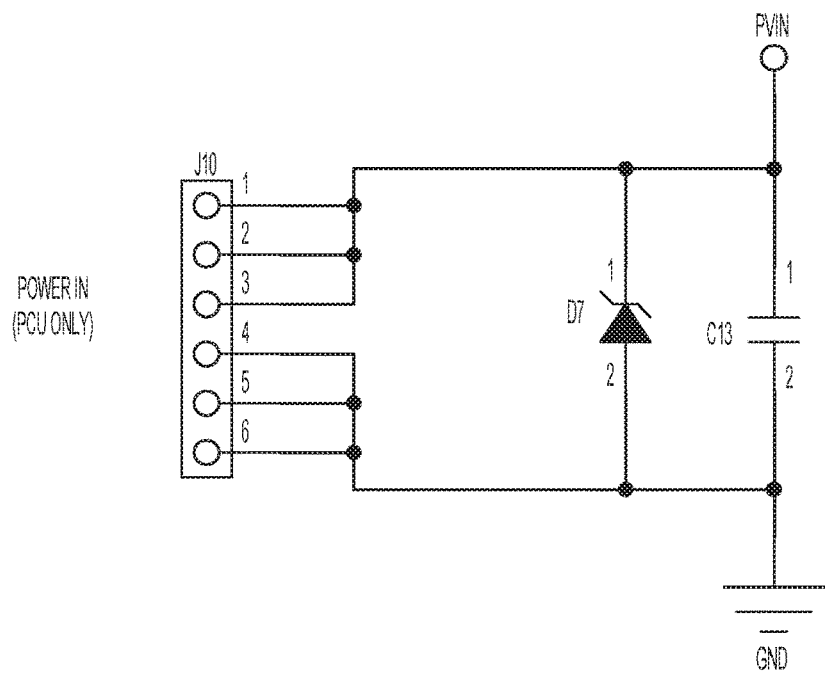
Figure 193F:
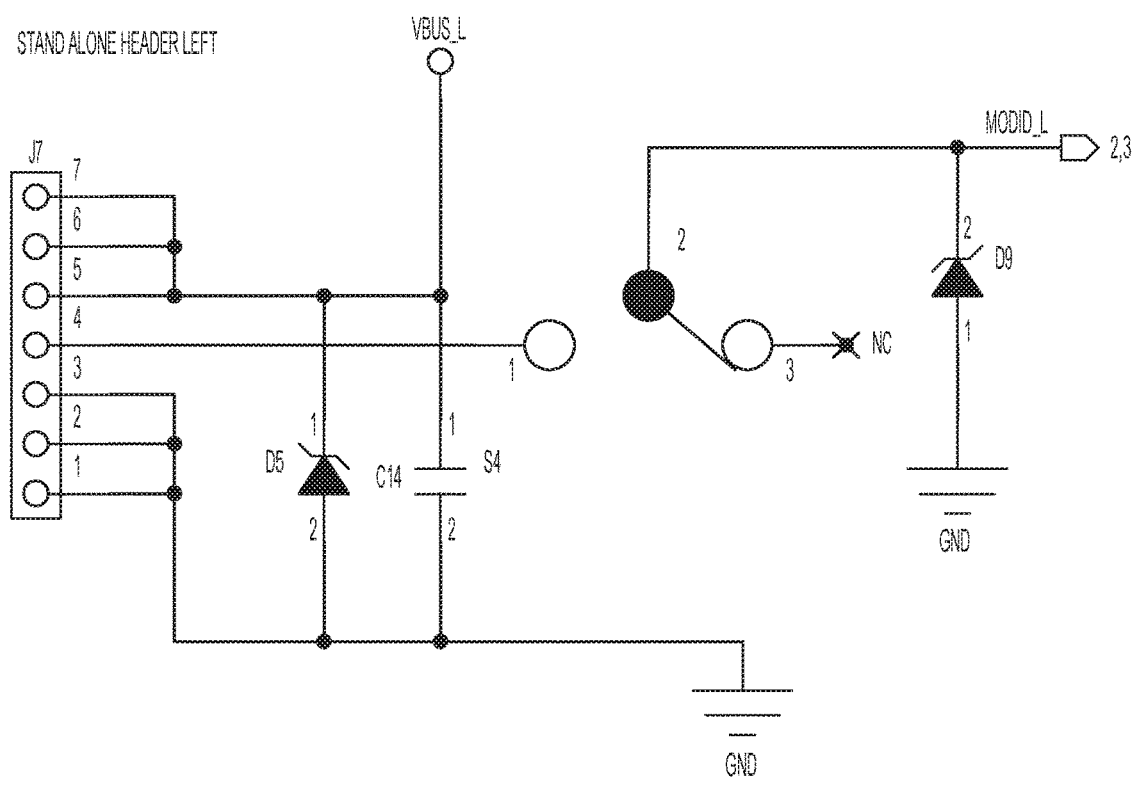
Figure 193G:
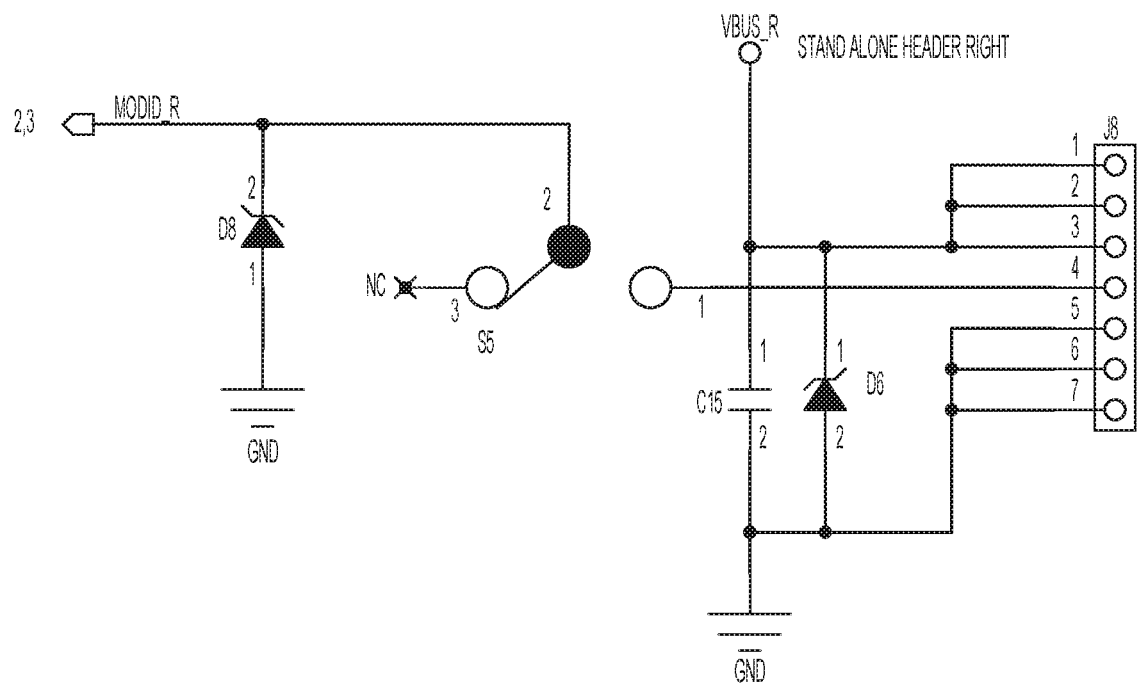
Figure 193H:
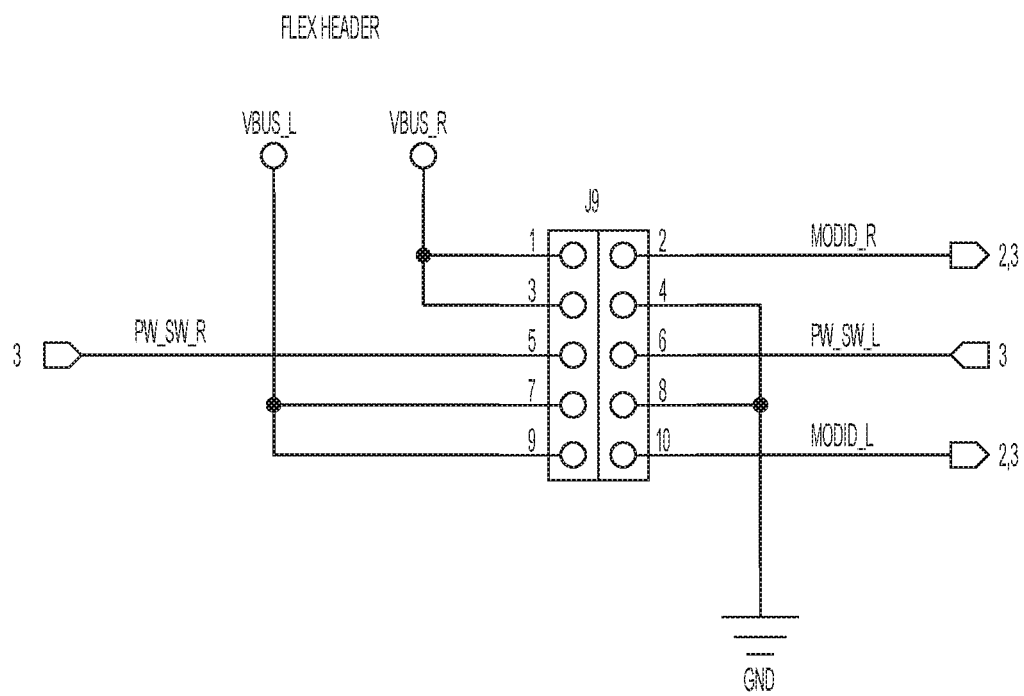
Figure 193I:
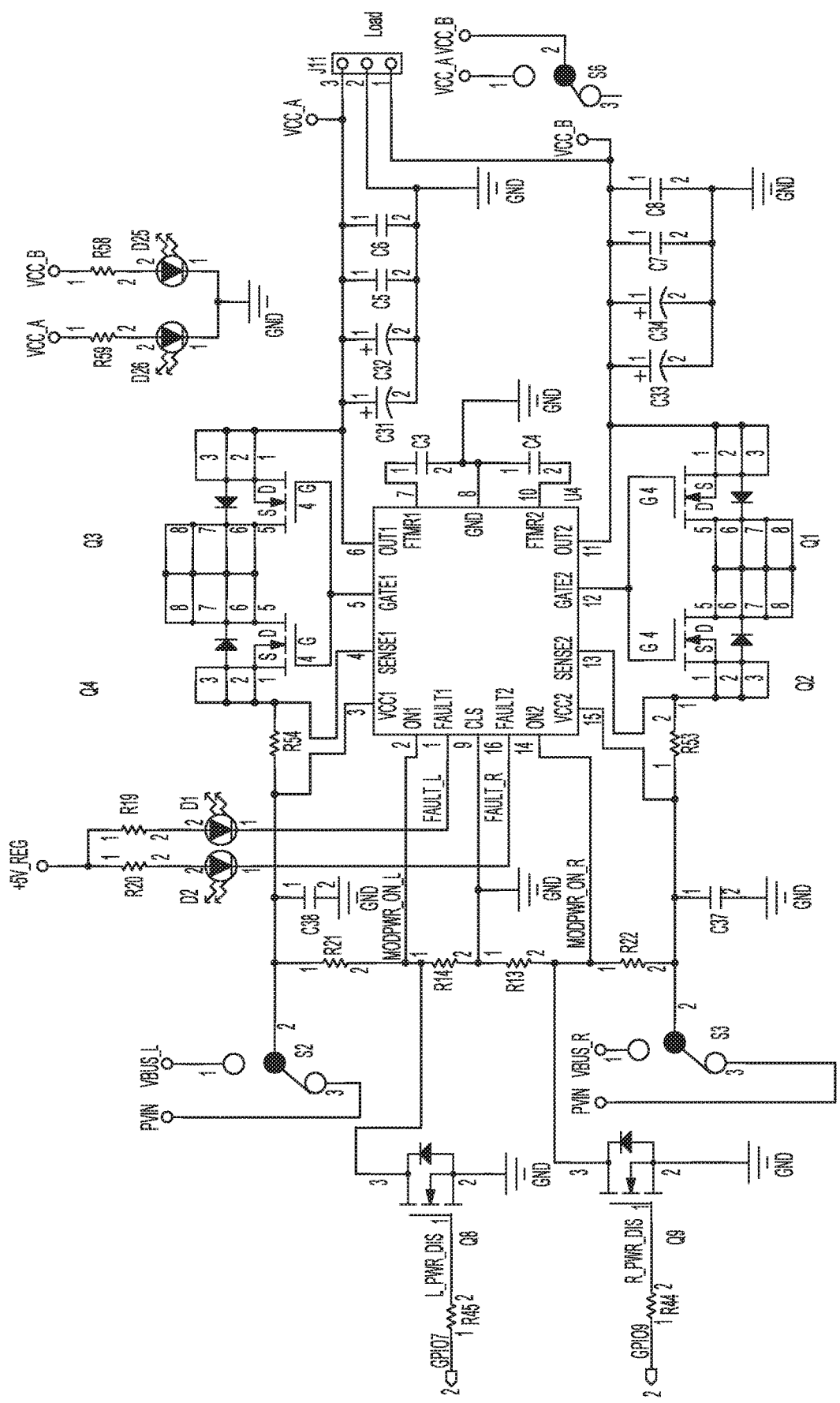
Figure 193J:
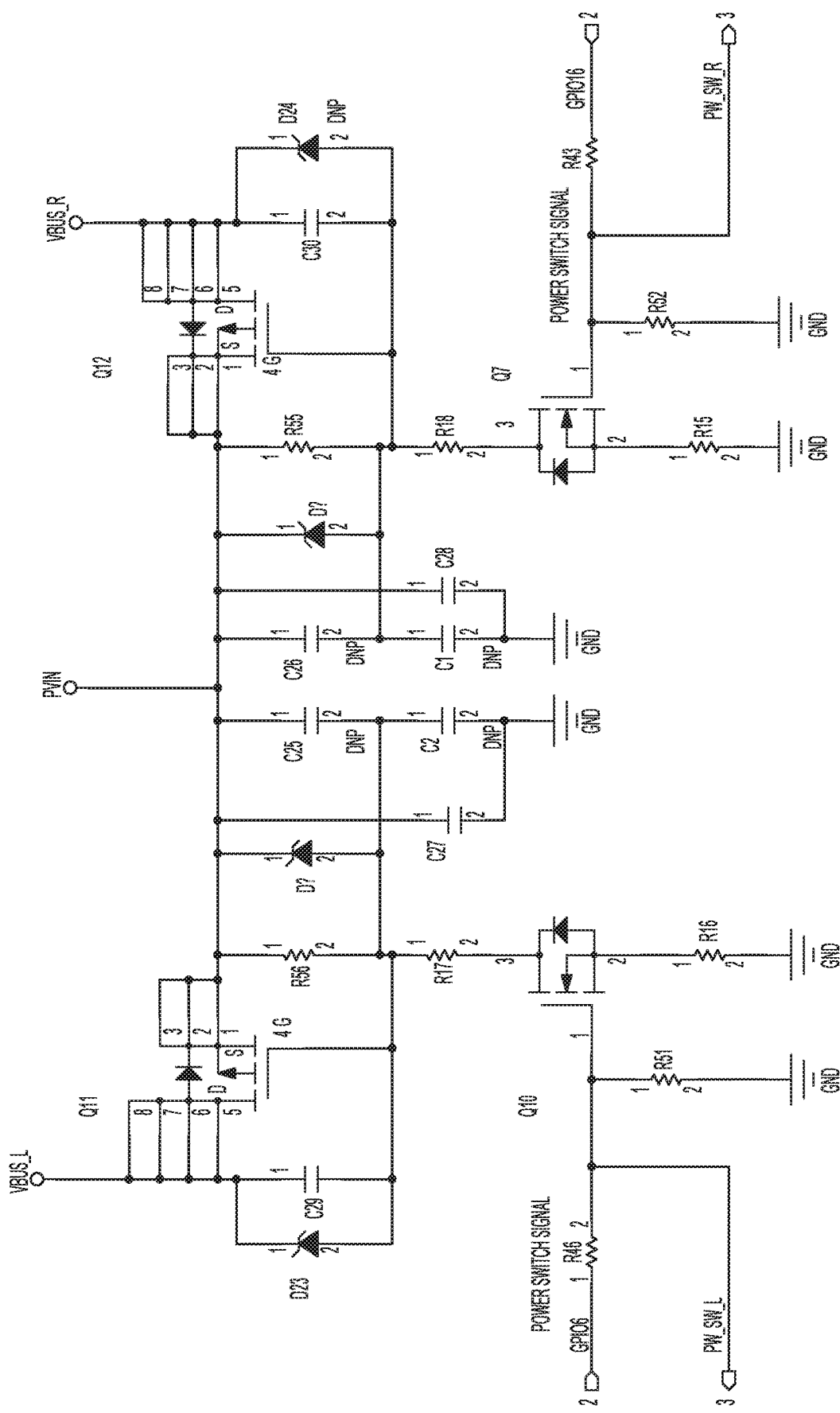

FIG. 193B shows the controller U5. The controller U5 may be part number SLG46721V of Dialog Semiconductor of 100 Longwater Avenue, Green Park, Reading RG2 6GP, United Kingdom. FIG. 193C shows a debugging header. FIG. 193D shows the voltage regulator for the central unit or modular assembly. FIG. 193E shows a power conditioning circuit. FIG. 193F and 103G shows power conditioning circuits. FIG. 193H shows another debugging header. FIG. 193I shows the dual hot-swap controller. The device U4, may be part number LTC4226IMS-2 #PBF made by Analog Devices of One Technology Way, P. O. Box 9106, Norwood, Mass. 02062-9106, United States of America. FIG. 193J shows the cross-bar switch.

Figure 194:
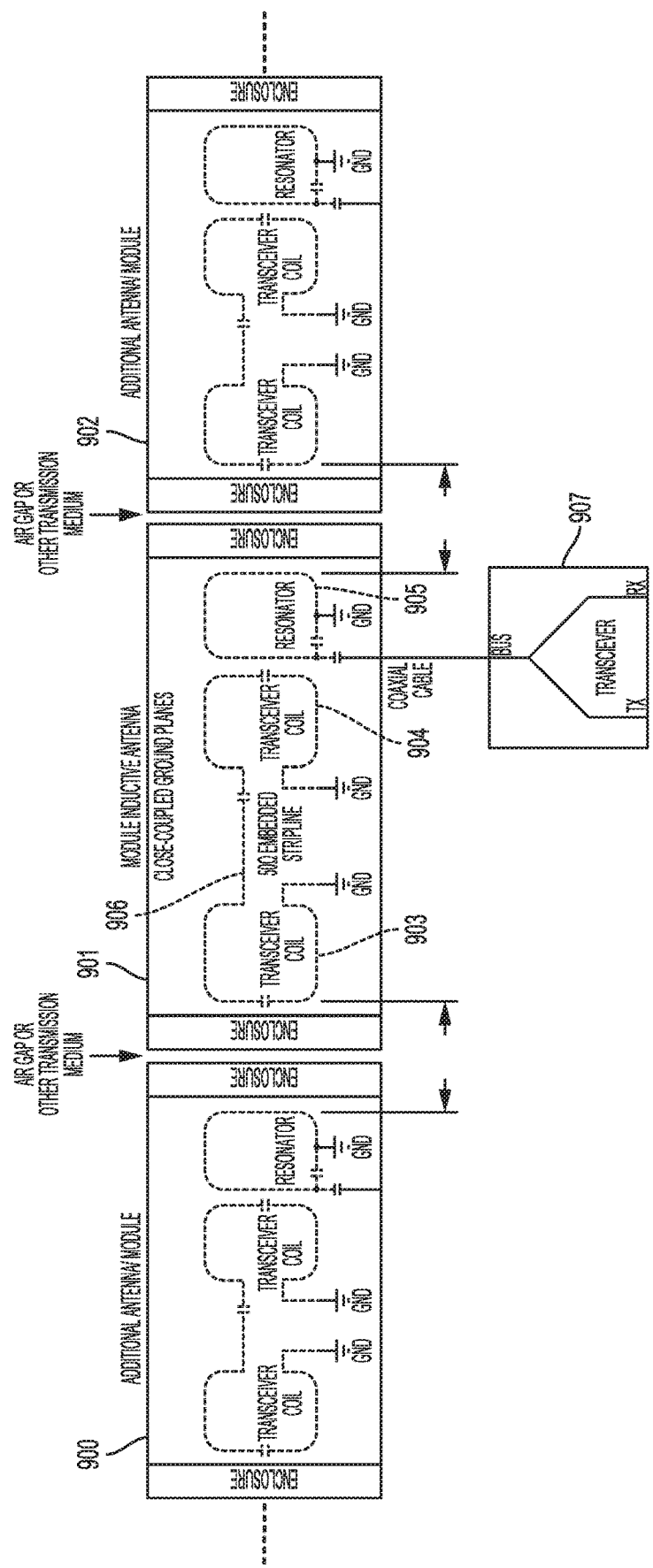
FIG. 194 shows a block diagram of the communication circuitry of the modular pump system in accordance with an embodiment of the present disclosure.

FIG. 194 shows a block diagram of the communication circuitry of the modular pump system. The communication module 900, 901 and 902 are shown. The modules 900, 901, and 902 may each be part of a central unit or an assembly. The module 901 includes a RF stripline 906 which forms the a communications bus. The communications bus may be dual use with the start-up sequence described above. One end of the bus includes a transceiver coil 903. On the other end is another transceiver coil 904 coupled to a resonator 905. The resonator communication with another module via an air gap as shown in FIG. 194. A top is coupled to the resonator 905 to interface with the bus via transceiver 907.

Figure 195:
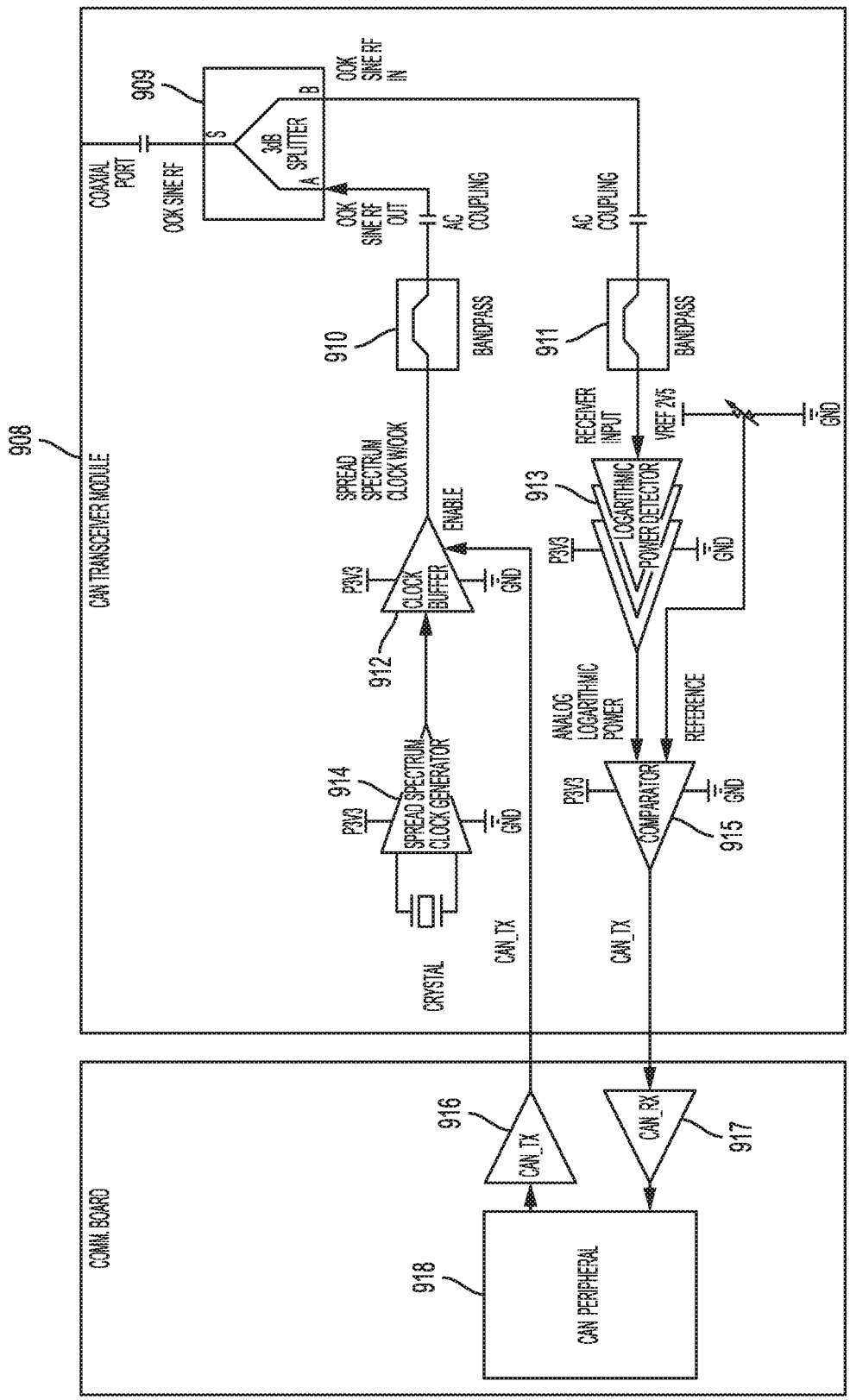
FIG. 195 shows a diagram of the circuitry for interfacing into the communications bus of the modular pump system in accordance with an embodiment of the present disclosure.

FIG. 195 shows a diagram of the circuitry for interfacing into the communications bus of the modular pump system. A CAN peripheral 918 is coupled to a buffer 916 for transmitting and another buffer 917 for receiving a signal.

Figure 196:
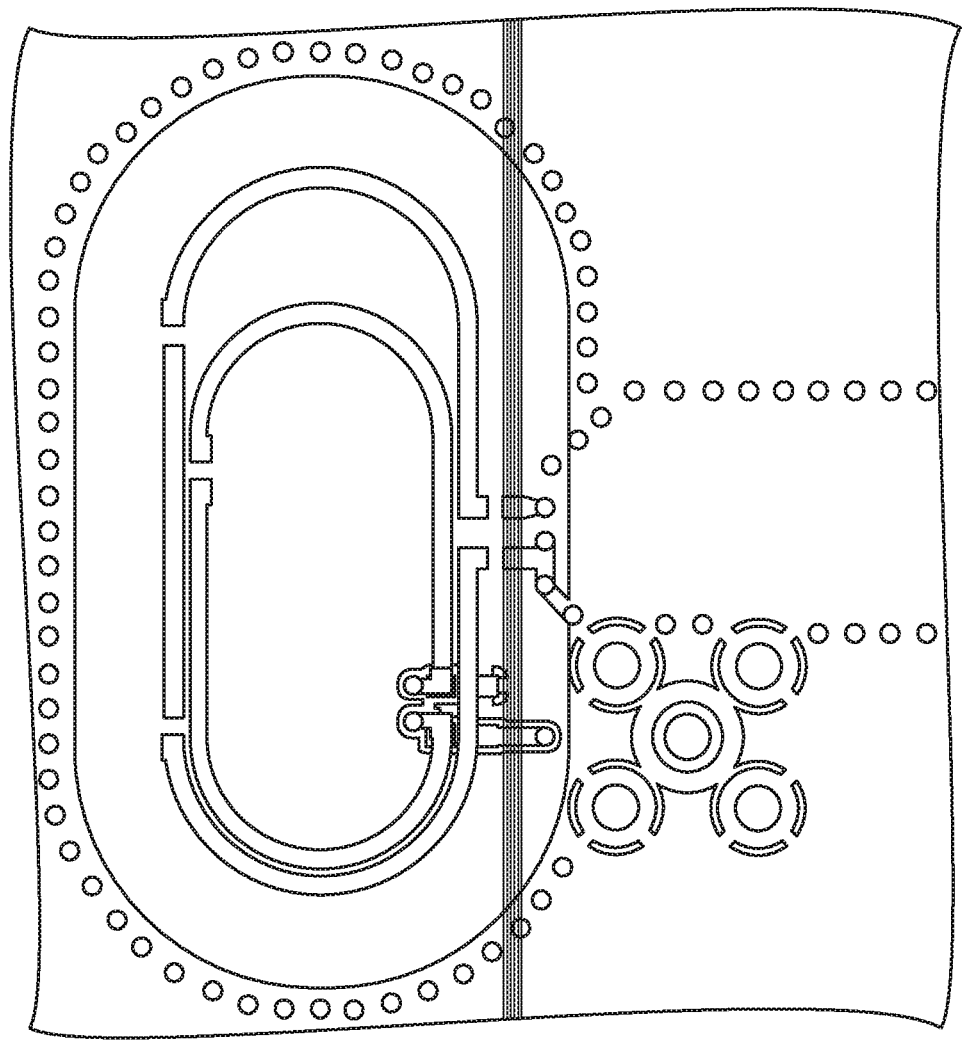
FIG. 196 shows an antenna design to couple a module to another module to extend the communications bus of the modular pump system in accordance with an embodiment of the present disclosure.

The transceiver module 908 modules the CAN values on an On-Off keying carrier signal. For transmission, the carrier frequency is generated using a spread-spectrum clock generator 914, which is on-off modulated with a clock buffer 912. A band pass filter 910 isolates the circuitry and the splitter 909 allows the signal to interface with the bus. The on-off carrier signal is also received by the splitter 909, which goes through a band pass filter 911 and is demodulated by a power detector 913. A comparator 915 translates the broadband signal to CAN on-off signals for being received by the buffer 917. FIG. 196 shows a PCB diagram of the resonator 905.

In alternative embodiments, the central unit generates the broad-spectrum signal and each of the assemblies grounds the signal to on-off keying modulation to communicate the on-off values needed for CAN communications.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g., "a," "an," or "the," this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. An apparatus, comprising:
    a carriage housing comprising a carriage rotatable within the carriage housing, and at least one tube retainer offset from an axis of rotation of the carriage, the at least one tube retainer configured to receive and retain a fluid tube in a substantially stationary position while the carriage rotates within the carriage housing, the carriage comprising a guide surface;
    a pivot mechanism coupled to the carriage and configured to connect to a rotating device to rotate the carriage about the axis in response to rotation of the rotating device; and
    a removable tube clamp being retainable by the at least one tube retainer for rotation inside the carriage housing by the carriage such that, when the fluid tube is retained by the at least one tube retainer and the carriage rotates about the axis, the removable tube clamp constricts or opens the tube depending on the direction of rotation of the carriage, the removable tube clamp comprising a stabilizer, the stabilizer facilitating insertion of the removable tube clamp into the retainer, the guide surface and the stabilizer interacting with one another to inhibit the removable tube clamp from pinching the fluid tube during insertion of the removable tube clamp into the retainer when the fluid tube is retained by the at least one tube retainer.

2. The apparatus of claim 1, wherein the at least one tube retainer comprises respective tube retainers aligned through at least a portion of a top and a bottom of the carriage housing at respective vertically aligned locations.

3. The apparatus of claim 1, further comprising:
    a light emitting device, and
    an optical sensor,
    wherein the carriage housing is configured with a window to receive light from the light emitting device, and to pass at least a portion of the received light through the carriage housing to the sensor when the removable tube clamp is received into the carriage housing, the portion of the received light comprising a pattern defined by one or more holes in the removable tube clamp.

* * * * *